US008623997B2

(12) United States Patent
Bosanac et al.

(10) Patent No.: US 8,623,997 B2
(45) Date of Patent: Jan. 7, 2014

(54) VARIANT HHIP1 PROTEIN AND METHODS AND USES THEREOF

(75) Inventors: Ivan Bosanac, San Mateo, CA (US); Sarah G. Hymowitz, San Francisco, CA (US); Robert A. Lazarus, Millbrae, CA (US); Henry R. Maun, San Francisco, CA (US); Suzanna J. Scales, San Mateo, CA (US); Xiaohui Wen, Palo Alto, CA (US)

(73) Assignees: Curis, Inc., Lexington, MA (US); Genentech, Inc., South San Francisco, CA (US)

( * ) Notice: Subject to any disclaimer, the term of this patent is extended or adjusted under 35 U.S.C. 154(b) by 164 days.

(21) Appl. No.: 12/995,442

(22) PCT Filed: Jun. 1, 2009

(86) PCT No.: PCT/US2009/045880
§ 371 (c)(1),
(2), (4) Date: Feb. 9, 2011

(87) PCT Pub. No.: WO2009/146463
PCT Pub. Date: Dec. 3, 2009

(65) Prior Publication Data
US 2011/0129457 A1 Jun. 2, 2011

Related U.S. Application Data

(60) Provisional application No. 61/057,762, filed on May 30, 2008.

(51) Int. Cl.
C07K 14/00 (2006.01)
(52) U.S. Cl.
USPC ......................................................... 530/350
(58) Field of Classification Search
USPC ......................................................... 530/350
See application file for complete search history.

(56) References Cited

U.S. PATENT DOCUMENTS

| 6,514,724 | B1 | 2/2003 | McMahon et al. |
| 7,115,394 | B2 | 10/2006 | McMahon et al. |
| 7,585,671 | B2 | 9/2009 | McMahon et al. |
| 2003/0143595 | A1 | 7/2003 | McMahon et al. |

FOREIGN PATENT DOCUMENTS

| WO | WO 98/12326 A1 | 3/1998 |
| WO | WO 01/30798 A1 | 5/2001 |
| WO | WO03042661 | * 5/2003 |

OTHER PUBLICATIONS

Skolnick et al. (Trends in Biotechnology 2000; 18: 34-39).*
Bowie et al. (Science 1990; 257: 1306-1310).*
Burgess et al. (Journal of Cell Biology 1990; 111: 2129-2138).*
Lazar et al. (Molecular and Cellular Biology, 1988, 8: 1247-1252).*
Luque et al. (Biochemistry. Nov. 19, 2002; 41 (46): 13663-13671).*
Vucic et al. (J. Biol. Chem. Dec. 18, 1998; 273 (51): 33915-33921).*
Takada et al. (Mol. Endocrinol. 2000; 14 (5): 733-740).*
Guo et al. (Proc. Natl. Acad. Sci. USA. Jun. 22, 2004; 101 (25): 9205-9210).*
Bosanac et al. (Nat Struct Mol Biol. Jul. 2009; 16 (7): 691-7).*
Beachy, Philip A., et al., "Tissue Repair and Stem Cell Renewal in Carcinogenesis," Nature, 432:324-331 (2004).
Bochtler, Matthias, et al., "Similar Active Sites in Lysostaphins and D-Ala-D-Ala Metallopeptidases," Protein Science, 13:854-861 (2004).
Bussiere, Dirksen, E., et al., "The Structure of VanX Reveals a Novel Amino-Dipeptidase Involved in Mediating Transposon-Based Vancomycin Resistance," Molecular Cell, 2:75-84 (1998).
Chen, Yu and Struhl, Gary, "Dual Roles for Patched in Sequestering and Transducing Hedgehog," Cell, 87:553-563 (1996).
Chuang, Pao-Tien and McMahon, Andrew P., "Vertebrate Hedgehog Signalling Modulated by Induction of a Hedgehog-Binding Protein," Nature, 397:617-621 (1999).
Chuang, Pao-Tien, et al., "Feedback control of Mammalian Hedgehog Signaling by the Hedgehog-Binding Protein, Hip1, Modulates Fgf Signaling During Branching Morphogenesis of the Lung," Genes & Development, 17:342-347 (2003).
Coulombe, J., et al., Hedgehog Interacting Protein in the Mature Brain: Membrane-Associated and Soluble Forms, Molecular and Cellular Neuroscience, 25:323-333 (2004).
Ericson, Johan, et al., "Two Critical Periods of Sonic Hedgehog Signaling Required for the Specification of Motor Neuron Identity," Cell, 87:661-673 (1996).
Frank-Kamenetsky, Maria, et al., "Small-Molecule Modulators of Hedgehog Signaling: Identification and Characterization of Smoothened Agonists and Antagonists," Journal of Biology, 1:10 (2002).
Fuse, Naoyuki, et al., "Sonic Hedgehog Protein Signals not as a Hydrolytic Enzyme but as an Apparent Ligand for Patched," Proc. Natl. Acad. Sci. USA, 96:10992-10999 (1999).
Hall, Tracy M. Tanaka, et al., "A Potential Catalytic Site Revealed by the 1.7Åp Crystal Structure of the Amino-Terminal Signalling Domain of Sonic Hedgehog," Nature, 378:212-216 (1995).
Ingham, Philip W. and McMahon, Andrew P., "Hedgehog Signalling in Animal Development: Paradigms and Principles," Genes & Development, 15:3059-3087 (2001).
Kiselyov, Alex S., et al., "Small-Molecule Modulators of Hh and Wnt Signaling Pathways," Expert Opinion, 11(8):1087-1101 (2007).
Lee, John J., et al., "Autoproteolysis in Hedgehog Protein Biogenesis," Science, 266:1528-1537 (1994).
Mammalian Gene Collection (MGC) Program Team, "Generation and initial analysis of more than 15,000 full-length human and mouse cDNA sequences," PNAS, vol. 99(26), pp. 16899-16903 (2002).
Marigo, Valeria, et al., "Biochemical Evidence that Patched is the Hedgehog Receptor," Nature, 384:176-179 (1996).
McLellan, Jason S., et al., "Structure of a Heparin-Dependent Complex of Hedgehog and Ihog," PNAS, 103(46):17208-17213 (2006).

(Continued)

Primary Examiner — Stephen Rawlings
(74) Attorney, Agent, or Firm — Ropes & Gray LLP

(57) ABSTRACT

The present invention is directed to derivatives of Hhip1 and methods of using the same for treatment and diagnosis of cancer in mammals.

16 Claims, 28 Drawing Sheets

(56) References Cited

OTHER PUBLICATIONS

Olsen, Catherine L., et al., "Hedgehog-Interacting Protein is Highly Expressed in Endothelial Cells but Down-Regulated During Angiogenesis and in Several Human Tumors," BMC Cancer, 4:43 (2004).

Pasca di Magliano, Marina and Hebrok, Matthias, "Hedgehog Signalling in Cancer Formation and Maintenance," Nature Reviews—Cancer, 3:903-911 (2003).

Pepinsky, R. Blake et al., "Mapping Sonic Hedgehog-Receptor Interactions in Steric Interference," The Journal of Biological Chemistry, vol. 275(15), pp. 10995-11001 (2000).

Pepinsky, R. Blake, et al., "Identification of a Palmitic Acid-modified Form of Human Sonic Hedgehog," The Journal of Biological Chemistry, 273(22):14037-14045 (1998).

Porter, Jeffery A., et al., "Hedgehog Patterning Activity: Role of a Lipophilic Modification Mediated by the Carboxy-Terminal Autoprocessing Domain," Cell, 86:21-34 (1996).

Porter, Jeffery, et al., "Cholesterol Modification of Hedgehog Signaling Proteins in Animal Development," Science, 274:255-259 (1996).

Porter, Jeffery, et al., "The Product of Hedgehog Autoproteolytic Cleavage Active in Local and Long-Range Signalling," Nature, 374:363-366 (1995).

Rawlings, Neil D., et al., "MEROPS: The Peptide Database," Nucleic Acids Research, 36:D320-D325 (2008).

Rohatgi, Rajat and Scott, Matthew P., "Patching the Gaps in Hedgehog Signalling," Nature Cell Biology, 9(9):1005-1009 (2007).

Rubin, Lee L. and de Sauvage, Frederic, "Targeting the Hedgehog Pathway in Cancer," Nature Reviews Drug Discovery, 5:1026-1033 (2006).

Stanton, Benjamin Z., et al., "A Small Molecule that Binds Hedgehog and Blocks its Signalling in Human Cells," Nature Chemical Biology, 5(3)154-156 (2009).

Stone, Donna M., et al., The Tumour-Suppressor Gene Patched Encodes a Candidate Receptor for Sonic Hedgehog, Nature, 384:129-133 (1996).

Yao, Shenqin, et al., "The Ihog Cell-Surface Proteins Bind Hedgehog and Mediate Pathway Activation," Cell, 125:343-357 (2006).

Yauch, Robert L., A Paracrine Requirement for Hedgehog Signalling in Cancer, Nature, 455:406 (2008).

Briscoe et al., "A Hedgehog-Insensitive Form of Patched Provides Evidence for Direct Long-Range Morphogen Activity of Sonic Hedgehog in the Neural Tube," Molecular Cell, vol. 7(6), pp. 1279-1291 (2001).

Nakamura et al., "Anti-patched-1 Antibodies Suppress Hedgehog Signaling Pathway and Pancreatic Cancer Proliferation," Anticancer Research, vol. 27(6A), pp. 3743-3747 (2007).

\* cited by examiner

Figure 1A

```
  1 gagaagctgc agccgccggc agaggagacc tcagcatcat ctagagccca gcgctggccc
 61 tgcctccgcc tgccccgccg ccgccgtcgc cgtttctgtt cctgctactg tcccacctaa
121 acaactcccg ttacacggac aagtgaacat ctgtggctgt cctctccttt tcttcctcct
181 cttccaactc cttctcctcc tcccacttcc cagccgcagc agaaagcccc caacccaact
241 gacactggca caactgcaaa cggtgtcatc cgcacaactt tatctcgctc ctcgggctcc
301 cctaaggcat ggaccccatc gccgcgtctt ttatttttg caaagttgca tcgctgtaca
361 tatttttgtc cccgccacct ccctctgtct ctggagtgcc ctacagcccc gcaaactcct
421 cctggagctg cgccctagtg cccctgctgg gcagtggcgt tccccccat cctcccgcgc
481 ccagcccctg ctgctctggg cagacg
```

| | | | | | | | | | | | | | | | | |
|---|---|---|---|---|---|---|---|---|---|---|---|---|---|---|---|---|
| atg | ctg | aag | atg | ctc | tcc | ttt | aag | ctg | ctg | ctg | ctg | gcc | gtg | gct | ctg | ggc | ttc | ttt |
| M | L | K | M | L | S | F | K | L | L | L | L | A | V | A | L | G | F | F |
| | | | | 5 | | | | | 10 | | | | | 15 | | | | |

| gaa | gga | gat | gct | aag | ttt | ggg | gaa | aga | aac | gaa | ggg | agc | gga | gca | agg | agg | aga | agg |
|---|---|---|---|---|---|---|---|---|---|---|---|---|---|---|---|---|---|---|
| E | G | D | A | K | F | G | E | R | N | E | G | S | G | A | R | R | R | R |
| 20 | | | | | 25 | | | | | 30 | | | | | 35 | | | |

| tgc | ctg | aat | ggg | aac | ccc | ccg | aag | cgc | ctg | aaa | agg | aga | gac | agg | agg | atg | atg | tcc |
|---|---|---|---|---|---|---|---|---|---|---|---|---|---|---|---|---|---|---|
| C | L | N | G | N | P | P | K | R | L | K | R | R | D | R | R | M | M | S |
| | 40 | | | | | 45 | | | | | 50 | | | | | 55 | | |

| cag | ctg | gag | ctg | ctg | agt | ggg | gga | gag | atg | ctg | tgc | ggt | ggc | ttc | tac | cct | cgg | ctg |
|---|---|---|---|---|---|---|---|---|---|---|---|---|---|---|---|---|---|---|
| Q | L | E | L | L | S | G | G | E | M | L | C | G | G | F | Y | P | R | L |
| | | 60 | | | | | 65 | | | | | 70 | | | | | 75 | |

| tcc | tgc | tgc | ctg | cgg | agt | gac | agc | ccg | ggg | cta | ggg | cgc | ctg | gag | aat | aag | ata | ttt |
|---|---|---|---|---|---|---|---|---|---|---|---|---|---|---|---|---|---|---|
| S | C | C | L | R | S | D | S | P | G | L | G | R | L | E | N | K | I | F |
| | | | 80 | | | | | 85 | | | | | 90 | | | | | 95 |

| tct | gtt | acc | aac | aac | aca | gaa | tgt | ggg | aag | tta | ctg | gag | gaa | atc | aaa | tgt | gca | ctt |
|---|---|---|---|---|---|---|---|---|---|---|---|---|---|---|---|---|---|---|
| S | V | T | N | N | T | E | C | G | K | L | L | E | E | I | K | C | A | L |
| | | | | 100 | | | | | 105 | | | | | 110 | | | | |

| tgc | tct | cca | cat | tct | caa | agc | ctg | ttc | cac | tca | cct | gag | aga | gaa | gtc | ttg | gaa | aga |
|---|---|---|---|---|---|---|---|---|---|---|---|---|---|---|---|---|---|---|
| C | S | P | H | S | Q | S | L | F | H | S | P | E | R | E | V | L | E | R |
| 115 | | | | | 120 | | | | | 125 | | | | | 130 | | | |

| gac | cta | gta | ctt | cct | ctg | ctc | tgc | aaa | gac | tat | tgc | aaa | gaa | ttc | ttt | tac | act | tgc |
|---|---|---|---|---|---|---|---|---|---|---|---|---|---|---|---|---|---|---|
| D | L | V | L | P | L | L | C | K | D | Y | C | K | E | F | F | Y | T | C |
| | 135 | | | | | 140 | | | | | 145 | | | | | 150 | | |

| cga | ggc | cat | att | cca | ggt | ttc | ctt | caa | aca | act | gcg | gat | gag | ttt | tgc | ttt | tac | tat |
|---|---|---|---|---|---|---|---|---|---|---|---|---|---|---|---|---|---|---|
| R | G | H | I | P | G | F | L | Q | T | T | A | D | E | F | C | F | Y | Y |
| | | 155 | | | | | 160 | | | | | 165 | | | | | 170 | |

| gca | aga | aaa | gat | ggt | ggg | ttg | tgc | ttt | cca | gat | ttt | cca | aga | aaa | caa | gtc | aga | gga |
|---|---|---|---|---|---|---|---|---|---|---|---|---|---|---|---|---|---|---|
| A | R | K | D | G | G | L | C | F | P | D | F | P | R | K | Q | V | R | G |
| | | | 175 | | | | | 180 | | | | | 185 | | | | | 190 |

| cca | gca | tct | aac | tac | ttg | gac | cag | atg | gaa | gaa | tat | gac | aaa | gtg | gaa | gag | atc | agc |
|---|---|---|---|---|---|---|---|---|---|---|---|---|---|---|---|---|---|---|
| P | A | S | N | Y | L | D | Q | M | E | E | Y | D | K | V | E | E | I | S |
| | | | | 195 | | | | | 200 | | | | | 205 | | | | |

Figure 1B

```
aga aag cac aaa cac aac tgc ttc tgt att cag gag gtt gtg agt ggg ctg cgg cag
 R   K   H   K   H   N   C   F   C   I   Q   E   V   V   S   G   L   R   Q
210             215             220             225 ccc gtt ggt gcc ctg cat agt ggg gat ggc tcg caa cgt ctc ttc att ctg gaa aaa
 P   V   G   A   L   H   S   G   D   G   S   Q   R   L   F   I   L   E   K
    230             235             240             245 gaa ggt tat gtg aag ata ctt acc cct gaa gga gaa att ttc aag gag cct tat ttg
 E   G   Y   V   K   I   L   T   P   E   G   E   I   F   K   E   P   Y   L
        250             255             260             265 gac att cac aaa ctt gtt caa agt gga ata aag gga gga gat gaa aga gga ctg cta
 D   I   H   K   L   V   Q   S   G   I   K   G   G   D   E   R   G   L   L
            270             275             280             285 agc ctc gca ttc cat ccc aat tac aag aaa aat gga aag ttg tat gtg tcc tat acc
 S   L   A   F   H   P   N   Y   K   K   N   G   K   L   Y   V   S   Y   T
                290             295             300 acc aac caa gaa cgg tgg gct atc ggg cct cat gac cac att ctt agg gtt gtg gaa
 T   N   Q   E   R   W   A   I   G   P   H   D   H   I   L   R   V   V   E
305             310             315             320 tac aca gta tcc aga aaa aat cca cac caa gtt gat ttg aga aca gcc aga gtc ttt
 Y   T   V   S   R   K   N   P   H   Q   V   D   L   R   T   A   R   V   F
    325             330             335             340 ctt gaa gtt gca gaa ctc cac aga aag cat ctg gga gga caa ctg ctc ttt ggc cct
 L   E   V   A   E   L   H   R   K   H   L   G   G   Q   L   L   F   G   P
        345             350             355             360 gac ggc ttt ttg tac atc att ctt ggt gat ggg atg att aca ctg gat gat atg gaa
 D   G   F   L   Y   I   I   L   G   D   G   M   I   T   L   D   D   M   E
            365             370             375        ↑       * gaa atg gat ggg tta agt gat ttc aca ggc tca gtg cta cgg ctg gat gtg gac aca
 E   M   D   G   L   S   D   F   T   G   S   V   L   R   L   D   V   D   T
 ↑   *   *       385     *       390             395 gac atg tgc aac gtg cct tat tcc ata cca agg agc aac cca cac ttc aac agc acc
 D   M   C   N   V   P   Y   S   I   P   R   S   N   P   H   F   N   S   T
400             405             410             415 aac cag ccc ccc gaa gtg ttt gct cat ggg ctc cac gat cca ggc aga tgt gct gtg
 N   Q   P   P   E   V   F   A   H   G   L   H   D   P   G   R   C   A   V
    420             425             430             435 gat aga cat ccc act gat ata aac atc aat tta acg ata ctg tgt tca gac tcc aat
 D   R   H   P   T   D   I   N   I   N   L   T   I   L   C   S   D   S   N
        440             445             450             455 gga aaa aac aga tca tca gcc aga att cta cag ata ata aag ggg aaa gat tat gaa
 G   K   N   R   S   S   A   R   I   L   Q   I   I   K   G   K   D   Y   E
            460             465             470             475
```

Figure 1C

```
agt gag cca tca ctt tta gaa ttc aag cca ttc agt aat ggt cct ttg gtt ggt gga
 S   E   P   S   L   L   E   F   K   P   F   S   N   G   P   L   V   G   G
            480             485                     490 ttt gta tac cgg ggc tgc cag tca gaa aga ttg tat gga agc tac gtg ttt gga gat
 F   V   Y   R   G   C   Q   S   E   R   L   Y   G   S   Y   V   F   G   D
495                     500             505                     510 cgt aat ggg aat ttc cta act ctc cag caa agt cct gtg aca aag cag tgg caa gaa
 R   N   G   N   F   L   T   L   Q   Q   S   P   V   T   K   Q   W   Q   E
    515             520             525                     530 aaa cca ctc tgt ctc ggc act agt ggg tcc tgt aga ggc tac ttt tcc ggt cac atc
 K   P   L   C   L   G   T   S   G   S   C   R   G   Y   F   S   G   H   I
        535                 540             545                     550 ttg gga ttt gga gaa gat gaa cta ggt gaa gtt tac att tta tca agc agt aaa agt
 L   G   F   G   E   D   E   L   G   E   V   Y   I   L   S   S   S   K   S
            555             560             565                     570 atg acc cag act cac aat gga aaa ctc tac aaa att gta gat ccc aaa aga cct tta
 M   T   Q   T   H   N   G   K   L   Y   K   I   V   D   P   K   R   P   L
                575             580             585 atg cct gag gaa tgc aga gcc acg gta caa cct gca cag aca ctg act tca gag tgc
 M   P   E   E   C   R   A   T   V   Q   P   A   Q   T   L   T   S   E   C
590             595             600             605 tcc agg ctc tgt cga aac ggc tac tgc acc ccc acg gga aag tgc tgc tgc agt cca
 S   R   L   C   R   N   G   Y   C   T   P   T   G   K   C   C   C   S   P
    610             615             620                     625 ggc tgg gag ggg gac ttc tgc aga act gca aaa tgt gag cca gca tgt cgt cat gga
 G   W   E   G   D   F   C   R   T   A   K   C   E   P   A   C   R   H   G
            630             635             640                     645 ggt gtc tgt gtt aga ccg aac aag tgc ctc tgt aaa aaa gga tat ctt ggt cct caa
 G   V   C   V   R   P   N   K   C   L   C   K   K   G   Y   L   G   P   Q
            650             655             660                     665 tgt gaa caa gtg gac aga aac atc cgc aga gtg acc agg gca ggt att ctt gat cag
 C   E   Q   V   D   R   N   I   R   R   V   T   R   A   G   I   L   D   Q
                670             675             680 atc att gac atg aca tct tac ttg ctg gat cta aca agt tac att gta tag
 I   I   D   M   T   S   Y   L   L   D   L   T   S   Y   I   V   ---
685             690             695             700
```

```
MLKMLSFKLLLLAVALGFF                                    19  (Leader)

EGDAKFGERNEGSGARRRRCLNGNPPKRLKR          50
RDRRMMSQLELLSGGEMLCGGFYPRLSCCLRSDSPGLGRLENKIFSVTNN    100
TECGKLLEEIKCALCSPHSQSLFHSPEREVLERDLVLPLLCKDYCKEFFY    150 (Fz Domain)
TCRGHIPGFLQTTADEFCFYYARKDGGLCFPDFPRKQVRGPA            192

SNYLDQME    200
EYDKVEEISRKHKHNCFCIQEVVSGLRQPVGALHSGDGSQRLFILEKEGY    250
VKILTPEGEIFKEPYLDIHKLVQSGIKGGDERGLLSLAFHPNYKKNGKLY    300 (β-propeller)
VSYTTNQERWAIGPHDHILRVVEYTVSRKNPHQVDLRTARVFLEVAELHR    350
KHLGGQLLFGPDGFLYIILGDGMITLDDMEEMDGLSDFTGSVLRLDVDTD    400 (L2 Loop)
MCNVPYSIPRSNPHFNSTNQPPEVFAHGLHDPGRCAVDRHPTDININLTI    450
LCSDSNGKNRSSARILQIIKGKDYESEPSLLEFKPFSNGPLVGGFVYRGC    500
QSERLYGSYVFGDRNGNFLTLQQSPVTKQWQEKPLCLGTSGSCRGYFSGH    550
ILGFGEDELGEVYILSSSKSMTQTHNGKLYKIVDPKRPLMPEECRATVQP    600
AQTLTSE                                               607

CSRLCRNGYCTPTGKCCCSPGWEGDFCRTA                637 (EGF1)

KCEPACRHGGVCV         650
RPNKCLCKKGYLGPQCE                                     667 (EGF2)

QVDRNIRRVTRAGILDQIIDMTSYLLDLTSYIV       700 (GPI &
        Cytosolic
                                                          Domains)
```

B

| | |
|---|---|
| Hip1 (human) | MITLDDMEEMDGLSDFTG |
| Ptch (human) | QLTKQRLVDADGIINPSA |
| Ptch (mouse) | QLTKQRLVDADGIINPSA |
| Ptch (chick) | QLTKQRLVDADGIINPNA |
| Ptch (zebrafish) | QLTSRRLVDGDGLIPPEV |
| Ptch (fly) | LVLTNRLVNSDGIINQRA |
| Ptch (worm) | RVGKIRLVDASGIINSDG |
| Ptch2 (human) | QLTTRKLVDREGLIPPEL |
| Ptch2 (mouse) | QLTTRKLVDKEGLIPPEL |

Figure 3
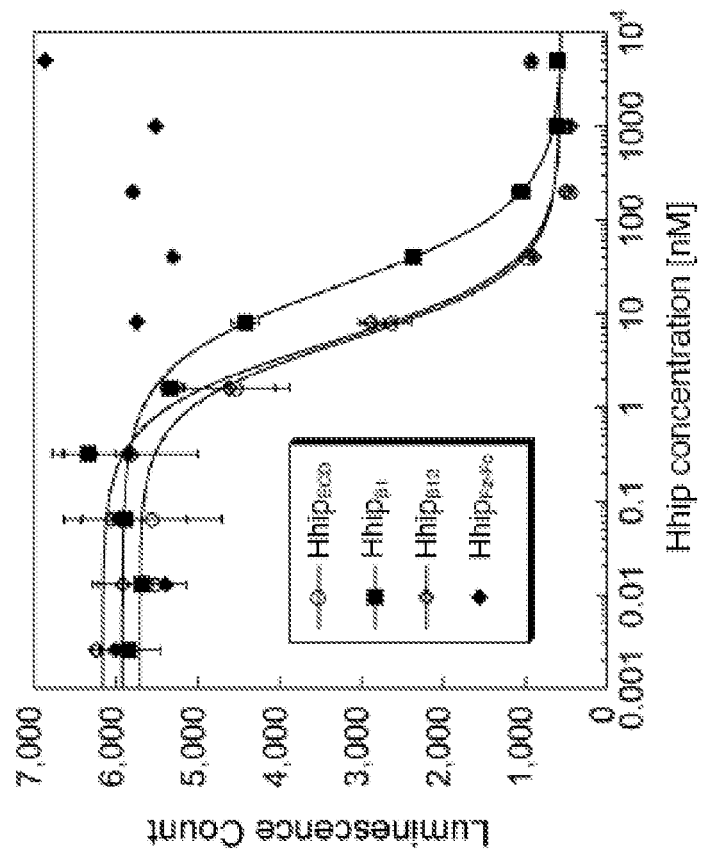
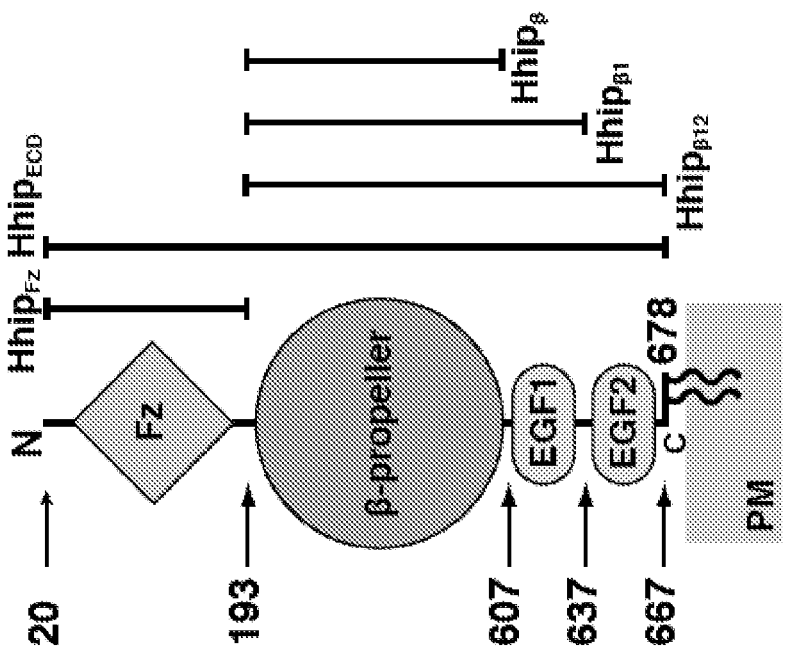

Figure 4
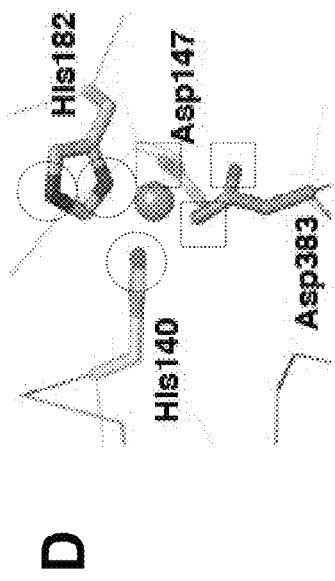
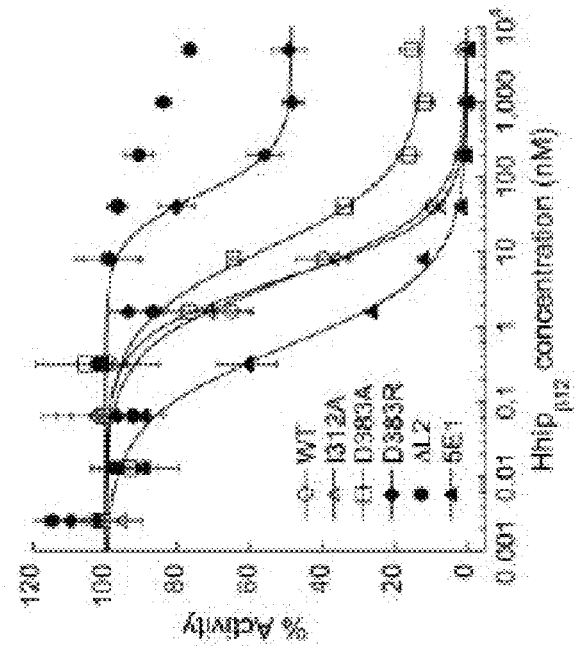
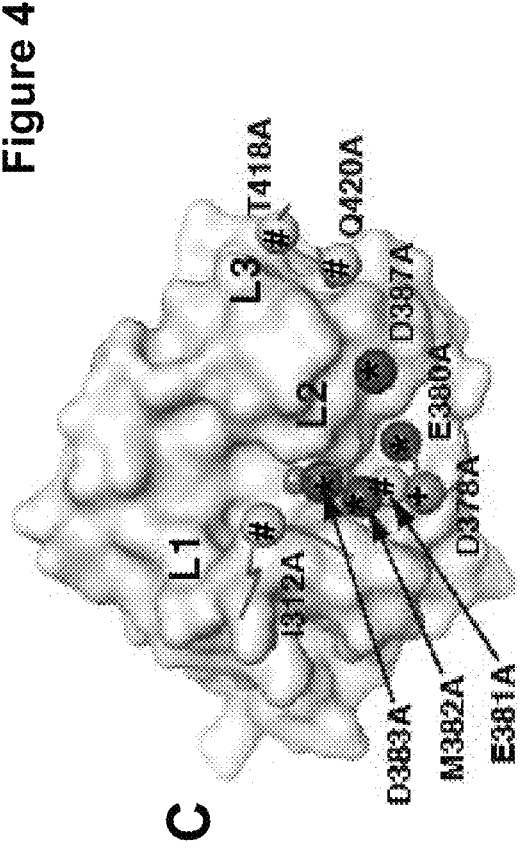
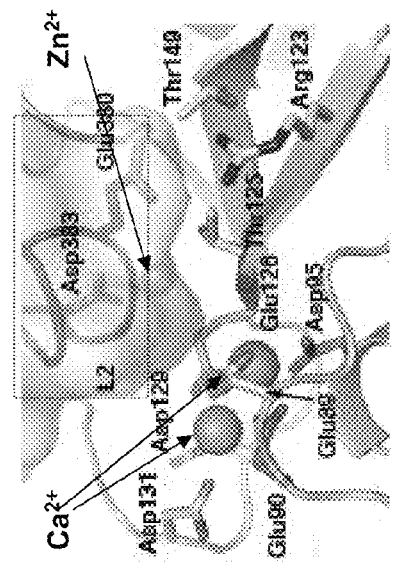

Figure 5B

| | | |
|---|---|---|
| Hip_human | MITLDDMEEMDGLSDFTG | SEQ ID NO: 7 |
| Ptch1_human | QLTKQRLIVDADGIINPSA | SEQ ID NO: 17 |
| Ptch1_mouse | QLTKQRLIVDADGIINPSA | SEQ ID NO: 18 |
| Ptch1_chick | QLTKQRLIVDADGIINPMA | SEQ ID NO: 19 |
| Ptch1_zebrafish | QITSRRLVDGDGLIPPEV | SEQ ID NO: 20 |
| Ptch1_fruit_fly | LVLTNRLIVNSDGIINQRA | SEQ ID NO: 21 |
| Ptch1_worm | RVGKIRLVDASGIINSDG | SEQ ID NO: 22 |
| Ptch2_human | QLTTRKLVDREGLIPPEL | SEQ ID NO: 23 |
| Ptch2_mouse | QLTTRKLVDREGLIPPEL | SEQ ID NO: 24 |

```
Shh  24   CGPGRG-FG-KRRHPKKLTPLAYKQF-IP
Ihh  28   CGPGRV-VGSRRRPPRKLVPLAYKQFSP
Dhh  23   CGPGRGPVGRRRYARKQLVPLLYKQFVP

Shh  81   NPDIIFKDEENTGADRLMTQRCKDKLNA
Ihh  86   NPDIIFKDEENTGADRLMTQRCKDRLNS
Dhh  82   NPDIIFKDEENSGADRLMTERCKERVNA

Shh  140  HYEGRAVDITTSDRDRSKYGMLARLAVE
Ihh  146  HYEGRAVDITTSDRDNKYGLLARLAVE
Dhh  141  HYEGRALDITTSDRDNKYGLLARLAVE
```

Figure 8B (part 1)

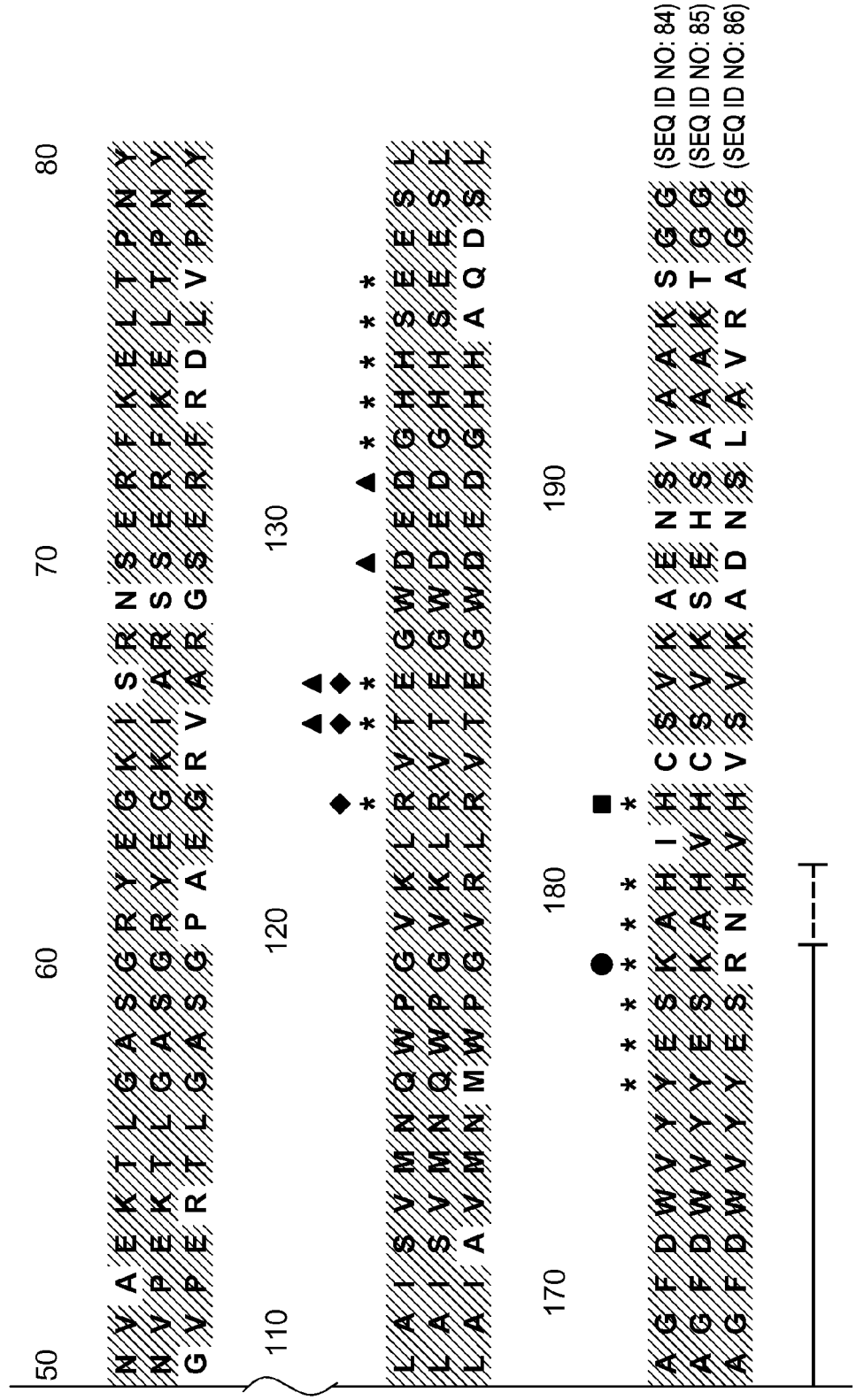
Figure 8B (part 2)

| | | |
|---|---|---|
| Hip_Homo | MITDDMEIDGLSDFTG | SEQ ID NO: 7 |
| Hip_Macac | MITDDMEIDGLSDFTG | SEQ ID NO: 25 |
| Hip_Pan | MITDDMEIDGLSDFTG | SEQ ID NO: 26 |
| Hip_Equus | MITDDMEIDGLSDFTG | SEQ ID NO: 27 |
| Hip_Monod | MITDDMEIDGLSDFTG | SEQ ID NO: 28 |
| Hip_Mus | MITDDMEIDGLSDFTG | SEQ ID NO: 29 |
| Hip_Bos | MITDDMEIDGLSDFTG | SEQ ID NO: 30 |
| Hip_Canis | MITDDMEIDGLSDFTG | SEQ ID NO: 31 |
| Hip_Rattu | MITDDMEIDGLSDFTG | SEQ ID NO: 32 |
| Hip_Ornit | MITDDMEIDGLSDFTG | SEQ ID NO: 33 |
| Hip_Fugu | MITDDMEIDGLSDFTG | SEQ ID NO: 34 |
| Hip_Tetra | MITDDMEIDGLSDFTG | SEQ ID NO: 35 |
| Hip_Danio | MITDDMEIDGLSDFTG | SEQ ID NO: 36 |
| Hip_Galli | MITDDMEIDGLSDFTG | SEQ ID NO: 37 |
| Hip_Xenop | MITDDMEIDGLSDFTG | SEQ ID NO: 38 |

B

MITDDMEIDGLSDFTG    SEQ ID NO: 7

Figure 14
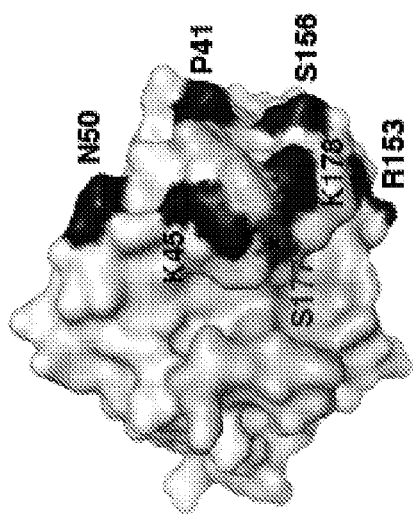
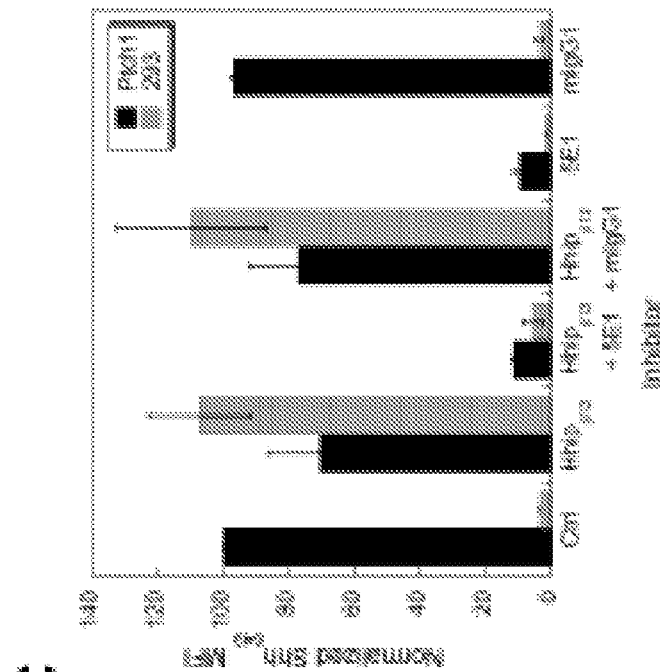
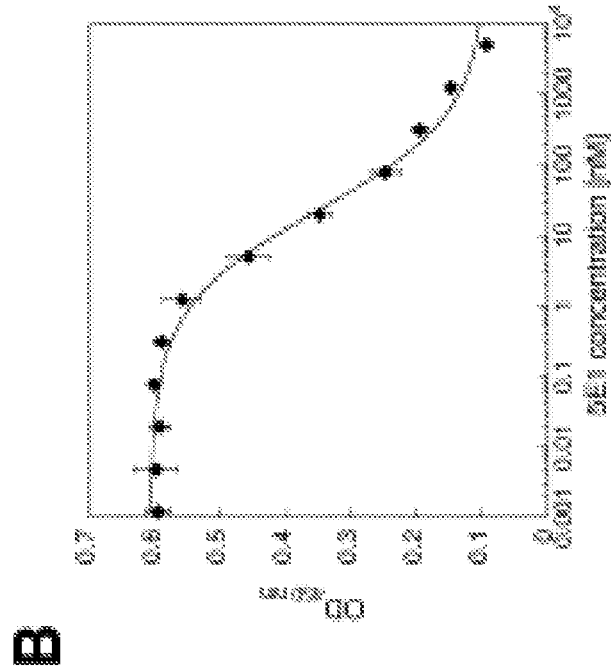

VARIANT HHIP1 PROTEIN AND METHODS AND USES THEREOF

CROSS-REFERENCE TO RELATED APPLICATIONS

This Application claims benefit of U.S. Provisional Application No. 61/057,762, filed May 30, 2008, the content of which are hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on May 13, 2013, is named CIBT-219-301_SL.txt and is 72,467 bytes in size.

FIELD OF THE INVENTION

The present invention is directed to compositions of matter useful for the diagnosis and treatment of tumors in mammals and to methods of using those compositions of matter for the same.

BACKGROUND OF THE INVENTION

The highly conserved homologs of the secreted morphogen Hedgehog (Hh) are responsible for proper cellular differentiation during embryogenesis of both invertebrates and vertebrates (reviewed in Ingham and McMahon (2001) *Genes Dev.* 15:3059-3087). In mammals, three Hedgehog genes have been identified encoding Sonic Hedgehog (Shh), Indian Hedgehog (Ihh) and Desert Hedgehog (Dhh) proteins. Their roles range from left-right asymmetry, neural tube patterning, limb patterning and branching morphogenesis to bone formation and spermatogenesis. Mutations of pathway components can lead to dramatic developmental disorders. While Hh signaling is mostly quiescent in adults, it has been implicated in many cancers, suggesting that inhibition of this pathway may have therapeutic benefit (reviewed in Beachy, P. A. et al. (2004) *Nature* 432:324-331; Pasca di Magliano and Hebrok (2003) *Nat. Rev. Cancer* 3:903-911; Rubin and de Sauvage (2006) *Nat Rev Drug Discov.* 5(12):1026-33).

Activation of the Hedgehog pathway through overexpression of Hedgehog is a hallmark of many cancers. The literature shows that overexpression of Hedgehog has been detected in many human tumor biopsies and cell lines of different types, including, for example, small cell lung cancer (SCLC), gastric and upper gastrointestinal tract cancer, pancreatic cancer, and prostate cancer.

The mature Hh amino terminal domain, responsible for proper short- and long-range signaling of Shh (sometimes referred to as Shh-N), is produced by autoproteolytic cleavage of the C-terminal intein-like domain (Lee, J. J. et al. (1994) *Science* 266:1528-1537; Porter, J. A. et al. (1995) *Nature* 374:363-366; Porter, J. A. et al. (1996) *Cell* 86:21-34) followed by addition of cholesterol at the C-terminus and palmitoylation at the N-terminus (Pepinsky et al. (1998) *J. Biol. Chem.* 273:14037-14045; Porter, J. A. et al. (1996) *Science* 274:255-259). The crystal structure of murine Shh revealed a tetrahedrally coordinated $Zn^{2+}$ cation (Hall, T. M. et al. (1995) *Nature* 378:212-216) with an overall topology similar to those of the MD clan of metalloproteases (Rawlings, N. D. et al. (2008) *Nucleic Acids Res.* 36:D320-325), which include bacterial lysostahins (Bochtler, M. et al. (2004) *Protein Sci.* 13:854-861), and the VanX dipeptidase (Bussiere, D. E. et al. (1998) *Mol. Cell.* 2:75-84). Although Shh contains a metalloprotease pseudo-active site, mutations in the active site do not adversely affect biological assays signaling activity, suggesting that Shh acts as binding partner for membrane-bound receptors rather than as an enzymatically active protease (Fuse, N. et al. (1999) *Proc. Natl. Acad. Sci. USA* 96:10992-10999).

At the cell surface, the Hh signal is relayed by two multi-transmembrane prteins. The 12-pass transmembrane protein Patched (Ptch) is a negative regulator of the pathway, which in the absence of ligand prevents signaling by repressing the 7-passtranmembrane protein Smoothened (Smo) (Chen and Struhl (1996) *Cell* 87:553-563; Marigo, V. et al. (1996) *Nature* 384:176-179; Stone, D. M. et al. (1996) *Nature* 384:129-134). Binding of Shh to Ptch relieves the inhibition of Smo, allowing it to translocate to the primary cilium (Rohatgi and Scott (2007) *Nat. Cell Biol.* 9:1005-1009), where still poorly understood downstream signaling events ultimately lead to the activation of a family of Zn-finger transcription factors called Gli (Ingham and McMahon (2001) *Genes Devel.* 15: 3059-3087).

Regulation of the Hh signal at the cell surface by Ptch is finely tuned by a number of additional cell surface molecules such as the invertebrate proteins Ihog (interference Hedgehog) (Lum, L. et al. (2003) *Science* 299:2039-2045; Yao, S. et al. (2006) *Cell* 125:343-357) and Boi (brother of Ihog) (Yao, S. et al. (2006) *Cell* 125:343-357) and their corresponding vertebrate homologs Cdon (Kang, J. S. et al. (1997) *J. Cell. Biol.* 138:203-213; Zhang, W. et al. (2006) *Dev. Cell* 10: 657-65) and Boc (bioregional Cdon-binding protein) (Kang, J. S. et al. (2002) *EMBO J.* 21:114-124; Tenzen, T. et al. (2006) *Dev. Cell* 10:647-656). The co-receptors Ihog/Boi Cdon/Boc, and Gas1 (Growth arrest-specific-1 protein), which lacks a known homolog in *Drosophila*, are pathway agonists that enhance signal reception (Allen Allen, B. L. et al. (2007) *Genes Dev.* 21:1244-1257).

Like Ptch, Hedgehog-interacting protein (Hhip1, also known as Hip) is a negative regulator of the pathway and its transcription is upregulated in response to Hh signaling (Chuang, P. T. et al. (2003) *Genes Dev.* 17:342-347; Chuang, P. T. et al. (1999) *Nature* 397:617-621). Binding affinities for Shh to Hhip1 and Ptch on cells are similar, with $K_D$ values of 5 nM for Hhip1 and 4 nM for Ptch (Chuang and McMahon (1999) *Nature* 397:617-621). Decreased expression levels of Hhip1 have been noted in several human tumor tissue types, suggesting an important role for Hhip1 in suppressing tumor development (Olsen, C. L. et al. (2004) *BMC Cancer* 4:43).

Hhip1 is a 700 residue protein with an N-terminal signal peptide and a large extracellular region that ends with a hydrophobic C-terminal stretch (Chuang and McMahon (1999) *Nature* 397:617-621). In addition to the predominantly membrane-associated form, a soluble form of Hhip1 has also been detected in mature brains of adult rodents (Coulombe, J. et al. (2004) *Mol. Cell. Neurosci.* 25:323-333). Other than the likely presence of two epidermal growth factor (EGF) domains and four potential N-linked glycosylation sites (Chuang and McMahon (1999) *Nature* 397:617-621), nothing is known about the structural arrangement of the Hhip1 extracellular domain (ECD).

Although the structure of Shh has been known for some time, a precise understanding of the molecular interactions with its membrane-associated receptors has remained elusive. Recently, a comparison of structures of fibronectin type III (FNIII) domain 1 of Ihog and FNIII domain 3 of Cdon in complex with *Drosphila* Hh and vertebrate Shh, respectively, have revealed completely different binding modes (McLellan, J. S. et al. (2006) *Proc. Natl. Acad. Sci. USA* 103:17208-17213).

Until now, the crystal structure of Hhip1 has remained unsolved and it was not known how Hhip1 interacted with Hh to exert its effect. Likewise, Ptch has not been crystallized, so it was also unknown how Ptch interacted with Hh.

Thus, in order to effectively combat Hedgehog pathway-associated tumors, there is an urgent need in the art to better understand the precise interaction of Hh with Hh-controlling molecules such as Hhip1 and Ptch. A more complete understanding of the structural/functional relationship of the members of the Hedgehog signaling pathway, and more specifically, a better understanding of the molecular interaction between Ptch and Hhip1 with Hh would provide the necessary information for the rational design of small molecule and large molecule inhibitors of Hh and therapies for Hh-related cancers and conditions.

SUMMARY OF THE INVENTION

In order to better understand the regulation of Shh by Hhip1, we determined crystal structures of a truncated form of the Hhip1 ectodomain both alone and in complex with Shh. The complex structure revelas a critical interaction between a loop in the Hhip1 β-propeller and the $Zn^{2+}$-containing groove of the Shh pseudo-active site. Remarkably, a similar motif is found in Ptch, suggesting that Ptch and Hhip1 compete for binding to the Shh pseudo-active site. This would explain the negative regulation by Hhip1 as a structural decoy for Shh, preventing Ptch binding and pathway activation. The data also lend insight into the effect of mutations in and around the pseudo-active site in Hh proteins that are linked to human disease (Dubourg et al. (2004); Gao and He (2004)). Taken together, the data allow us to propose a model for regulation of Hh activity via receptor interactions and suggest novel approaches for developing antagonists of Hh signaling.

Thus, this specification describes a Hedgehog interacting protein (Hhip1) variant, lacking a putative frizzled domain, herein referred to as "$Hhip1_{β12}$" and the crystal structure of the same. It has been surprisingly discovered that the $Hhip1_{β12}$ protein provides the $Hhip1_{β12}$ protein with increased stability while completely maintaining Hh-inhibitory activity. Thus, the crystal structure of $Hhip1_{β12}$ has been solved and the interaction with Hh and other proteins, such at Ptch, has been analyzed. $Hhip1_{β12}$ contains critical amino acids that interact with Hh and Ptch allowing for the design of interacting molecules such as, for example, polypeptide agonists and antagonists, immunoadhesins, antibodies, and small molecule inhibitors and agonists.

Accordingly, in one embodiment of the present invention, the invention provides an isolated nucleic acid molecule having a nucleotide sequence that encodes a $Hhip1_{β12}$ polypeptide or biologically active fragment thereof (collectively "$Hhip1_{β12}$ polypeptides").

In certain aspects, the isolated nucleic acid molecule comprises a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule encoding a full-length $Hhip1_{β12}$ polypeptide (b) a $Hhip1_{β12}$ extracellular domain (ECD) polypeptide ("$Hhip1_{β12ECD}$") (i.e., $Hhip1_{β12}$ also lacking the putative GPI anchor signal sequence) having an amino acid sequence as disclosed herein; (c) a $Hhip1_{β1}$ polypeptide (i.e., lacking the signal peptide, putative $_{Fz}$ domain, the EGF2 domain, and putative GPI anchor signal sequence) having the amino acid sequence as disclosed herein; (d) a $Hhip1_{β}$ polypeptide (i.e., lacking the signal peptide, putative Fz domain, the EGF domains, and the putative GPI anchor signal sequence) having the amino acid sequence as disclosed herein; (e) a $Hhip1_{FzB}$ polypeptide (i.e., lacking the signal peptide, the EGF domains, and the putative GPI anchor signal sequence); (f) a $Hhip1_{Fz}$ polypeptide (i.e., lacking the signal peptide, the propeller domain, the EGF domains, and the putative GPI anchor signal sequence); or any other specifically defined fragment of a full-length Hhip1 polypeptide amino acid sequence as disclosed herein, or (b) the complement of any of the above DNA molecules.

Another aspect of the invention provides an isolated nucleic acid molecule comprising a nucleotide sequence encoding a Hhip1 polypeptide which has either the putative GPI signal sequence deleted or inactivated, or is complementary to such encoding nucleotide sequence, wherein the putative GPI signal sequence of such polypeptide(s) are disclosed herein. Therefore, soluble extracellular domains of the herein described Hhip1 polypeptides are contemplated.

In other aspects, the present invention is directed to isolated nucleic acid molecules which hybridize to (a) a nucleotide sequence encoding a Hhip1 polypeptide having a full-length amino acid sequence as disclosed herein, a Hhip1 polypeptide amino acid sequence lacking the signal peptide as disclosed herein, a $Hhip1_{β12}$ amino acid sequence as disclosed herein, an extracellular domain of a $Hhip1_{β12}$ polypeptide, as disclosed herein or any other specifically defined fragment of a full-length Hhip1 polypeptide amino acid sequence as disclosed herein, or (b) the complement of the nucleotide sequence of (a). In this regard, an embodiment of the present invention is directed to fragments of a full-length Hhip1 polypeptide coding sequence, or the complement thereof, as disclosed herein, that may find use as, for example, hybridization probes useful as, for example, diagnostic probes, PCR primers, antisense oligonucleotide probes, or for encoding fragments of a full-length Hhip1 polypeptide that may optionally encode a polypeptide comprising a binding site for an anti-Hip polypeptide antibody, a $Hhip1_{β12}$ binding oligopeptide (agonist or antagonist) or other small organic molecule that binds to a $Hhip1_{β12}$ polypeptide (agonist or antagonist). Such nucleic acid fragments are usually at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length. Moreover, such nucleic acid fragments are usually comprised of consecutive nucleotides derived from the full-length coding sequence of a Hhip1 polypeptide or the complement thereof. It is noted that novel fragments of a $Hhip1_{β12}$ polypeptide-encoding nucleotide sequence, or the complement thereof, may be determined in a routine manner by aligning the $Hhip1_{β12}$ polypeptide-encoding nucleotide sequence with other known nucleotide sequences using any of a number of well known sequence alignment programs and determining which $Hhip1_{β12}$ polypeptide-encoding nucleotide sequence fragment(s), or the complement thereof, are novel. All of such novel fragments of Hhip1$_{\beta 12}$ polypeptide-encoding nucleotide sequences, or the complement thereof, are contemplated herein. Also contemplated are the Hhip1 polypeptide fragments encoded by these nucleotide molecule fragments, preferably those Hhip1 polypeptide fragments that comprise a binding site for an anti-Hhip1$_{\beta 12}$ antibody, a Hhip1$_{\beta 12}$ binding oligopeptide or other small organic molecule that binds to a Hhip1$_{\beta 12}$ polypeptide, and Hhip1$_{\beta 12}$ peptides that bind Hh.

In another embodiment, the invention provides isolated Hhip1 polypeptides encoded by any of the isolated nucleic acid sequences hereinabove identified.

In a certain aspect, the invention concerns an isolated Hhip1$_{\beta 12}$ polypeptide, comprising an amino acid sequence having at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% amino acid sequence identity, to a Hhip1$_{\beta 12}$ polypeptide having a full-length amino acid sequence as disclosed herein, an amino acid sequence encoded by any of the nucleic acid sequences disclosed herein or any other specifically defined fragment of a full-length Hhip1 polypeptide amino acid sequence as disclosed herein.

In a yet further aspect, the invention concerns an isolated Hhip1 polypeptide comprising an amino acid sequence that is encoded by a nucleotide sequence that hybridizes to the complement of a DNA molecule encoding (a) a Hhip1$_{\beta 12}$ polypeptide having a full-length Hhip1$_{\beta 12}$ amino acid sequence as disclosed herein, (b) an extracellular domain of a Hhip1$_{\beta 12}$ polypeptide protein as disclosed herein, (c) an amino acid sequence encoded by any of the nucleic acid sequences disclosed herein or (d) any other specifically defined fragment of a full-length Hhip1$_{\beta 12}$ polypeptide amino acid sequence as disclosed herein.

In a specific aspect, the invention provides an isolated Hhip1$_{\beta 12}$ polypeptide; an isolated Hhip1$_{\beta 12ECD}$; an isolated Hip$_{\beta 1}$ polypeptide; an isolated Hip$_{\beta}$; each encoded by a nucleotide sequence that encodes such an amino acid sequence as herein described. Processes for producing the same are also herein described, wherein those processes comprise culturing a host cell comprising a vector which comprises the appropriate encoding nucleic acid molecule under conditions suitable for expression of the Hhip1$_{\beta 12}$ polypeptide and recovering the Hhip1 polypeptide from the cell culture.

Another aspect of the invention provides an isolated Hhip1$_{\beta 12ECD}$ polypeptide. Processes for producing the same are also herein described, wherein those processes comprise culturing a host cell comprising a vector which comprises the appropriate encoding nucleic acid molecule under conditions suitable for expression of the Hhip1$_{\beta 12}$ polypeptide and recovering the Hhip1$_{\beta 12}$ polypeptide from the cell culture.

In other embodiments of the present invention, the invention provides vectors comprising DNA encoding any of the herein described polypeptides. Host cells comprising any such vector are also provided. By way of example, the host cells may be mammalian cells, CHO cells, insect cells, E. coli cells, or yeast cells. A process for producing any of the herein described polypeptides is further provided and comprises culturing host cells under conditions suitable for expression of the desired polypeptide and recovering the desired polypeptide from the cell culture.

In other embodiments, the invention provides isolated chimeric polypeptides comprising any of the herein described Hhip1$_{\beta 12}$ polypeptides (including, for example, Hhip1$_{\beta 12}$, Hip$_{\beta 1}$, Hip$_{\beta}$, and Hhip1$_{Fz\beta}$) fused to a heterologous (non-Hip) polypeptide. Examples of such chimeric molecules comprise any of the Hhip1$_{\beta 12}$ polypeptides descried herein fused to a heterologous polypeptide such as, for example, an epitope tag sequence or an Fc region of an immunoglobulin.

In another embodiment, the invention provides an antibody which binds, preferably specifically, to any of the above or below described polypeptides. Optionally, the antibody is a monoclonal antibody, antibody fragment, chimeric antibody, humanized antibody, single-chain antibody or antibody that competitively inhibits the binding of an anti-Hhip1$_{\beta 12}$ polypeptide antibody to its respective antigenic epitope. Antibodies of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies of the present invention may optionally be produced in CHO cells or bacterial cells and preferably inhibit the growth or proliferation of or induce the death of a cell to which they bind. For diagnostic purposes, the antibodies of the present invention may be detectably labeled, attached to a solid support, or the like.

In some embodiments, the antibodies of the invention interfere with the interaction between Hh and Hhip1 or Hh and Ptch. In some embodiments, the antibodies are other than 5E1. In other embodiments, the antibodies stimulate Hh signaling.

In other embodiments of the present invention, the invention provides vectors comprising DNA encoding any of the herein described antibodies. Host cell comprising any such vector are also provided. By way of example, the host cells may be CHO cells, E. coli cells, or yeast cells. A process for producing any of the herein described antibodies is further provided and comprises culturing host cells under conditions suitable for expression of the desired antibody and recovering the desired antibody from the cell culture.

In some embodiments the oligopeptides interfere with the interaction between Hh and Hhip1 or Ptch. In other embodiments the oligopeptides stimulate Hh signaling by binding to Ptch.

In another embodiment, the invention provides oligopeptides ("Hhip1$_{\beta 12}$ binding oligopeptides") which bind, preferably specifically, to any of the described Hhip1$_{\beta 12}$ polypeptides. Optionally, the Hhip1$_{\beta 12}$ binding oligopeptides of the present invention may be conjugated to a growth inhibitory agent or cytotoxic agent such as a toxin, including, for example, a maytansinoid or calicheamicin, an antibiotic, a radioactive isotope, a nucleolytic enzyme, or the like. The Hhip1$_{\beta 12}$ binding oligopeptides of the present invention may optionally be produced in CHO cells or bacterial cells and preferably inhibit the growth or proliferation of or induce the death of a cell to which they bind. For diagnostic purposes, the Hhip1$_{\beta 12}$ binding oligopeptides of the present invention may be detectably labeled, attached to a solid support, or the like.

In another embodiment, the invention provides oligopeptides ("Hhip1 L2 Loop mimicking oligopeptides") which bind, preferably specifically, to Hh polypeptides. Optionally, the Hhip1 L2 Loop mimicking oligopeptides of the present invention may be conjugated to a growth inhibitory agent or cytotoxic agent such as a toxin, including, for example, a maytansinoid or calicheamicin, an antibiotic, a radioactive isotope, a nucleolytic enzyme, or the like. The Hhip1 L2 Loop mimicking oligopeptides of the present invention may optionally be produced in CHO cells or bacterial cells and preferably inhibit the growth or proliferation of or induce the death of a cell to which they bind. For diagnostic purposes, the Hhip1 L2 Loop mimicking oligopeptides of the present invention may be detectably labeled, attached to a solid support, or the like.

In other embodiments of the present invention, the invention provides vectors comprising DNA encoding any of the herein described Hhip1$_{\beta 12}$ binding oligopeptides and Hhip1 L2 Loop mimicking oligopeptides. Host cell comprising any such vector are also provided. By way of example, the host cells may be CHO cells, *E. coli* cells, or yeast cells. A process for producing any of the herein described Hhip1$_{\beta 12}$ binding and Hhip1 L2 Loop mimicking oligopeptides is further provided and comprises culturing host cells under conditions suitable for expression of the desired oligopeptide and recovering the desired oligopeptide from the cell culture.

In another embodiment, the invention provides small organic molecules ("Hhip1$_{\beta 12}$ binding organic molecules") which bind, preferably specifically, to any of the above or below described Hhip1$_{\beta 12}$ polypeptides. Optionally, the Hhip1$_{\beta 12}$ binding organic molecules of the present invention may be conjugated to a growth inhibitory agent or cytotoxic agent such as a toxin, including, for example, a maytansinoid or calicheamicin, an antibiotic, a radioactive isotope, a nucleolytic enzyme, or the like. The Hhip1$_{\beta 12}$ binding organic molecules of the present invention preferably inhibit the growth or proliferation of or induce the death of a cell to which they bind. For diagnostic purposes, the Hhip1$_{\beta 12}$ binding organic molecules of the present invention may be detectably labeled, attached to a solid support, or the like.

In some embodiments, the small organic molecules interfere with the interaction between Hh and Hhip or Ptch. In some embodiments, the small molecules are other than robotnikinin (Stanton et al. (2009) *Nat. Chem. Biol.* 5(3):154-156). In other embodiments, the small molecules stimulate Hh signaling.

In yet another embodiment, the invention provides small organic molecules ("Hhip1 L2 Loop mimicking organic molecules") which bind, preferably specifically, to Hh polypeptides. Optionally, the Hhip1 L2 Loop mimicking organic molecules of the present invention may be conjugated to a growth inhibitory agent or cytotoxic agent such as a toxin, including, for example, a maytansinoid or calicheamicin, an antibiotic, a radioactive isotope, a nucleolytic enzyme, or the like. The Hhip1 L2 Loop mimicking organic molecules of the present invention preferably inhibit the growth or proliferation of or induce the death of a cell to which they bind. For diagnostic purposes, the Hhip1 L2 Loop mimicking organic molecules of the present invention may be detectably labeled, attached to a solid support, or the like.

In a still further embodiment, the invention concerns a composition of matter comprising a Hhip1$_{\beta 12}$ polypeptides as described herein, a chimeric Hhip1$_{\beta 12}$ polypeptide as described herein, an anti-Hhip1$_{\beta 12}$ antibody as described herein, a Hhip1$_{\beta 12}$ binding oligopeptide as described herein, a Hhip1 L2 Loop mimicking oligopeptide as described herein, a Hhip1$_{\beta 12}$ binding organic molecule as described herein, or a Hhip1 L2 Loop mimicking organic molecule as described herein in combination with a carrier. Optionally, the carrier is a pharmaceutically acceptable carrier.

In yet another embodiment, the invention concerns an article of manufacture comprising a container and a composition of matter contained within the container, wherein the composition of matter may comprise a Hhip1$_{\beta 12}$ polypeptide or derivative thereof as described herein, a chimeric Hhip1$_{\beta 12}$ polypeptide or derivative thereof as described herein, an anti-Hhip1$_{\beta 12}$ antibody as described herein, a Hhip1$_{\beta 12}$ binding oligopeptide as described herein, or a Hhip1$_{\beta 12}$ binding organic molecule as described herein. The article may further optionally comprise a label affixed to the container, or a package insert included with the container, that refers to the use of the composition of matter for the therapeutic treatment or diagnostic detection of a tumor.

Another embodiment of the present invention is directed to the use of a Hhip1 polypeptide as described herein, a chimeric Hhip1 polypeptide as described herein, an anti-Hhip1 polypeptide antibody as described herein, a Hhip1$_{\beta 12}$ binding oligopeptide as described herein, a Hhip1 L2 Loop mimicking oligopeptide as described herein, a Hhip1$_{\beta 12}$ binding organic molecule as described herein, or a a Hhip1 L2 Loop mimicking organic molecule as described herein for the preparation of a medicament useful in the treatment of a condition which is responsive to Hh signaling.

ADDITIONAL EMBODIMENTS

Another embodiment of the present invention is directed to a method for inhibiting the growth of a cell that expresses a Hhip1 and/or Ptch polypeptide, wherein the method comprises contacting the cell with an antibody, an oligopeptide or a small organic molecule that binds to the Hhip1$_{\beta 12}$ and/or Ptch polypeptide, and wherein the binding of the antibody, oligopeptide or organic molecule to the Hhip1 and/or Ptch polypeptide causes inhibition of the growth of the cell expressing the Hhip1 and/or Ptch polypeptide. In preferred embodiments, the cell is a cancer cell and binding of the antibody, oligopeptide or organic molecule to the Hhip1 and/or Ptch polypeptide causes death of the cell expressing the Hhip1 and/or Ptch polypeptide. Optionally, the antibody is a monoclonal antibody, antibody fragment, chimeric antibody, humanized antibody, or single-chain antibody. Antibodies, Hhip1$_{\beta 12}$ L2 Loop binding oligopeptides and Hhip1$_{\beta 12}$ L2 Loop binding organic molecules employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies and Hhip1$_{\beta 12}$ L2 Loop binding oligopeptides employed in the methods of the present invention may optionally be produced in CHO cells or bacterial cells.

Yet another embodiment of the present invention is directed to a method of therapeutically treating a mammal having a cancerous tumor comprising cells that express a Hhip1 and/or Ptch polypeptide, wherein the method comprises administering to the mammal a therapeutically effective amount of an anti-Hhip1$_{\beta 12}$ antibody, a Hhip1$_{\beta 12}$ L2 Loop binding oligopeptide or a Hhip1$_{\beta 12}$ L2 Loop binding small organic molecule antagonist that binds to the Hhip1 and/or Ptch polypeptide, thereby resulting in the effective therapeutic treatment of the tumor. Optionally, the antibody is a monoclonal antibody, antibody fragment, chimeric antibody, humanized antibody, or single-chain antibody. Antibodies, Hhip1$_{\beta 12}$ L2 Loop binding oligopeptides and Hhip1$_{\beta 12}$ binding organic molecules employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies and oligopeptides employed in the methods of the present invention may optionally be produced in CHO cells or bacterial cells.

Yet another embodiment of the present invention is directed to a method of determining the presence of a Hhip1 and/or Ptch polypeptide in a sample suspected of containing the Hhip1 and/or Ptch polypeptide, wherein the method comprises exposing the sample to an antibody, oligopeptide or small organic molecule that binds to the Hhip1 and/or Ptch polypeptide and determining binding of the antibody, oligopeptide or organic molecule to the Hhip1 and/or Ptch polypeptide in the sample, wherein the presence of such binding is indicative of the presence of the Hhip1 and/or Ptch polypeptide in the sample. Optionally, the sample may contain cells (which may be cancer cells) suspected of expressing the Hhip1 and/or Ptch polypeptide. The antibody, Hhip1$_{\beta12}$ binding L2 Loop biding oligopeptide or Hhip1$_{\beta12}$ L2 Loop binding organic molecule employed in the method may optionally be detectably labeled, attached to a solid support, or the like.

A further embodiment of the present invention is directed to a method of diagnosing the presence of a tumor in a mammal, wherein the method comprises detecting the level of expression of a gene encoding a Hhip1 polypeptide (a) in a test sample of tissue cells obtained from said mammal, and (b) in a control sample of known normal non-cancerous cells of the same tissue origin or type, wherein a higher level of expression of the Hhip1 polypeptide in the test sample, as compared to the control sample, is indicative of the presence of tumor in the mammal from which the test sample was obtained. Probes for such assays are derived from Hhip1$_{\beta12}$-encoding nucleic acids.

Another embodiment of the present invention is directed to a method of diagnosing the presence of a tumor in a mammal, wherein the method comprises (a) contacting a test sample comprising tissue cells obtained from the mammal with a anti-Hhip1$_{\beta12}$ antibody, Hhip1$_{\beta12}$ L2 Loop binding oligopeptide or Hhip1$_{\beta12}$ L2 Loop binding small organic molecule that binds to a Hhip1 and/or Ptch polypeptide and (b) detecting the formation of a complex between the antibody, oligopeptide or small organic molecule and the Hhip1 and/or Ptch polypeptide in the test sample, wherein the formation of a complex is indicative of the presence of a tumor in the mammal Optionally, the antibody, Hhip1$_{\beta12}$ L2 Loop binding oligopeptide, or Hhip1$_{\beta12}$ L2 Loop binding organic molecule employed is detectably labeled, attached to a solid support, or the like, and/or the test sample of tissue cells is obtained from an individual suspected of having a cancerous tumor.

Yet another embodiment of the present invention is directed to a method for treating or preventing a cell proliferative disorder associated with altered, preferably increased, expression or activity of a Hhip1 and/or Ptch polypeptide, the method comprising administering to a subject in need of such treatment an effective amount of an antagonist of a Hhip1 and/or Ptch polypeptide. Preferably, the cell proliferative disorder is cancer and the antagonist of the Hhip1 and/or Ptch polypeptide is an anti-Hhip1$_{\beta12}$ antibody, a Hhip1$_{\beta12}$ L2 Loop binding oligopeptide, a Hhip1$_{\beta12}$ L2 Loop binding organic molecule or antisense oligonucleotide. Effective treatment or prevention of the cell proliferative disorder may be a result of direct killing or growth inhibition of cells that express a Hhip1 and/or Ptch polypeptide or by antagonizing the cell growth potentiating activity of a Hhip1 and/or Ptch polypeptide.

Yet another embodiment of the present invention is directed to a method of binding an anti-Hhip1$_{\beta12}$ antibody, an Hhip1$_{\beta12}$ L2 Loop binding oligopeptide or Hhip1$_{\beta12}$ L2 Loop binding small organic molecule to a cell that expresses a Hhip1 and/or Ptch polypeptide, wherein the method comprises contacting a cell that expresses a Hhip1 and/or Ptch polypeptide with said antibody, oligopeptide or small organic molecule under conditions which are suitable for binding of the antibody, oligopeptide or small organic molecule to said Hhip1 and/or Ptch polypeptide and allowing binding therebetween. In preferred embodiments, the antibody is labeled with a molecule or compound that is useful for qualitatively and/or quantitatively determining the location and/or amount of binding of the antibody, oligopeptide or small organic molecule to the cell.

Other embodiments of the present invention are directed to the use of (a) a Hhip1$_{\beta12}$ polypeptide, (b) a nucleic acid encoding a Hhip1$_{\beta12}$ polypeptide or a vector or host cell comprising that nucleic acid, (c) an anti-Hhip1$_{\beta12}$ polypeptide antibody, (d) a Hhip1$_{\beta12}$ L2 Loop binding oligopeptide, or (e) a Hhip1$_{\beta12}$ L2 Loop binding small organic molecule in the preparation of a medicament useful for (i) the therapeutic treatment or diagnostic detection of a cancer or tumor, or (ii) the therapeutic treatment or prevention of a cell proliferative disorder.

Yet further embodiments of the present invention will be evident to the skilled artisan upon a reading of the present specification.

Concise Statement of the Invention

1. An isolated nucleic acid having a nucleotide sequence that has at least 80% nucleic acid sequence identity to a DNA molecule encoding the amino acid sequence of any one of SEQ ID NOS:11, 12, 13, 14, 15, 16, or the complement thereof.

2. An isolated nucleic acid having a nucleotide sequence encoding the amino acid sequence shown in any one of SEQ ID NOS:11, 12, 13, 14, 15, 16, or the complement thereof.

3. An expression vector comprising the nucleic acid of 1 or 2.

4. The expression vector of 3, wherein said nucleic acid is operably linked to control sequences recognized by a host cell transformed with the vector.

5. A host cell comprising the expression vector of 3.

6. The host cell of 5 which is a CHO cell, an *E. coli* cell or a yeast cell.

7. A process for producing a polypeptide comprising culturing the host cell of 5 under conditions suitable for expression of said polypeptide and recovering said polypeptide from the cell culture.

8. An isolated polypeptide having at least 80% amino acid sequence identity to the polypeptide having an amino acid sequence of any one of SEQ ID NOs: 11, 12, 13, 14, 15, 16.

9. An isolated polypeptide having an amino acid sequence of any one of SEQ ID NOs: 11, 12, 13, 14, 15, 16.

10. A chimeric polypeptide comprising the polypeptide of 8 or 9 fused to a heterologous polypeptide.

11. The chimeric polypeptide of 10, wherein said heterologous polypeptide is an epitope tag sequence or an Fc region of an immunoglobulin.

12. An isolated oligopeptide that binds to a polypeptide having an amino acid sequence of any one of SEQ ID NOs: 7, 17, 19-25, 38, 53-55, and 72-82.

13. The oligopeptide of 12 which is conjugated to a growth inhibitory agent.

14. The oligopeptide of 12 which is conjugated to a cytotoxic agent.

15. The oligopeptide of 14, wherein the cytotoxic agent is selected from the group consisting of toxins, antibiotics, radioactive isotopes and nucleolytic enzymes.

16. The oligopeptide of 14, wherein the cytotoxic agent is a toxin.

17. The oligopeptide of 16, wherein the toxin is selected from the group consisting of maytansinoid and calicheamicin.

18. The oligopeptide of 16, wherein the toxin is a maytansinoid.

19. The oligopeptide of 12 which induces death of a cell to which it binds.

20. The oligopeptide of 12 which is detectably labeled.

21. A Hhip1 L2 Loop mimicking oligopeptide comprising a peptide having an amino acid sequence of SEQ ID NO:39 and which binds a Hedgehog polypeptide.

22. The oligopeptide of 21 wherein said oligopeptide comprises an amino acid sequence of SEQ ID NO:56-71.

23. The oligopeptide of 21 which is conjugated to a growth inhibitory agent.

24. The oligopeptide of 21 which is conjugated to a cytotoxic agent.

25. The oligopeptide of 24, wherein the cytotoxic agent is selected from the group consisting of toxins, antibiotics, radioactive isotopes and nucleolytic enzymes.

26. The oligopeptide of 25, wherein the cytotoxic agent is a toxin.

27. The oligopeptide of 26, wherein the toxin is selected from the group consisting of maytansinoid and calicheamicin.

28. The oligopeptide of 26, wherein the toxin is a maytansinoid.

29. The oligopeptide of 21 which induces death of a cell to which it binds.

30. The oligopeptide of 21 which is detectably labeled.

31. An organic small molecule comprising a compound that binds to an L2 Loop of a Hhip1 or Ptch protein wherein said molecule inhibits the binding of Hh polypeptide to Hhip1 or Ptch.

32. The small molecule of 31 wherein said molecule is other than robotnikinin.

33. An organic small molecule comprising a compound that mimics an L2 Loop of a Hhip1 or Ptch protein wherein said molecule binds to Hh polypeptide and inhibits Hh signaling.

34. An organic small molecule comprising a compound that binds to the L2 Loop of a Ptch protein and agonizes Hh signaling.

35. A composition of matter comprising:
(a) the polypeptide of 8;
(b) the polypeptide of 9;
(c) the chimeric polypeptide of 10;
(d) the oligopeptide of 12;
(e) the oligopeptide of 21;
(f) the organic molecule of 31;
(g) the organic molecule of 32;
(h) the organic molecule of 33; or
(i) the organic molecule of 34.
in combination with a pharmaceutically acceptable carrier.

36. An article of manufacture comprising:
(a) a container; and
(b) the composition of matter of 35 contained within said container.

37. The article of manufacture of 36 further comprising a label affixed to said container, or a package insert included with said container, referring to the use of said composition of matter for the therapeutic treatment of or the diagnostic detection of a cancer.

38. A method of inhibiting the growth of a cell that expresses Hhip1 or Ptch comprising contacting said cell with an oligopeptide or organic molecule that binds to said Hhip1 or Ptch, the binding of said oligopeptide or organic molecule to said Hhip1 or Ptch thereby causing an inhibition of growth of said cell.

39. The method of 38, wherein said oligopeptide or organic molecule is conjugated to a growth inhibitory agent.

40. The method of 38, wherein said oligopeptide or organic molecule is conjugated to a cytotoxic agent.

41. The method of 40, wherein said cytotoxic agent is selected from the group consisting of toxins, antibiotics, radioactive isotopes and nucleolytic enzymes.

42. The method of 40, wherein the cytotoxic agent is a toxin.

43. The method of 42, wherein the toxin is selected from the group consisting of maytansinoid and calicheamicin.

44. The method of 42, wherein the toxin is a maytansinoid.

45. The method of 38, wherein said cell is a cancer cell.

46. The method of 45, wherein said cancer cell is further exposed to radiation treatment or a chemotherapeutic agent.

47. The method of 45, wherein said cancer cell is selected from the group consisting of a breast cancer cell, a colorectal cancer cell, a lung cancer cell, an ovarian cancer cell, a central nervous system cancer cell, a liver cancer cell, a bladder cancer cell, a pancreatic cancer cell, a cervical cancer cell, a melanoma cell and a leukemia cell.

48. The method of 45, wherein said protein is more abundantly expressed by said cancer cell as compared to a normal cell of the same tissue origin.

49. The method of 38 which causes the death of said cell.

50. A method of therapeutically treating a mammal having a cancerous tumor comprising cells that express a Hhip1 or Ptch protein, said method comprising administering to a subject in need of such treatment an effective amount of a $Hhip1_{\beta12}$ L2 Loop binding antibody, a $Hhip1_{\beta12}$ L2 Loop anti-idiotypic antibody, a $Hhip1_{\beta12}$ binding oligopeptide, $Hhip1_{\beta12}$ binding organic molecule a $Hhip1_{\beta12}$ L2 Loop mimicking oligopeptide, a $Hhip1_{\beta12}$ L2 Loop mimicking organic molecule, thereby, thereby effectively treating said mammal.

51. The method of 50, wherein said antibody, oligopeptide or organic molecule is conjugated to a growth inhibitory agent.

52. The method of 50, wherein said antibody, oligopeptide or organic molecule is conjugated to a cytotoxic agent.

53. The method of 52, wherein said cytotoxic agent is selected from the group consisting of toxins, antibiotics, radioactive isotopes and nucleolytic enzymes.

54. The method of 52, wherein the cytotoxic agent is a toxin.

55. The method of 54, wherein the toxin is selected from the group consisting of maytansinoid and calicheamicin.

56. The method of 54, wherein the toxin is a maytansinoid.

57. The method of 50, wherein said tumor is further exposed to radiation treatment or a chemotherapeutic agent.

58. The method of 50, wherein said tumor is a breast tumor, a colorectal tumor, a lung tumor, an ovarian tumor, a central nervous system tumor, a liver tumor, a bladder tumor, a pancreatic tumor, or a cervical tumor.

59. The method of 50, wherein said protein is more abundantly expressed by the cancerous cells of said tumor as compared to a normal cell of the same tissue origin.

60. A method for treating or preventing a cell proliferative disorder in cells expressing Hhip1 or Ptch protein, said method comprising administering to a subject in need of such treatment an effective amount of a $Hhip1_{\beta12}$ L2 Loop binding antibody, a $Hhip1_{\beta12}$ L2 Loop anti-idiotypic antibody, a $Hhip1_{\beta12}$ binding oligopeptide, $Hhip1_{\beta12}$ binding organic molecule a $Hhip1_{\beta12}$ L2 Loop mimicking oligopeptide, a $Hhip1_{\beta12}$ L2 Loop mimicking organic molecule, thereby effectively treating or preventing said cell proliferative disorder.

61. The method of 60, wherein said cell proliferative disorder is cancer.

62. A method of inhibiting the growth of a cell comprising administering to a cell expressing Ptch or Hhip1, an effective amount of a Hhip1$_{\beta12}$ L2 Loop binding antibody or a Hhip1$_{\beta12}$ L2 Loop anti-idiotypic antibody.

63. The method of 62, wherein said antibody is a monoclonal antibody.

64. The method of 62, wherein said antibody is an antibody fragment.

65. The method of 62, wherein said antibody is a chimeric or a humanized antibody.

66. The method of 62, wherein said antibody, oligopeptide or organic molecule is conjugated to a growth inhibitory agent.

67. The method of 62, wherein said antibody, oligopeptide or organic molecule is conjugated to a cytotoxic agent.

68. The method of 67, wherein said cytotoxic agent is selected from the group consisting of toxins, antibiotics, radioactive isotopes and nucleolytic enzymes.

69. The method of 67, wherein the cytotoxic agent is a toxin.

70. The method of 69, wherein the toxin is selected from the group consisting of maytansinoid and calicheamicin.

71. The method of 69, wherein the toxin is a maytansinoid.

72. The method of 62, wherein said antibody is produced in bacteria.

73. The method of 62, wherein said antibody is produced in CHO cells.

74. The method of 62, wherein said cell is a cancer cell.

75. The method of 74, wherein said cancer cell is further exposed to radiation treatment or a chemotherapeutic agent.

76. The method of 74, wherein said cancer cell is selected from the group consisting of a breast cancer cell, a colorectal cancer cell, a lung cancer cell, an ovarian cancer cell, a central nervous system cancer cell, a liver cancer cell, a bladder cancer cell, a pancreatic cancer cell, a cervical cancer cell, a melanoma cell and a leukemia cell.

77. The method of 75, wherein said protein is more abundantly expressed by said cancer cell as compared to a normal cell of the same tissue origin.

78. The method of 62 which causes the death of said cell.

79. Use of an oligopeptide in any of 12 to 30 in the preparation of a medicament for the therapeutic treatment of a cancer.

80. Use of an oligopeptide in any of 12 to 30 in the preparation of a medicament for treatment or prevention of a cell proliferative disorder.

81. An anti-Hip L2 Loop antibody.

82. An anti-idiotypic Hhip1 L2 Loop antibody

83. An anti-Ptch L2 Loop antibody.

84. An anti-idiotypic Ptch L2 Loop antibody

85. Use of an antibody in any of 81-84 in the preparation of a medicament for the therapeutic treatment of a cancer.

86. Use of an antibody in any of 81-84 in the preparation of a medicament for treating a tumor.

87. Use of an antibody in any of 81-84 in the preparation of a medicament for treatment or prevention of a cell proliferative disorder.

88. Use of a Hhip1$_{\beta12}$ binding organic molecule of 31 in the preparation of a medicament for the therapeutic treatment or diagnostic detection of a cancer.

89. Use of a Hhip1$_{\beta12}$ binding organic molecule of 31 in the preparation of a medicament for treating a tumor.

90. Use of a Hhip1$_{\beta12}$ binding organic molecule of 31 in the preparation of a medicament for treatment or prevention of a cell proliferative disorder.

91. Use of a Hhip1 L2 Loop mimicking organic molecule of 33 in the preparation of a medicament for the therapeutic treatment of a cancer.

92. Use of a Hhip1 L2 Loop mimicking organic molecule of 33 in the preparation of a medicament for treating a tumor.

93. Use of a Hhip1 L2 Loop mimicking organic molecule of 33 in the preparation of a medicament for treatment or prevention of a cell proliferative disorder.

94. Use of a composition of matter of 34 in the preparation of a medicament for the therapeutic treatment of a cancer.

95. Use of a composition of matter of 34 in the preparation of a medicament for treating a tumor.

96. Use of a composition of matter of 35 in the preparation of a medicament for treatment or prevention of a cell proliferative disorder.

97. Use of an article of manufacture of 36 in the preparation of a medicament for the therapeutic treatment of a cancer.

98. Use of an article of manufacture of 36 in the preparation of a medicament for treating a tumor.

99. Use of an article of manufacture of 36 in the preparation of a medicament for treatment or prevention of a cell proliferative disorder.

100. A method of inhibiting Hedgehog signaling in a cell comprising administering to a Hedgehog-producing cell or Hedgehog responsive tissue an oligopeptide of at least 8 to 15 amino acids in length and comprising an amino acid sequence of any one of SEQ ID NOs: 17-44.

101. The method of 100 wherein the oligopeptide comprises the amino acid sequence of any of SEQ ID NOs: 39-44.

102. The method of 100, wherein said amino acid sequence comprises conservative substitutions of amino acids at positions X with respect to the amino acids at the same positions of SEQ ID NO:60.

103. The method of 100 wherein said oligopeptide is between 8 and 12 amino acids in length.

104. The method of 100 wherein said oligopeptide is between 8 and 10 amino acids in length.

105. An oligopeptide of at least 8 to 15 amino acids in length and comprising an amino acid sequence of any one of SEQ ID NOs: 17-44.

106. The oligopeptide of 105 wherein said oligopeptide is between 8 and 12 amino acids in length.

107. The oligopeptide of 105 wherein said oligopeptide is between 8 and 10 amino acids in length.

108. The oligopeptide of 105 wherein the oligopeptide comprises the amino acid sequence of any of SEQ ID NOs: 39-44.

109. The oligopeptide of 108 wherein said amino acid sequence comprises conservative substitutions of amino acids at positions X with respect to the amino acids at the same positions of SEQ ID NO:60.

110. A pharmaceutical composition comprising an oligopeptide of at least 8 to 15 amino acids in length and comprising an amino acid sequence of any one of SEQ ID NOs: 17-44 and a pharmaceutically acceptable carrier.

111. The pharmaceutical composition of 110 wherein said oligopeptide is between 8 and 12 amino acids in length.

112. The pharmaceutical composition of 110 wherein said oligopeptide is between 8 and 10 amino acids in length.

113. The pharmaceutical composition of 110 wherein the oligopeptide comprises the amino acid sequence of any of SEQ ID NOs: 39-44.

114. The pharmaceutical composition of 113 wherein said amino acid sequence comprises conservative substitutions of amino acids at positions X with respect to the amino acids at the same positions of SEQ ID NO:60.

115. The method of 100 wherein said oligopeptide is linear.

116. The method of 100 wherein said oligopeptide is cyclic.

117. The oligopeptide of 105 wherein said oligopeptide is linear.

118. The oligopeptide of 105 wherein said oligopeptide is cyclic.

119. The pharmaceutical composition of 110 wherein said oligopeptide is linear.

120. The pharmaceutical composition of 110 wherein said oligopeptide is cyclic.

121. An antibody that specifically binds to an epitope comprising the L2 loop of Hhip.

122. An antibody that specifically binds to an epitope comprising the L2 loop of Ptch.

123. An antibody that specifically binds to an epitope comprising the pseudo-active site of Hh.

124. The antibody of 123 wherein said antibody is other than 5E1.

BRIEF DESCRIPTION OF THE DRAWINGS

FIG. 1A-C shows an alignment of the human cDNA for Hhip1$_{β12}$ (SEQ ID NO:1) and the deduced amino acid sequence (SEQ ID NO:2). 1B also shows the L2 Loop (shaded) with important amino acid residues marked by ↑ and ★.

FIG. 2 shows putative location of regions of Hip: 2A shows the amino acid sequence of Hhip1$_{β12}$ showing putative locations of the leader (SEQ ID NO:3); Putative Fz domain (SEQ ID NO:4); linker (SEQ ID NO:5); β-propeller (SEQ ID NO:6); L2 loop (SEQ ID NO:7); EGF1 Domain (SEQ ID NO:8); EGF2 Domain (SEQ ID NO:9); and putative GPI signal sequence (SEQ ID NO:10). 2B shows alignments of L2 Loop regions of human Hhip1$_{β12}$ (SEQ ID NO:7), human Ptch (SEQ ID NO:17), mouse Ptch (SEQ ID NO:18), chick Ptch (SEQ ID NO:19), zebrafish Ptch (SEQ ID NO:20), *Drosophila* Ptch (SEQ ID NO:21), worm Ptch (SEQ ID NO:22), human Ptch2 (SEQ ID NO:23), and mouse Ptch2 (SEQ ID NO:24).

FIG. 11 shows an alignment of Hhip1 sequences corresponding to L2 loop showing 15 vertebrate species of Hhip1 type 1. Highlighted are the residues in the only two non-identical positions. A conservation plot, as in described in FIG. 5B, is shown below the alignment. Residue conservation was generated with ConSurf (consurf.tau.ac.il).

FIG. 14 shows that monoclonal antibody 5E1 competes with Hhip1$_{\beta 12}$ for Shh binding. Panel A shows that the 5E1 epitope on Shh overlaps with Hhip and Ptch1 binding sites. Surface representation of Shh shows residues within 4.5 Å of Hhip (light gray) and residues where mutation alters Ptch1 activity (dark gray). The critical residue for 5E1 binding, S177 shown marked with an asterisk (*), resides in the area of Shh that interacts with both Hhip and Ptch1. Numbering refers to human Shh (Fuse, N. et al. (1999) *Proc. Natl. Acad. Sci. USA* 96:10992-10999; Pepinsky R. B. et al. (2000) *J. Biol. Chem.* 275:10995-11001). Panel B shows competitive binding between biotinylated Shh$_{N-Cys}$ and 5E1 for immobilized Hhip1$_{\beta 12}$ by ELISA. The curve drawn represents data fit to a 4-parameter equation, from which the IC$_{50}$ of 23 nM was derived. Panel C shows that at high concentrations Hhip1$_{\beta 12}$ (520 nM shown here) and Hhip1$_{\beta 12}$-Fc (data not shown) bind nonspecifically to 293 cells (light gray bars), recruiting Shh$_{649}$ (15 nM) in a Ptch1-independent manner Hhip1$_{\beta 12}$ was thus present at 35-fold excess compared to Shh649. This recruitment is competed by 520 nM 5E1 (but not control mIgG1), demonstrating that 5E1 competes with Hhip1$_{\beta 12}$ for Shh$_{649}$ binding. Black bars show binding to Ptch1 cells for comparison. Data are the average mean fluorescence intensity and SDs of two independent (duplicate and triplicate) experiments normalized to Shh$_{649}$ binding to Ptch1 cells in the absence of other proteins ("Ctrl") in the same way as FIG. 15J. Shh$_{649}$ and Hhip1$_{\beta 12}$ are present at 45- and 10-fold higher concentrations respectively than in FIG. 15J in order to detect the Ptch1-independent binding of Shh$_{649}$ to Hhip1$_{\beta 12}$.

DETAILED DESCRIPTION OF THE INVENTION

I. Definitions

Figure 3:
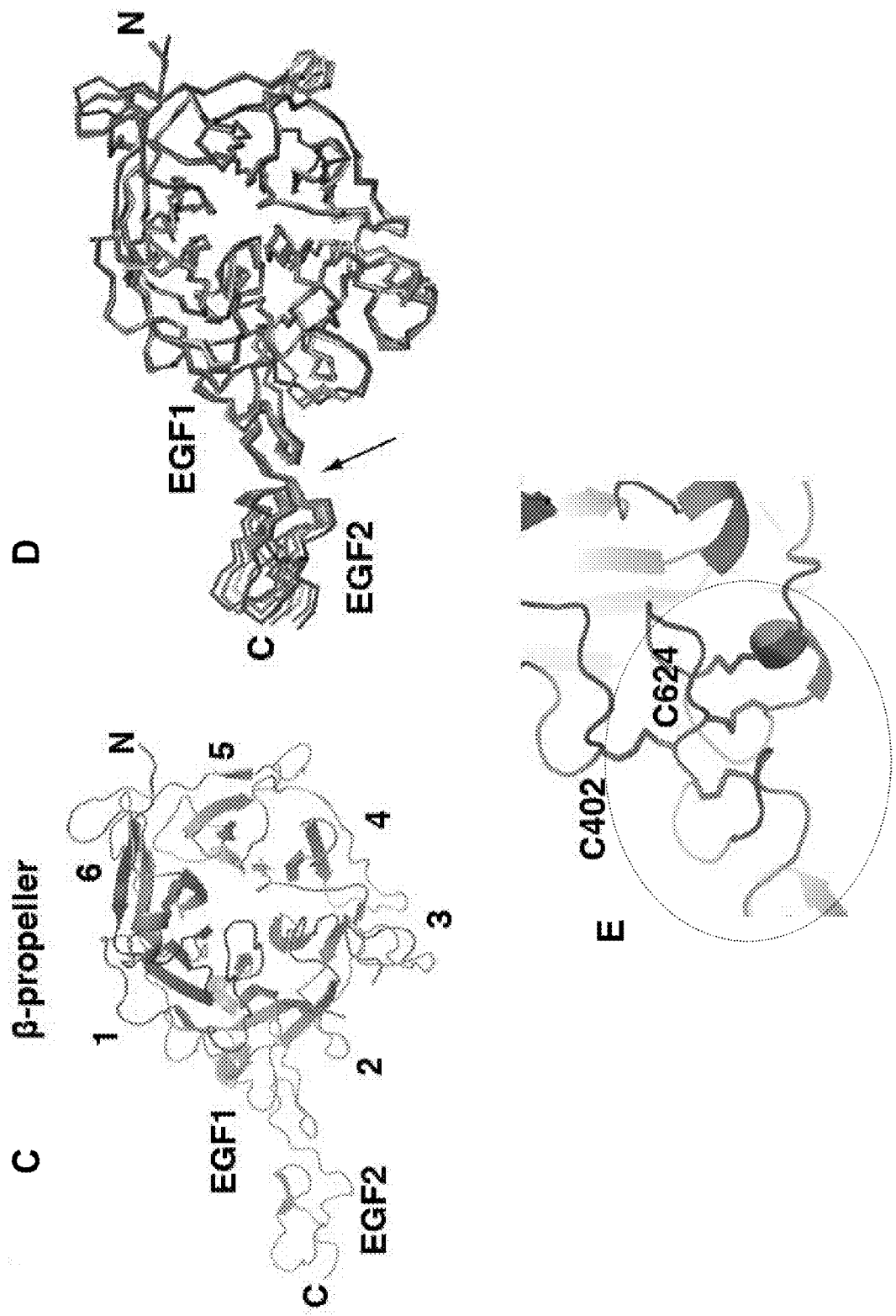
FIG. 3 shows a characterization of the Hhip1$_{ECD}$ minimal region required for Hedgehog pathway inhibition. Panel A: Hhip1 domain architecture predicted from bioinformatic analysis. Residues defining domain boundaries for constructs use in the study are shown. The lines within the plasma membrane (PM) represent the lipid tails of the GPI anchor. Constructs containing Hhip1$_{ECD}$ (SEQ ID NO:11), Hhip1$_{β12}$ (SEQ ID NO:12), Hip$_{β1}$ (SEQ ID NO:13), Hip$_β$ (SEQ ID NO:14) and Hhip1$_{Fz}$ (SEQ ID NO:16) encompass residues 20-667, 193-667, residues 193-637 and 193-607 and 20-193 of SEQ ID NO:2, respectively; Panel B: Inhibition of Shh signaling by different domains of Hhip1$_{ECD}$ in Gli-luciferase co-culture signaling assays. In this assay, Shh-producing HT-29 cells were overlaid on stably expressing Gli-luciferase S12 fibroblasts followed by incubation with Hhip1 domains and measurement of luciferase activity as described in experimental procedures. The results are plotted as the average of three independent triplicates±standard deviation; Panel C: Overall cartoon representation of the Hhip1$_{β12}$ structure. Hhip1$_{ECD}$ contains six-bladed β-propeller and two EGF domains. N-terminus and C-terminus are shown; Panel D: Superimposition of five models of Hhip1$_{β12}$ from free and Shh-bound crystal structures including the trigonal system and the orthorhombic system. Arrow indicates the flexible region between the two EGF domains; Panel E: Close-up view of β-propeller and EGF1 (inset in oval) interaction highlighting inter-domain disulfide bond between C402 and C624.

The terms "Hhip1," "Hhip" and "Hip" may be used herein interchangeably.

The terms "$Hhip1_{β12}$ polypeptides" and "$Hhip1_{β12}$ derivatives" or $Hip_{β12}$ refer to various polypeptides, derived from full-length $Hhip1_{β12}$ (SEQ ID NO:83) that is lacking the putative Frizzled domain of Hhip1. The term encompasses specifically identified fragments defined herein by SEQ ID NOs. and by designations such as $Hhip1_{β12ECD}$ (SEQ ID NO:12), $Hip_{β1}$ (SEQ ID NO:13) and $Hip_{β}$ (SEQ ID NO:14), for example. Further, where the term appears with specified amino acids (e.g., Hhip1 14-67) this refers to the amino acids specifically designated with reference to the full-length Hhip1 polypeptide (SEQ ID NO:2). The $Hhip1_{β12}$ polypeptides described herein may be isolated from a variety of sources, such as from human tissue types or from another source, or prepared by recombinant or synthetic methods. The term "$Hhip1_{β12}$ polypeptide" refers to each individual $Hhip1_{β12}$/number polypeptide disclosed herein. All disclosures in this specification which refer to the "$Hhip1_{β12}$ polypeptide derivatives" refer to each of the polypeptides individually as well as jointly. For example, descriptions of the preparation of, purification of, derivation of, formation of antibodies to or against, formation of $Hhip1_{β12}$ binding oligopeptides to or against, formation of $Hhip1_{β12}$ binding organic molecules to or against, administration of, compositions containing, treatment of a disease with, etc., pertain to each polypeptide of the invention individually. The term "$Hhip1_{β12}$ polypeptide variants" refers to variants of the $Hhip1_{β12}$ polypeptide and derivatives disclosed herein including. The sequence of full-length Hhip1 polypeptide is provided in SEQ ID NO:2. The sequence of full-length $Hhip1_{β12}$ polypeptide is provided as SEQ ID NO:83.

A "native sequence Hhip1 polypeptide" comprises a polypeptide having the same amino acid sequence as the corresponding Hhip1 polypeptide derived from nature. Such native sequence Hhip1 polypeptides can be isolated from nature or can be produced by recombinant or synthetic means. The term "native sequence Hhip1 polypeptide" specifically encompasses naturally-occurring truncated or secreted forms of the specific Hhip1 polypeptide (e.g., an extracellular domain sequence), naturally-occurring variant forms (e.g., alternatively spliced forms) and naturally-occurring allelic variants of the polypeptide.

The Hhip1 polypeptide "extracellular domain" or "ECD" refers to a form of the Hhip1 polypeptide which is essentially free of the putative GPI signal sequence which is removed when the polypeptide is anchored via a GPI-linkage (abbreviated herein as "$Hhip1_{ECD}$"). It will be understood that any putative GPI signal sequence identified for the Hhip1 polypeptides of the present invention are identified pursuant to criteria routinely employed in the art for identifying that type of domain. The exact boundaries of a GPI signal sequence may vary but most likely by no more than about 5 amino acids at either end of the domain as initially identified herein. In a specific example, $Hhip1_{ECD}$ has the amino acid sequence of SEQ ID NO:11. Optionally, therefore, an extracellular domain of a Hhip1 polypeptide may contain from about 5 or fewer amino acids on either side of the putative GPI signal sequence domain/extracellular domain boundary as identified in the Examples or specification and such polypeptides, with or without the associated signal peptide, and nucleic acid encoding them, are contemplated by the present invention. Similarly, $Hhip1_{β12ECD}$ refers to the $Hhip1_{β12}$ polypeptide essentially free of the putative GPI signal sequence (abbreviated herein as "$Hhip1_{β12ECD}$").

The approximate location of the "signal peptides," "signal sequence," or "leader sequence," used synonymously herein, of the various Hhip1 polypeptides disclosed herein may be shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6 (1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"$Hhip1_{β12}$ polypeptide variant" means a $Hhip1_{β12}$ polypeptide, preferably an active $Hhip1_{β12}$ polypeptide, as defined herein having at least about 80% amino acid sequence identity with a full-length native sequence $Hhip1_{β12}$ polypeptide sequence as disclosed herein, an extracellular domain of a $Hhip1_{β12}$ polypeptide, or any other fragment of a full-length $Hhip1_{β12}$ polypeptide sequence as disclosed herein (such as those encoded by a nucleic acid that represents only a portion of the complete coding sequence for a full-length $Hhip1_{β12}$ polypeptide). Such $Hhip1_{β12}$ polypeptide variants include, for instance, $Hhip1_{β12}$ polypeptides wherein one or more amino acid residues are added, or deleted, at the N- or C-terminus of the full-length native amino acid sequence. Ordinarily, a $Hhip1_{β12}$ polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence Hhip1$_{\beta 12}$ polypeptide sequence as disclosed herein, an extracellular domain of a Hhip1$_{\beta 12}$ polypeptide, as disclosed herein or any other specifically defined fragment of a full-length Hhip1 polypeptide sequence as disclosed herein. Ordinarily, Hhip1$_{\beta 12}$ variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, Hhip1$_{\beta 12}$ variant polypeptides will have no more than one conservative amino acid substitution as compared to the native Hhip1$_{\beta 12}$ polypeptide sequence, alternatively no more than 2, 3, 4, 5, 6, 7, 8, 9, or 10 conservative amino acid substitution as compared to the native Hhip1$_{\beta 12}$ polypeptide sequence.

"Percent (%) amino acid sequence identity" with respect to the Hhip1 polypeptide sequences identified herein is defined as the percentage of amino acid residues in a candidate sequence that are identical with the amino acid residues in the specific Hhip1 polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc. and the source code shown in U.S. Pat. No. 7,361,732, and has been filed with user documentation in the U.S. Copyright Office, Washington D.C., 20559, where it is registered under U.S. Copyright Registration No. TXU510087. The source code is incorporated herein by reference. The ALIGN-2 program is publicly available through Genentech, Inc., South San Francisco, Calif. or may be compiled from the source code provided in U.S. Pat. No. 7,361,732. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "Hhip1$_{\beta 12}$", wherein "Hhip1$_{\beta 12}$" represents the amino acid sequence of a hypothetical Hhip1$_{\beta 12}$ polypeptide of interest, "Comparison Protein" represents the amino acid sequence of a polypeptide against which the "Hhip1$_{\beta 12}$" polypeptide of interest is being compared, and "X," "Y" and "Z" each represent different hypothetical amino acid residues. Unless specifically stated otherwise, all % amino acid sequence identity values used herein are obtained as described in the immediately preceding paragraph using the ALIGN-2 computer program.

"Hhip1$_{\beta 12}$ variant polynucleotide" or "Hhip1$_{\beta 12}$ variant nucleic acid sequence" means a nucleic acid molecule which encodes a Hhip1$_{\beta 12}$ polypeptide, preferably an active Hhip1$_{\beta 12}$ polypeptide, as defined herein and which has at least about 80% nucleic acid sequence identity with a nucleotide acid sequence encoding a full-length Hhip1$_{\beta 12}$ polypeptide sequence as disclosed herein, an extracellular domain of a Hhip1$_{\beta 12}$ polypeptide, or any other fragment of a full-length Hhip1 polypeptide sequence as disclosed herein (such as those encoded by a nucleic acid that represents only a portion of the complete coding sequence for a full-length Hhip1 polypeptide). Ordinarily, a Hhip1$_{\beta 12}$ variant polynucleotide will have at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length Hhip1$_{\beta 12}$ polypeptide sequence as disclosed herein, an extracellular domain of a Hhip1$_{\beta 12}$ polypeptide, or any other fragment of a full-length Hhip1 polypeptide sequence as disclosed herein. Such variants encompass Hhip1$_{\beta 12}$ variants. Variants do not encompass the native nucleotide sequence.

Ordinarily, Hhip1$_{\beta 12}$ variant polynucleotides are at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Percent (%) nucleic acid sequence identity" with respect to Hhip1$_{\beta 12}$-encoding nucleic acid sequences identified herein is defined as the percentage of nucleotides in a candidate sequence that are identical with the nucleotides in the Hhip1$_{\beta 12}$ nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program as described above.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 3 and 4, demonstrate how to calculate the % nucleic acid sequence identity of the nucleic acid sequence designated "Comparison DNA" to the nucleic acid sequence designated "Hhip1$_{\beta12}$-DNA", wherein "Hhip1$_{\beta12}$-DNA" represents a hypothetical Hip-encoding nucleic acid sequence of interest, "Comparison DNA" represents the nucleotide sequence of a nucleic acid molecule against which the "Hhip1$_{\beta12}$-DNA" nucleic acid molecule of interest is being compared, and "N", "L" and "V" each represent different hypothetical nucleotides. Unless specifically stated otherwise, all % nucleic acid sequence identity values used herein are obtained as described in the immediately preceding paragraph using the ALIGN-2 computer program.

In other embodiments, Hhip1$_{\beta12}$ variant polynucleotides are nucleic acid molecules that encode a Hhip1$_{\beta12}$ polypeptide and which are capable of hybridizing, preferably under stringent hybridization and wash conditions, to nucleotide sequences encoding a full-length Hhip1 polypeptide as disclosed herein. Hhip1$_{\beta12}$ variant polypeptides may be those that are encoded by a Hhip1$_{\beta12}$ variant polynucleotide The term "full-length coding region" when used in reference to a nucleic acid encoding a Hhip1$_{\beta12}$ polypeptide refers to the sequence of nucleotides which encode the full-length Hhip1$_{\beta12}$ polypeptide of the invention (which is often shown between start and stop codons, inclusive thereof, in the accompanying figures).

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the Hhip1$_{\beta12}$ polypeptide natural environment will not be present. Ordinarily, however, isolated polypeptide will be prepared by at least one purification step.

An "isolated" Hhip1$_{\beta12}$ polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., CURRENT PROTOCOLS IN MOLECULAR BIOLOGY, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with a 10 minute wash at 42° C. in 0.2×SSC (sodium chloride/ sodium citrate) followed by a 10 minute high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a $Hhip1_{\beta 12}$ polypeptide or anti-$Hhip1_{\beta 12}$ antibody fused to a "tag polypeptide." The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of a $Hhip1_{\beta 12}$ polypeptide which retain a biological and/or an immunological activity of native or naturally-occurring Hhip1, wherein "biological" activity refers to a biological function of a native or naturally-occurring Hhip1 other than the ability to induce the production of an antibody against an antigenic epitope possessed by a native or naturally-occurring Hhip1 and an "immunological" activity refers to the ability to induce the production of an antibody against an antigenic epitope possessed by a native or naturally-occurring Hip.

The term "antagonist" is used in the broadest sense, and includes any molecule that partially or fully blocks, inhibits, or neutralizes a biological activity of a native Hhip1 polypeptide disclosed herein. In a similar manner, the term "agonist" is used in the broadest sense and includes any molecule that mimics a biological activity of a native Hhip1 polypeptide disclosed herein. Suitable agonist or antagonist molecules specifically include agonist or antagonist antibodies or antibody fragments, fragments or amino acid sequence variants of native Hhip1 polypeptides, peptides, antisense oligonucleotides, small organic molecules, etc. Methods for identifying agonists or antagonists of a Hhip1 polypeptide may comprise contacting a Hhip1 polypeptide with a candidate agonist or antagonist molecule and measuring a detectable change in one or more biological activities normally associated with the Hhip1 polypeptide.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for a cancer, for example, if, after receiving a therapeutic amount of a $Hhip1_{\beta 12}$ oligopeptide, or $Hhip1_{\beta 12}$ immunoadhesin, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; inhibition of Hedgehog signaling and/or relief to some extent, one or more of the symptoms associated with the specific cancer; reduced morbidity and mortality, and improvement in quality of life issues. To the extent the anti-$Hhip1_{\beta 12}$ antibody or $Hhip1_{\beta 12}$ oligopeptide may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

For bladder cancer, which is a more localized cancer, methods to determine progress of disease include urinary cytologic evaluation by cystoscopy, monitoring for presence of blood in the urine, visualization of the urothelial tract by sonography or an intravenous pyelogram, computed tomography (CT) and magnetic resonance imaging (MRI). The presence of distant metastases can be assessed by CT of the abdomen, chest x-rays, or radionuclide imaging of the skeleton.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of the treatment of, alleviating the symptoms of or diagnosis of a cancer refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

By "solid phase" or "solid support" is meant a non-aqueous matrix to which an antibody, $Hhip1_{\beta12}$ oligopeptide or $Hhip1_{\beta12}$ L2-mimicking organic molecule of the present invention can adhere or attach. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a $Hhip1_{\beta12}$ polypeptide, an antibody thereto or a $Hhip1_{\beta12}$ oligopeptide to a mammal. The components of the liposome are commonly arranged in a bilayer formation, similar to the lipid arrangement of biological membranes A "small" molecule or "small" organic molecule is defined herein to have a molecular weight below about 500 Daltons.

An "effective amount" of a polypeptide, antibody, $Hhip1_{\beta12}$ oligopeptide, Hip-mimicking organic molecule or an agonist or antagonist thereof as disclosed herein is an amount sufficient to carry out a specifically stated purpose. An "effective amount" may be determined empirically and in a routine manner, in relation to the stated purpose.

The term "therapeutically effective amount" refers to an amount of an antibody, polypeptide, $Hhip1_{\beta12}$ oligopeptide, $Hhip1_{\beta12}$ L2-mimicking organic molecule or other drug effective to "treat" a disease or disorder in a subject or mammal In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; inhibit Hedgehog signaling; and/or relieve to some extent one or more of the symptoms associated with the cancer. See the definition herein of "treating." To the extent the drug may prevent growth and/or kill existing cancer cells, it may be cytostatic and/or cytotoxic.

A "growth inhibitory amount" of an anti-$Hhip1_{\beta12}$ antibody, $Hhip1_{\beta12}$ polypeptide, $Hhip1_{\beta12}$ oligopeptide or $Hhip1_{\beta12}$ L2-mimicking organic molecule is an amount capable of inhibiting the growth of a cell, especially tumor, e.g., cancer cell, either in vitro or in vivo. A "growth inhibitory amount" of an anti-$Hhip1_{\beta12}$ antibody, Hhip1 polypeptide, Hhip1 binding oligopeptide or Hhip1 binding organic molecule for purposes of inhibiting neoplastic cell growth may be determined empirically and in a routine manner.

A "cytotoxic amount" of an anti-$Hhip1_{\beta12}$ antibody, $Hhip1_{\beta12}$ polypeptide, $Hhip1_{\beta12}$ oligopeptide or $Hhip1_{\beta12}$ L2-mimicking organic molecule is an amount capable of causing the destruction of a cell, especially tumor, e.g., cancer cell, either in vitro or in vivo. A "cytotoxic amount" of an anti-$Hhip1_{\beta12}$ antibody, $Hhip1_{\beta12}$ polypeptide, $Hhip1_{\beta12}$ oligopeptide or $Hhip1_{\beta12}$ L2-mimicking organic molecule for purposes of inhibiting neoplastic cell growth may be determined empirically and in a routine manner.

The term "antibody" is used in the broadest sense and specifically covers, for example, single anti-$Hhip1_{\beta12}$ monoclonal antibodies (including agonist, antagonist, and neutralizing antibodies), anti-$Hhip1_{\beta12}$ antibody compositions with polyepitopic specificity, polyclonal antibodies, single chain anti-$Hhip1_{\beta12}$ antibodies, and fragments of anti-$Hhip1_{\beta12}$ antibodies (see below) as long as they exhibit the desired biological or immunological activity. The term "immunoglobulin" (Ig) is used interchangeable with antibody herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, e.g., BASIC AND CLINICAL IMMUNOLOGY, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in CH sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., SEQUENCES OF PROTEINS OF IMMUNOLOGICAL INTEREST, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the VL, and around about 1-35 (H1), 50-65 (H2) and 95-102 (H3) in the VH; Kabat et al., SEQUENCES OF PROTEINS OF IMMUNOLOGICAL INTEREST, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the VL, and 26-32 (H1), 53-55 (H2) and 96-101 (H3) in the VH; Chothia and Lesk (1987) *J. Mol. Biol.* 196: 901-917).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler and Milstein (1975) *Nature* 256: 495, or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., (1991) *Nature* 352:624-628 and Marks et al., (1991) *J. Mol. Biol.*, 222:581-597, for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., (1984) *Proc. Natl. Acad. Sci. USA* 81:6851-6855). Chimeric antibodies of interest herein include "primatized" antibodies comprising variable domain antigen-binding sequences derived from a non-human primate (e.g., Old World Monkey, Ape etc.), and human constant region sequences.

An "intact" antibody is one which comprises an antigen-binding site as well as a CL and at least heavy chain constant domains, CH1, CH2 and CH3. The constant domains may be native sequence constant domains (e.g., human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870, Example 2; Zapata et al., (1995) *Protein Eng.* 8(10): 1057-1062); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in THE PHARMACOLOGY OF MONOCLONAL ANTIBODIES, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., *Proc. Natl. Acad. Sci. USA*, 90:6444-6448 (1993).

Anti-idiotypic antibodies are antibodies that bind to the antigen binding region of a subject antibody. Such anti-idiotypic antibodies may mimic the epitope that is bound by the subject antibody. For example, a Hhip1$_{β12}$ antibody that specifically binds the L2 loop of Hhip1, may mimic the portion of Hedgehog that binds to L2. Thus, an anti-idiotypic antibody raised against this subject antibody (and specifically against the antigen binding portion, may therefore recognize and specifically bind Hedgehog in the manner that the L2 portion of Hhip1 binds Hedgehog.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al. (1986) *Nature* 321:522-525; Riechmann et al. (1988) *Nature* 332:323-329; and Presta, (1992) *Curr. Op. Struct. Biol.* 2:593-596.

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1 \times 10^{-7}$ M, preferably no more than about $1 \times 10^{-8}$ and most preferably no more than about $1 \times 10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

A "Hhip1$_{β12}$ oligopeptide" is an oligopeptide that binds, preferably specifically, to a Hedgehog polypeptide. Hhip1$_{β12}$ binding oligopeptides may be chemically synthesized using known oligopeptide synthesis methodology or may be prepared and purified using recombinant technology. Hhip1$_{β12}$ oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a Hedgehog polypeptide as described herein. Some Hhip1$_{β12}$ oligopeptides are described herein. Other Hhip1$_{β12}$ oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762; 5,750,373; 4,708,871; 4,833,092; 5,223,409; 5,403,484; 5,571,689; 5,663,143; PCT Publication Nos. WO 84/03506 and WO84/03564; Geysen et al., (1984) *Proc. Natl. Acad. Sci. USA* 81:3998-4002; Geysen et al., (1985) *Proc. Natl. Acad. Sci. USA* 82:178-182 (1985); Geysen et al., in SYNTHETIC PEPTIDES AS ANTIGENS, 130-149 (1986); Geysen et al., (1987) *J. Immunol. Meth.* 102:259-274; Schoofs et al. (1988) *J. Immunol.* 140:611-616, Cwirla, S. E. et al. (1990) *Proc. Natl. Acad. Sci. USA* 87:6378; Lowman, H. B. et al. (1991) *Biochemistry* 30:10832; Clackson, T. et al. (1991) *Nature,* 352:624; Marks, J. D. et al. (1991) *J. Mol. Biol.* 222:581; Kang, A. S. et al. (1991) *Proc. Natl. Acad. Sci. USA* 88:8363, and Smith, G. P. (1991) *Current Opin. Biotechnol.* 2:668).

A "Hhip1$_{β12}$ L2 Loop binding oligopeptide" is a form of a Hhip1$_{β12}$ oligopeptide that binds, preferably specifically, to a Hhip1 polypeptide at the portion of Hhip1 that interacts with Hh in nature (i.e., the L2 Loop) and/or to the analogous portion of Ptch. Hhip1$_{β12}$ L2 Loop binding oligopeptides may be chemically synthesized using known oligopeptide synthesis methodology or may be prepared and purified using recombinant technology. Hhip1$_{β12}$ L2 Loop binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a Hhip1 and/or Ptch polypeptide as described herein.

A "Hhip1$_{β12}$ L2 Loop binding organic molecule" is an organic molecule other than an oligopeptide or antibody as defined herein that binds, preferably specifically, to a Hhip1$_{β12}$ L2 Loop motif in a protein, including analogous motifs in Ptch and Ptch2 polypeptides as described herein. Hhip1$_{β12}$ L2 Loop binding organic molecules may be identified and chemically synthesized using known methodology (see, e.g., PCT Publication Nos. WO 00/00823 and WO 00/39585). Hhip1$_{β12}$ L2 Loop binding organic molecules are usually less than about 2000 daltons in size, alternatively less than about 1500, 750, 500, 250 or 200 daltons in size, wherein such organic molecules that are capable of binding, preferably specifically, to a Hhip1 and or Ptch polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO 00/00823 and WO 00/39585). Such molecules may have an agonist or antagonist effect on Hhip1 and/or Ptch due to the structural similarity of the Hhip1 L2 and Ptch L2 domains.

"Hhip1$_{\beta12}$ L2 Loop mimicking oligopeptide" is a peptide that binds, preferably specifically, to a Hh polypeptide at the portion of Hh that interacts with Hhip1 in nature. Hhip1$_{\beta12}$ L2 Loop mimicking oligopeptides may be chemically synthesized using known oligopeptide synthesis methodology or may be prepared and purified using recombinant technology. Hhip1$_{\beta12}$ L2 Loop mimicking oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a Hh polypeptide as described herein.

A "Hhip1$_{\beta12}$ L2 mimicking organic molecule" is an organic molecule other than an oligopeptide or antibody as defined herein that binds, preferably specifically, to a Hedgehog polypeptide as described herein. Hhip1$_{\beta12}$ L2-mimicking organic molecules may be identified and chemically synthesized using known methodology (see, e.g., PCT Publication Nos. WO 00/00823 and WO 00/39585). Hhip1$_{\beta12}$ L2-mimicking organic molecules are usually less than about 2000 daltons in size, alternatively less than about 1500, 750, 500, 250 or 200 daltons in size, wherein such organic molecules that are capable of binding, preferably specifically, to a Hedgehog polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO 00/00823 and WO 00/39585).

An antibody, oligopeptide or other organic molecule "which binds" an antigen of interest, e.g. a tumor-associated polypeptide antigen target, is one that binds the antigen with sufficient affinity such that the antibody, oligopeptide or other organic molecule is useful as a diagnostic and/or therapeutic agent in targeting a cell or tissue expressing the antigen, and does not significantly cross-react with other proteins. In such embodiments, the extent of binding of the antibody, oligopeptide or other organic molecule to a "non-target" protein will be less than about 10% of the binding of the antibody, oligopeptide or other organic molecule to its particular target protein as determined by fluorescence activated cell sorting (FACS) analysis or radioimmunoprecipitation (RIA). With regard to the binding of an antibody, oligopeptide or other organic molecule to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target.

The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

The structural similarity of Hhip1 L2 and Ptch L2 Loops permits cross-reactivity of anti-Hhip1$_{\beta12}$ antibodies that target the L2 loop. Thus, in certain embodiments, anti-Hhip1$_{\beta12}$ antibodies that bind the Hhip1$_{\beta12}$ L2 loop may also specifically bind the Ptch L2 loop. Likewise, small organic molecules designed to bind Hhip1$_{\beta12}$ L2 loop or to the portion of Hedgehog that interacts with the Hhip1$_{\beta12}$ L2 loop may also bind to the structurally analogous portion of Ptch L2.

"Patched" or "Ptch" as used herein includes both Ptch and Ptch2 polypeptides when referring to the antibodies, oligopeptides, and small organic molecules and various methods using the same as described herein.

An antibody, oligopeptide or other organic molecule that "inhibits the growth of tumor cell" or a "growth inhibitory" antibody, oligopeptide or other organic molecule is one which results in measurable growth inhibition of cancer cells responsive to Hedgehog stimulation. Preferred growth inhibitory anti-Hhip1$_{\beta12}$ antibodies, oligopeptides or organic molecules inhibit growth of Hedgehog-responsive tumor cells by greater than 20%, preferably from about 20% to about 50%, and even more preferably, by greater than 50% (e.g., from about 50% to about 100%) as compared to the appropriate control, the control typically being tumor cells not treated with the antibody, oligopeptide or other organic molecule being tested. In one embodiment, growth inhibition can be measured at an antibody concentration of about 0.1 to 30 µg/ml or about 0.5 nM to 200 nM in cell culture, where the growth inhibition is determined 1-10 days after exposure of the tumor cells to the antibody. The antibody is growth inhibitory in vivo if administration of the anti-Hhip1$_{\beta12}$ antibody about 1 µg/kg to about 100 mg/kg body weight results in reduction in tumor size or tumor cell proliferation within about 5 days to 3 months from the first administration of the antibody, preferably within about 5 to 30 days.

The tumor cell is usually one that is responsive to Hedgehog signaling. Preferably the tumor cell, is, for example, basal cell carcinoma, prostate, breast, ovarian, stomach, endometrial, lung, kidney, colon, bladder cell.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet (1991) *Annu. Rev. Immunol.* 9:457-492. An in vitro ADCC assay, such as that described in U.S. Pat. No. 5,500,362 or 5,821,337, may be performed to assess ADCC activity of a molecule of interest. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. (1998) *Proc. Natl. Acad. Sci. USA* 95(2):652-656.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, (1997) *Annu. Rev. Immunol.* 15:203-234). FcRs are reviewed in Ravetch and Kinet (1991) *Annu. Rev. Immunol.* 9:457-492; Capel et al. (1994) *Immunomethods* 4:25-34; and de Haas et al. (1995) *J. Lab. Clin. Med.* 126:330-341. Other FcRs, including those to be identified in the future, are encompassed by the term "FcR" herein. The term also includes the neonatal receptor, FcRn, which is responsible for the transfer of maternal IgGs to the fetus (Guyer et al. (1976) *J. Immunol.* 117:587 and Kim et al. (1994) *J. Immunol.* 24:249).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass) which are bound to their cognate antigen. To assess complement activation, a CDC assay, e.g., as described in Gazzano-Santoro et al., (1996) *J. Immunol. Methods* 202:163, may be performed.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, basal cell carcinoma (BCC) pancreatic ductal adenocarcinoma (PDA) and associated metastases.

The terms "cell proliferative disorder" and "proliferative disorder" refer to disorders that are associated with some degree of abnormal cell proliferation. In one embodiment, the cell proliferative disorder is cancer.

"Tumor," as used herein, refers to all neoplastic cell growth and proliferation, whether malignant or benign, and all pre-cancerous and cancerous cells and tissues.

An antibody, oligopeptide or other organic molecule which "induces cell death" is one which causes a viable cell to become nonviable. The cell is one which is responsive to Hedgehog signaling, such as one that expresses Hhip1 and/or Ptch, preferably a cell that overexpresses Ptch polypeptide as compared to a normal cell of the same tissue type. Preferably, the cell is a cancer cell, e.g., a basal cell, pancreatic, breast, ovarian, stomach, endometrial, salivary gland, lung, kidney, colon, thyroid, or bladder cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody, oligopeptide or other organic molecule is able to induce cell death, loss of membrane integrity as evaluated by uptake of propidium iodide (PI), trypan blue (see Moore et al. (1995) *Cytotechnology* 17:1-11) or 7AAD can be assessed relative to untreated cells. Preferred cell death-inducing antibodies, oligopeptides or other organic molecules are those which induce PI uptake in the PI uptake assay in BT474 cells.

A "Hhip1$_{\beta12}$-expressing cell" is a cell which expresses an endogenous or transfected Hhip1$_{\beta12}$ polypeptide either on the cell surface or in a secreted form. A "Hedgehog-responsive cancer" is a cancer comprising cells that have a Hhip1 polypeptide and/or Ptch polypeptide present on the cell surface. A "Hedgehog-responsive cancer" produces sufficient levels Hh receptor polypeptides on the surface of cells thereof, such that an anti-Hhip1$_{\beta12}$ antibody (e.g., an antibody that binds to an L2 loop of Hhip1 and Ptch and inhibit Hh binding), an oligopeptide or other organic molecule can bind thereto and have a therapeutic effect with respect to the cancer.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The word "label" when used herein refers to a detectable compound or composition which is conjugated directly or indirectly to the antibody, oligopeptide or other organic molecule so as to generate a "labeled" antibody, oligopeptide or other organic molecule. The label may be detectable by itself (e.g. radioisotope labels or fluorescent labels) or, in the case of an enzymatic label, may catalyze chemical alteration of a substrate compound or composition which is detectable.

The term "cytotoxic agent" as used herein refers to a substance that inhibits or prevents the function of cells and/or causes destruction of cells. The term is intended to include radioactive isotopes (e.g., At211, I131, I125, Y90, Re186, Re188, Sm153, Bi212, P32 and radioactive isotopes of Lu), chemotherapeutic agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew (1994) *Chem. Intl. Ed. Engl.* 33:183-186); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxy-doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body, treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell, especially a Hip- or Ptch-expressing cancer cell (i.e., a Hedgehog-responsive cancer cell), either in vitro or in vivo. Thus, the growth inhibitory agent may be one which significantly reduces the percentage of Hip-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in THE MOLECULAR BASIS OF CANCER, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anti-cancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

TABLE 1

| | | |
|---|---|---|
| Hhip1$_{\beta 12}$ | XXXXXXXXXXXXXXX | (Length = 15 amino acids) |
| Comparison Protein | XXXXXYYYYYY | (Length = 12 amino acids) |

% amino acid sequence identity = (the number of identically matching amino acid residues between the two polypeptide sequences as determined by ALIGN-2) divided by (the total number of amino acid residues of the Hhip1$_{\beta 12}$ polypeptide) = 5 divided by 15 = 33.3%

TABLE 2

| | | |
|---|---|---|
| Hhip1$_{\beta 12}$ | XXXXXXXXXX | (Length = 10 amino acids) |
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the Hhip1$_{\beta 12}$ polypeptide) = 5 divided by 10 = 50%

TABLE 3

| Hhip1$_{\beta12}$-DNA | NNNNNNNNNNNNNN | (Length = 14 nucleotides) |
|---|---|---|
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the Hip-DNA nucleic acid sequence) = 6 divided by 14 = 42.9%

TABLE 4

| Hhip1$_{\beta12}$-DNA | NNNNNNNNNNNN | (Length = 12 nucleotides) |
|---|---|---|
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the Hip-DNA nucleic acid sequence) = 4 divided by 12 = 33.3%

II. Compositions and Methods of the Invention

A. Hhip1$_{\beta12}$ Polypeptides

In some embodiments of the invention, the Hhip1$_{\beta12}$ polypeptides are isolated polypeptides having an amino acid sequence selected from SEQ ID NO:83, SEQ ID NO:6, SEQ ID NO:7, SEQ ID NO:8, SEQ ID NO:9, SEQ ID NO:12, SEQ ID NO:13, SEQ ID NO:14, SEQ ID NO:15, and SEQ ID NO:16. In other embodiments, the invention provides Hhip1$_{\beta12}$-derived polypeptides, such as the individual domains having the amino acid sequences of SEQ ID NO:3, SEQ ID NO:4, SEQ ID NO:5, SEQ ID NO:6, SEQ ID NO:7, SEQ ID NO:8, SEQ ID NO:9 and SEQ ID NO:10.

Nucleic acid sequences encoding these polypeptides may be cloned into appropriate expression vectors and transfected into appropriate host cells. Expressed polypeptides may be isolated using a variety of methods known in that art and described herein.

B. Anti-Hhip1$_{\beta12}$ Antibodies

In one embodiment, the present invention provides anti-Hhip1$_{\beta12}$ antibodies which may find use herein as therapeutic and/or diagnostic agents. In some embodiments, the anti-Hhip1$_{\beta12}$ antibodies are produced by immunizing animals with Hhip1$_{\beta12}$ polypeptides and such antibodies specifically bind to epitopes on native Hhip1 that could not be elicited through immunization with native Hhip1 protein (containing the putative Frizzled domain). In a specific example, the antibodies include antibodies against the L2 Loop of Hhip1 and anti-idiotypic antibodies thereof. Exemplary antibodies include polyclonal, monoclonal, humanized, bispecific, anti-idiotypic and heteroconjugate antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, SOCl$_2$, or R$^1$N═C═NR, where R and R$^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler and Milstein (1975) Nature, 256:495, or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, MONOCLONAL ANTIBODIES: PRINCIPLES AND PRACTICE, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection (ATCC), Manassas, Va., USA. Human myeloma and mouse-human heteromyeloma cell lines also have been described for the production of human monoclonal antibodies (Kozbor (1984) J. Immunol. 133:3001); and Brodeur et al., MONOCLONAL ANTIBODY PRODUCTION TECHNIQUES AND APPLICATIONS, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., (1980) *Anal. Biochem.* 107:220.

Once hybridoma cells that produce antibodies of the desired specificity, affinity, and/or activity are identified, the clones may be subcloned by limiting dilution procedures and grown by standard methods (Goding, Monoclonal Antibodies: PRINCIPLES AND PRACTICE, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G Sepharose®) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., (1993) *Curr. Opinion in Immunol.* 5:256-262 (1993) and Plückthun (1992) *Immunol. Revs.* 130:151-188.

In a further embodiment, monoclonal antibodies or antibody fragments can be isolated from antibody phage libraries generated using the techniques described in McCafferty et al. (1990) *Nature* 348:552-554. Clackson et al. (1991) *Nature* 352:624-628 and Marks et al. (1991) *J. Mol. Biol.* 222:581-597 describe the isolation of murine and human antibodies, respectively, using phage libraries. Subsequent publications describe the production of high affinity (nM range) human antibodies by chain shuffling (Marks et al. (1992) *Bio/Technology* 10:779-783), as well as combinatorial infection and in vivo recombination as a strategy for constructing very large phage libraries (Waterhouse et al. (1993) *Nuc. Acids. Res.* 21:2265-2266). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain (CH and CL) sequences for the homologous murine sequences (U.S. Pat. No. 4,816,567; and Morrison, et al. (1984) *Proc. Natl. Acad. Sci. USA* 81:6851), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-Hhip1 antibodies of the invention may further comprise humanized antibodies or human antibodies.

Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al. (1986) *Nature* 321:522-525; Riechmann et al. (1988) *Nature* 332:323-329; and Presta (1992) *Curr. Op. Struct. Biol.* 2:593-596).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-329; Verhoeyen et al. (1988) *Science* 239:1534-1536), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al. (1993) *J. Immunol.* 151:2296; Chothia et al. (1987) *J. Mol. Biol.* 196:901). Another method uses a particular framework region derived from the consensus sequence of all human antibodies of a particular subgroup of light or heavy chains. The same framework may be used for several different humanized antibodies (Carter et al., (1992) *Proc. Natl. Acad. Sci. USA* 89:4285; Presta et al. (1993) *J. Immunol.* 151:2623).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized antibodies are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al. (1993) *Proc. Natl. Acad. Sci. USA* 90:2551; Jakobovits et al. (1993) *Nature* 362:255-258; Bruggemann et al. (1993) *Year in Immuno.* 7:33; U.S. Pat. Nos. 5,545,806, 5,569,825, 5,591,669 (all of GenPharm); 5,545,807; and WO 97/17852.

Alternatively, phage display technology (McCafferty et al. (1990) *Nature* 348:552-553) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, K. S., et al. (1993) *Current Opinion in Structural Biology* 3:564-571. Several sources of V-gene segments can be used for phage display. Clackson et al. (1991) *Nature* 352:624-628 isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al. (1991) *J. Mol. Biol.* 222:581-597, or Griffith et al. (1993) *EMBO J.* 12:725-734. See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al. (1992) *J. Biochem. Biophys. Methods* 24:107-117; and Brennan et al. (1985) *Science* 229:81). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab')_2$ fragments (Carter et al., (1992) *Bio/Technology* 10:163-167). According to another approach, $F(ab')_2$ fragments can be isolated directly from recombinant host cell culture. Fab and $F(ab')_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv (See ANTIBODY ENGINEERING, ed. Borrebaeck, supra). The antibody fragment may also be a "linear antibody", e.g., as described in U.S. Pat. No. 5,641,870 for example. Such linear antibody fragments may be monospecific or bispecific.

5. Bispecific Antibodies

Bispecific antibodies are antibodies that have binding specificities for at least two different epitopes. Exemplary bispecific antibodies may bind to two different epitopes of a $Hhip1_{\beta12}$ polypeptide as described herein. Other such antibodies may combine a $Hhip1_{\beta12}$ binding site with a binding site for another protein. Alternatively, a target-specific arm (e.g., an L2-specific arm) may be combined with an arm which binds to a triggering molecule on a leukocyte such as a T-cell receptor molecule (e.g., CD3), or Fc receptors for IgG (FcγR), such as FcγRI (CD64), FcγRII (CD32) and FcγRIII (CD16), so as to focus and localize cellular defense mechanisms to the Hip- or Ptch-expressing cell. Bispecific antibodies may also be used to localize cytotoxic agents to cells which express Hhip1 and/or Ptch. These antibodies possess a Hip- or Ptch-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., $F(ab')_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody. Thus, methods for making bispecific antibodies are known in the art. Traditional production of full length bispecific antibodies is based on the co-expression of two immunoglobulin heavy chain-light chain pairs, where the two chains have different specificities (Millstein et al. (1983) *Nature* 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al. (1991) *EMBO J.* 10:3655-3659.

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, CH2, and CH3 regions. It is preferred to have the first heavy-chain constant region (CH1) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al. (1986) *Meth. Enzymol.* 121:210.

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al. (1985) *Science* 229:81 describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al. (1992) *J. Exp. Med.* 175: 217-225 describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers (Kostelny et al. (1992) *J. Immunol.* 148(5):1547-1553). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al. (1993) *Proc. Natl. Acad. Sci. USA* 90:6444-6448 has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al. (1994) *J. Immunol.* 152:5368.

Antibodies with more than two valencies are contemplated. For example, trispecific antibodies can be prepared. Tutt et al. (1991) *J. Immunol.* 147:60.

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al. (1992) *J. Exp Med.* 176:1191-1195 and Shopes, B. J. (1992) *Immunol.* 148: 2918-2922. Homodimeric antibodies with enhanced anti-tumor activity may also be prepared using heterobifunctional cross-linkers as described in Wolff et al. (1993) *Cancer Res.* 53:2560-2565. Alternatively, an antibody can be engineered which has dual Fc regions and may thereby have enhanced complement lysis and ADCC capabilities. See Stevenson et al. (1989) *Anti-Cancer Drug Design* 3:219-230.

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

9. Immunoconjugates

The invention also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate)

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include 212Bi, 131I, 131In, 90Y, and 186Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. (1987) *Science* 238:1098. Carbon-14-labeled 1-isothiocyanatobenzyl-3-methyldiethylene triaminepentaacetic acid (MX-DTPA) is an exemplary chelating agent for conjugation of radionucleotide to the antibody (See WO 94/11026).

Conjugates of an antibody and one or more small molecule toxins, such as a calicheamicin, maytansinoids, a trichothene, and CC1065, and the derivatives of these toxins that have toxin activity, are also contemplated herein.

i. Maytansine and Maytansinoids

In one preferred embodiment, an anti-Hhip1$_{\beta12}$ antibody (full length or fragments) of the invention is conjugated to one or more maytansinoid molecules.

Maytansinoids are mitototic inhibitors which act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al. (1996) *Proc. Natl. Acad. Sci. USA* 93:8618-

8623 described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al. (1992) *Cancer Res.* 52:127-131 describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-Hhip1$_{\beta 12}$ antibody-maytansinoid conjugates are prepared by chemically linking an anti-Hhip1$_{\beta 12}$ antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0425235B1, Chari et al. (1992) *Cancer Res.* 52:127-131, and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al. (1978) *Biochem. J.* 173:723-737) and N-succinimidyl-4-(2-pyridylthio)-pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hyrdoxymethyl, the C-15 position modified with a hydroxyl group, and the C-20 position having a hydroxyl group. In a preferred embodiment, the linkage is formed at the C-3 position of maytansinol or a maytansinol analogue.

ii. Auristatins and Dolostatins

In some embodiments, the immunoconjugate comprises an antibody of the invention conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) *Antimicrob. Agents and Chemother.* 45(12):3580-3584) and have anticancer (U.S. Pat. No. 5,663,149) and antifungal activity (Pettit et al. (1998) *Antimicrob. Agents Chemother.* 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF (i.e., MMAE and MMAF), disclosed in "Senter et al., *Proceedings of the American Association for Cancer Research*, Volume 45, Abstract Number 623, presented Mar. 28, 2004, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, THE PEPTIDES, volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al. (1989) *J. Am. Chem. Soc.* 111:5463-5465; Pettit et al. (1998) *Anti-Cancer Drug Design* 13:243-277; Pettit, G. R., et al. (1996) *Synthesis* 6:719-725; Pettit et al (1996) *J. Chem. Soc. Perkin Trans.* 1 5:859-863; and Doronina (2003) *Nat. Biotechnol.* 21(7):778-784.

iii. Calicheamicin

Another immunoconjugate of interest comprises an anti-Hhip1$_{\beta 12}$ antibody conjugated to one or more calicheamicin molecules. The calicheamicin family of antibiotics are capable of producing double-stranded DNA breaks at subpicomolar concentrations. For the preparation of conjugates of the calicheamicin family, see U.S. Pat. Nos. 5,712,374; 5,714,586; 5,739,116; 5,767,285; 5,770,701; 5,770,710; 5,773,001; 5,877,296 (all to American Cyanamid Company). Structural analogues of calicheamicin which may be used include, but are not limited to, γ1I, α2I, α3I, N-acetyl-γ1I, PSAG and θI1 (Hinman et al. (1993) *Cancer Res.* 53:3336-3342; Lode et al. (1998) *Cancer Res.* 58:2925-2928 and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

iv. Other Cytotoxic Agents

Other antitumor agents that can be conjugated to the anti-Hhip1$_{\beta12}$ antibodies of the invention include BCNU, streptozoicin, vincristine and 5-fluorouracil, the family of agents known collectively LL-E33288 complex described in U.S. Pat. Nos. 5,053,394; 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecene (See, for example, WO 93/21232 published Oct. 28, 1993).

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-Hhip1$_{\beta12}$ antibodies. Examples include $^{211}$At, $^{131}$I, $^{125}$I, $^{90}$Y, $^{186}$Re, $^{188}$Re, $^{153}$Sm, $^{212}$Bi, $^{32}$P, $^{212}$Pb, and radioactive isotopes of Lu. When the conjugate is used for diagnosis, it may comprise a radioactive atom for scintigraphic studies, for example tc99m or $^{123}$I, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as tc99m or $^{123}$I, $^{186}$Re, $^{188}$Re and $^{111}$In can be attached via a cysteine residue in the peptide. Yttrium-90 can be attached via a lysine residue. The IODOGEN method (Fraker et al. (1978) *Biochem. Biophys. Res. Commun.* 80:49-57 can be used to incorporate iodine-123. MONOCLONAL ANTIBODIES IN IMMUNOSCINTIGRAPHY, Chatal, CRC Press, 1989, describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. (1987) *Science* 238:1098. Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al. (1992) *Cancer Res.* 52:127-131; U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone) benzoate) which are commercially available (e.g., from Pierce Biotechnology, Inc., Rockford, Ill., U.S.A, see pages 467-498 of the 2003-2004 Applications Handbook and Catalog).

Alternatively, a fusion protein comprising the anti-Hhip1$_{\beta12}$ antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The anti-Hhip1$_{\beta12}$ antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al. (1985) *Proc. Natl. Acad. Sci. USA* 82:3688; Hwang et al. (1980) *Proc. Natl. Acad. Sci. USA* 77:4030; U.S. Pat. Nos. 4,485,045 and 4,544,545; and WO 97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. (1982) *J. Biol. Chem.* 257:286-288 via a disulfide interchange reaction. A chemotherapeutic agent is optionally contained within the liposome (See Gabizon et al. (1989) *J. National Cancer Inst.* 81(19): 1484).

B. Hhip1 Binding Oligopeptides

Hhip1$_{\beta12}$ oligopeptides of the present invention are oligopeptides that bind, preferably specifically, to a Hhip1 polypeptide. Hhip1 binding oligopeptides may be chemically synthesized using known oligopeptide synthesis methodology or may be prepared and purified using recombinant technology. Hhip1 binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a Hhip1 polypeptide. Certain Hhip1$_{\beta12}$ oliopeptides are described in detail herein. Other Hhip1$_{\beta12}$ oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762; 5,750,373; 4,708,871; 4,833,092; 5,223, 409; 5,403,484; 5,571,689; 5,663,143; PCT Publication Nos. WO 84/03506 and WO 84/03564; Geysen et al. (1984) *Proc. Natl. Acad. Sci. USA* 81:3998-4002; Geysen et al. (1985) *Proc. Natl. Acad. Sci. USA* 82:178-182; Geysen et al., in SYNTHETIC PEPTIDES AS ANTIGENS, Portland, R. and Whelan J., Eds., John Wiley, Chichester, 130-149 (1986); Geysen et al. (1987) *J. Immunol. Meth.* 102:259-274; Schoofs et al. (1988) *J. Immunol.* 140:611-616, Cwirla, S. E. et al. (1990) *Proc. Natl. Acad. Sci. USA* 87:6378; Lowman, H. B. et al. (1991) *Biochemistry* 30:10832; Clackson, T. et al. (1991) *Nature* 352:624; Marks, J. D. et al. (1991) *J. Mol. Biol.* 222:581; Kang, A. S. et al. (1991) *Proc. Natl. Acad. Sci. USA* 88:8363; and Smith, G. P. (1991) *Current Opin. Biotechnol.* 2:668).

In this regard, bacteriophage (phage) display is one well known technique which allows one to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) *Science* 249:386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) *Proc. Natl. Acad. Sci. USA* 87:6378) or protein (Lowman, H. B. et al. (1991) *Biochemistry* 30:10832; Clackson, T. et al. (1991) *Nature,* 352:624; Marks, J. D. et al. (1991), *J. Mol. Biol.* 222:581; Kang, A. S. et al. (1991) *Proc. Natl. Acad. Sci. USA* 88:8363) libraries on phage have been used for screening millions of polypeptides or oligopeptides for ones with specific binding properties (Smith, G. P. (1991) *Current Opin. Biotechnol.* 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409; 5,403,484; 5,571,689; and 5,663,143.

Although most phage display methods have used filamentous phage, lambdoid phage display systems (WO 95/34683; U.S. Pat. No. 5,627,024), T4 phage display systems (Ren et al. (1998) *Gene* 215:439; Zhu et al. (1998) *Cancer Res.* 58(15):3209-3214; Jiang et al. (1997) *Inf. Immun.* 65(11): 4770-4777; Ren et al. (1997) *Gene* 195(2):303-311; Ren (1996) *Protein Sci.* 5:1833; Efimov et al. (1995) *Virus Genes* 10:173) and T7 phage display systems (Smith and Scott (1993) *Meth. Enzymol.* 217:228-257; and U.S. Pat. No. 5,766, 905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphylococcus aureus* protein A as an affinity tag has also been reported (Li et al. (1998) *Mol. Biotech.* 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538; 5,432,018; and WO 98/15833.

Methods of generating peptide libraries and screening these libraries are also disclosed in U.S. Pat. Nos. 5,723,286; 5,432,018; 5,580,717; 5,427,908; 5,498,530; 5,770,434; 5,734,018; 5,698,426; 5,763,192; and 5,723,323.

In certain embodiments, the Hhip1$_{\beta12}$ binding oligopeptides bind to the L2 Loop of Hhip1 and as such are Hhip1$_{\beta12}$L2 Loop binding oligopeptides. These peptides bind to the L2 Loop of Hhip1 and/or Ptch due to the conserved nature of the L2 Loop motif of Hhip1. In some embodiments, the oligopeptides interfere with Hh binding to Hhip1 and/or Ptch and prevent Hh signaling. In other embodiments, the oligopeptides themselves may bind to Hhip1 and/or Ptch and thereby drive Hh signaling by mimicking Hh binding to Ptch.

C. Hhip1$_{\beta12}$ L2 Loop Mimicking Oligopeptides

In certain embodiments, the Hhip1$_{\beta12}$ oligopeptides are based on the L2 loop of Hhip1 (SEQ ID NO:54). The L2 loop of Hhip1$_{\beta12}$ is the portion that binds to Hedgehog and which contains residues that are conserved with an analogous portion of Ptch that also binds Hedgehog. Therefore, the invention provides oligopeptides based on the amino acid sequence of the L2 loop of the β-propeller domain of Hhip1 that interacts with Hedgehog. These oligopeptides may be expressed in recombinant systems or chemically synthesized by any method known in the art. The oligopeptides may be linear or made to be cyclic. The oligopeptides generally are at least 8 amino acids in length. In some embodiments, the oligopeptides between 9-21 amino acids in length including embodiments that are 9, 10, 11, 12 13, 14, 15, 16, 17, 18, 19, 20 or 21 amino acids in length.

The oligopeptides of the invention comprise at least the following amino acid sequence:

(SEQ ID NO: 39)
[I/L/V]XXXX[M/L]X[D/E/N]X[D/S/E]G[L/I]

In which X can be any amino acid, and the amino acid in brackets represents alternative amino acids for that position. Preferably, the amino acid at position X one that is either identical to, or is a conservative substitution of the amino acid at that position of the L2 loop of Hhip1. Examples of some oligopeptides include:

```
IXXXX[M/L]X[D/E/N]X[D/S/E]G[L/I]      (SEQ ID NO: 56)
LXXXX[M/L]X[D/E/N]X[D/S/E]G[L/I]      (SEQ ID NO: 57)
IXXXXMX[D/E/N]X[D/S/E]G[L/I]          (SEQ ID NO: 58)
LXXXXLX[D/E/N]X[D/S/E]G[L/I]          (SEQ ID NO: 59)
IXXXXMXEX[D/S/E]G[L/I]                (SEQ ID NO: 60)
LXXXXLXDX[D/S/E]G[L/I]                (SEQ ID NO: 61)
IXXXXMXEXDG[L/I]                      (SEQ ID NO: 62)
LXXXXLXDXDG[L/I]                      (SEQ ID NO: 63)
LXXXXLXDXSG[L/I]                      (SEQ ID NO: 64)
LXXXXLXDXEG[L/I]                      (SEQ ID NO: 65)
IXXXXMXEXDGL                          (SEQ ID NO: 66)
LXXXXLXDXDGL                          (SEQ ID NO: 67)
LXXXXLXDXSGL                          (SEQ ID NO: 68)
LXXXXLXDXEGL                          (SEQ ID NO: 69)
LXXXXLXDXDGI                          (SEQ ID NO: 70)
LXXXXLXDXSGI                          (SEQ ID NO: 71)
LXXXXLXDXEGI                          (SEQ ID NO: 72)
```

In which X can be any amino acid, but preferably one that is either identical to, or is a conservative substitution of the amino acid at that position of the L2 loop of Hhip1 or Ptch. Examples of some oligopeptides include:

```
ITLDDMEEMDGL     (SEQ ID NO: 73)
LTKQRLVDADGI     (SEQ ID NO: 74)
LTTRKLVDREGL     (SEQ ID NO: 75)
LLTNRLVNSDGI     (SEQ ID NO: 76)
LTTRKLVDKEGL     (SEQ ID NO: 77)
```

In which X can be any amino acid, but preferably one that is either identical to, or is a conservative substitution of the amino acid at that position of the L2 loop of Hhip1 or Ptch.

Specific examples of L2 loop oligopeptides include the following (listed with their source and core region from SEQ ID NO:39 shaded), for example:

```
MITLDDMEEMDGLSDFTG (Human Hhip1 L2 Loop)
                   (SEQ ID NO: 7)
MITLDDMEEMDGLSDFTG (macaque Hhip1 L2 Loop)
                   (SEQ ID NO: 25)
MITLDDMEEMDGLSDFTG (Chimpanzee Hhip1 L2 Loop)
                   (SEQ ID NO: 26)
MITLDDMEEMDGLSDFTG (Horse Hhip1 L2 Loop)
                   (SEQ ID NO: 27)
MITLDDMEEMDGLSDFTG (Opossum Hhip1 L2 Loop)
                   (SEQ ID NO: 28)
MITLDDMEEMDGLSDFTG (mouse Hhip1 L2 Loop)
                   (SEQ ID NO: 29)
MITLDDMEEMDGLSDFTG (cattle Hhip L2 Loop)
                   (SEQ ID NO: 30)
MITLDDMEEMDGLSDFTG (Dog Hhip1 L2 Loop)
                   (SEQ ID NO: 31)
```

-continued

```
    MITLDDMEEMDGLSDFTG (rat Hhip1 L2 Loop)
                       (SEQ ID NO: 32)
    MITLDDMEEMDGLSDFTG (Platypus Hhip1 L2 Loop)
                       (SEQ ID NO: 33)
    MITLDDMEEMDGLSDFTG (Fugu Hhip1 L2 Loop)
                       (SEQ ID NO: 34)
    MITLDDMEEMDGLSDFTG (Tetraodon Hhip1 L2 Loop)
                       (SEQ ID NO: 35)
    MITLDDMEEMDGLSDFTG (zebrafish Hhip1 L2 Loop)
                       (SEQ ID NO: 36)
    MITLDDMEEMDGLSDFTG (chicken Hhip1 L2 Loop)
                       (SEQ ID NO: 37)
    MITIDDMEEMDGLSDFTG (frog Hhip1 L2 Loop)
                       (SEQ ID NO: 38)
     ITLDDMEEMDGLSD    (human Hhip1 L2 Loop)
                       (SEQ ID NO: 55)
GCGMITLDDMEEMDGLSDFCG (Human Hhip1 L2 Loop
                       derived disulfide-
                       bridged peptide)
                       (SEQ ID NO: 54)
```

In other embodiments, the oligopeptides of the invention comprise at least the following amino acid sequence:

```
LVXXXGXIX      (SEQ ID NO: 78)
```

In which X can be any amino acid, but preferably one that is either identical to, or is a conservative substitution of the amino acid at that position of the L2 loop of Ptch. Examples of some oligopeptides include:

```
LVDXXGXIX      (SEQ ID NO: 79)
LVDAXGXIN      (SEQ ID NO: 80)
LVDAXGXINP     (SEQ ID NO: 81)
LVDADGIINP     (SEQ ID NO: 82)
```

For example, and not by way of limitation, specific examples of L2 loop oligopeptides include the following (listed with their source, and with base sequence (SEQ ID NO:78) shaded):

```
  QLTKQRLVDADGIINPSA (Human Ptch L2 Loop)
                     (SEQ ID NO: 17)
  QLTKQRLVDADGIINPSA (mouse Ptch L2 Loop)
                     (SEQ ID NO: 18)
  QLTKQRLVDADGIINPNA (chicken Ptch L2 Loop)
                     (SEQ ID NO: 19)
  QLTSRRLVDGDGLIPPEV (zebrafish Ptch L2 Loop)
                     (SEQ ID NO: 20)
  LVLTNRLVNSDGIINQRA (Drosophila Ptch L2 Loop)
                     (SEQ ID NO: 21)
  RVGKIRLVDASGIINSDG (C. elegans Ptch L2 Loop)
                     (SEQ ID NO: 22)
  QLTTRKLVDREGLIPPEL (human Ptch2 L2 Loop)
                     (SEQ ID NO: 23)
  QLTTRKLVDKEGLIPPEL (mouse Ptch2 L2 Loop)
                     (SEQ ID NO: 24)
GCQLTKQRLVDADGIINPCG (human Ptch2 L2 Loop
                     derived disulfide-bridged
                     peptide)
                     (SEQ ID NO: 53)
```

While not wishing to be bound by any particular theory of operability, the oligopeptides of the invention are designed to mimic the L2 loop of Hhip1 and/or Ptch, and therefore, interact with Hedgehog. The oligopeptides of the invention are useful for binding to Hedgehog and thereby inhibiting binding of Hedgehog to Ptch and Hhip1 receptors on the surface of cells, such as cancer cells. Thus, inhibiting or halting the growth of Hedgehog-responsive cells (e.g., cancer cells).

The peptides of the invention are also useful as antigens in the generation of L2 loop-specific antibodies. Such antibodies may bind native Hhip1 and/or Ptch and prevent binding of Hedgehog to these receptors (without stimulating the receptors themselves) and inhibit of halt growth of Hedgehog-responsive cells (e.g., cancer cells). In addition anti-idiotypic antibodies against anti-L2 Loop antibodies may be made which mimic the Hhip1 or Ptch L2 Loop and therefore would bind Hedgehog. Such antibodies are also useful in preventing binding of Hedgehog to Ptch or Hhip1 and inhibit of halt growth of Hedgehog-responsive cells. These antibodies are useful in treating Hedgehog related cancers.

Alternatively, in some embodiments, anti-L2-specific antibodies are useful as agonists of Hedgehog signaling and may be useful as Hedgehog agonists in such applications as, for example, regulation of growth of neural tissues, bone and cartilage formation and repair, regulation of spermatogenesis, regulation of smooth muscle, regulation of lung, liver and other organs arising from the primitive gut, regulation of hematopoietic function, regulation of skin and hair growth.

D. Hhip1$_{\beta12}$ Binding and Hhip1$_{\beta12}$ L2 Loop Mimicking Organic Molecules Hhip1 binding organic molecules are organic molecules other than oligopeptides or antibodies as defined herein that bind, preferably specifically, to a Hhip1 polypeptide and or Ptch polypeptide and modulate Hedgehog signaling. In other embodiments, the small organic molecules are designed based on Hhip1$_{\beta12}$ L2 loop structure in the Hedgehog-binding region to bind to Hedgehog polypeptide and modulate Hedgehog signaling.

In some embodiments, the organic molecules bind Hedgehog and act as Hedgehog antagonists (i.e., prevent Hedgehog signaling in a Hedgehog responsive cell). In other embodiments, the organic molecules bind Hedgehog and act as Hedgehog agonists (i.e., stimulate Hedgehog signaling in a Hedgehog responsive cell). In other embodiments, the organic molecules bind Hhip1 and/or pateched and act as Hedgehog signaling antagonists (i.e., prevent Hedgehog signaling in a Hedgehog responsive cell). In other embodiments, the organic molecules bind Hhip1 and/or Ptch and act as Hedgehog agonists (i.e., stimulate Hedgehog signaling in a Hedgehog responsive cell).

Rational design of drugs based on structure of proteins is known in the art and strategies to design drugs based on the information provided herein for Hhip1$_{\beta12}$ may be used by those of skill in the art through routine experimentation. Guidance for such methods and techniques may be found in, for example, Greer J. et al. (1994) "Application of the three-dimensional structures of protein target molecules in structure-based drug design" *J Med. Chem.* 37(8):1035-1054 and Gubernator K., and H. J. Böhm STRUCTURE-BASED LIGAND DESIGN, METHODS AND PRINCIPLES IN MEDICINAL CHEMISTRY, Weinheim: Wiley-VCH, 1998.

Hhip1 binding organic molecules may be identified and chemically synthesized using known methodology (see, e.g., PCT Publication Nos. WO 00/00823 and WO 00/39585). Hhip1 binding organic molecules are usually less than about 2000 daltons in size, alternatively less than about 1500, 750, 500, 250 or 200 daltons in size, wherein such organic molecules that are capable of binding, preferably specifically, to a Hhip1 polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO 00/00823 and WO 00/39585). Hhip1 L2 binding organic molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

E. Screening for Anti-Hhip1$_{\beta12}$ Antibodies, Hhip1 Oligopeptides and Hhip1 Binding Organic Molecules with the Desired Properties Techniques for generating antibodies, oligopeptides and organic molecules that bind to Hhip1 polypeptides have been described above. One may further select antibodies, oligopeptides or other organic molecules with certain biological characteristics, as desired.

The growth inhibitory effects of an anti-Hhip1$_{\beta12}$ antibody, oligopeptide or other organic molecule of the invention may be assessed by methods known in the art, e.g., using cells which express a Hhip1$_{\beta12}$ polypeptide either endogenously or following transfection with the Hhip1$_{\beta12}$ gene. For example, appropriate tumor cell lines and Hip-transfected cells may treated with an anti-Hhip1$_{\beta12}$ monoclonal antibody, Hhip1$_{\beta12}$ oligopeptide or other Hhip1$_{\beta12}$ organic molecule of the invention at various concentrations for a few days (e.g., 2-7) days and stained with crystal violet or MTT or analyzed by some other colorimetric assay. Another method of measuring proliferation would be by comparing $^3$H-thymidine uptake by the cells treated in the presence or absence an anti-Hhip1$_{\beta12}$ antibody, Hhip1$_{\beta12}$ oligopeptide or Hhip1$_{\beta12}$ organic molecule of the invention. After treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of tumor cells in vivo can be determined in various ways known in the art. Preferably, the tumor cell is one that overexpresses a Hhip1 polypeptide. Preferably, the anti-Hhip1$_{\beta12}$ antibody, Hhip1$_{\beta12}$ oligopeptide or Hhip1$_{\beta12}$ organic molecule will inhibit cell proliferation of a Hip-expressing tumor cell in vitro or in vivo by about 25-100% compared to the untreated tumor cell, more preferably, by about 30-100%, and even more preferably by about 50-100% or 70-100%, in one embodiment, at an antibody concentration of about 0.5 to 30 μg/ml. Growth inhibition can be measured at an antibody concentration of about 0.5 to 30 μg/ml or about 0.5 nM to 200 nM in cell culture, where the growth inhibition is determined 1-10 days after exposure of the tumor cells to the antibody. The antibody is growth inhibitory in vivo if administration of the anti-Hhip1$_{\beta12}$ antibody at about 1 μg/kg to about 100 mg/kg body weight results in reduction in tumor size or reduction of tumor cell proliferation within about 5 days to 3 months from the first administration of the antibody, preferably within about 5 to 30 days.

To select for an anti-Hhip1$_{\beta12}$ antibody, Hhip1$_{\beta12}$ oligopeptide or Hhip1$_{\beta12}$ organic molecule which induces cell death, loss of membrane integrity as indicated by, e.g., propidium iodide (PI), trypan blue or 7AAD uptake may be assessed relative to control. A PI uptake assay can be performed in the absence of complement and immune effector cells. Hhip1 polypeptide-expressing tumor cells are incubated with medium alone or medium containing the appropriate anti-Hhip1$_{\beta12}$ antibody (e.g, at about 10 μg/ml), Hhip1 binding oligopeptide or Hhip1 binding organic molecule. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 μg/ml). Samples may be analyzed using a FACSCAN® flow cytometer and FACSCONVERT® CellQuest software (Becton Dickinson). Those anti-Hhip1 antibodies, Hhip1 binding oligopeptides or Hhip1 binding organic molecules that induce statistically significant levels of cell death as determined by PI uptake may be selected as cell death-inducing anti-Hhip1$_{\beta12}$ antibodies, Hhip1$_{\beta12}$ oligopeptides or Hhip1$_{\beta12}$ organic molecules.

To screen for antibodies, oligopeptides or other organic molecules which bind to an epitope on a Hhip1 polypeptide bound by an antibody of interest, a routine cross-blocking assay such as that described in ANTIBODIES, A LABORATORY MANUAL, Cold Spring Harbor Laboratory, Ed Harlow and David Lane (1988), can be performed. This assay can be used to determine if a test antibody, oligopeptide or other organic molecule binds the same site or epitope as a known anti-Hhip1$_{\beta12}$ antibody. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of a Hhip1 polypeptide can be used in competition assays with the test antibodies or with a test antibody and an antibody with a characterized or known epitope.

F. Antibody Dependent Enzyme Mediated Prodrug Therapy (ADEPT)

The antibodies of the present invention may also be used in ADEPT by conjugating the antibody to a prodrug-activating enzyme which converts a prodrug (e.g., a peptidyl chemotherapeutic agent, see WO 81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey (1987) *Nature* 328:457-458). Antibody-abzyme conjugates can be prepared as described herein for delivery of the abzyme to a tumor cell population.

The enzymes of this invention can be covalently bound to the anti-Hhip1 antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al. (1984) *Nature* 312:604-608).

G. Full-Length Hhip1$_{\beta12}$ Polypeptides

The present invention also provides newly identified and isolated nucleotide sequences encoding polypeptides referred to in the present application as Hhip1$_{\beta12}$ polypeptides. In particular, cDNAs (partial and full-length) encoding various Hhip1 polypeptides are encompassed by the invention. The nucleotide sequences encoding the polypeptides of the invention may be determined with reference to FIG. 1 which shows an alignment of the nucleic acid sequence encoding Hhip1 and the deduced amino acid sequence. Further, SEQ ID NO:83 shows the amino acid sequence of full-length Hhip1$_{\beta12}$ and SEQ ID NO:52 shows the cDNA sequence of human Hhip1. The smaller fragments of Hhip1$_{\beta12}$ may be encoded by any polynucleotide sequence encoding the amino acid sequence, but the specific example of the nucleic acid sequence provides one of skill in the art with at least one reference sequence.

H. Anti-Hhip1$_{\beta12}$ Antibody and Hhip1 Polypeptide Variants

In addition to the anti-Hhip1$_{\beta12}$ antibodies and full-length sequence Hhip1$_{\beta12}$ and other Hhip1$_{\beta12}$ polypeptides described herein, it is contemplated that anti-Hhip1$_{\beta12}$ antibody and Hhip1$_{\beta12}$ polypeptide variants can be prepared. Anti-Hhip1$_{\beta12}$ antibody and Hhip1 polypeptide variants can be prepared by introducing appropriate nucleotide changes into the encoding DNA, and/or by synthesis of the desired antibody or polypeptide. Those skilled in the art will appreciate that amino acid changes may alter post-translational processes of the anti-Hhip1$_{\beta12}$ antibody or Hhip1$_{\beta12}$ polypeptide, such as changing the number or position of glycosylation sites or altering the membrane anchoring characteristics.

Variations in the anti-Hhip1 antibodies and Hhip1 polypeptides described herein, can be made, for example, using any of the techniques and guidelines for conservative and non-conservative mutations set forth, for instance, in U.S. Pat. No. 5,364,934. Variations may be a substitution, deletion or insertion of one or more codons encoding the antibody or polypeptide that results in a change in the amino acid sequence as compared with the native sequence antibody or polypeptide. Optionally the variation is by substitution of at least one amino acid with any other amino acid in one or more of the domains of the anti-Hhip1$_{\beta12}$ antibody or Hhip1 polypeptide. Guidance in determining which amino acid residue may be inserted, substituted or deleted without adversely affecting the desired activity may be found by comparing the sequence of the anti-Hhip1$_{\beta12}$ antibody or Hhip1$_{\beta12}$ polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Anti-Hhip1$_{\beta 12}$ antibody and Hhip1$_{\beta 12}$ polypeptide fragments are provided herein. Such fragments may be truncated at the N-terminus or C-terminus, or may lack internal residues, for example, when compared with a full length native antibody or protein. Certain fragments lack amino acid residues that are not essential for a desired biological activity of the anti-Hhip1$_{\beta 12}$ antibody or Hhip1$_{\beta 12}$ polypeptide.

Anti-Hhip1$_{\beta 12}$ antibody and Hhip1$_{\beta 12}$ polypeptide fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR. Preferably, anti-Hhip1$_{\beta 12}$ antibody and Hhip1$_{\beta 12}$ polypeptide fragments share at least one biological and/or immunological activity with the native anti-Hhip1$_{\beta 12}$ antibody or Hhip1$_{\beta 12}$ polypeptide disclosed herein.

In particular embodiments, conservative substitutions of interest are shown in Table 5 under the heading of preferred substitutions. If such substitutions result in a change in biological activity, then more substantial changes, denominated exemplary substitutions in Table 5, or as further described below in reference to amino acid classes, are introduced and the products screened.

TABLE 5

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser, Ala | Ser |
| Gln (Q) | Asn; Glu | Asn |
| Glu (E) | Asp, Gln | Asp |
| Gly (G) | Pro; Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Leu |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in function or immunological identity of the anti-Hhip1$_{\beta 12}$ antibody or Hhip1 polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: Norleucine, Met, Ala, Val, Leu, Ile;
(2) neutral hydrophilic: Cys, Ser, Thr; Asn; Gln
(3) acidic: Asp, Glu;
(4) basic: His, Lys, Arg;
(5) residues that influence chain orientation: Gly, Pro; and
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis (Carter et al., (1986) *Nucl. Acids Res.* 13:4331; Zoller et al. (1987) *Nucl. Acids Res.* 10:6487), cassette mutagenesis (Wells et al. (1985) *Gene* 34:315), restriction selection mutagenesis (Wells et al. (1986) *Philos. Trans. R. Soc. London SerA* 317:415) or other known techniques can be performed on the cloned DNA to produce the anti-Hhip1$_{\beta 12}$ antibody or Hhip1 polypeptide variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant (Cunningham and Wells (1989) *Science* 244:1081-1085). Alanine is also typically preferred because it is the most common amino acid. Further, it is frequently found in both buried and exposed positions (Creighton, THE PROTEINS, W.H. Freeman & Co., N.Y.); Chothia (1976) *J. Mol. Biol.* 150:1). If alanine substitution does not yield adequate amounts of variant, an isoteric amino acid can be used.

Any cysteine residue not involved in maintaining the proper conformation of the anti-Hhip1$_{\beta 12}$ antibody or Hhip1 polypeptide also may be substituted, generally with serine, to improve the oxidative stability of the molecule and prevent aberrant crosslinking. Conversely, cysteine bond(s) may be added to the anti-Hhip1$_{\beta 12}$ antibody or Hhip1$_{\beta 12}$ polypeptide to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human Hhip1 polypeptide. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the anti-Hhip1$_{\beta 12}$ antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-Hhip1$_{\beta 12}$ antibody.

I. Modifications of Anti-Hhip1 Antibodies and Hhip1$_{\beta 12}$ Polypeptide Covalent modifications of anti-Hhip1$_{\beta 12}$ antibodies and Hhip1$_{\beta 12}$ polypeptides are included within the scope of this invention. One type of covalent modification includes reacting targeted amino acid residues of an anti-Hhip1$_{\beta 12}$ antibody or Hhip1$_{\beta 12}$ polypeptide with an organic derivatizing agent that is capable of reacting with selected side chains or the N- or C-terminal residues of the anti-Hhip1$_{\beta 12}$ antibody or Hhip1$_{\beta 12}$ polypeptide. Derivatization with bifunctional agents is useful, for instance, for crosslinking anti-Hhip1$_{\beta 12}$ antibody or Hhip1 polypeptide to a water-insoluble support matrix or surface for use in the method for purifying anti-Hhip1 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (T. E. Creighton, PROTEINS: STRUCTURE AND MOLECULAR PROPERTIES, W.H. Freeman & Co., San Francisco, pp. 79-86, 1983), acetylation of the N-terminal amine, and amidation of any C-terminal carboxyl group.

Another type of covalent modification of the anti-Hhip1$_{\beta 12}$ antibody or Hhip1 polypeptide included within the scope of this invention comprises altering the native glycosylation pattern of the antibody or polypeptide. "Altering the native glycosylation pattern" is intended for purposes herein to mean deleting one or more carbohydrate moieties found in native sequence anti-Hhip1$_{\beta 12}$ antibody or Hhip1$_{\beta 12}$ polypeptide (either by removing the underlying glycosylation site or by deleting the glycosylation by chemical and/or enzymatic means), and/or adding one or more glycosylation sites that are not present in the native sequence anti-Hhip1$_{\beta 12}$ antibody or Hhip1$_{\beta 12}$ polypeptide. In addition, the phrase includes qualitative changes in the glycosylation of the native proteins, involving a change in the nature and proportions of the various carbohydrate moieties present.

Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the anti-Hhip1$_{\beta 12}$ antibody or Hhip1 polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original anti-Hhip1$_{\beta 12}$ antibody or Hhip1$_{\beta 12}$ polypeptide (for O-linked glycosylation sites). The anti-Hhip1$_{\beta 12}$ antibody or Hhip1$_{\beta 12}$ polypeptide amino acid sequence may optionally be altered through changes at the DNA level, particularly by mutating the DNA encoding the anti-Hhip1$_{\beta 12}$ antibody or Hhip1 polypeptide at preselected bases such that codons are generated that will translate into the desired amino acids.

Another means of increasing the number of carbohydrate moieties on the anti-Hhip1$_{\beta 12}$ antibody or Hhip1$_{\beta 12}$ polypeptide is by chemical or enzymatic coupling of glycosides to the polypeptide. Such methods are described in the art, e.g., in WO 87/05330 published 11 Sep. 1987, and in Aplin and Wriston, CRC CRIT. REV. BIOCHEM., pp. 259-306, 1981.

Removal of carbohydrate moieties present on the anti-Hhip1$_{\beta 12}$ antibody or Hhip1$_{\beta 12}$ polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al. (1987) *Arch. Biochem. Biophys.* 259:52 and by Edge et al. (1981) *Anal. Biochem.* 118:131. Enzymatic cleavage of carbohydrate moieties on polypeptides can be achieved by the use of a variety of endo- and exo-glycosidases as described by Thotakura et al. (1987) *Meth. Enzymol.* 138: 350.

Another type of covalent modification of anti-Hhip1$_{\beta 12}$ antibody or Hhip1$_{\beta 12}$ polypeptide comprises linking the antibody or polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791, 192 or 4,179,337. The antibody or polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in REMINGTON'S PHARMACEUTICAL SCIENCES, 16TH EDITION, Oslo, A., Ed., 1980.

The anti-Hhip1$_{\beta 12}$ antibody or Hhip1$_{\beta 12}$ polypeptide of the present invention may also be modified in a way to form chimeric molecules comprising an anti-Hhip1$_{\beta 12}$ antibody or Hhip1$_{\beta 12}$ polypeptide fused to another, heterologous polypeptide or amino acid sequence.

In one embodiment, such a chimeric molecule comprises a fusion of the anti-Hhip1$_{\beta12}$ antibody or Hhip1$_{\beta12}$ polypeptide with a tag polypeptide which provides an epitope to which an anti-tag antibody can selectively bind. The epitope tag is generally placed at the amino- or carboxyl-terminus of the anti-Hhip1$_{\beta12}$ antibody or Hhip1$_{\beta12}$ polypeptide. The presence of such epitope-tagged forms of the anti-Hhip1$_{\beta12}$ antibody or Hhip1 polypeptide can be detected using an antibody against the tag polypeptide. Also, provision of the epitope tag enables the anti-Hhip1$_{\beta12}$ antibody or Hhip1$_{\beta12}$ polypeptide to be readily purified by affinity purification using an anti-tag antibody or another type of affinity matrix that binds to the epitope tag. Various tag polypeptides and their respective antibodies are well known in the art. Examples include polyhistidine (poly-his) or poly-histidine-glycine (poly-his-gly) tags; the flu HA tag polypeptide and its antibody 12CA5 (Field et al. (1988) *Mol. Cell. Biol.* 8:2159-2165); the c-myc tag and the 8F9, 3C7, 6E10, G4, B7 and 9E10 antibodies thereto (Evan et al., (1985) *Mol. Cell. Biol.* 5:3610-3616); and the Herpes Simplex virus glycoprotein D (gD) tag and its antibody (Paborsky et al. (1990) *Pro. Engineer.* 3(6):547-553). Other tag polypeptides include the Flag-peptide (Hopp et al. (1988) *BioTechnology* 6:1204-1210); the KT3 epitope peptide (Martin et al. (1992) *Science* 255:192-194); an α-tubulin epitope peptide (Skinner et al. (1991) *J. Biol. Chem.* 266:15163-15166); and the T7 gene 10 protein peptide tag (Lutz-Freyermuth et al. (1990) *Proc. Natl. Acad. Sci. USA* 87:6393-6397).

In an alternative embodiment, the chimeric molecule may comprise a fusion of the anti-Hhip1$_{\beta12}$ antibody or Hhip1$_{\beta12}$ polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an anti-Hhip1$_{\beta12}$ antibody or Hhip1 polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

J. Preparation of Anti-Hhip1$_{\beta12}$ Antibodies and Hhip1$_{\beta12}$ Polypeptides The description below relates primarily to production of anti-Hhip1$_{\beta12}$ antibodies and Hhip1 polypeptides by culturing cells transformed or transfected with a vector containing anti-Hhip1$_{\beta12}$ antibody- and Hhip1 polypeptide-encoding nucleic acid. It is, of course, contemplated that alternative methods, which are well known in the art, may be employed to prepare anti-Hhip1 antibodies and Hhip1 polypeptides. For instance, the appropriate amino acid sequence, or portions thereof, may be produced by direct peptide synthesis using solid-phase techniques (see, e.g., Stewart et al., SOLID-PHASE PEPTIDE SYNTHESIS, W.H. Freeman Co., San Francisco, Calif. (1969); Merrifield, (1963) *J. Am. Chem. Soc.* 85:2149-2154). In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the anti-Hhip1$_{\beta12}$ antibody or Hhip1$_{\beta12}$ polypeptide may be chemically synthesized separately and combined using chemical or enzymatic methods to produce the desired anti-Hhip1$_{\beta12}$ antibody or Hhip1$_{\beta12}$ polypeptide.

1. Isolation of DNA Encoding Anti-Hhip1$_{\beta12}$ Antibody or Hhip1$_{\beta12}$ Polypeptide DNA encoding anti-Hhip1$_{\beta12}$ antibody or Hhip1$_{\beta12}$ polypeptide may be obtained from a cDNA library prepared from tissue believed to possess the anti-Hhip1$_{\beta12}$ antibody or Hhip1$_{\beta12}$ polypeptide mRNA and to express it at a detectable level. Accordingly, human anti-Hhip1$_{\beta12}$ antibody or Hhip1$_{\beta12}$ polypeptide DNA can be conveniently obtained from a cDNA library prepared from human tissue. The anti-Hhip1$_{\beta12}$ antibody- or Hhip1$_{\beta12}$ polypeptide-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., MOLECULAR CLONING: A LABORATORY MANUAL, Cold Spring Harbor Laboratory Press, NY, 1989). An alternative means to isolate the gene encoding anti-Hhip1$_{\beta12}$ antibody or Hhip1$_{\beta12}$ polypeptide is to use PCR methodology (Sambrook et al., supra; Dieffenbach et al., PCR PRIMER: A LABORATORY MANUAL, Cold Spring Harbor Laboratory Press, NY, 1995).

Techniques for screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for anti-Hhip1$_{\beta12}$ antibody or Hhip1$_{\beta12}$ polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in MAMMALIAN CELL BIOTECHNOLOGY: A PRACTICAL APPROACH, M. Butler, ed., IRL Press, 1991 and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., (1983) *Gene* 23:315 and WO 89/05859 published Jun. 29, 1989. For mammalian cells without such cell walls, the calcium phosphate precipitation method of Graham and van der Eb (1978) *Virol.* 52:456-457 can be employed. General aspects of mammalian cell host system transfections have been described in U.S. Pat. No. 4,399,216. Transformations into yeast are typically carried out according to the method of Van Solingen et al., (1977) *J. Bacteriol.* 130:946 (1977) and Hsiao et al. (1979) *Proc. Natl. Acad. Sci. USA* 76:3829. However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al. (1990) *Meth. Enzymol.* 185:527-537 and Mansour et al. (1988) *Nature* 336:348-352.

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac) 169 degP ompT kanr; *E. coli* W3110 strain 37D6, which has the complete genotype tonA ptr3 phoA E15 (argF-lac) 169 degP ompT rbs7 ilvG kanr; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued Aug. 7, 1990. Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation regio (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for anti-Hhip1$_{\beta 12}$ antibody- or Hhip1$_{\beta 12}$ polypeptide-encoding vectors. *Saccharomyces cerevisiae* is a commonly used lower eukaryotic host microorganism. Others include *Schizosaccharomyces pombe* (Beach and Nurse (1981) *Nature* 290:140; EP 139,383 published May 2, 1985); *Kluyveromyces* hosts (U.S. Pat. No. 4,943,529; Fleer et al., (1991) *Bio/Technology*, 9:968-975) such as, e.g., *K. lactis* (MW98-8C, CBS683, CBS4574; Louvencourt et al., (1983) *J. Bacteriol.* 154(2):737-742); *K. fragilis* (ATCC 12,424); *K. bulgaricus* (ATCC 16,045); *K. wickeramii* (ATCC 24,178); *K. waltii* (ATCC 56,500); *K. drosophilarum* (ATCC 36,906; Van den Berg et al. (1990) *Bio/Technology*, 8:135); *K. thermotolerans*; and *K. marxianus*; *Yarrowia* (EP 402,226); *Pichia pastoris* (EP 183,070; Sreekrishna et al. (1988) *J. Basic Microbiol.* 28:265-278); *Candida*; *Trichoderma reesia* (EP 244,234); *Neurospora crassa* (Case et al. (1979) *Proc. Natl. Acad. Sci. USA* 76:5259-5263); *Schwanniomyces* such as *Schwanniomyces occidentalis* (EP 394,538 published Oct. 31, 1990); and filamentous fungi such as, e.g., *Neurospora*, *Penicillium*, *Tolypocladium* (WO 91/00357 published Jan. 10, 1991), and *Aspergillus* hosts such as *A. nidulans* (Ballance et al. (1983) *Biochem. Biophys. Res. Commun.*, 112:284-289; Tilburn et al. (1983) *Gene* 26:205-221; Yelton et al. (1984) *Proc. Natl. Acad. Sci. USA* 81: 1470-1474) and *A. niger* (Kelly and Hynes (1985) *EMBO J.* 4:475-479). Methylotropic yeasts are suitable herein and include, but are not limited to, yeast capable of growth on methanol selected from the genera consisting of *Hansenula*, *Candida*, *Kloeckera*, *Pichia*, *Saccharomyces*, *Torulopsis*, and *Rhodotorula*. A list of specific species that are exemplary of this class of yeasts may be found in C. Anthony, THE BIOCHEMISTRY OF METHYLOTROPHS, Academic Press, London, p. 269, 1982.

Suitable host cells for the expression of glycosylated anti-Hhip1$_{\beta 12}$ antibody or Hhip1 polypeptide are derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silkworm) have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al. (1977) *J. Gen Virol.* 36:59); baby hamster kidney cells (BHK, ATCC CCL 10); Chinese hamster ovary cells/–DHFR(CHO, Urlaub et al. (1980) *Proc. Natl. Acad. Sci. USA* 77:4216); mouse sertoli cells (TM4, Mather (1980) *Biol. Reprod.* 23:243-251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al. (1982) *Annals N.Y. Acad. Sci.* 383:44-68); MRC 5 cells; FS4 cells; and a human hepatoma line (Hep G2).

Host cells are transformed with the above-described expression or cloning vectors for anti-Hhip1$_{\beta12}$ antibody or Hhip1 polypeptide production and cultured in conventional nutrient media modified as appropriate for inducing promoters, selecting transformants, or amplifying the genes encoding the desired sequences.

3. Selection and Use of a Replicable Vector

The nucleic acid (e.g., cDNA or genomic DNA) encoding anti-Hhip1$_{\beta12}$ antibody or Hhip1 polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The Hhip1$_{\beta12}$ polypeptides may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the anti-Hhip1$_{\beta12}$ antibody- or Hhip1$_{\beta12}$ polypeptide-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the anti-Hhip1$_{\beta12}$ antibody- or Hhip1 polypeptide-encoding nucleic acid, such as DHFR or thymidine kinase. An appropriate host cell when wild-type DHFR is employed is the CHO cell line deficient in DHFR activity, prepared and propagated as described by Urlaub et al. (1980) *Proc. Natl. Acad. Sci. USA,* 77:4216. A suitable selection gene for use in yeast is the trp1 gene present in the yeast plasmid YRp7 (Stinchcomb et al. (1979) *Nature* 282:39; Kingsman et al. (1979) *Gene* 7:141; Tschemper et al. (1980) *Gene* 10:157). The trp1 gene provides a selection marker for a mutant strain of yeast lacking the ability to grow in tryptophan, for example, ATCC No. 44076 or PEP4-1 (Jones, (1977) *Genetics* 85:12).

Expression and cloning vectors usually contain a promoter operably linked to the anti-Hhip1$_{\beta12}$ antibody- or Hhip1 polypeptide-encoding nucleic acid sequence to direct mRNA synthesis. Promoters recognized by a variety of potential host cells are well known. Promoters suitable for use with prokaryotic hosts include the β-lactamase and lactose promoter systems (Chang et al. (1978) *Nature* 275:615); Goeddel et al. (1979) *Nature* 281:544), alkaline phosphatase, a tryptophan (trp) promoter system (Goeddel (1980) *Nucl. Acids Res.* 8:4057; EP 36,776), and hybrid promoters such as the tac promoter (deBoer et al. (1983) *Proc. Natl. Acad. Sci. USA* 80:21-25). Promoters for use in bacterial systems also will contain a Shine-Dalgarno (S.D.) sequence operably linked to the DNA encoding anti-Hhip1$_{\beta12}$ antibody or Hhip1 polypeptide.

Examples of suitable promoting sequences for use with yeast hosts include the promoters for 3-phosphoglycerate kinase (Hitzeman et al. (1980) *J. Biol. Chem.* 255:2073) or other glycolytic enzymes (Hess et al. (1968) *J. Adv. Enzyme Reg.* 7:149; Holland, (1978) *Biochemistry* 17:4900) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Anti-Hhip1$_{\beta12}$ antibody or Hhip1$_{\beta12}$ polypeptide transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the anti-Hhip1$_{\beta12}$ antibody or Hhip1$_{\beta12}$ polypeptide by higher eukaryotes may be increased by inserting an enhancer sequence into the vector Enhancers are cis-acting elements of DNA (usually about from 10 to 300 bp) that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the anti-Hhip1$_{\beta12}$ antibody or Hhip1$_{\beta12}$ polypeptide coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-Hhip1$_{\beta12}$ antibody or Hhip1$_{\beta12}$ polypeptide.

Still other methods, vectors, and host cells suitable for adaptation to the synthesis of anti-Hhip1$_{\beta12}$ antibody or Hhip1$_{\beta12}$ polypeptide in recombinant vertebrate cell culture are described in Gething et al. (1981) *Nature* 293:620-625; Mantei et al. (1979) *Nature* 281:40-46; EP 117,060; and EP 117,058.

4. Culturing the Host Cells

The host cells used to produce the anti-Hhip1$_{\beta12}$ antibody or Hhip1$_{\beta12}$ polypeptide of this invention may be cultured in a variety of media. Commercially available media such as Ham's F10 (Sigma), Minimal Essential Medium (MEM) (Sigma), RPMI-1640 (Sigma), and Dulbecco's Modified Eagle Medium (DMEM) (Sigma) are suitable for culturing the host cells. In addition, any of the media described in Ham et al. (1979) *Meth. Enzymol.* 58:44, Barnes et al. (1980) *Anal. Biochem.* 102:255, U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA (Thomas, (1980) *Proc. Natl. Acad. Sci. USA* 77:5201-5205), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal Conveniently, the antibodies may be prepared against a sequence Hhip1$_{\beta12}$ polypeptide or against a synthetic peptide based on the DNA sequences provided herein or against exogenous sequence fused to Hhip1$_{\beta12}$ DNA and encoding a specific antibody epitope.

6. Purification of Anti-Hhip1$_{\beta12}$ Antibody and Hhip1 Polypeptide

Forms of anti-Hhip1$_{\beta12}$ antibody and Hhip1$_{\beta12}$ polypeptide may be recovered from culture medium or from host cell lysates. If membrane-bound, it can be released from the membrane using a suitable detergent solution (e.g., Triton-X 100) or by enzymatic cleavage. Cells employed in expression of anti-Hhip1$_{\beta12}$ antibody and Hhip1$_{\beta12}$ polypeptide can be disrupted by various physical or chemical means, such as freeze-thaw cycling, sonication, mechanical disruption, or cell lysing agents.

It may be desired to purify anti-Hhip1$_{\beta12}$ antibody and Hhip1$_{\beta12}$ polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex® G-75; protein A Sepharose® columns to remove contaminants such as IgG; and metal chelating columns to bind epitope-tagged forms of the anti-Hhip1$_{\beta12}$ antibody and Hhip1$_{\beta12}$ polypeptide. Various methods of protein purification may be employed and such methods are known in the art and described for example in Deutscher (1990) Meth. Enzymol. 182:83-90; Scopes, PROTEIN PURIFICATION: PRINCIPLES AND PRACTICE, Springer-Verlag, New York, 1982. The purification step(s) selected will depend, for example, on the nature of the production process used and the particular anti-Hhip1$_{\beta12}$ antibody or Hhip1$_{\beta12}$ polypeptide produced.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al. (1992) *Bio/Technology* 10:163-167 describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2 or γ4 heavy chains (Lindmark et al. (1983) *J. Immunol. Meth.* 62:1-13). Protein G is recommended for all mouse isotypes and for human γ3 (Guss et al. (1986) *EMBO J.* 5:1567-1575). The matrix to which the affinity ligand is attached is most often agarose, but other matrices are available. Mechanically stable matrices such as controlled pore glass or poly (styrenedivinyl) benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

J. Pharmaceutical Formulations

Therapeutic formulations of the anti-Hhip1 antibodies, Hhip1$_{\beta12}$ oligopeptides, Hhip1$_{\beta12}$ organic molecules and/or Hhip1$_{\beta12}$ polypeptides used in accordance with the present invention are prepared for storage by mixing the antibody, polypeptide, oligopeptide or organic molecule having the desired degree of purity with optional pharmaceutically acceptable carriers, excipients or stabilizers (REMINGTON'S PHARMACEUTICAL SCIENCES 16TH EDITION, OSol, A. Ed., 1980), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG). The antibody preferably comprises the antibody at a concentration of between 5-200 mg/ml, preferably between 10-100 mg/ml.

The formulations herein may also contain more than one active compound as necessary for the particular indication being treated, preferably those with complementary activities that do not adversely affect each other. For example, in addition to an anti-Hhip1$_{\beta12}$ antibody, Hhip1$_{\beta12}$ oligopeptide, or Hhip1$_{\beta12}$ organic molecule, it may be desirable to include in the one formulation, an additional antibody, e.g., a second anti-Hhip1$_{\beta12}$ antibody which binds a different epitope on the Hhip1$_{\beta12}$ polypeptide, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in REMINGTON'S PHARMACEUTICAL SCIENCES, 16TH EDITION, Osol, A. Ed., 1980.

Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly (2-hydroxyethyl-methacrylate), or poly (vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

K. Diagnosis and Treatment with Anti-Hhip1$_{\beta12}$ Antibodies, Hhip1$_{\beta12}$ Oligopeptides and Hhip1$_{\beta12}$ Organic Molecules In one embodiment, Hedgehog-related tumors may be analyzed by immunohistochemistry (IHC). Parrafin embedded tissue sections from a tumor biopsy may be subjected to the IHC assay and accorded a Hhip1 and/or Ptch protein staining intensity criteria as follows:

Score 0— no staining is observed or membrane staining is observed in less than 10% of tumor cells.

Score 1+—a faint/barely perceptible membrane staining is detected in more than 10% of the tumor cells. The cells are only stained in part of their membrane.

Score 2+—a weak to moderate complete membrane staining is observed in more than 10% of the tumor cells.

Score 3+—a moderate to strong complete membrane staining is observed in more than 10% of the tumor cells.

Those tumors with 0 or 1+ scores for Hhip1 and/or Ptch polypeptide expression may be characterized as not overexpressing Hhip1 and/or Ptch, whereas those tumors with 2+ or 3+ scores may be characterized as overexpressing Hip and/or Ptch.

Alternatively, or additionally, FISH assays such as the INFORM® (sold by Ventana, Ariz.) or PATHVISION® (Vysis, Ill.) may be carried out on formalin-fixed, paraffin-embedded tumor tissue to determine the extent (if any) of Hhip1 and/or Ptch overexpression in the tumor.

Hhip1 and/or Ptch overexpression or amplification may be evaluated using an in vivo diagnostic assay, e.g., by administering a molecule (such as an antibody, oligopeptide or organic molecule) which binds the molecule to be detected and is tagged with a detectable label (e.g., a radioactive isotope or a fluorescent label) and externally scanning the patient for localization of the label.

Without wishing to be bound by any particular theory of operability, it is believed that the anti-Hhip1$_{\beta 12}$ antibodies of the invention that bind the Hhip1 L2 loop may cross-react with the analogous loop of Ptch and therefore detect overexpression of Ptch as well as Hip.

As described above, the anti-Hhip1$_{\beta 12}$ antibodies, oligopeptides and organic molecules of the invention have various non-therapeutic applications. The anti-Hhip1$_{\beta 12}$ antibodies, oligopeptides and organic molecules of the present invention can be useful for diagnosis and staging of Hip- or Ptch-expressing cancers (e.g., in radioimaging). The antibodies, oligopeptides and organic molecules are also useful for purification or immunoprecipitation of Hhip1 and Hhip1$_{\beta 12}$ polypeptide from cells, for detection and quantitation of Hhip1 polypeptide in vitro, e.g., in an ELISA or a Western blot, to kill and eliminate Hip-expressing cells from a population of mixed cells as a step in the purification of other cells.

Currently, depending on the stage of the cancer, cancer treatment involves one or a combination of the following therapies: surgery to remove the cancerous tissue, radiation therapy, and chemotherapy. Anti-Hhip1$_{\beta 12}$ antibody, oligopeptide or organic molecule therapy may be especially desirable in elderly patients who do not tolerate the toxicity and side effects of chemotherapy well and in metastatic disease where radiation therapy has limited usefulness. The tumor targeting anti-Hhip1$_{\beta 12}$ antibodies, oligopeptides and organic molecules of the invention are useful to alleviate Hip-expressing cancers upon initial diagnosis of the disease or during relapse. For therapeutic applications, the anti-Hhip1$_{\beta 12}$ antibody, oligopeptide or organic molecule can be used alone, or in combination therapy with, e.g., hormones, antiangiogens, or radiolabelled compounds, or with surgery, cryotherapy, and/or radiotherapy. Anti-Hhip1$_{\beta 12}$ antibody, oligopeptide or organic molecule treatment can be administered in conjunction with other forms of conventional therapy, either consecutively with, pre- or post-conventional therapy. Chemotherapeutic drugs such as TAXOTERE® (docetaxel), TAXOL® (palictaxel), estramustine and mitoxantrone are used in treating cancer, in particular, in good risk patients. In the present method of the invention for treating or alleviating cancer, the cancer patient can be administered anti-Hhip1$_{\beta 12}$ antibody, oligopeptide or organic molecule in conjuction with treatment with the one or more of the preceding chemotherapeutic agents. In particular, combination therapy with palictaxel and modified derivatives (see, e.g., EP0600517) is contemplated. The anti-Hhip1$_{\beta 12}$ antibody, oligopeptide or organic molecule will be administered with a therapeutically effective dose of the chemotherapeutic agent. In another embodiment, the anti-Hhip1$_{\beta 12}$ antibody, oligopeptide or organic molecule is administered in conjunction with chemotherapy to enhance the activity and efficacy of the chemotherapeutic agent, e.g., paclitaxel. THE PHYSICIANS' DESK REFERENCE (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

In one particular embodiment, a conjugate comprising an anti-Hhip1$_{\beta 12}$ antibody, oligopeptide or organic molecule conjugated with a cytotoxic agent is administered to the patient. Preferably, the immunoconjugate bound to the Hhip1 protein is internalized by the cell, resulting in increased therapeutic efficacy of the immunoconjugate in killing the cancer cell to which it binds. In a preferred embodiment, the cytotoxic agent targets or interferes with the nucleic acid in the cancer cell. Examples of such cytotoxic agents are described above and include maytansinoids, calicheamicins, ribonucleases and DNA endonucleases.

The anti-Hhip1$_{\beta 12}$ antibodies, oligopeptides, organic molecules or toxin conjugates thereof are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody, oligopeptide or organic molecule is preferred.

Other therapeutic regimens may be combined with the administration of the anti-Hhip1$_{\beta 12}$ antibody, oligopeptide or organic molecule. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-Hhip1$_{\beta 12}$ antibody or antibodies, oligopeptides or organic molecules, with administration of an antibody directed against another tumor antigen associated with the particular cancer.

In another embodiment, the therapeutic treatment methods of the present invention involves the combined administration of an anti-Hhip1$_{\beta 12}$ antibody (or antibodies), oligopeptides or organic molecules and one or more chemotherapeutic agents or growth inhibitory agents, including co-administration of cocktails of different chemotherapeutic agents. Chemotherapeutic agents include estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in CHEMOTHERAPY SERVICE Ed., M. C. Perry, Williams & Wilkins, Baltimore, Md., 1992.

The antibody, oligopeptide or organic molecule may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the anti-Hhip1$_{\beta 12}$ antibody, oligopeptide or organic molecule (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post antibody, oligopeptide or organic molecule therapy. Suitable dosages for any of the above co-administered agents are those presently used and may be lowered due to the combined action (synergy) of the agent and anti-Hhip1$_{\beta12}$ antibody, oligopeptide or organic molecule.

For the prevention or treatment of disease, the dosage and mode of administration will be chosen by the physician according to known criteria. The appropriate dosage of antibody, oligopeptide or organic molecule will depend on the type of disease to be treated, as defined above, the severity and course of the disease, whether the antibody, oligopeptide or organic molecule is administered for preventive or therapeutic purposes, previous therapy, the patient's clinical history and response to the antibody, oligopeptide or organic molecule, and the discretion of the attending physician. The antibody, oligopeptide or organic molecule is suitably administered to the patient at one time or over a series of treatments. Preferably, the antibody, oligopeptide or organic molecule is administered by intravenous infusion or by subcutaneous injections. Depending on the type and severity of the disease, about 1 µg/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-Hhip1$_{\beta12}$ antibody. However, other dosage regimens may be useful. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of nucleic acid encoding the antibody is encompassed by the expression "administering a therapeutically effective amount of an antibody." See, for example, WO 96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al. (1992) *Science* 256: 808-813. See also WO 93/25673 and the references cited therein.

The anti-Hhip1 antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies an antibody sequence is fused to a heterologous polypeptide sequence. The antibodies can be modified in the Fc region to provide desired effector functions. As discussed in more detail in the sections herein, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

In one embodiment, the antibody competes for binding or bind substantially to, the same epitope as the antibodies of the invention. Antibodies having the biological characteristics of the present anti-Hhip1$_{\beta12}$ antibodies of the invention are also contemplated, specifically including the in vivo tumor targeting and any cell proliferation inhibition or cytotoxic characteristics.

Methods of producing the above antibodies are described in detail herein.

The present anti-Hhip1$_{\beta12}$ antibodies, oligopeptides and organic molecules are useful for treating a Hip-expressing cancer or alleviating one or more symptoms of the cancer in a mammal. Such a cancer includes prostate cancer, cancer of the urinary tract, lung cancer, breast cancer, colon cancer and ovarian cancer, more specifically, prostate adenocarcinoma, renal cell carcinomas, colorectal adenocarcinomas, lung adenocarcinomas, lung squamous cell carcinomas, and pleural mesothelioma. The cancers encompass metastatic cancers of any of the preceding. The antibody, oligopeptide or organic molecule is able to bind to at least a portion of the cancer cells that express Hhip1 polypeptide in the mammal. In a preferred embodiment, the antibody, oligopeptide or organic molecule is effective to destroy or kill Hip-expressing tumor cells or inhibit the growth of such tumor cells, in vitro or in vivo, upon binding to Hhip1 polypeptide on the cell. Such an antibody includes a naked anti-Hhip1$_{\beta12}$ antibody (not conjugated to any agent). Naked antibodies that have cytotoxic or cell growth inhibition properties can be further harnessed with a cytotoxic agent to render them even more potent in tumor cell destruction. Cytotoxic properties can be conferred to an anti-Hhip1$_{\beta12}$ antibody by, e.g., conjugating the antibody with a cytotoxic agent, to form an immunoconjugate as described herein. The cytotoxic agent or a growth inhibitory agent is preferably a small molecule. Toxins such as calicheamicin or a maytansinoid and analogs or derivatives thereof, are preferable.

The invention provides a composition comprising an anti-Hhip1$_{\beta 12}$ antibody, oligopeptide or organic molecule of the invention, and a carrier. For the purposes of treating cancer, compositions can be administered to the patient in need of such treatment, wherein the composition can comprise one or more anti-Hhip1 antibodies present as an immunoconjugate or as the naked antibody. In a further embodiment, the compositions can comprise these antibodies, oligopeptides or organic molecules in combination with other therapeutic agents such as cytotoxic or growth inhibitory agents, including chemotherapeutic agents. The invention also provides formulations comprising an anti-Hhip1$_{\beta 12}$ antibody, oligopeptide or organic molecule of the invention, and a carrier. In one embodiment, the formulation is a therapeutic formulation comprising a pharmaceutically acceptable carrier.

Another aspect of the invention is isolated nucleic acids encoding the anti-Hhip1 antibodies. Nucleic acids encoding both the H and L chains and especially the hypervariable region residues, chains which encode the native sequence antibody as well as variants, modifications and humanized versions of the antibody, are encompassed.

The invention also provides methods useful for treating a Hhip1 polypeptide-expressing cancer or alleviating one or more symptoms of the cancer in a mammal, comprising administering a therapeutically effective amount of an anti-Hhip1$_{\beta 12}$ antibody, oligopeptide or organic molecule to the mammal. The antibody, oligopeptide or organic molecule therapeutic compositions can be administered short term (acute) or chronic, or intermittent as directed by physician. Also provided are methods of inhibiting the growth of, and killing a Hhip1 polypeptide-expressing cell.

The invention also provides kits and articles of manufacture comprising at least one anti-Hhip1$_{\beta 12}$ antibody, oligopeptide or organic molecule. Kits containing anti-Hhip1 antibodies, oligopeptides or organic molecules find use, e.g., for Hhip1 cell killing assays, for purification or immunoprecipitation of Hhip1 polypeptide from cells. For example, for isolation and purification of Hhip1, the kit can contain an anti-Hhip1$_{\beta 12}$ antibody, oligopeptide or organic molecule coupled to beads (e.g., Sepharose® beads). Kits can be provided which contain the antibodies, oligopeptides or organic molecules for detection and quantitation of Hhip1 in vitro, e.g., in an ELISA or a Western blot. Such antibody, oligopeptide or organic molecule useful for detection may be provided with a label such as a fluorescent or radiolabel.

L. Articles of Manufacture and Kits

Another embodiment of the invention is an article of manufacture containing materials useful for the treatment of anti-Hhip1 expressing cancer. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the cancer condition and may have a sterile access port (for example the container may be an intravenous solution bag or a vial having a stopper pierceable by a hypodermic injection needle). At least one active agent in the composition is an anti-Hhip1$_{\beta 12}$ antibody, oligopeptide or organic molecule of the invention. The label or package insert indicates that the composition is used for treating cancer. The label or package insert will further comprise instructions for administering the antibody, oligopeptide or organic molecule composition to the cancer patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for Hip-expressing cell killing assays, for purification or immunoprecipitation of Hhip1 polypeptide from cells. For isolation and purification of Hhip1 polypeptide, the kit can contain an anti-Hhip1$_{\beta 12}$ antibody, oligopeptide or organic molecule coupled to beads (e.g., Sepharose® beads). Kits can be provided which contain the antibodies, oligopeptides or organic molecules for detection and quantitation of Hhip1 polypeptide in vitro, e.g., in an ELISA or a Western blot. As with the article of manufacture, the kit comprises a container and a label or package insert on or associated with the container. The container holds a composition comprising at least one anti-Hhip1$_{\beta 12}$ antibody, oligopeptide or organic molecule of the invention. Additional containers may be included that contain, e.g., diluents and buffers, control antibodies. The label or package insert may provide a description of the composition as well as instructions for the intended in vitro or diagnostic use.

M. Uses for Hhip1 polypeptides and Hip-Polypeptide Encoding Nucleic Acids

Nucleotide sequences (or their complement) encoding Hhip1 polypeptides have various applications in the art of molecular biology, including uses as hybridization probes, in chromosome and gene mapping and in the generation of anti-sense RNA and DNA probes. Hip-encoding nucleic acid will also be useful for the preparation of Hhip1 polypeptides by the recombinant techniques described herein, wherein those Hhip1 polypeptides may find use, for example, in the preparation of anti-Hhip1 antibodies as described herein The full-length native sequence Hhip1 gene, or portions thereof, may be used as hybridization probes for a cDNA library to isolate the full-length Hhip1 cDNA or to isolate still other cDNAs (for instance, those encoding naturally-occurring variants of Hhip1 or Hhip1 from other species) which have a desired sequence identity to the native Hhip1 sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence Hhip1. By way of example, a screening method will comprise isolating the coding region of the Hhip1 gene using the known DNA sequence to synthesize a selected probe of about 40 bases. Hybridization probes may be labeled by a variety of labels, including radionucleotides such as $^{32}$P or $^{35}$S, or enzymatic labels such as alkaline phosphatase coupled to the probe via avidin/biotin coupling systems. Labeled probes having a sequence complementary to that of the Hhip1 gene of the present invention can be used to screen libraries of human cDNA, genomic DNA or mRNA to determine which members of such libraries the probe hybridizes to. Hybridization techniques are described in further detail in the Examples below. Any EST sequences disclosed in the present application may similarly be employed as probes, using the methods disclosed herein.

Other useful fragments of the Hip-encoding nucleic acids include antisense or sense oligonucleotides comprising a singe-stranded nucleic acid sequence (either RNA or DNA)

capable of binding to target Hhip1 mRNA (sense) or Hhip1 DNA (antisense) sequences. Antisense or sense oligonucleotides, according to the present invention, comprise a fragment of the coding region of Hhip1 DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (1988) *Cancer Res.* 48:2659 and van der Krol et al. (1988) *BioTechniques* 6:958.

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. Such methods are encompassed by the present invention. The antisense oligonucleotides thus may be used to block expression of Hhip1 proteins, wherein those Hhip1 proteins may play a role in the induction of cancer in mammals. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Preferred intragenic sites for antisense binding include the region incorporating the translation initiation/start codon (5'-AUG/5'-ATG) or termination/stop codon (5'-UAA, 5'-UAG and 5-UGA/5'-TAA, 5'-TAG and 5'-TGA) of the open reading frame (ORF) of the gene. These regions refer to a portion of the mRNA or gene that encompasses from about 25 to about 50 contiguous nucleotides in either direction (i.e., 5' or 3') from a translation initiation or termination codon. Other preferred regions for antisense binding include: introns; exons; intron-exon junctions; the open reading frame (ORF) or "coding region," which is the region between the translation initiation codon and the translation termination codon; the 5' cap of an mRNA which comprises an N7-methylated guanosine residue joined to the 5'-most residue of the mRNA via a 5'-5' triphosphate linkage and includes 5' cap structure itself as well as the first 50 nucleotides adjacent to the cap; the 5' untranslated region (5'UTR), the portion of an mRNA in the 5' direction from the translation initiation codon, and thus including nucleotides between the 5' cap site and the translation initiation codon of an mRNA or corresponding nucleotides on the gene; and the 3' untranslated region (3'UTR), the portion of an mRNA in the 3' direction from the translation termination codon, and thus including nucleotides between the translation termination codon and 3' end of an mRNA or corresponding nucleotides on the gene.

Specific examples of preferred antisense compounds useful for inhibiting expression of Hhip1 proteins include oligonucleotides containing modified backbones or non-natural internucleoside linkages. Oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides. Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included. Representative United States patents that teach the preparation of phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH.sub.2 component parts. Representative United States patents that teach the preparation of such oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In other preferred antisense oligonucleotides, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al. (1991) *Science* 254:1497-1500.

Preferred antisense oligonucleotides incorporate phosphorothioate backbones and/or heteroatom backbones, and in particular —$CH_2$—NH—O—$CH_2$—, —$CH_2$—N($CH_3$)—

O—CH$_2$-(known as a methylene (methylimino) or MMI backbone), —CH$_2$—O—N(CH$_3$)—CH$_2$—, —CH$_2$—N (CH$_3$)—N(CH$_3$)—CH$_2$— and —O—N(CH$_3$)—CH$_2$—CH$_2$— (wherein the native phosphodiester backbone is represented as —O—P—O—CH$_2$—) described in the above referenced U.S. Pat. No. 5,489,677, and the amide backbones of the above referenced U.S. Pat. No. 5,602,240. Also preferred are antisense oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-alkyl, S-alkyl, or N-alkyl; O-alkenyl, S-alkeynyl, or N-alkenyl; O-alkynyl, S-alkynyl or N-alkynyl; or O-alkyl-O-alkyl, wherein the alkyl, alkenyl and alkynyl may be substituted or unsubstituted C1 to C10 alkyl or C2 to C10 alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH2)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred antisense oligonucleotides comprise one of the following at the 2' position: C1 to C10 lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al. (1995) Helv. Chim. Acta 78:486-504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—CH$_2$—O—CH$_2$—N (CH$_2$).

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—CH$_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$ or —CH$_2$—C≡CH) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2': 4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in THE CONCISE ENCYCLOPEDIA OF POLYMER SCIENCE AND ENGINEERING, Kroschwitz, J. I., ed., John Wiley & Sons, 1990, pp. 858-859, and those disclosed by Englisch et al., ANGEWANDTE CHEMIE, INTERNATIONAL EDITION, Wiley-VCH, Germany, 1991, 30:613. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al. ANTISENSE RESEARCH AND APPLICATIONS, CRC Press, Boca Raton, 1993, pp. 276-278) and are preferred base substitutions, even more particularly when combined with 2'-O-methoxyethyl sugar modifications. Representative U.S. patents that teach the preparation of modified nucleobases include, but are not limited to: U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,681,941 and 5,750,692, each of which is herein incorporated by reference.

Another modification of antisense oligonucleotides chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, cation lipids, phospholipids, cationic phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Conjugate moieties include but are not limited to lipid moieties such as a cholesterol moiety (Letsinger et al. (1989) *Proc. Natl. Acad. Sci. USA* 86:6553-6556), cholic acid (Manoharan et al. (1994) *Bioorg. Med. Chem. Lett.* 4:1053-1060), a thioether, e.g., hexyl-S-tritylthiol (Manoharan et al. (1992) *Ann. N.Y. Acad. Sci.* 660: 306-309; Manoharan et al. (1993) *Bioorg. Med. Chem. Lett.* 3:2765-2770), a thiocholesterol (Oberhauser et al. (1992) *Nucl. Acids Res.* 20:533-538), an aliphatic chain, e.g., dodecandiol or undecyl residues (Saison-Behmoaras et al. (1991) *EMBO J.* 10:1111-1118; Kabanov et al. (1990) *FEBS Lett.* 259:327-330; Svinarchuk et al. (1993) *Biochimie* 75:49-54, a phospholipid, e.g., di-hexadecyl-rac-glycerol or triethyl-ammonium 1,2-di-O-hexadecyl-rac-glycero-3-H-phosphonate (Manoharan et al. (1995) *Tetrahedron Lett.* 36:3651-3654; Shea et al. (1990) *Nucl. Acids Res.* 18:3777-3783), a polyamine or a polyethylene glycol chain (Manoharan et al. (1995) *Nucleosides & Nucleotides* 14:969-973), or adamantane acetic acid (Manoharan et al. (1995) *Tetrahedron Lett.* 36:3651-3654), a palmityl moiety (Mishra et al. (1995) *Biochim. Biophys. Acta* 1264:229-237), or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,688,941 and 6,656,730, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the invention may be formed as composite structures of two or more oligonucleotides, modified oligonucleotides, oligonucleosides and/or oligonucleotide mimetics as described above. Preferred chimeric antisense oligonucleotides incorporate at least one 2' modified sugar (preferably 2'-O—(CH$_2$)$_2$—O—CH$_3$) at the 3' terminal to confer nuclease resistance and a region with at least 4 contiguous 2'-H sugars to confer RNase H activity. Such compounds have also been referred to in the art as hybrids or gapmers. Preferred gapmers have a region of 2' modified sugars (preferably 2'-O—(CH$_2$)$_2$—O—CH$_3$) at the 3'-terminal and at the 5' terminal separated by at least one region having at least 4 contiguous 2'-H sugars and preferably incorporate phosphorothioate backbone linkages. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521, 291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Other examples of sense or antisense oligonucleotides include those oligonucleotides which are covalently linked to organic moieties, such as those described in WO 90/10048, and other moieties that increase affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

The probes may also be employed in PCR techniques to generate a pool of sequences for identification of closely related Hhip1 coding sequences.

Nucleotide sequences encoding a Hhip1 can also be used to construct hybridization probes for mapping the gene which encodes that Hhip1 and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for Hhip1 encode a protein which binds to another protein (example, where the Hhip1 is a receptor), the Hhip1 can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor Hhip1 can be used to isolate correlative ligand(s). Screening assays can be designed to find lead compounds that mimic the biological activity of a native Hhip1 or a receptor for Hhip1. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode Hhip1 or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding Hhip1 can be used to clone genomic DNA encoding Hhip1 in accordance with established techniques and the genomic sequences used to generate transgenic animals that contain cells which express DNA encoding Hhip1. Methods for generating transgenic animals, particularly animals such as mice or rats, have become conventional in the art and are described, for example, in U.S. Pat. Nos. 4,736,866 and 4,870,009. Typically, particular cells would be targeted for $Hhip1_{\beta 12}$ transgene incorporation with tissue-specific enhancers. Transgenic animals that include a copy of a transgene encoding Hhip1 introduced into the germ line of the animal at an embryonic stage can be used to examine the effect of increased expression of DNA encoding Hhip1. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of Hhip1 can be used to construct a Hhip1 "knock out" animal which has a defective or altered gene encoding Hhip1 as a result of homologous recombination between the endogenous gene encoding Hhip1 and altered genomic DNA encoding Hhip1 introduced into an embryonic stem cell of the animal. For example, cDNA encoding Hhip1 can be used to clone genomic DNA encoding Hhip1 in accordance with established techniques. A portion of the genomic DNA encoding Hhip1 can be deleted or replaced with another gene, such as a gene encoding a selectable marker which can be used to monitor integration. Typically, several kilobases of unaltered flanking DNA (both at the 5' and 3' ends) are included in the vector (see e.g., Thomas and Capecchi (1987) Cell 51:503 for a description of homologous recombination vectors). The vector is introduced into an embryonic stem cell line (e.g., by electroporation) and cells in which the introduced DNA has homologously recombined with the endogenous DNA are selected (see e.g., Li et al. (1992) Cell 69:915). The selected cells are then injected into a blastocyst of an animal (e.g., a mouse or rat) to form aggregation chimeras (see e.g., Bradley, in TERATOCARCINOMAS AND EMBRYONIC STEM CELLS: A PRACTICAL APPROACH, E. J. Robertson, ed., IRL, Oxford, 1987, pp. 113-152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the Hhip1 polypeptide.

Nucleic acid encoding the Hhip1 polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., (1986) *Proc. Natl. Acad. Sci. USA* 83:4143-4146). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al. (1993) *Trends in Biotechnology* 11:205-210). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al. (1987) *J. Biol. Chem.* 262:4429-4432; and Wagner et al. (1990) *Proc. Natl. Acad. Sci. USA* 87:3410-3414. For review of gene marking and gene therapy protocols see Anderson et al. (1992) *Science* 256:808-813.

The nucleic acid molecules encoding the Hhip1 polypeptides or fragments thereof described herein are useful for chromosome identification. In this regard, there exists an ongoing need to identify new chromosome markers, since relatively few chromosome marking reagents, based upon actual sequence data are presently available. Each Hhip1 nucleic acid molecule of the present invention can be used as a chromosome marker.

The Hhip1$_{β12}$ polypeptides and nucleic acid molecules of the present invention may also be used diagnostically for tissue typing, wherein Hhip1 polypeptides may be differentially expressed in one tissue as compared to another, preferably in a diseased tissue as compared to a normal tissue of the same tissue type. Hhip1$_{β12}$ nucleic acid molecules will find use for generating probes for PCR, Northern analysis, Southern analysis and Western analysis.

This invention encompasses methods of screening compounds to identify those that mimic the Hhip1 polypeptide (Hedgehog antagonists) or prevent the effect of the Hhip1 polypeptide (agonists). Screening assays for antagonist drug candidates are designed to identify compounds that bind or complex with the Hhip1 polypeptides encoded by the genes identified herein, or otherwise interfere with the interaction of the encoded polypeptides with other cellular proteins, including e.g., inhibiting the expression of Hhip1 polypeptide from cells. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a Hhip1$_{β12}$ polypeptide encoded by a nucleic acid identified herein under conditions and for a time sufficient to allow these two components to interact.

In binding assays, the interaction is binding and the complex formed can be isolated or detected in the reaction mixture. In a particular embodiment, the Hhip1$_{β12}$ polypeptide encoded by the nucleic acid identified herein or the drug candidate is immobilized on a solid phase, e.g., on a microtiter plate, by covalent or non-covalent attachments. Non-covalent attachment generally is accomplished by coating the solid surface with a solution of the Hhip1$_{β12}$ polypeptide and drying. Alternatively, an immobilized antibody, e.g., a monoclonal antibody, specific for the Hhip1$_{β12}$ polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular Hhip1 polypeptide encoded by a nucleic acid identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns In addition, protein-protein interactions can be monitored by using a yeast-based genetic system described by Fields and co-workers (Fields and Song, (1989) *Nature* 340:245-246; Chien et al. (1991) *Proc. Natl. Acad. Sci. USA* 88:9578-9582) as disclosed by Chevray and Nathans (1991) *Proc. Natl. Acad. Sci. USA* 89:5789-5793. Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a $Hhip1_{\beta12}$ polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the $Hhip1_{\beta12}$ polypeptide may be added to a cell along with the compound to be screened for a particular activity and the ability of the compound to inhibit the activity of interest in the presence of the $Hhip1_{\beta12}$ polypeptide indicates that the compound is an antagonist to the $Hhip1_{\beta12}$ polypeptide. Alternatively, antagonists may be detected by combining the $Hhip1_{\beta12}$ polypeptide and a potential antagonist with membrane-bound $Hhip1_{\beta12}$ polypeptide receptors or recombinant receptors under appropriate conditions for a competitive inhibition assay. The $Hhip1_{\beta12}$ polypeptide can be labeled, such as by radioactivity, such that the number of $Hhip1_{\beta12}$ polypeptide molecules bound to the receptor can be used to determine the effectiveness of the potential antagonist. The gene encoding the receptor can be identified by numerous methods known to those of skill in the art, for example, ligand panning and FACS sorting. Coligan et al., Eds., CURRENT PROTOCOLS IN IMMUNOLOGY, 1(2): Chapter 5, 1991. Preferably, expression cloning is employed wherein polyadenylated RNA is prepared from a cell responsive to the $Hhip1_{\beta12}$ polypeptide and a cDNA library created from this RNA is divided into pools and used to transfect COS cells or other cells that are not responsive to the $Hhip1_{\beta12}$ polypeptide. Transfected cells that are grown on glass slides are exposed to labeled $Hhip1_{\beta12}$ polypeptide. The $Hhip1_{\beta12}$ polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

More specific examples of potential antagonists include an oligonucleotide that binds to the fusions of immunoglobulin with Hhip1 polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments.

Another potential Hhip1 polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example nucleic acids encoding $Hhip1_{\beta12}$ polypeptides herein, are used to design an antisense RNA oligonucleotide of from about 10 to 40 base pairs in length. A DNA oligonucleotide is designed to be complementary to a region of the gene involved in transcription (triple helix—see Lee et al. (1979) *Nucl. Acids Res.* 6:3073; Cooney et al. (1988) *Science* 241:456; Dervan et al. (1991) *Science* 251:1360), thereby preventing transcription and the production of the Hhip1 polypeptide. The antisense RNA oligonucleotide hybridizes to the mRNA in vivo and blocks translation of the mRNA molecule into the Hhip1 polypeptide (Okano (1991) *Neurochem.* 56:560); OLIGODEOXYNUCLEOTIDES AS ANTISENSE INHIBITORS OF GENE EXPRESSION, CRC Press, Boca Raton, Fla., 1988). The oligonucleotides described above can also be delivered to cells such that the antisense RNA or DNA may be expressed in vivo to inhibit production of the Hhip1 polypeptide. When antisense DNA is used, oligodeoxyribonucleotides derived from the translation-initiation site, e.g., between about −10 and +10 positions of the target gene nucleotide sequence, are preferred.

Potential antagonists of Hhip1 include small molecules that bind to the active site, the receptor binding site, or growth factor or other relevant binding site of the $Hhip1_{\beta12}$ L2 region, thereby blocking the normal biological activity of the Hhip1 polypeptide. Examples of small molecules include, but are not limited to, small peptides or peptide-like molecules, preferably soluble peptides, and synthetic non-peptidyl organic or inorganic compounds.

Potential agonists of Hedgehog signaling include small molecules that bind to the active site of Hip/Hedgehog binding, thereby blocking the normal biological activity of the Hhip1 polypeptide and prevent the inhibition of Hedgehog signaling. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi (1994) *Current Biology*, 4:469-471, and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Isolated Hhip1$_{\beta 12}$ polypeptide-encoding nucleic acid can be used herein for recombinantly producing Hhip1$_{\beta 12}$ polypeptide using techniques well known in the art and as described herein. In turn, the produced Hhip1$_{\beta 12}$ polypeptides can be employed for generating anti-Hhip1 antibodies using techniques well known in the art and as described herein.

Antibodies specifically binding a Hhip1$_{\beta 12}$ polypeptide identified herein, as well as other molecules identified by the screening assays disclosed hereinbefore, can be administered for the treatment of various disorders, including cancer, in the form of pharmaceutical compositions.

If the Hhip1 polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology (See, e.g., Marasco et al. (1993) *Proc. Natl. Acad. Sci. USA* 90:7889-7893).

The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated.

Example 1

Cloning and Expression of Hhip1$_{\beta 12}$ Variants

A. Sequence Analysis of Human Hip

To discern the underlying structural patterns that help reveal domain folds and boundaries, an evolutionarily diverse alignment of Hhip1 homologs was constructed by MUSCLE (Edgar, R. C. (2004) *Nucleic Acids Res.* 32:1792-1797) from sequences harvested from Genbank by iterative PSIBLAST runs (Schaffer et al. (2001) *Nucleic Acids Res.* 29:2994-3005. Secondary structure prediction of the aligned sequences was in turn performed by PSIPRED (McGuffin et al. (2000) *Bioinformatics* 16:404-405. Hhip1 sequence profiles and HMMs aimed at both sequence and structure databases were able to discern links between an N-terminal Cys-rich module (rich in predicted α-helices) and putative Frizzled domains, and likewise, between a central β-strand-rich section of Hhip1 and β-propeller domains. These relationships were corroborated by returns from fold recognition programs (dependent on profile-profile matches at both sequence and structural levels) like HHPred (Söding, J. (2005) *Bioinformatics* 21:951-960. Comparative models of the Hhip1 β-propeller domain were built with MODELLER (Sali and Blundell, 1993) *J. Mol. Biol.* 234:779-815. The presence of a C-terminal GPI-anchor sequence in Hhip1 rather than a transmembrane helix, with the concomitant prediction of the modification site residue, was detected by the big-PI server (mendel.imp.ac.at/gpi/gpi_server) (Eisenhaber et al. (1999) *J. Mol. Biol.* 292:741-758).

Computational analysis of the Hhip1$_{\beta 12ECD}$ sequence using sensitive structure prediction and fold recognition tools revealed the presence of four distinct globular domains: a Cysteine-rich N-terminal domain with a putative Frizzled (Fz) fold, a central six-bladed β-propeller and two C-terminal EGF repeats (FIG. 3A). Furthermore, in place of the single C-terminal transmembrane helix previously predicted for Hhip1 (Chuang and McMahon, 1999), we find a motif consistent with a putative glycosylphosphatidylinositol (GPI)-anchor attachment site (Eisenhaber et al. (1999) *J. Mol. Biol.* 292:741-758).

Alignment of the cDNA sequence encoding human Hhip1 and the deduced amino acid sequence is shown in FIG. 1A-C. FIG. 1B shows the L2 loop (shaded) of the putative propeller region and residues that are important for Hedgehog binding. These include D378, E380, E381, M382, D383, and D387. Residues marked with an asterisk (*) indicate amino acids that are of primary importance for Shh binding. Residues marked with an arrow (↑) indicate amino acids that are of minor or moderate importance for Shh binding.

The primary amino acid sequence may be further described in general terms into putative regions. These are shown in FIG. 2A. The figure shows the putative leader sequence (SEQ ID NO:3) from amino acids 1-19 of SEQ ID NO:2; the putative frizzed domain (SEQ ID NO:4) from amino acids 20-192 of SEQ ID NO:2; the putative linker region (SEQ ID NO:5) between amino acids 186-192 of SEQ ID NO:2; the putative β-propeller domain (SEQ ID NO:6) from amino acids 193-607 of SEQ ID NO:2 (including the L2 loop (SEQ ID NO:7) from amino acids 376-388 (shaded)); the EGF1 domain (SEQ ID NO:8) from amino acids 608-637 of SEQ ID NO:2; the EGF2 domain (SEQ ID NO:9) from amino acids 638-667 of SEQ ID NO:2); and the putative GPI signal sequence (SEQ ID NO:10) from amino acids 668-700 of SEQ ID NO:2. The absolute margins of these domains may be shifted by a few amino acids, including by 1, 2, 3, 4, or even 5 amino acids. These delineations provided in FIG. 2A are presented as a guide.

These domains are also discussed with reference to constructs that were produced for the studies presented herein. The construct Hhip1$_{ECD}$ (Hhip1$_{\beta 12}$ extracellular domain) (SEQ ID NO:11) encompasses residues 20-667 of SEQ ID NO:2; construct Hhip1$_{Fz\beta}$ (Fz-β-propeller) (SEQ ID NO:15) encompasses residues 20-607 of SEQ ID NO:2; construct Hhip1$_{Fz}$ ($_{Fz}$-domain) (SEQ ID NO:16) encompasses residues 20-189 of SEQ ID NO:2; construct Hip$_{\beta 12}$ (β-propeller-EGF1-EGF2) (SEQ ID NO:12) encompasses residues 193-667 of SEQ ID NO:2; construct Hip$_{\beta 1}$ (β-propeller-EGF1) (SEQ ID NO:13) encompasses residues 193-637 of SEQ ID NO:2; and construct Hip$_{\beta}$ (β-propeller) (SEQ ID NO:14) encompasses residues 193-607 of SEQ ID NO:2.

Figure 5:
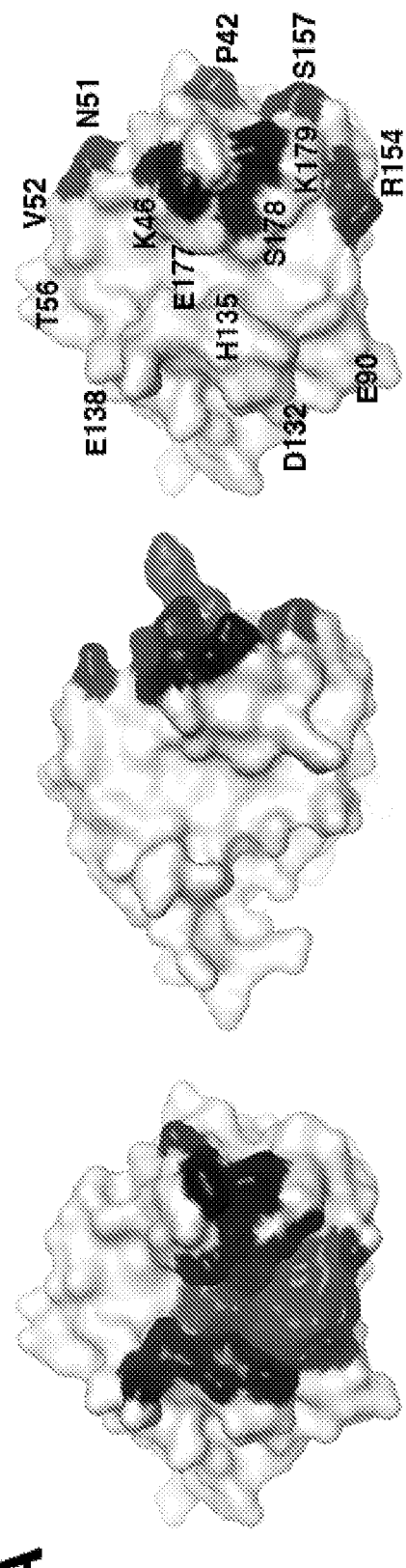
FIG. 5 shows the presence of an 'L2 loop' in Ptch. Panel A: Hhip1 and Ptch binding sites on Shh with Ihog binding site on Hh. Surface representation of Shh and Hh with residues within 4.5 Å of Hhip1 (left) and Ihog (center) colored dark gray. The right panel depicts the surface of Shh, where groups of mutated residues that affected Ptch activity are colored dark gray and those that did not are colored light gray; numbering refers to murine Shh (Fuse et al., 1999; Pepinsky et al., 2000). Mutations of Shh residues that had negligible impact on Ptch binding and signaling are colored yellow. Panel B shows a sequence alignment of Hhip1 and Ptch in the region corresponding to the Hhip1 L2 loop. Residue conservation within the L2 loop is plotted below. The plot was generated from the alignment of 15 vertebrate Hhip1 type 1 sequences (SEQ ID NOs: 7 and 25-38 of FIG. 11) and the Ptch sequences listed; for brevity only human Hhip1 (SEQ ID NO: 7) is shown. D383 of Hhip1 was arbitrarily chosen as a position 0. Residues of particular importance are denoted with an asterisk. Plot was created using WebLogo Panel C shows a competition ELISA of Hhip1-L2 peptide for Him binding to Shh. The data were fit to a 4-parameter equation from which the $IC_{50}$ was derived; Panel D shows a $^{15}N$, $^1H$-HSQC spectrum of Shh alone (gray) and in the presence of excess unlabeled Hip-L2 peptide (black); Panel E shows the same as panel D except Ptch-L2 peptide was used.

Analysis of the L2 loop of human Hhip1$_{\beta12}$ (SEQ ID NO:7) shows homology to similar regions in human Ptch (SEQ ID NO:17), mouse Ptch (SEQ ID NO:18), chick Ptch (SEQ ID NO:19), zebrafish Ptch (SEQ ID NO:20), *Drosophila* Ptch (SEQ ID NO:21), worm Ptch (SEQ ID NO:22), human Ptch2 (SEQ ID NO:23), and mouse Ptch2 (SEQ ID NO:24). These sequences are shown in FIG. 5B.

B. Expression and Purification of Hhip1$_{\beta12}$ Variants from Insect Cells

In order to identify domains that mediate interactions with Shh and inhibit cell signaling, full length and truncated versions of Hhip1$_{\beta12}$ were expressed in insect cells.

Thus, with reference to the amino acids shown in SEQ ID NO:2, N-terminally His$_6$ (SEQ ID NO: 87)-tagged Hhip1$_{ECD}$ (residues 20-667), Hip$_{\beta12}$ (residues 193-667), Hip$_{\beta1}$ (residues 193-637), and Hip$_\beta$ (residues 193-607) containing C-terminal His$_6$-tags (SEQ ID NO: 87) were cloned into the Gateway vector pENTR/D-TOPO (Invitrogen) including the honeybee melittin secretion signal to generate recombinant baculovirus via the Bac-to-Bac system (Invitrogen). Tni insect cells (1×10$^6$ per ml) in ESF921 medium (Expression Systems) were infected with recombinant baculovirus with a M.O.I. of three. After 72 hrs incubation Hhip1$_{\beta12}$ proteins were purified from the media by Ni-affinity (Ni-NTA Superflow, Qiagen) and size exclusion chromatography. Expression and purification of selenomethionine labeled Hip$_{\beta12}$ (Se-Met Hip1$_{\beta2}$) was carried out as described above using ESF921 methionine-free medium (Expression Systems). The medium was supplemented with 100 mg/L selenomethionine (Sigma Aldrich) 12 and 36 hrs after virus infection. The proteins were purified to homogeneity. The Hhip1$_{\beta12}$ construct to express only the putative β-propeller domain alone (Hip$_\beta$) (SEQ ID NO:6) did not express.

C. Cloning and Expression of Human Shh

Human Dhh (residues 24-198), Ihh (residues 29-202) Shh$_{N-Cys}$ (residues 24-197), Shh (residues 25-197) and Shh-Flag (residues 25-197 with C-terminal Flag-Tag) were cloned into pET101/D-TOPO (Invitrogen) according to the manufacturer's protocol with an N-terminal His$_6$-tag (SEQ ID NO: 87). Shh constructs were expressed in Rosetta 2 *E. coli* cells (Novagen) in LB medium for 20 hrs at 25° C. after induction with 1 mM IPTG. For expression of $^{15}$N-labeled Shh, cells were grown in minimal medium. Harvested cells were lysed and Shh was purified from the cystosolic fraction by Ni-affinity and size exclusion chromatography. For crystallization and NMR studies, Shh was incubated with 10 units of thrombin (Calbiochem) per mg of Shh in PBS overnight at 23° C., yielding Shh (residues 29-197) lacking the His$_6$-Tag (SEQ ID NO: 87). Finally, Shh was purified using a Mono S 5/5GL column (GE Healthcare) and eluted with a linear gradient from 0-1 M NaCl in 20 mM Hepes pH 7.2. Purification buffers for Shh$_{N-Cys}$ contained 5 mM β-mercaptoethanol during Ni-affinity chromatography and 0.5 mM DTT during size exclusion and cation exchange chromatography. Shh$_{N-Cys}$ was conjugated with EZ-Link Maleimide PEO$_2$-Biotin (Pierce) according to the manufacturer's protocol to yield biotinylated-Shh$_{N-Cys}$. Shh$_{C-Cys}$ was conjugated with DyLight 649 Maleimide (Pierce) to yield fluorescent Shh (Shh$_{649}$) according to the manufacturer's protocol. Expressed proteins were used in experiments described below.

Example 2

Hedgehog Binding to Hhip1$_{\beta12}$ Variants

The binding kinetics of the Hhip1$_{\beta12}$ fragments as well as Hhip1$_{\beta12}$ mutants were measured by bio-layer interferometry in the presence or absence of 10 mM EDTA on an Octet (Fortébio). Streptavidin high binding FA biosensors were loaded with biotinylated-Shh$_{N-Cys}$ in kinetic buffer (Fortébio). The loaded biosensors were washed and transferred to wells containing Hhip1$_{\beta12}$ protein at concentrations of 1.2, 1.0, 0.8 and 0.6 µM in kinetic buffer. Hhip1$_{\beta12}$ association and dissociation was measured for 30 and 20 min, respectively. Kinetic parameters ($k_{on}$ and $k_{off}$) and affinities ($K_D$) were calculated from a non-linear fit of the data based on a 1:1 binding model between Hhip1$_{\beta12}$ and Shh using the Octet software. Multiple independent measurements were performed.

The $K_D$ values for Shh binding to full length Hhip1$_{ECD}$, a truncated version lacking the putative $_{Fz}$ domain (Hip$_{\beta12}$), and Hhip1$_{\beta12}$ containing only the β-propeller and EGF1 domains (Hip$_{\beta1}$) were 67 nM, 220 nM and 150 nM, respectively, as determined by bio-layer interferometry (Table 6). Binding to all 3 mammalian homologs using competition was also assessed by ELISAs (see Example 3).

TABLE 6

Binding kinetics of Hhip1$_{\beta12}$ variants to Shh.

| | Hhip1$_{\beta12}$ variants[a] | $k_{on} \times 10^3$ [$M^{-1} \times s^{-1}$][b] | $k_{off} \times 10^{-4}$ [$s^{-1}$][b] | $K_D$ [nM][b] |
|---|---|---|---|---|
| | Hhip1$_{ECD}$ | 1.2 | 7.9 | 67 |
| | Hhip1$_{\beta12}$ | 4.3 | 9.4 | 220 |
| | Hhip1$_{\beta1}$ | 1.5 | 2.3 | 150 |
| Loop[c] | | | | |
| L1 | I312A | 1.5 | 4.8 | 320 |
| | D378A | 0.15 | 3.6 | 2400 |
| | E380A | n.d. | n.d. | n.d. |
| L2 | E381A | 1.1 | 3.3 | 300 |
| | M382A | n.d. | n.d. | n.d. |
| | D383A | n.d. | n.d. | n.d. |
| | D387A | n.d. | n.d. | n.d. |
| L3 | T418A | 3.4 | 9.0 | 270 |
| | Q420A | 2.1 | 11.0 | 500 |

[a]All Hhip1$_{\beta12}$ alanine variants are made in the Hhip1$_{\beta12}$ construct.
[b]n.d stands for no binding detected.
[c]Loop residues in Hhip1$_{\beta12}$ are as follows:

Example 3

A. Gli Luciferase Signaling Co-Culture Assay and Hip-Fc Assay

Due to the lack of both N- and C-terminal lipid modifications of Shh and the absence of other cellular components, the in vitro assays may not fully recapitulate Hip-Shh interactions occurring in a cellular environment. Therefore, a co-culture assay consisting of murine S12 fibroblasts stably transfected with a Gli luciferase reporter gene and (Frank-Kamenetsky et al. (2002) *J. Biol.* 1:10) and human colorectal adenocarcinoma HT29 cells that secrete fully lipid-modified Shh (Yauch et al. (2008) *Nature* 455:406) was used to determine which extracellular domains of Hhip1$_{\beta12}$ mediate inhibition of Shh signaling in mammalian cells.

Briefly, S12 cells, which are 10T1/2 fibroblasts stably transfected with 8× Gli-binding sites fused to a luciferase reporter (Frank-Kamenetsky et al. (2002) *J. Biol.* 1:10), were plated at 10,000 cells/well of a white-walled clear bottomed 96-well plate (Costar 3610) for 48 hrs in regular growth medium (HG-DMEM, 10% FBS, 1% glutamine). After 24 h, the media was removed and Shh-producing HT29 cells at 20,000 cells/well were plated and the co-culture was grown in regular media. After 24 h, the media was changed to 0.5% serum HG-DMEM±Hhip1$_{\beta 12}$ fragments and further incubated for 24 hrs to stimulate signaling. Gli-luciferase activity was measured using a HTS-Steady Lite luciferase detection kit (Perkin Elmer); multiple assays were carried out, each in triplicate. Data were fit to a 4-parameter sigmoidal equation, from which the IC$_{50}$ was derived using Kaleidagraph (Synergy Software). The results are shown in FIG. 3B.

Hhip1$_{ECD}$ and Hhip1$_{\beta 12}$ were equally potent inhibitors of Hh signaling with IC$_{50}$ values of 5.3 nM and 5.0 nM, respectively, while Hip$_{\beta 1}$ had an IC$_{50}$ of 20.3 nM, only about 4-fold higher than Hhip1$_{ECD}$ (FIG. 3B).

To confirm that the putative Fz domain (Hhip1$_{Fz}$) is dispensable for inhibition in this assay, we expressed and purified it as an Fc-fusion protein (Hhip1$_{Fz\text{-}Fc}$). Briefly, human Hhip1$_{\beta 12}$ (20-193) was cloned into expression vector pRK5 (Genentech) with an N-terminal gD-secrection signal (MG-GAAARLGAVILFVVIVGLHGVRG) (SEQ ID NO:41) and a C-terminal human Fc-fragment (IgG$_1$). The construct was expressed in 293 cells by transient transfection using FuGENE 6 (Roche) and after 5 days of incubation purified using protein A resin (GE Healthcare) followed by size exclusion chromatography (S-200 column, GE Healthcare). Consistent with the data above, the Fc fusion construct lacked any inhibitory activity (FIG. 3B). Overall, these data reveal that the minimal region of the Hhip1$_{\beta 12}$ ECD required for binding all three mammalian Hedgehogs and mediating its full antagonistic effect is contained within the β-propeller and EGF domains, with the EGF2 domain playing only a minor role.

B. Peptide Competition ELISA

Figure 8A:
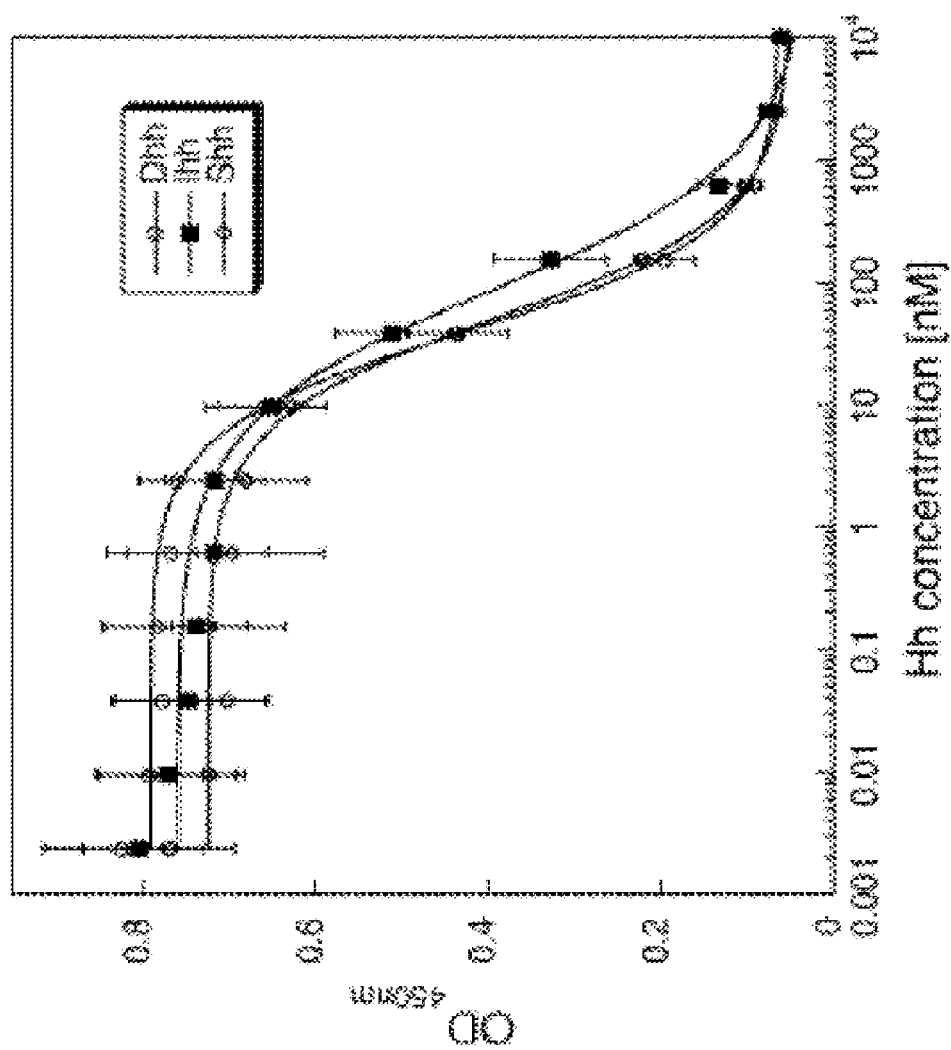
FIG. 8 shows Hhip1$_{\beta 12}$ competition binding ELISA with Dhh, Ihh and Shh. Panel A: Competitive binding between biotinylated Shh$_{N-Cys}$ and non-labeled Dhh, Ihh and Shh for immobilized Hip$_{\beta 12}$ in ELISA format is shown in which the data and curve fits are shown for Dhh (○), Ihh (■) and Shh (◇) with IC$_{50}$ values of 40 nM, 53 nM and 87 nM, respectively. The lines drawn represent data fit to a 4-parameter equation, from which the IC$_{50}$ was derived; Panel B: sequence alignment of Shh, Dhh and Ihh. Residues in contact with Hhip1 are denoted with an asterisk. Residues that coordinate Ca$^{2+}$ (▲) and Zn$^{2+}$ (■) cations as well as those implicated in brachydactyly type A1 for Ihh (♦) are also denoted. The 5E1 epitope maps to Ser177 (●) of human Shh$_{1,2}$ and the Shh peptide protected by 5E1 from tryptic digestion is underlined. The dashed extension indicates the putative extended epitope based on the lower affinity of 5E1 for Dhh compared to Ihh or Shh.

Binding to all 3 mammalian Hh homologs using competition was also assessed by ELISAs. Briefly, 96-well Nunc-Immuno MaxiSorp plates (Nalge Nunc International) were coated with 100 µl of Hhip1$_{\beta 12}$ at 2 µg/ml in 50 mM sodium carbonate buffer pH 9.6 at 4° C. overnight. Plates were blocked for 1 hr at room temperature with 100 µL blocking buffer (PBS containing 0.5% BSA and 15 PPM Proclin) on a plate shaker. The blocking buffer was removed and a serial dilution of either Dhh, Ihh, or Shh (starting at 10 µM, 1:4 dilution) containing 5 nM biotinylated-Shh$_{N\text{-}Cys}$ in a final volume of 100 µL was added to the wells to compete for binding to immobilized Hhip1. After incubation for 1 hr at room temperature on a plate shaker, the wells were washed with wash buffer (50 mM Hepes pH 7.2, 150 mM NaCl, 0.1% Tween) and incubated for 1 hr with Streptavidin-HRP (Pierce) according to the manufacturer's protocol in blocking buffer. After that, the plate was washed again with wash buffer and incubated with 100 µL of BD OptEIA reagent mix (1:1 ratio, BD Bioscience) until the solution turned light blue. The reaction was then quenched by addition of 100 µL acid (1 M H$_3$PO$_3$) and the optical density at 450 nm (OD$_{450}$) was measured with a SpectraMAX plate reader (Molecular Devices). The OD$_{450}$ was plotted versus the concentration of Ihh, Dhh and Shh and the IC$_{50}$ of the curves were determined in triplicate by a 4-parameter sigmoidal fit to the data using Kaleidagraph (Synergy Software). The results are shown in FIG. 8A.

The affinity of Hip$_{\beta 12}$ for Ihh (IC$_{50}$=87 nM), Dhh (IC$_{50}$=40 nM) or Shh (IC$_{50}$=53 nM) (FIG. 8A), are consistent with previously published results for full length Hhip1 (Chuang and McMahon (1999) *Nature* 397:617-621; Pathi, S. et al. (2001) *Mech. Dev.* 106:107-117).

C. Competition of Shh Binding to Ptch1 by Hhip

Shh$_{649}$, conjugated to Dylight 649 (Pierce) at its C-terminus (vide supra), was incubated at 0.33 or 1 nM for 1 h on ice with various Hhip or control proteins prior to incubation with HEK-293 cells (293) or 293 cells expressing full length human Patched-1 (Ptch1-293 clone 10) (Carpenter D. et al. (1998) *Proc. Natl. Acad. Sci. USA* 95:13630-13634) in FACS buffer (3% FBS in PBS) for 1 h on ice. After washing 3 times in FACS buffer, live cells (sorted by propidium iodide exclusion) were analyzed by flow cytometry in the APC channel using a FACSCalibur (BD Biosciences). Control proteins included His6-Shh, His6-Ihh, HGF β-His639, Trastuzumab (Genentech, Inc.) as a human IgG1 isotype control for Hhip1$_{\beta 12}$-Fc, and mIgG1 (Molecular Probes Z25105) as a murine Mab control for anti-Shh 5E1 Mab34. The results are shown in FIG. 14C.

D. 5E1 Epitope Mapping

5E1 bound to agarose beads was incubated with Shh, partially digested with trypsin, then undigested peptides were eluted and identified by mass spectrometry as previously described (Kiselyov, A. S. et al. (2007) *Expert Opin. Ther. Targets* 11:1087-1101). This revealed peptide 158-178 (FIG. 8b) in agreement with previous data that encompasses the S177 residue (Fuse N. et al. (1999) *Proc. Natl. Acad. Sci.* 96:10992-10999; Pepinsky, R. B. et al. (2000) *J. Biol. Chem.* 5:154-156). The epitope likely extends past the tryptic cleavage site at K178 encompassing the residues that differ between Shh/Ihh and Dhh to account for the lower affinity for Dhh (vide infra).

E. Binding Affinity of 5E1 to Shh by Surface Plasmon Resonance

Affinity determinations for human Shh (25-197), Dhh, or Ihh binding to 5E1 were performed by surface plasmon resonance using a BIAcore™-2000. IgG (882 to 991 RU) was immobilized in 10 mM sodium acetate pH 4.8 on a CM5 sensor chip and serial 3-fold dilutions of the various forms of Shh (0.3-1000 nM) in PBST were injected at a flow rate of 30 µl/min. Each sample was analyzed with 4-minute association time and 10-minute dissociation time. After each injection the chip was regenerated using 10 mM glycine pH 1.7. Binding response was corrected by subtracting the control IgG flow cell 1 from the 5E1 flow cells. A 1:1 Languir model of simultaneous fitting of k$_{on}$ and k$_{off}$ was used for kinetics analysis. 5E1 bound with similar affinity (~3 nM) to Shh and Ihh, but had significantly lower affinity for Dhh.

Example 4

Crystallization, Data Collection and Structure Solution

A. Crystal Formation and Characteristics

Having defined the Hip$_{\beta 12}$ domain as essential for Shh binding and inhibition of signaling, we explored the molecular basis for this activity by determining the structures of the Hhip1 and Hip-Shh complexes.

Crystals of apo Hip$_{\beta 12}$ were grown by atypical hanging-drop vapor diffusion at 19° C. by placing protein samples (0.3-2 µl) over 500 µl of reservoir solution of 20 mM Hepes pH 7.2 and 3 M NaCl. Rectangular crystals appeared within 48 hrs and were grown for one week, with the longest dimension exceeding 0.8 mm. The best diffracting crystals (typically 0.25×0.25×0.10 mm$^3$) were transferred to a 2 µl drop of 20 mM Hepes pH 7.2 and 3 M NaCl and placed over a 500 µl reservoir solution of 20 mM Hepes pH 7.2 and 5 M NaCl.

After 16-24 hrs of dehydration, crystals were soaked for 30 sec in 20 mM Hepes pH 7.2, 5M NaCl prior to flash cooling in liquid nitrogen. Three-wavelength Se-Met based MAD was collected at 100 K at Stanford Synchrotron Radiation Laboratory (SSRL) 9-2 beamline. Crystallography statistics are summarized in Table 7.

A different form of apo Hhip1$_{\beta12}$ crystal was grown by hanging-drop vapor diffusion at 19° C. by combining 1.5 µl of protein solution with 1.5 µl of reservoir solution (0.1 M sodium acetate, 0.2 M ammonium sulfate, 22-24% PEG 4000 and 1-2% dioxane). Crystals appeared within a week and grew to full size in 7-14 days. Prior to flash cooling in liquid nitrogen, crystals were cryoprotected in a reservoir solution supplemented with glycerol in a step-wise fashion (v/v glycerol final concentration of 5%, 10%, 15% and 20%). Native data were collected at 100 K at Advanced Light Source (ALS) 5.0.2 beamline.

Initial crystals of Hip$_{\beta12}$-Shh complex were generated by hanging-drop vapor diffusion at 19° C. by combining 1 l of protein sample and 1 µl of reservoir solution (0.1 M bis-Tris propane pH 7.0 and 2.8-3.0 M sodium formate). They appeared after 4 days and grew large with the longest dimension exceeding 0.3 mm. These crystals were of very poor quality and a series of microseeding and macroseeding steps were required for crystals suitable for data collection. A succession of streak seeding into a pre-equilibrated (48 h) protein drop improved crystal quality such that macroseeding was feasible. Small crystals with dimensions of about 0.02 mm were washed and transferred into a pre-equilibrated drop with a reservoir solution containing 0.1 M bis-Tris propane pH 7.0 and 2.2 M sodium formate. Since slow growth was essential for getting crystals suitable for X-ray diffraction, complex and lengthy multistage procedures were implemented using NeXtal screw-cap 24 well plates. Typically, crystals were incubated over reservoir solution for 4-7 days before being transferred to conditions where the sodium formate concentration was raised by 0.1 M. This process was repeated four times with a final reservoir containing 0.1 M bis-Tris propane pH 7.0 and 2.5 M sodium formate. The best quality crystals measuring 0.09×0.09×0.05 mm$^3$ were produced in a period of 4-6 weeks. Anisotropic native data were collected at SSRL 11-1 beamline.

All data sets were processed using HKL2000 (Otwinowski and Minor (1997) *Methods Enzymol.* 276: 307-325). Nine selenium sites were located and phase refinement for apo Hip$_{\beta12}$ crystallized in the P3$_1$21 space group was performed with autoSHARP (Bricogne, G. et al. (2003) *Acta Crystallogr. D Biol. Crystallogr.* 59: 2023-30). Solvent flattening with 66% solvent content significantly improved experimental map quality. Manual atomic model building into experimental electron density was done in Coot (Emsley and Cowtan (2004) *Acta Crystallogr. D. Biol. Crystallogr.* 60: 2126-2132). The structures of apo Hhip1$_{\beta12}$ in the C222$_1$ space group and the Hhip1$_{\beta12}$-Shh complex were solved by molecular replacement with Phaser (McCoy, A. J. et al. (2005) *Acta Crystallogr. D. Biol. Crystallogr.* 61: 458-464) using the refined coordinates of the P3$_1$21 crystal form as a search model for the Hhip1$_{\beta12}$ and Shh crystal structure (PDB code 1VHH). Refinement of all structures was done with Refmac (Winn, M. D. et al. (2001) *Acta Crystallogr. D. Biol. Crystallogr.* 57: 122-133). Crystallography statistics are summarized in Table 7.

Purified Hhip1$_{\beta12}$ crystallized in both trigonal (space group P3$_1$21) and orthorhombic (space group C222$_1$) systems with final models refined to 3.1 Å and 2.9 Å resolution, respectively (structural statistics are summarized in Table 7). The following discussion on the apo Hhip1$_{\beta12}$ structure is based on observations from the trigonal crystals with any differences between the two forms highlighted accordingly.

The high affinity between Hip$_{\beta12}$ and Shh allowed isolation of a stable complex with 1:1 stoichiometry was isolated by size exclusion chromatography. Surprisingly, the complex crystallized in the same trigonal space group as that of the apo crystal with nearly identical unit cell parameters and diffracted to 3.0 Å resolution (Table 7). The asymmetric unit contained two Hhip1$_{\beta12}$ molecules in the same orientation as in the apo form, and two Shh molecules, each creating a 1:1 heterodimeric complex. However, the density for one of the Shh molecules was extremely poor due to the lack of stabilizing crystal packing interactions; this copy of Shh was not included in the final model.

TABLE 7

Crystallographic Statistics.

| Protein | Apo Se-Met Hhip1$_{\beta12}$ | Se Inflection | Se Remote | Apo Hhip1$_{\beta12}$ | Hhip1$_{\beta12}$-Shh complex |
|---|---|---|---|---|---|
| Data Collection | | | | | |
| | Se Peak | | | | |
| Space group | P3$_1$21 | | | C222$_1$ | P3$_1$21 |
| Unit cell dimension (Å) | a = 101.0, b = 101.0, c = 304.9 | | | a = 86.2, b = 118.0, c = 126.3 | a = 101.6, b = 101.6, c = 302.8 |
| Wavelength (Å) | 0.97940 | 0.97955 | 0.91176 | 1.0000 | 0.97839 |
| Resolution (Å) | 30-3.1 | 30-3.1 | 30-3.1 | 30-2.8 | 50-3.0 |
| Completeness (%)$^a$ | 99.8 (99.2) | 99.8 (99.3) | 99.6 (98.9) | 99.8 (100) | 99.8 (100) |
| Unique reflections | 33,657 | 33,672 | 33,626 | 14,755 | 37,106 |
| Redundancy | 5.3 (5.1) | 5.3 (5.1) | 5.2 (4.9) | 4.7 (4.8) | 8.7 (8.9) |
| Rsym (%)$^b$ | 7.4 (56.8) | 7.6 (60.1) | 7.7 (64.4) | 8.9 (49.1) | 8.5 (58.9) |
| <I>/<σ(I)> | 21.2 (2.9) | 20.7 (2.8) | 20.6 (2.4) | 14.4 (3.5) | 24.2 (4.3) |
| Phasing statistics | | | | | |
| Phasing power (iso) | 0.328 | 0.415 | 0 | | |
| Phasing power (anom) | 0.487 | 0.454 | 0.273 | | |
| FOM acentric, centric | 0.25/0.2 | | | | |
| Refinement Statistics | | | | | |
| Resolution (Å) | 30-3.1 | | | 30-2.9 | 30-3.0 |
| Rcryst (%)$^c$ | 22.1 | | | 26.1 | 23.6 |

TABLE 7-continued

Crystallographic Statistics.

| Protein | Apo Se-Met Hhip1$_{\beta12}$ | Se Inflection | Se Remote | Apo Hhip1$_{\beta12}$ | Hhip1$_{\beta12}$-Shh complex |
|---|---|---|---|---|---|
| Rfree (%) | 25.2 | | | 30.7 | 29.5 |
| No. of protein atoms | 6,590 | | | 3,364 | 7,876 |
| No. of ion atoms | | | | | 4 |
| Average B factor (Å$^2$) | 71.3 | | | 93.8 | 61.5 |
| Rmsd bonds (Å) | 0.008 | | | 0.007 | 0.008 |
| Rmsd angles (°) | 1.3 | | | 1.15 | 1.223 |
| Ramachandran plot (%)[d] | 80.8, 16.7, 1.7, 0.8 | | | 78.2, 17.9, 2.5, 1.4 | 84.4, 13.7, 0.9, 0.9 |

[a]Numbers in parentheses refer to the highest resolution shell.
[b]$R_{sym} = \Sigma |I - <I>|/\Sigma I$. $<I>$ is the average intensity of symmetry-related observations of a unique reflection.
[c]$R = \Sigma |F_o - F_c|/\Sigma F_o$.
[d]Percentage of residues in the most favored, additionally allowed, generously allowed, and disallowed regions of a Ramachandran plot.

The Hhip1$_{\beta12}$ fragment present in our crystal structures contains a canonical six-bladed β-propeller domain and two EGF domains, with the overall structure resembling a lollipop (FIG. 3C). The β-propeller domain represents the head (65×50×50 Å$^3$) of the lollipop and the two EGF domains create the stalk (40×15×15 Å$^3$). Four intra-domain disulfide bonds are present within the β-propeller and three within each of the EGF domains. The structures of Shh and the Hhip1$_{\beta12}$β-propeller core remain largely unchanged upon complex formation (Shh rmsd=0.38 Å (residues 40-187); (Hhip1$_{\beta12}$ rmsd=0.39 Å (residues 215-606), with the exception of peripheral Shh-binding loops in Hhip1$_{\beta12}$ which are generally more well-defined in the complex.

A search of the Protein Data Bank (PDB) with the SSM program (Krissinel and Henrick, 2004) revealed that the Hhip1$_{\beta12}$ β-propeller domain superimposed best with X-ray structures of soluble quinoprotein glucose dehydrogenases from bacteria and archea (PDB codes 2ISM, 2G8S and 1CRU), with rmsds ranging from 2.2-2.4 Å over 271-284 aligned C$_\alpha$ positions with a sequence identity of 23%. These proteins are members of a larger family of bacterial and archael enzymes that notably utilize a highly reactive pyrroloquinoline quinone (PQQ) cofactor that binds in the central cavity of their six-bladed β-propeller folds (Oubrie, 2003). Close inspection of the superimposed β-propellers of Hhip1 and these select dehydrogenases reveal that Hhip1 lacks the PQQ-coordinating residues and the corresponding binding pocket is both smaller and more solvent-exposed. The observed structural relationship of Hhip1 with a clan of bacterial PQQ-dependent enzymes raises the interesting question of whether the mammalian Hhip1 family is a very divergent branch that has lost enzyme function but gained a new protein interaction role.

All structural figures were generated using Pymol (DeLano, W. L. (2002) The PyMOL Molecular Graphics System, Palo Alto, Calif., USA, DeLano Scientific) which may be found on the Worldwide Web with a URL address of pymol.com.

B. The EGF1 Domain Intimately Associates with the β-propeller

Figure 9:
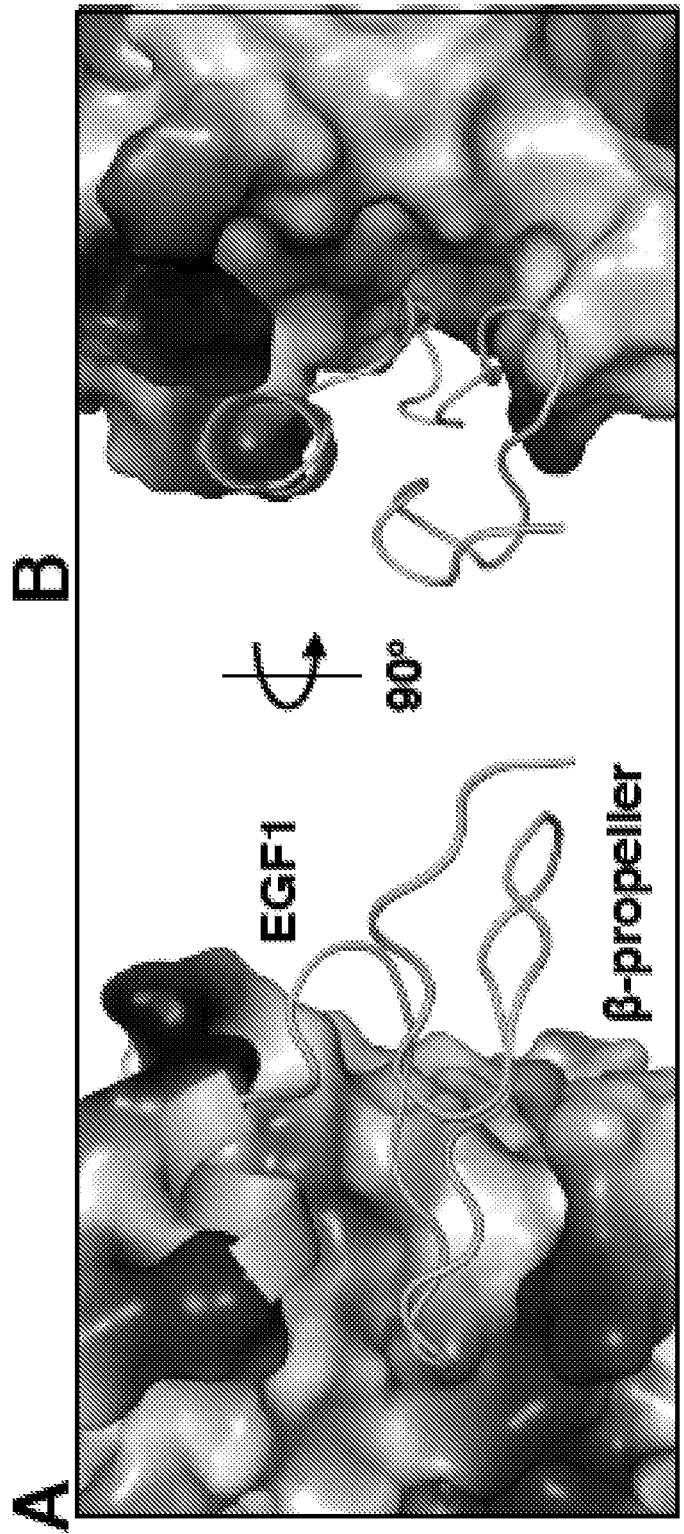
FIG. 9 shows the nature of the association between the β-propeller and EGF1. Panel A: the association between the β-propeller (shown as surface with electrostatic properties, positive in light gray and negative in dark gray) and EGF1 (cartoon representation) in line and ribbon; Panel B: shows the view in Panel A rotated by 90°.

In the five crystallographically independent structures of Hhip1, three for the apo form and two bound to Shh, the β-propeller and EGF1 domains superimpose well, suggesting that they form a rigid unit (FIG. 3D). EGF1 is spatially restrained by an intimate interaction with blades 2 and 3 of the β-propeller. The resulting interface between the two domains is hydrophilic as well as hydrophobic in nature, with a disulfide bond formed between C402 in blade 3 of the β-propeller and C624 in EGF1 (FIG. 3E). The intimate nature of this interaction explains the instability of the Hip$_p$ construct lacking the EGF1 domain (FIG. 9). The close interaction between the Hhip β-propeller and EGF1 domain resembles the contacts made between the second and third blade of the six-bladed β-propeller domain of low-density lipoprotein receptor (LDLR) and its C-terminal EGF domain (Jeon et al., 2001). Notably, the interface is considerably larger in the case of LDLR with hydrophobic side chains predominating. Unlike EGF1, the orientation of EGF2 with respect to the β-propeller shows significant variation, probably due to the inherent flexibility of the linker region between the two EGF domains (FIG. 3D). The flexibility here and most likely between EGF2 domain and the membrane implies there is some conformational freedom in the Hhip1$_{\beta12ECD}$ with respect to the plasma membrane.

C. Hhip1$_{\beta12}$ Interacts with Shh Via Three Loops

Figure 4:
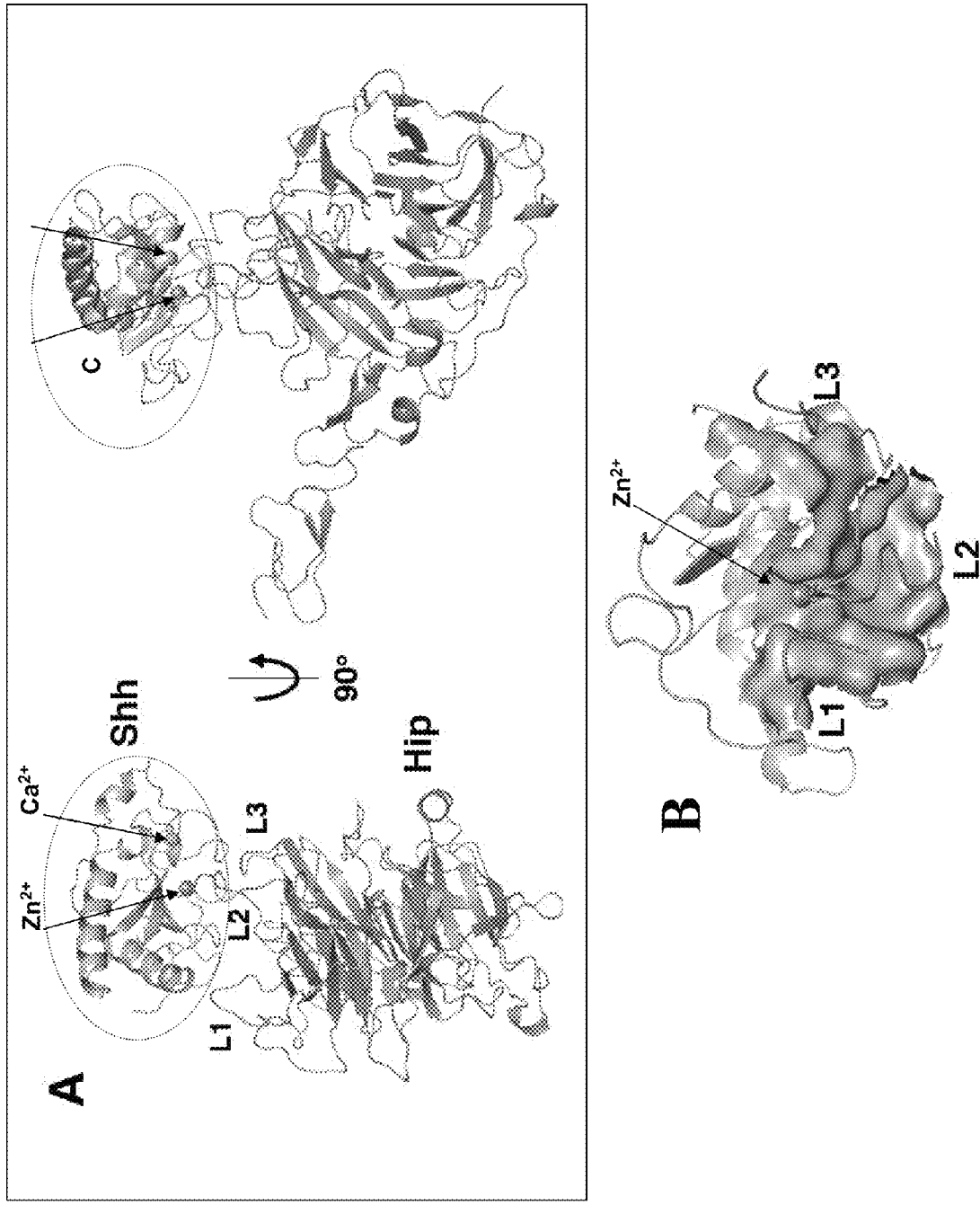
FIG. 4 shows structure and function of the Hhip-Shh complex. Panel A: Cartoon representation of the complex of Hhip1$_{β12}$ and Shh (inset in oval). The three loops from Hhip1$_{β12}$ contacting Shh are labeled L1-L3. $Zn^{2+}$ and $Ca^{2+}$ cations are shown with arrows Only one $Ca^{2+}$ cation is shown). A 90° rotated view is also shown. The N- and C-termini of Shh, as well as the C-terminus of Hhip are all on the same side of the complex, suggesting that both components could be anchored to the same cell membrane. Panel B shows a surface representation of Shh contacting the three loops from Hhip1$_{β12}$; Panel C: Alanine mutants in Hhip loops contacting Shh. Residues mutated to alanine in three Hhip loops are shown as spheres, with those that abolished Shh binding shown with an asterisk (*), those that had significant impact shown with a plus sign (+) and those with minimal consequence shown with a hatch sign (#). Panel D: Coordination of the $Zn^{2+}$ cation by residues from Shh and Hhip$_{β12}$. $Zn^{2+}$ (gray sphere) is coordinated by residues H140, D147 and H182 from Shh and D383 from Hhip$_{β12}$. Panel E: The Shh $Zn^{2+}$-containing groove and the $Ca^{2+}$ binding site are distinct. Shh and Hhip (inset in square), with a transparent surface shown for the Hhip L2 loop. $Zn^{2+}$ and $Ca^{2+}$ cations are shown with arrows. Shh residues, which in Ihh are genetically associated with brachydactyly type A1, are shown as sticks and carbon atoms are numbered according to the human Shh sequence. Panel F: Inhibition of Shh signaling in Gli-luciferase co-culture assays by Hhip$_{β12}$ mutants. Assays were carried out as in FIG. 3B. Results are plotted as the average of three independent triplicates normalized to 100% for no inhibitor±standard deviation.

The Shh binding site is localized at the periphery of the Hhip1$_{\beta12}$β-propeller domain, distant from the EGF stalk (FIGS. 4 A and B). Three loops from the second and third blades of Hhip1$_{\beta12}$ (L1: 309-314, L2: 376-388 and L3: 417-422) contact a region of Shh centered on the Zn$^{2+}$-containing groove (FIG. 4 A-C). The L1 and L2 loops show evidence of multiple conformations in the apo Hhip1$_{\beta12}$ structures, indicating that binding Shh restricts their conformation. The interface is large, comprising 23 Hhip1 residues and 29 Shh residues accounting for 870 Å$^2$ and 780 Å$^2$ buried solvent accessible surface area, respectively. The location and the extent of the interaction is consistent with our in vitro binding data, which show that the minimal region for binding resides within the protein fragment encompassing the β-propeller and EGF1 (Table 6). Although the EGF1 domain does not contact Shh, it is nonetheless required since it stabilizes the β-propeller (vide supra). Interestingly, the N- and C-termini of Shh, which are lipid-modified in vivo, as well as the C-terminus of Hhip1$_{\beta12}$ are all on the same side of the complex, suggesting that both components could be anchored to the same cell membrane.

The Hhip1$_{\beta12}$ L2 loop inserts deeply into the Zn$^{2+}$-containing groove of Shh and constitutes the heart of the interaction. Approximately 500 Å$^2$ of the Hhip1$_{\beta12}$ L2 surface is in direct contact with Shh, which accounts for ~60% of total Hhip1$_{\beta12}$ surface in contact with Shh. Extensive side chain interactions between Shh and the Hhip1$_{\beta12}$ L2 loop are present in addition to some main chain-side chain interactions. Intriguingly, D383 in the L2 loop of Hhip1$_{\beta12}$ directly interacts with the Zn$^{2+}$ cation in Shh, resulting in tetrahedral coordination (FIG. 4D). In the high-resolution apo murine Shh structure (Hall, T.

M. et al. (1995) *Nature* 378:212-216) a water molecule replaces D383 while the $Zn^{2+}$-coordinating residues H141, D148, and H183 in Shh (H140, D147, H182 in human Shh) are identical in the bound and apo structures (FIGS. 4D and 8B). In contrast to the extensive interactions made by the Hhip1$_{\beta 12}$ L2 loop, the L1 and L3 loops' contacts appear more superficial and involve significantly smaller surface area on the periphery of the binding site (FIG. 4C). Notably, the Hhip binding site on Shh includes residues E176-K178, deletion of which is associated with clinical presentation of microcephaly and a partial corpus collosum (Dubourg et al., 2004).

The interactions of Hhip1$_{\beta 12}$ with Hedgehog demonstrated herein are believed to be the same interactions that occur between native Hhip1 and Hedgehog.

Example 5

A. $Zn^{2+}$ and Hip-Shh Interaction

To characterize the importance of the $Zn^{2+}$ cation in mediating Hip-Shh interactions, we performed binding studies in the presence of EDTA. $^{15}$N-labeled Shh was prepared the same way as the native protein (see Example 1D) with $^{15}NH_4Cl$-supplemented M9 media. $^{15}$N, H—HSQC spectra were recorded with 90 mM $^{15}$N-Shh in PBS buffer supplemented with 10% (v/v) $D_2O$, at 32° C. on Bruker DRX600 MHZ spectrometer equipped with 5 mm inverse triple-resonance cryoprobe. The $Zn^{2+}$ studies of $^{15}$N-labeled Shh were carried out in the presence or absence of 10 mM EDTA.

Figure 10:
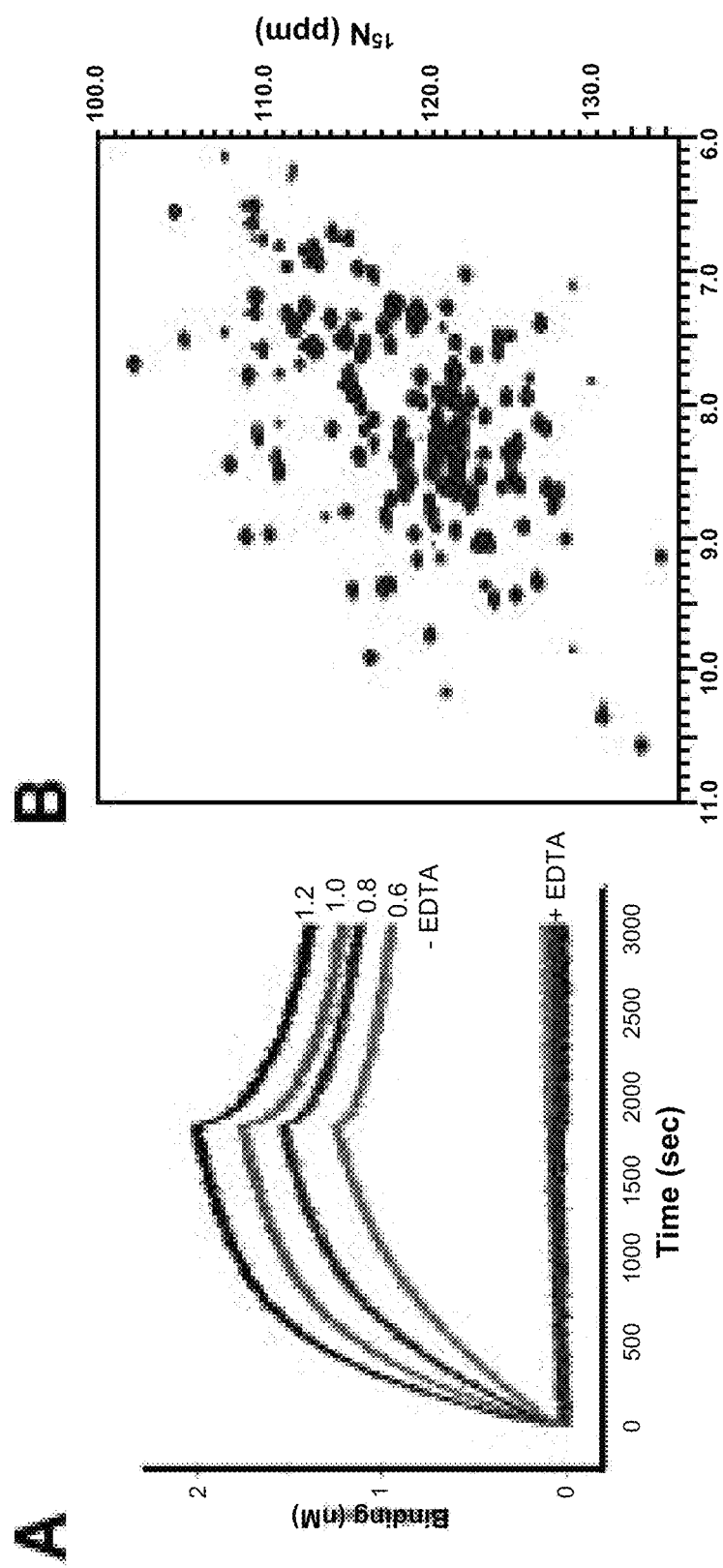
FIG. 10 shows Binding of Hip$_{\beta 1}$ to biotinylated Shh$_{N-Cys}$ in the absence and the presence of EDTA measured by bio-layer interferometry. Panel A: sensorgram binding curves of four different concentrations of Hip$_{\beta 1}$ (1.2, 1.0, 0.8 and 0.6 μM) in the absence and presence of 10 mM EDTA; Panel B: $^{15}$N, $^{1}$H-HSQC spectrum of Shh alone and in the presence of 10 mM EDTA; Panel C: shows the human Shh (light gray) from the Hip-Shh complex structure is superimposed on the *Drosophila* Hh (dark gray, PDB accession number 2IBG, residues 49-196). The Zn$^{2+}$ cation is only present in Shh and is shown as a gray sphere. For clarity, the Ca$^{2+}$ cations are omitted from the Shh structure. The rmsd of the superimposition is 0.6 Å; Panel D: shows a close up view of human Shh and *Drosophila* Hh structures highlighting Zn$^{2+}$ coordination in Shh. Residues in *Drosophila* Hh equivalent to Shh Zn$^{2+}$-coordinating residue positions are shown. The color selection is the same as that in Panel C.
Figure 10:
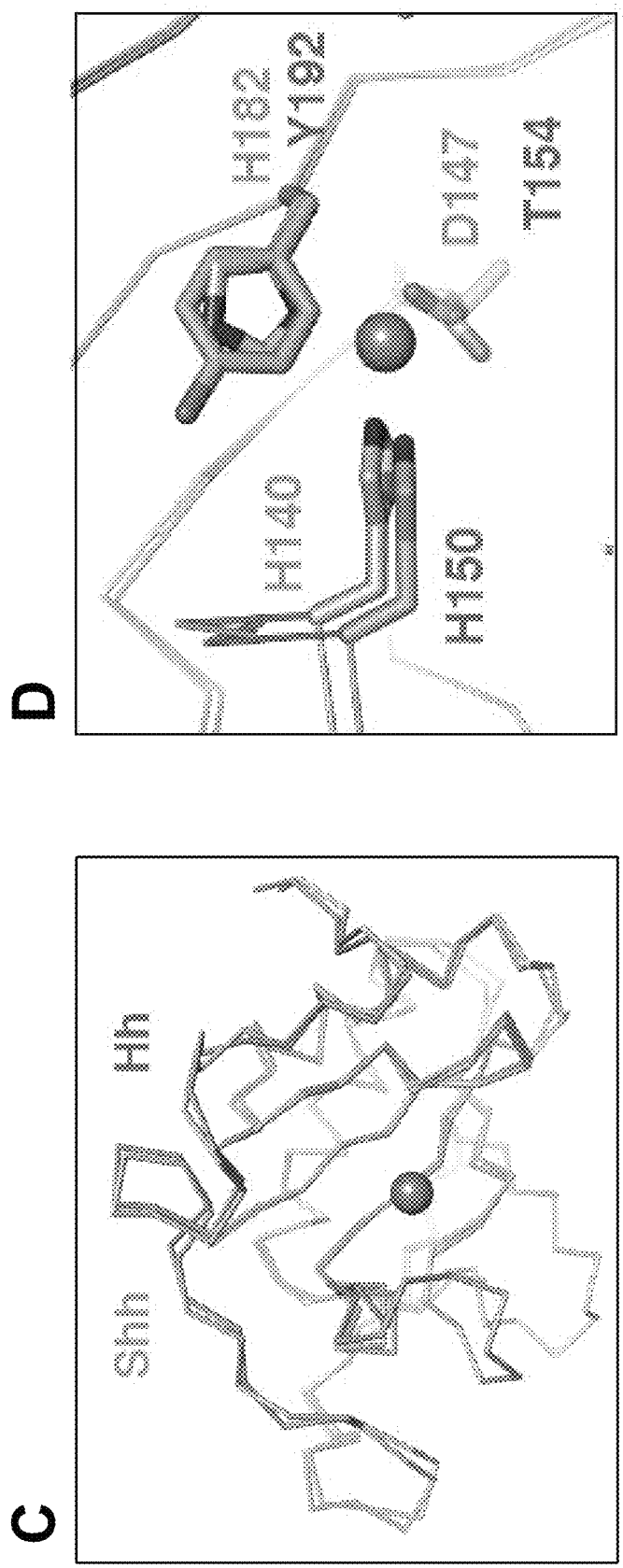

Consistent with the notion that interaction of Hip$_{\beta 1}$ with Shh is dependent upon $Zn^{2+}$, binding was completely abolished in the presence of EDTA (FIG. 10A). Importantly, loss of the $Zn^{2+}$ cation does not have a significant effect on Shh structure or stability, as shown by virtually identical NMR spectra in the absence or presence of EDTA (FIG. 10B). Minor spectral differences are consistent with local changes to the zinc-binding residues upon displacement of $Zn^{2+}$. Furthermore, the tertiary structure of Shh is nearly identical to that of *Drosophila* Hh (McLellan, J. S. et al. (2006) *Proc. Natl. Acad. Sci. USA* 103:17208-17213), which is incapable of binding $Zn^{2+}$ at the homologous site due to differences in groove residues (FIGS. 10 C and D). Although EDTA can also sequester other divalent cations (see $Ca^{2+}$ site below) we believe that $Zn^{2+}$ interaction is critical for complex assembly since the $Zn^{2+}$ is the only Shh-bound divalent cation that directly interacts with Hhip1.

B. Role of L1, L2 and L3 in Hedgehog Binding

In order to assess the contribution of residues in the Hhip1 L1, L2 and L3 loops for binding to Shh, a series of single alanine Hip$_{\beta 12}$ mutants were made using the QuickChange DNA mutagenesis kit (Stratagene) using the manufacturer's protocol, and their affinity for Shh was measured by bio-layer interferometry (as described in Example 2B). These mutations included Hhip1$_{\beta 12}$ mutants I312A, E381A, M382A, D383A, D378A, T418A, Q420A, E380A, D387A and ΔL2.

The results are shown in Table 6 and FIGS. 4E and 4F. As expected, deletion of the entire L2 loop (Hhip1$_{\Delta L 2}$) abrogated binding to Shh. The importance of the $Zn^{2+}$ cation for bridging the interaction between Hhip1$_{\beta 12}$ and Shh was also further highlighted by the inability of the D383A L2 and D383R Hhip L2 mutants to bind Shh. Alanine substitutions at L2 residues E380, M382, and D387 also abolished binding to Shh. Residues E380 and D387 have direct interactions with Shh, while M382 does not contact Shh and likely functions by stabilizing the L2 loop in a conformation that is competent for binding. Two other mutations in L2, D378A and E380A, had minor to moderate effects on Shh binding (Table 6, FIG. 4E). Unlike the changes in the L2 loop, single alanine mutations in the L1 (I312A) or L3 (T418A, Q420A) loops had little effect on Shh, binding with $K_D$ values comparable to WT Hhip1$_{\beta 12}$ (Table 6, FIG. 4F). The alanine mutant affinity data are consistent with the hypothesis that the L2 loop is the major energetic determinant for Shh binding.

Somewhat unexpectedly, the D383A mutant retained activity in the more complex and physiologically relevant Gli-luciferase co-culture assay (See Example 3A for protocol), having an $IC_{50}$ ~10 nM, only 2-fold higher than observed for wildtype Hip$_{\beta 12}$. However, the inhibition was incomplete (~85%) at saturating conditions (FIG. 4F).

Figure 12:
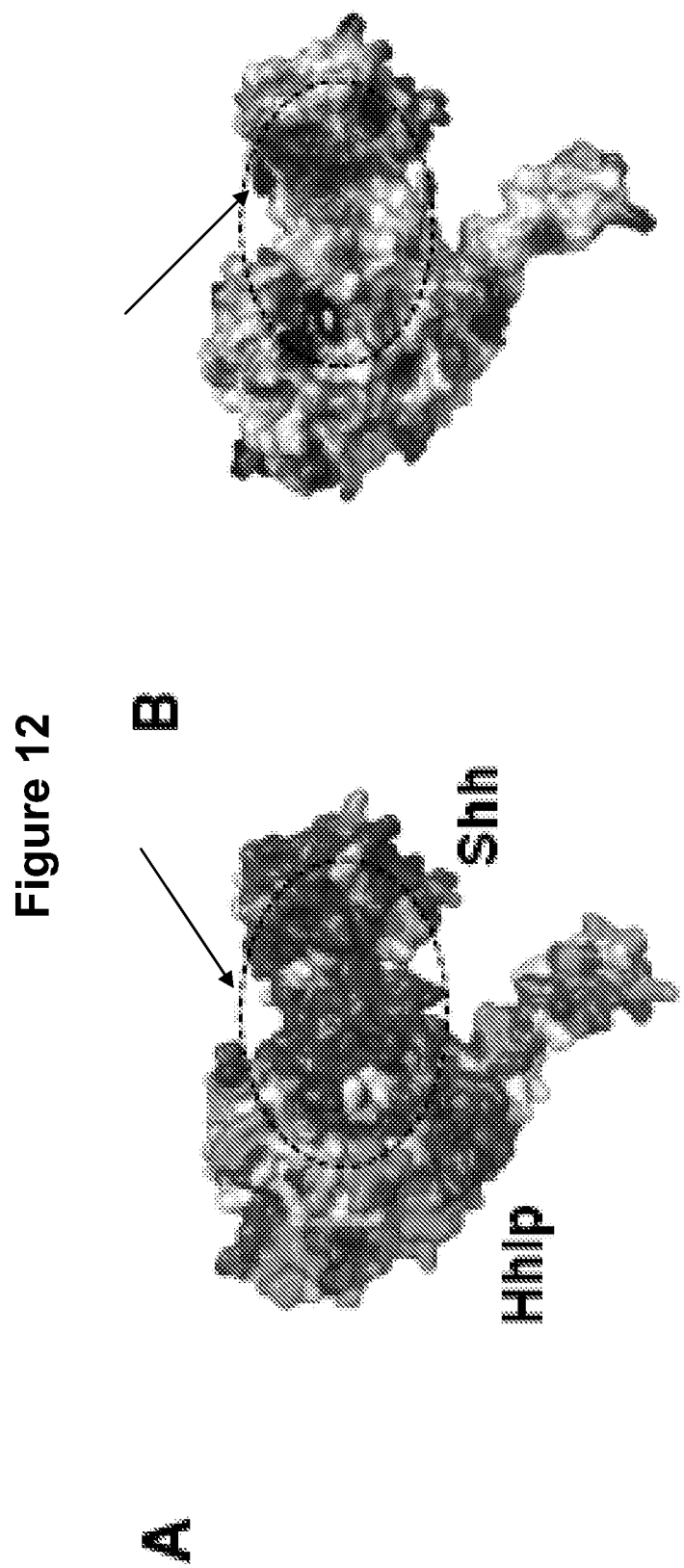
FIG. 12 shows a conserved surface patch on Hhip-Shh complex: Panel A shows a surface residue sequence conservation determined for Hhip1 (15 sequences in FIG. 11) and Shh (25 sequences in Swiss-Prot), illustrated with a color gradient from dark gray (identical residues) to light gray (least conserved residues). Areas within the dashed oval refer to the highly conserved patch. Panel B shows that the conserved surface patch contains a highly acidic region. The surface electrostatic potential is depicted with positive charge in light gray and negative charge in dark gray. Areas within the dashed oval refer to the highly conserved patch shown in Panel A. Residue conservation was generated with ConSurf (consurf.tau.ac.il).
Figure 13:
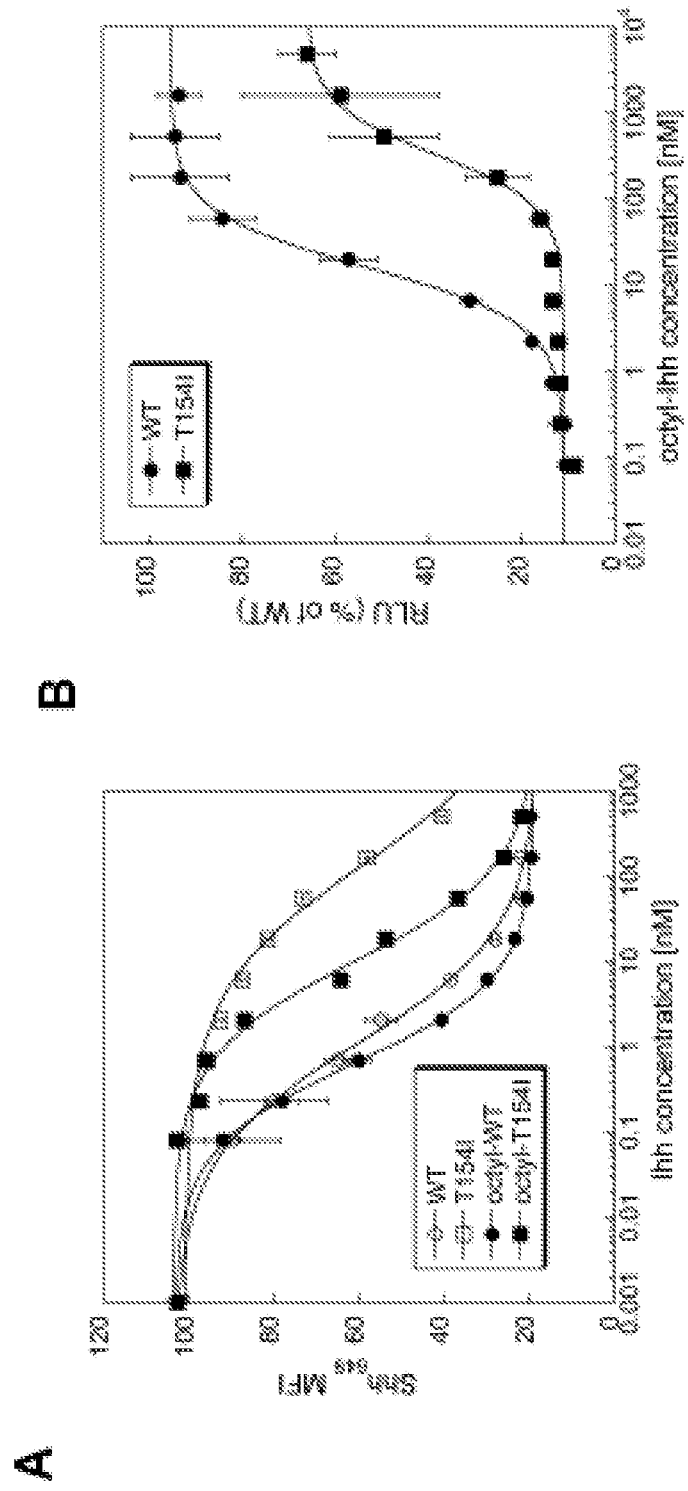
FIG. 13 shows that the type A1 brachydactyly mutant Ihh T154I is impaired in both binding to Ptch1 and activation of Hh signaling. Panel A shows that Ihh T154I is a weaker competitor than wildtype of Shh binding to Ptch1. Shh$_{649}$ (1 nM) preincubated with indicated proteins was bound to Ptch1 expressing cells, washed and analyzed by FACS. The average mean Shh$_{649}$ fluorescence intensity (MFI) of two independent dilution series was plotted versus inhibitor concentration, with error bars denoting standard deviations. Ihh and octyl-Ihh inhibit similarly (respective IC$_{50}$ values of 1.1 and 0.64 nM), whereas inhibition by T154I and octyl-T154I (IC$_{50}$ values of 140 nM and 10 nM, respectively) is impaired. Panel B shows activation of Hh signaling in S12 Gli luciferase assays. Assays were carried out using octylated Ihh wildtype and T154I proteins. Concentration dependent relative luciferase units (RLU) are plotted as the average of four independent dilution series±standard deviation and normalized to the maximal Ihh WT stimulation on each plate as 100%. The curve drawn represents data fit to a 4-parameter equation, from which EC$_{50}$ values of 16 and 330 nM were derived for Ihh and Ihh T154, respectively. The data is representative of three independent experiments.

Adverse steric and charge effects at this position (D383R) resulted in a ~13-fold reduction in $IC_{50}$ (57 nM) and maximal inhibition of only ~50%. As expected, there was no inhibitory activity observed with the Hhip$\Delta$L2 mutant (FIG. 4F). Since no additional divalent metal ions were added in the protein binding assays, sub-saturating concentrations could explain differences found in the cell-based assay; further Hhip-Shh binding studies are needed to better define the dependence on divalent metal ions. The complexity of Hhip-Shh interactions in cell-based assays could also arise from interactions absent in binding assays, e.g., lipid modifications on Shh. Moreover, the presence of a highly conserved acidic area on the surface of the Hhip-Shh complex suggests a potential interaction site for additional regulators (FIG. 12).

Another mutant, I312A, that bound Shh similar to wildtype Hhip1$_{\beta 12}$ (Table 6) was essentially identical to wildtype Hhip1$_{\beta 12}$ in the cell-based activity (FIG. 4F). The complexity of Hip-Shh interaction in cell-based assays may include additional or compensatory interactions absent in the binding assay, which uses unmodified recombinant Shh. The N-terminal palmitoyl and C-terminal cholesterol modifications of Shh present in the cell-based assays likely anchor Shh to the cell membrane, restricting its mobility and priming it for Hhip1$_{\beta 12}$ binding. Furthermore, the Hhip1 EGF2 domain may mediate additional interactions as it has a small effect on inhibition in the co-culture assay, even though it does not directly contact Shh in the crystal structure and does not appear to contribute to binding in vitro (FIG. 3B, Table 6).

Example 6

The Complex Suggests a Rationale for Type A1 Brachydactyly Ihh Genetic Mutations Genetic data on Hh and other Hh family members highlights the importance of the Shh pseudo-active site groove and the $Ca^{2+}$ binding site. These mutations can have a profound effect, although it is unclear for most of them whether this is due to impaired interactions with Ptch1 and/or with modulatory receptors. For instance, deletion of E176-K178, which contributes to one wall of the pseudo-active site groove, is associated with microcephaly and a partial corpus collosum. In addition, several Ihh mutations (E95G/K, D100E/N, R128Q, T130N, E131K and T154I corresponding to Shh residues E90, D95, R123, T125, E126 and T149, respectively; FIG. 8B) are associated with brachydactyly type A1, an autosomal dominant hereditary disorder characterized by shortening of the middle phalanges[43,44,45,47,48,49]. These mutations map to two sites in Shh: the pseudo-active site (R123, T125, T149) and the adjacent $Ca^{2+}$ binding site (E90, D95, E126) (FIG. 4D). In the $Zn^{2+}$-binding groove T125 and T149 both pack against R123 and contribute to the groove surface. In addition, R123 provides a complementary charge for residue E380 in Hhip (FIG. 4D). The Ihh mutations T1541, R128Q, T130N are all solvent exposed and are unlikely to alter the Ihh fold although the R128Q mutation may diminish electrostatic interactions with binding partners. The relatively benign nature of these three heterozygous mutations contrasts with the embryonic lethality in mice of the Ihh knockout[50].

The other type A1 bradydactyly-associated mutations in Ihh (E95G/K, D100E/N and E131K (Gao B. et al. (2001) *Nat. Genet.* 28:386-388; Kirkpatrick T. J. et al. (2003) *J. Med. Genet.* 40:42-44; McCready et al. (2002) *Hum. Genet.* 111: 368-375)) fom part of a novel divalent cation binding site in Shh adjacent to the $Zn^{2+}$-binding groove. Shh side chains E90, D95 and E126, corresponding to the Ihh residues above, and the backbone carbonyl of W128, coordinate a putative $Ca^{2+}$ cation (FIG. 4G). Alteration of any of these acidic side chains will likely adversely affect divalent cation binding to Shh or Ihh. The evolutionary association between the cation-coordinating side chains and this inheritable disease suggest that this site is functionally important in Hh signaling.

Example 7

Hip-Shh Interactions Resemble Inhibitor-Metalloprotease Interactions

Although both the geometry of $Zn^{2+}$ cation coordination and the overall Shh fold is topologically similar to the MD clan of metalloproteases (Bochtler, M. et al. (2004) *Protein Sci.* 13:854-861; Bussiere, D. E. et al. (1998) *Mol. Cell.* 2:75-84; Hall, T. M. et al. (1995) *Nature* 378:212-216; Rawlings, N. D. et al. (2008) *Nucl. Acids Res.* 36:D320-325), no enzymatic activity has been reported for Shh (Fuse, N. et al. (1999) *Proc. Natl. Acad. Sci. USA* 96:10992-10999). Mutation of key residues at the pseudo-active site has shown that Shh functions as a ligand for Ptch and not as a protease (Fuse, N. et al. (1999) *Proc. Natl. Acad. Sci. USA* 96:10992-10999). Our Hip-Shh complex structure is therefore the first example of Shh utilizing its metalloprotease-like fold to regulate the Hh pathway. The $Zn^{2+}$-containing groove of Shh, which is akin to the protease substrate/inhibitor binding cleft, is occupied by the L2 loop of Hhip1$_{β12}$ with D383 coordinating the $Zn^{2+}$. This mode of interaction is analogous to that of the TIMP1-MMP3 complex (Gomis-Ruth, F. X. et al. (1997) *Nature* 389:77-81), where the MMP3 active site groove is occupied by a continuous loop from its inhibitor, TIMP1. In the TIMP-MMP3 structure, as in the Hip-Shh complex, the inhibitor completes the $Zn^{2+}$ coordination sphere. The Hip-Shh structure suggests that Shh may have evolved from a catalytically competent ancestor which lost its proteolytic activity while retaining some aspects of the protease-inhibitor binding mode to regulate pathway activity. Involvement of non-catalytic proteases as a binding partner has been observed in other important signaling pathways. For instance, hepatocyte growth factor (HGF) is a plasminogen-like α/β-heterodimeric growth factor and the ligand for Met, a receptor tyrosine kinase (Birchmeier, C. et al. (2003) *Nature Rev. Mol. Cell. Biol.* 4:915-925). The HGF β-chain serine protease-like domain interacts with the β-propeller of the Met receptor via its pseudo-active site, yet HGF lacks any catalytic activity (Kirchhofer, D. et al. (2004) *J. Biol. Chem.* 279:39915-39924; Stamos, J. et al. (2004) *EMBO J.* 23:2325-2335).

If Hhip acts as a decoy receptor for Shh, preventing it from binding to Ptch1 and thereby inhibiting signaling, then Hhip1 and Ptch1 should compete for Shh. We therefore examined whether soluble Hhip1$_{β12}$ could compete Shh from binding to Ptch1-expressing 293 cells by FACS. Fluorescent Shh$_{649}$ bound specifically to Ptch1-293 cells with an EC50 of ~2 nM (data not shown) and could be competed with unlabeled Shh or Ihh in a dose dependent manner (FIG. 15J).

Figure 15:
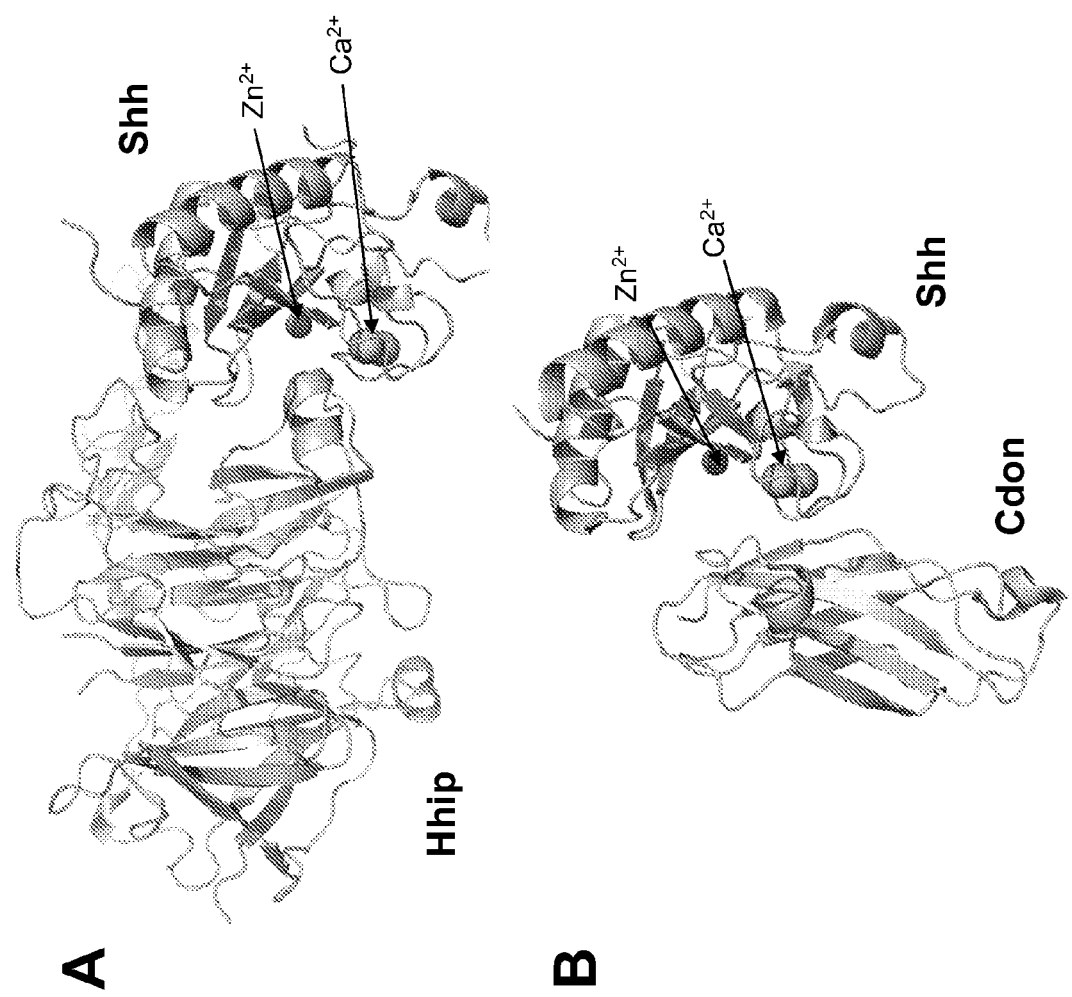
FIG. 15 shows Hhip and Ptch1 competitively bind at the Shh pseudo-active site groove. Panel A shows a cartoon representation of Hhip-Shh complex as shown in FIG. 4A. Panel B shows a cartoon representation of the complex between third FNIII domain of Cdon and Shh (PDB accession number 3D1M). Shh is in the same orientation as in the Hhip-Shh complex in Panel A. Zn$^{2+}$ and Ca$^{2+}$ cations are shown. Panel C shows overlapping binding sites for Hhip and Cdon on Shh. Surface representation of Shh with residues within 4.5 Å of Hhip (shaded gray) and Cdon (hatched areas). Area within dotted boarder indicates the boundaries of the Cdon footprint, which overlaps the Hhip binding surface. Panel D shows five histidine residues at the Shh pseudo-active site are proximal to the Hhip L2 loop. Shh histidine residues are shown as sticks with nitrogen atoms shaded dark. The Hhip L2 loop is shown in transparent surface and Zn$^{2+}$ cation is shown. Histidine 35 is not shown since the ordered portion of the Shh structure begins at L40. Panel E shows $^{13}$C, $^{1}$H-HSQC spectrum of Shh alone (gray) and in the presence of 10 mM EDTA (black). The spectral region of the histidine side chains is shown. Panel F shows the same as in Panel E except in the presence of 2 mM Hhip L2 peptide instead of EDTA. Panel G shows the same as in Panel E except in the presence of 2 mM Ptch1 L2-like peptide instead of EDTA. Panel H shows Hhip L2 peptide displaces Ptch1 L2-like peptide from Shh, indicating that they compete for Shh (2 mM Hhip L2 peptide was added to a sample containing Shh and 2 mM Ptch1 L2-like peptide (black) resulting in displacement of Ptch1 L2-like peptide from Shh, as shown by appearance of another spectrum (compare Panel G to Panel H showing presence of new spots), which is indicative of Hhip L2 peptide binding to Shh. Panel I shows that Hhip and Ptch1 compete for Shh binding. After preincubation of 1 nM $Shh_{649}$ with various proteins, Ptch1 expressing cells were incubated, washed and analyzed by FACS. The average mean Shh649 fluorescence intensity (MFI) of two independent dilution series was plotted versus protein concentration, with error bars denoting standard deviations. Ctrl refers to the His-6 (SEQ ID NO: 87) tagged HGF β protein. Panel J shows Hhip competition for Shh binding to Ptch1 is specific. Shh649 (0.33 nM) was preincubated with 56 nM (170-fold excess) of $Hhip_{β12}$ wildtype or L2 mutant proteins, 5E1 or controls then bound to Ptch1 cells (black) or 293 cells (gray), washed and analyzed by FACS. Shh649 binding to Ptch1 cells in the absence of inhibitors was normalized to 100% and the data expressed as a percentage of this signal (average of two independent duplicates with standard deviations). Ctrl and CtrlFc refer to HGF β and the IgG1 isotype control Trastuzumab, respectively. The data is representative of at least three independent experiments.
Figure 15:
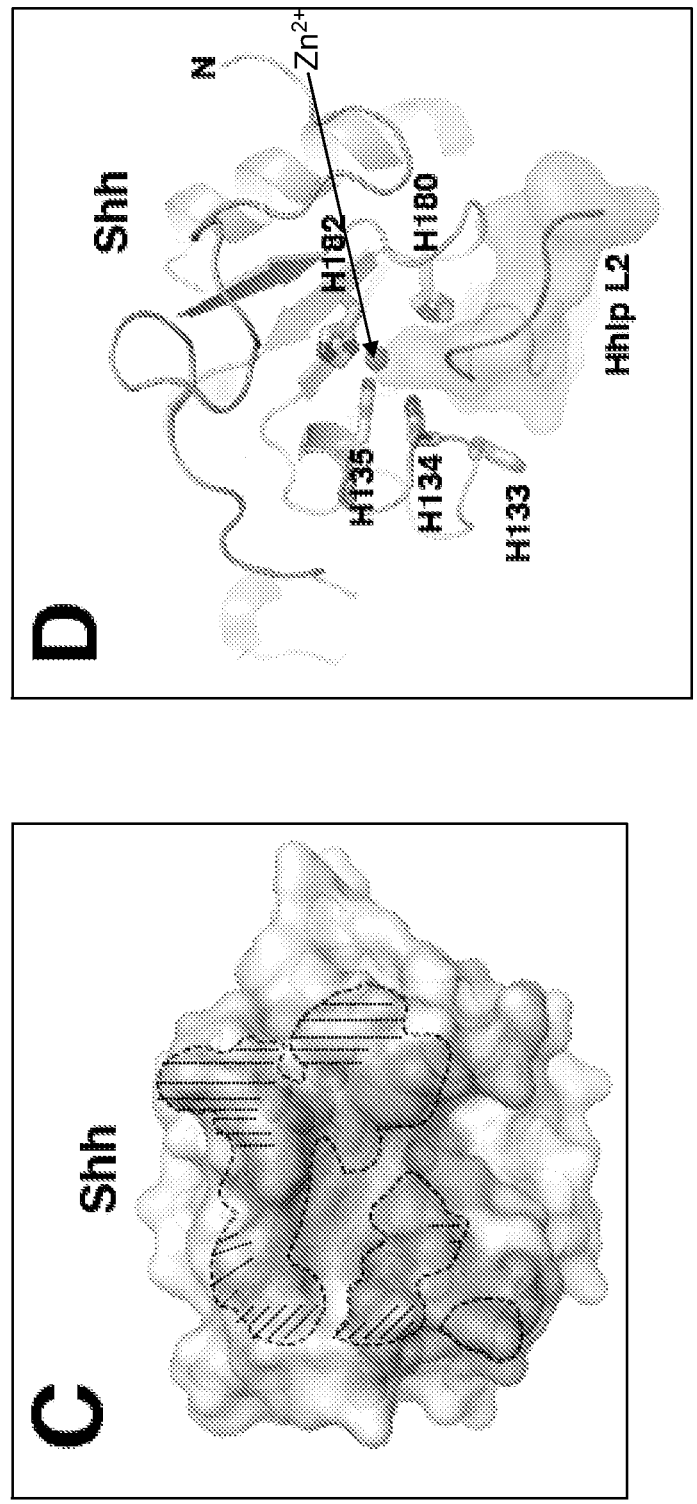
Figure 15:
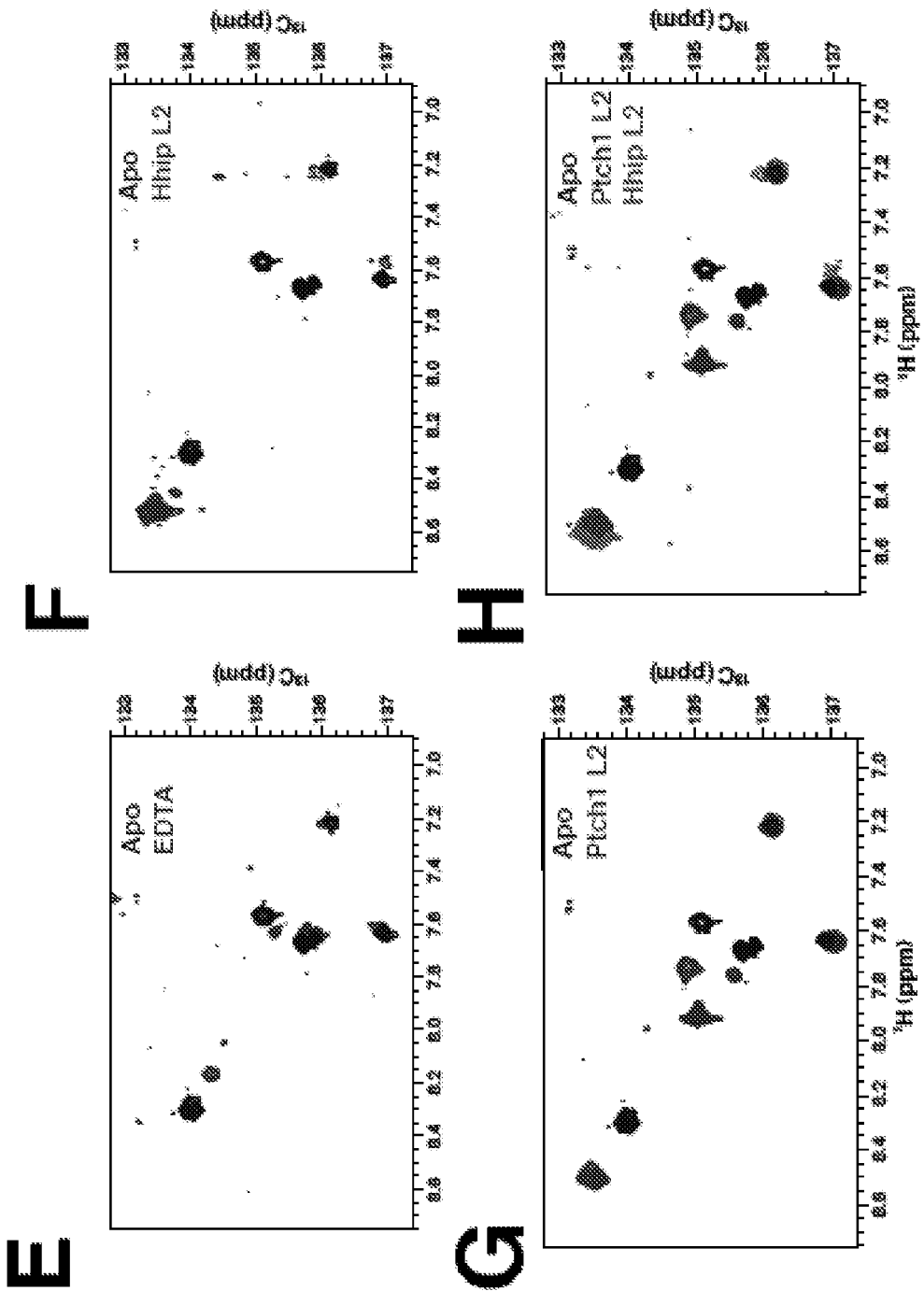
Figure 15:
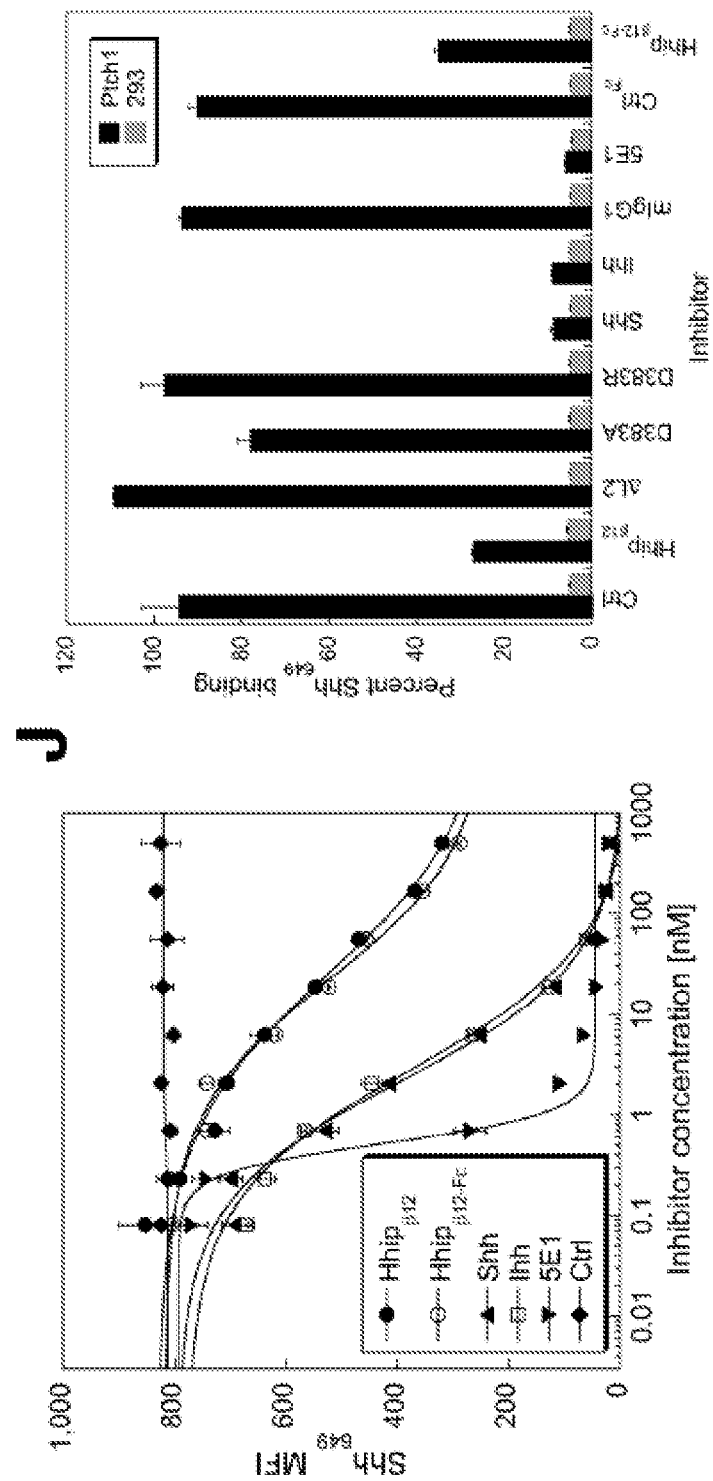

Indeed both Hhip1$_{β12}$ and Hhip1$_{β12}$-FC inhibit Ptch1-specific Shh cell binding in a dose-dependent manner (FIGS. 15I and 15J). In contrast, mutants that do not bind to Shh (Table 6), such as HhipΔL2 or Hhip1$_{β12}$ D383R, and His$_6$-(SEQ ID NO: 87) or Fc-tagged controls show no inhibition (FIG. 15J). The high affinity neutralizing anti-Shh monoclonal antibody 5E134 also competes Shh binding to Ptch1 (FIGS. 15I and 15J) as well as to Hhip1$_{β12}$ (FIG. 15). Moreover, the 5E1 epitope on Shh partially overlaps with the Hhip binding site (FIG. 14). Thus, since the Hhip1$_{β12}$, Ptch1 and 5E1 binding sites overlap, this further confirms that Ptch1 and Hhip compete for Shh and indicates that they either share a common binding site or have binding sites in close proximity such that steric hindrance results in competition.

Example 8

Hhip1$_{β12}$ Binding to Shh Differs from Ihog Interaction with *Drosophila* Hh

The interaction observed between Hhip1$_{β12}$ and Shh differs from that of *Drosophila* Hh and Ihog (McLellan, J. S. et al. (2006) *Proc. Natl. Acad. Sci. USA* 103:17208-17213), the only other Hh-receptor complex structure available to date. The two complexes differ both in their types and location of intermolecular interactions. The Ihog-Hh complex requires heparin, which not only bridges the two binding partners, but also facilitates Ihog dimerization. In contrast, the Hip-Shh interaction is heparin-independent and the presence of heparin, at least in vitro, does not lead to the formation of higher order Hhip oligomers (data not shown).

Despite the structural homology between *Drosophila* Hh and Shh, Ihog and Hhip1$_{β12}$ bind to distinct surfaces on these ligands. Hhip1$_{β12}$ binds Shh at its pseudo-active site whereas Ihog binds to a surface localized to the side of the molecule around the second helix (FIG. 5A). Moreover, the structural elements of Ihog and Hhip1$_{β12}$ responsible for ligand binding are fundamentally different. While Ihog uses one of its fibronectin type III (FNIII) domains to bind *Drosophila* Hh, the Hhip1$_{β12}$β-propeller mediates interactions with Shh. The two mammalian homologs of Ihog, Cdon and Boc, have been suggested to bind Shh in an Ihog-like manner (Yao, S. et al. (2006) *Cell* 125:343-357), which does not involve the $Zn^{2+}$-containing groove, thereby leaving this surface available to interact with Hhip1. Although Hhip1 and Ihog have distinct binding sites on Shh and Hh, respectively (FIG. 5A), superposition of the two complexes reveals adverse steric interactions of the FNIII domain with Hhip1 that occur away from the binding site. This suggests that either Hhip1 and Cdon/Boc cannot bind simultaneously to Shh or if they can, that Cdon/Boc do not bind Shh in an Ihog-like manner (vide infra).

The crucial role of Hh signaling in development, disease and cancer clearly illustrates the need for tight regulation. A number of plasma membrane-associated receptors are involved in relaying the Hh signal. To better understand the mechanism by which Hhip1 inhibits Shh signaling, we determined the structure of the complex between Hhip1$_{β12}$ and Shh, which led to several important and unexpected findings. First, the $Zn^{2+}$-containing groove in the pseudo-active site of Shh does indeed play a critical biochemical and biological role. Hhip1 utilizes this site to regulate the biological activity of Shh. Second, binding of Shh to a Ptch peptide, homologous to the Hhip1 L2 loop, suggests that Hhip1 and Ptch share a common binding mode to Hh homologs and strengthens the notion that Hhip1 acts as a competitive decoy receptor for Ptch. Finally, other Shh receptors such as Cdon/Boc can bind to the Hip-Shh complex, which permits us to begin putting the biological function of these proteins into a structural context. We propose that Cdon/Boc act as co-receptors for Shh, which leads to either signaling or inhibition of the pathway.

Here we show that a soluble fragment of Hhip1 (Hip$_{\beta12}$) that tightly binds Shh is a potent inhibitor of Hh signaling. While most reported Hh signaling inhibitors are small molecules that bind to Smo (Kiselyov et al. (2007) *Expert Opin. Ther. Targets* 11:1087-1101), the monoclonal antibody 5E1 remains the only potent pathway inhibitor that binds Hh ligands (Ericson et al. (1996) *Cell* 87:661-663). The critical interactions of Hhip1 with the Shh pseudo-active site can be captured by a peptide derived from its L2 loop as well as a peptide from Ptch. Thus antibodies, peptides or small molecules that bind with high affinity to the Shh pseudo-active site should all inhibit Hh signaling. Antibodies directed towards the Shh binding site on Ptch may do the same. This opens up several new opportunities to design novel antagonists of Hh signaling for use in cell biology and therapeutic areas.

Example 9

Ptch Binding to Shh

Mapping the Hhip1$_{\beta12}$ and Ihog binding sites on Shh and *Drosophila* Hh shows there are at least two distinct binding sites between surface receptors and Hh homologs (FIG. 5A). Ptch interactions with Shh have been defined by affinity and activity of Shh surface mutants (Fuse, N. et al. (1999) *Proc. Natl. Acad. Sci. USA* 96: 10992-10999; Pepinsky, R. B. et al. (2000) *J. Biol. Chem.* 275:10995-11001) (FIG. 5A, right panel). Since Cdon/Boc directly binds to Shh and enhances signaling through Ptch (Tenzen, T. et al. (2006) Dev. Cell 10: 647-56; Yao, S. et al. (2006) *Cell* 125:343-357), Shh mutants that abrogate Cdon/Boc binding may have indirect consequences on Ptch interaction with Shh and downstream signaling. In order to determine candidate regions of Ptch that might contact Shh, we looked for sequence similarities between Ptch and Hhip1, as well as between Ptch and Ihog. This analysis identified a stretch of residues in the second ectodomain of Ptch, between transmembrane helices 7 and 8, which had striking sequence similarity with the Hhip1$_{\beta12}$ L2 loop, thereby suggesting the presence of a similar loop in Ptch (FIG. 5B). Asp or Glu residues occupy position 0, except in *C. elegans* where Ser is found. In all cases, Gly is found at position 1 and Thr is the predominant residue in the −8 position. Moreover, the overwhelming presence of hydrophobic residues at positions −7, −4, −1 and 2 is consistent with a role in stabilizing an L2-like loop. In agreement with our analysis, removal of the entire extracellular domain between transmembrane helices 7 and 8 of Ptch results in a loss of Shh binding, while conserving the ability to repress Smo (Briscoe et al. (2001) *Mol. Cell.* 7:1279-1291; Taipale et al. (2002) *Nature* 418:892-897).

To explore further, we synthesized disulfide-containing cyclic peptides corresponding to the Hhip1$_{\beta12}$ and Ptch L2 loops and characterized their interactions with Shh using NMR spectroscopy. Briefly, $^{15}$N-labeled Shh was prepared the same way as the native protein with $^{15}$NH$_4$Cl-supplemented M9 media. $^1$H, $^{15}$N-HSQC spectra were recorded with 90 μM $^{15}$N-Shh in PBS buffer supplemented with 10% (v/v) D$_2$O, at 32° C. on Bruker DRX600 MHZ spectrometer equipped with 5 mm inverse triple-resonance cryoprobe. The peptide studies were done in the presence of disulfide-containing cyclic peptides for Ptch L2 (GCQLTKQRLVDADGI-INPCG) (SEQ ID NO:53) and Hhip1$_{\beta12}$ L2 (GCGMITLD-DMEEMDGLSDFCG) (SEQ ID NO:54) peptide, both unlabeled at 2 mM.

The addition of either peptide resulted in significant changes to the $^{15}$N, $^1$H HSQC spectra of Shh (FIGS. 5D and E), indicative of peptide binding. The similarity of the HSQC fingerprint between the two complexes suggests that the Ptch L2 peptide indeed binds Shh in a manner similar to that of the Hhip1$_{\beta12}$ L2 peptide.

In a competition assay, a peptide derived from the Hhip1$_{\beta12}$ L2 loop competed with Hip$_{\beta1}$ for Shh binding. Briefly, 96-well Nunc-Immuno MaxiSorp plates (Nalge Nunc International) were coated with 100 μl of anti-Flag M2 antibody (Sigma) at 5 μg/ml in 50 mM sodium carbonate buffer pH 9.6 at 4° C. overnight. Plates were blocked and washed as described for Shh competition ELISA followed by incubation with 100 μL of Shh-Flag at 50 μg/ml for 1 h. After plate washing a serial dilution of Hip-L2 peptide (GDGMITLD-DMEEMDGLSDFTG) (SEQ ID NO:46) starting at 1.2 mM (1:3 dilution) containing 800 nM Hhip1$_{\beta12}$ in a final volume of 100 μL was added to the wells to compete for binding to Shh-Flag. After incubation for 1 hr, wells were washed and incubated with anti-His-HRP conjugate (Qiagen, 1:2000 dilution) in blocking buffer. Plate was developed and the data were fit to a 4-parameter equation and the IC$_{50}$ calculated as described above; assays were carried out in triplicate.

Figure 5C:
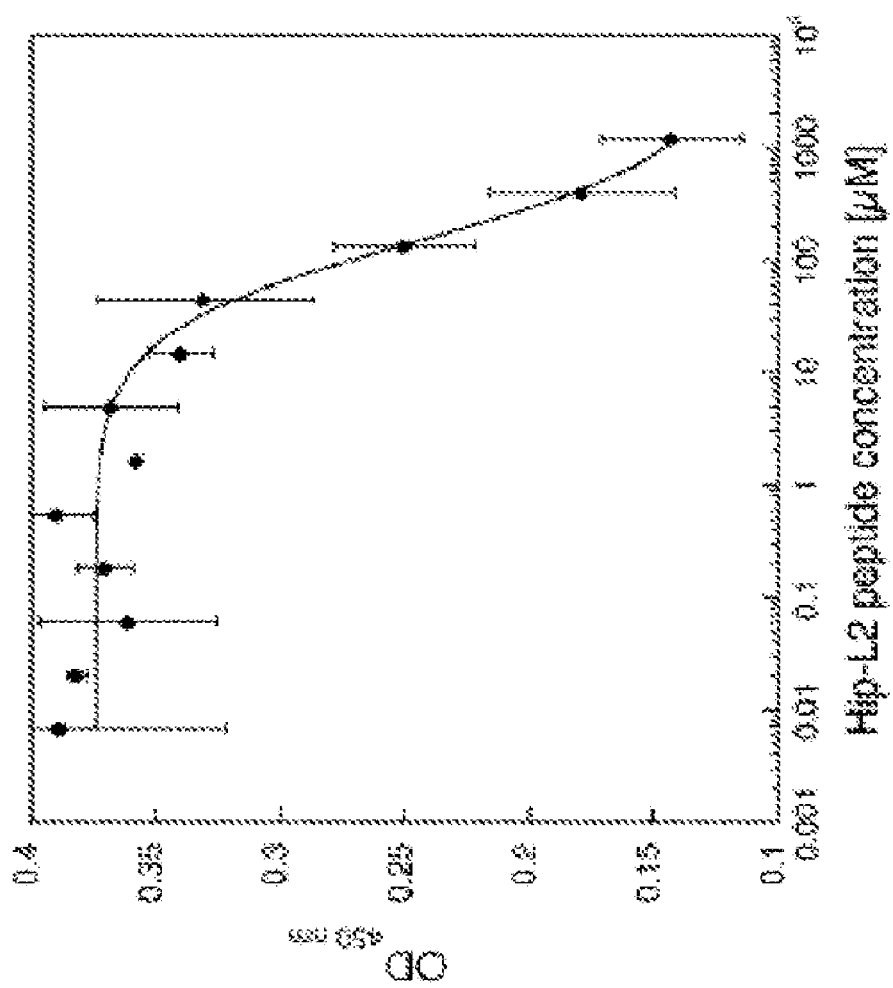
Figure 5:
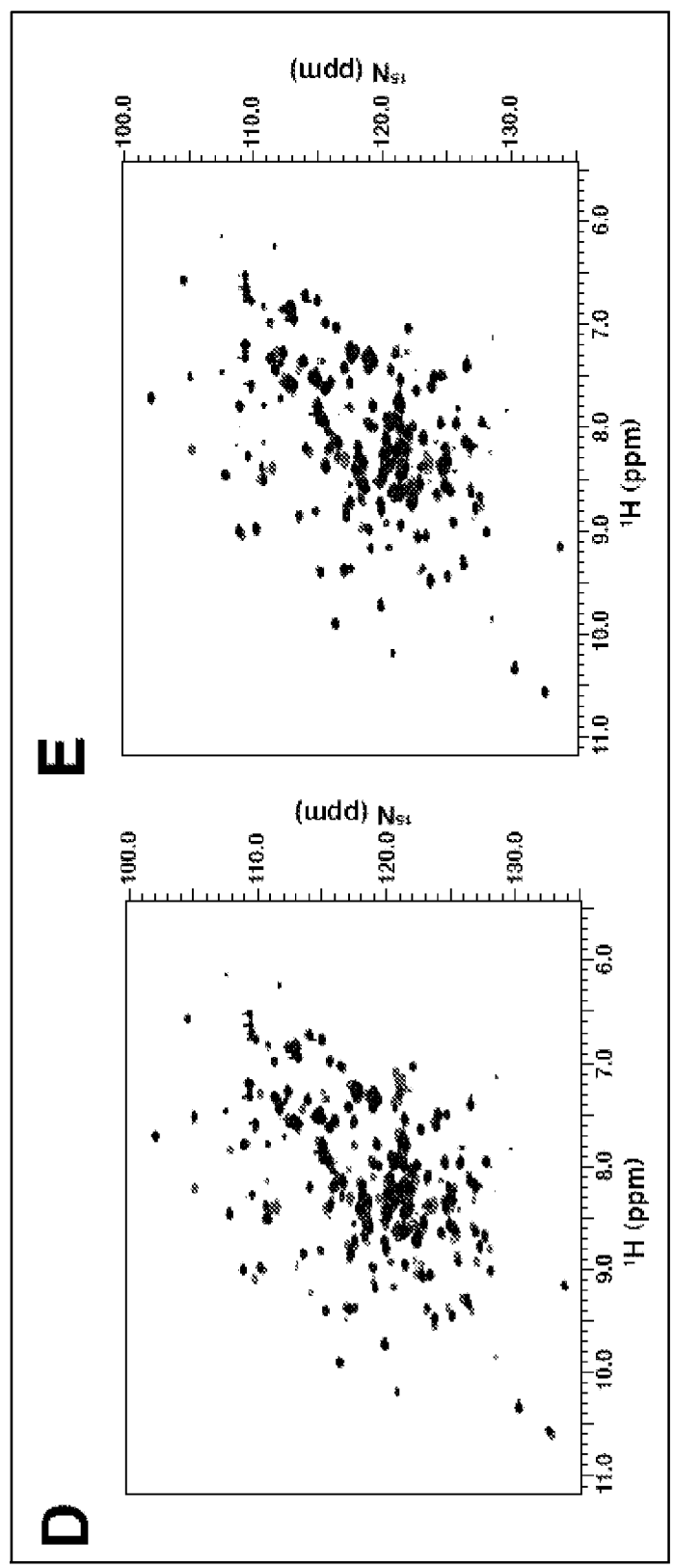

The peptide derived from the Hhip1$_{\beta12}$ L2 loop competed with Hip$_{\beta1}$ for Shh binding with an IC$_{50}$ of 150 μM (FIG. 5C), consistent with the notion that the peptide binds the same region on Shh as Hhip1. The Ptch L2-derived peptide was of lower affinity and thus unable to compete with Hip$_{\beta1}$ for Shh binding. Due to affinity and solubility limitations of these peptides, we were unable to test their effect on Shh signaling in the cell-based Gli-luciferase assays. Taken together, (i) the sequence similarity between the Hhip1$_{\beta12}$ L2 and Ptch peptides, (ii) the ability of the Hhip1$_{\beta12}$ L2 peptide to compete with Hip$_{\beta1}$ for Shh binding, and (iii) the similarity in the Shh HSQC spectra in the presence of both peptides suggests that Ptch may bind Shh at its pseudo-active site, thus providing us with a "patch for Patched." We propose a primary role for Hhip1 in Hh signaling as an inhibitory structural decoy receptor for Hh ligands (FIG. 12).

Example 10

Role of Cdon in Hhip1$_{\beta12}$ Interactions with Shh

Recent studies have shown that Cdon/Boc enhance Shh signaling through Ptch and suggested the possible existence of a multi-component complex between Hh homologs, Cdon/Boc (or Ihog in *Drosophila*) and Ptch (Tenzen, T. et al. (2006) *Dev. Cell* 10:647-56; Yao, S. et al. (2006) Cell 125: 343-57). The binding site on Cdon/Boc for Shh residues withion the third (membrane proximal) FNIII domain (Tenzen et al. (2006) *Dev. Cell* 10:647-56), which shares 98.0% sequence identity between human and murine proteins. In order to evaluate whether Cdon/Boc could play a minor role with Shh and Hhip1, we examined the ability of recombinant Cdon to interact with the Shh-Hhip1$_{\beta12}$ complex. A competition binding assay revealed that a fragment of murine Cdon containing its 3 FNIII domains fused to thioredoxin (mCdon$_{FN1-3}$) does not compete with Hhip1 for binding to Shh (data not shown).

In order to find a possible binding site for Cdon/Boc (or other interactors in vivo), we mapped the sequence conservation among Shh and Hhip1 orthologs. Sequence analysis revealed a highly-conserved acidic area on the surface of the Shh-Hhip1$_{\beta12}$ complex (FIG. 12B). We propose that this region contains a potential interaction site for additional signaling binding partners such as Cdon/Boc.

Figure 6:
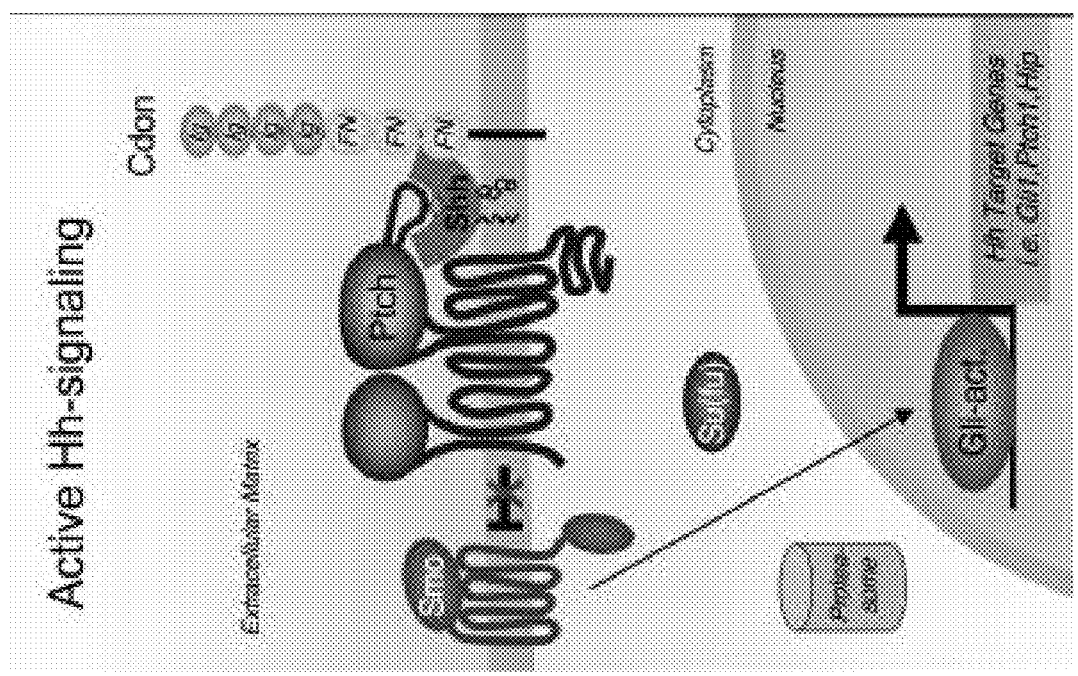
FIG. 6 shows the model of Shh-receptor complexes that lead to pathway regulation. When the Hh pathway is active, membrane-bound Shh forms a multimeric complex with Cdon and Ptch that relieves inhibition of Smo. This leads to translocation of the active form of Gli to the nucleus initiating transcription of Hh target genes. Ptch binding to Shh will likely involves interaction between the Ptch L2-equivalent loop and the Shh $Zn^{2+}$-containing groove.
Figure 7:
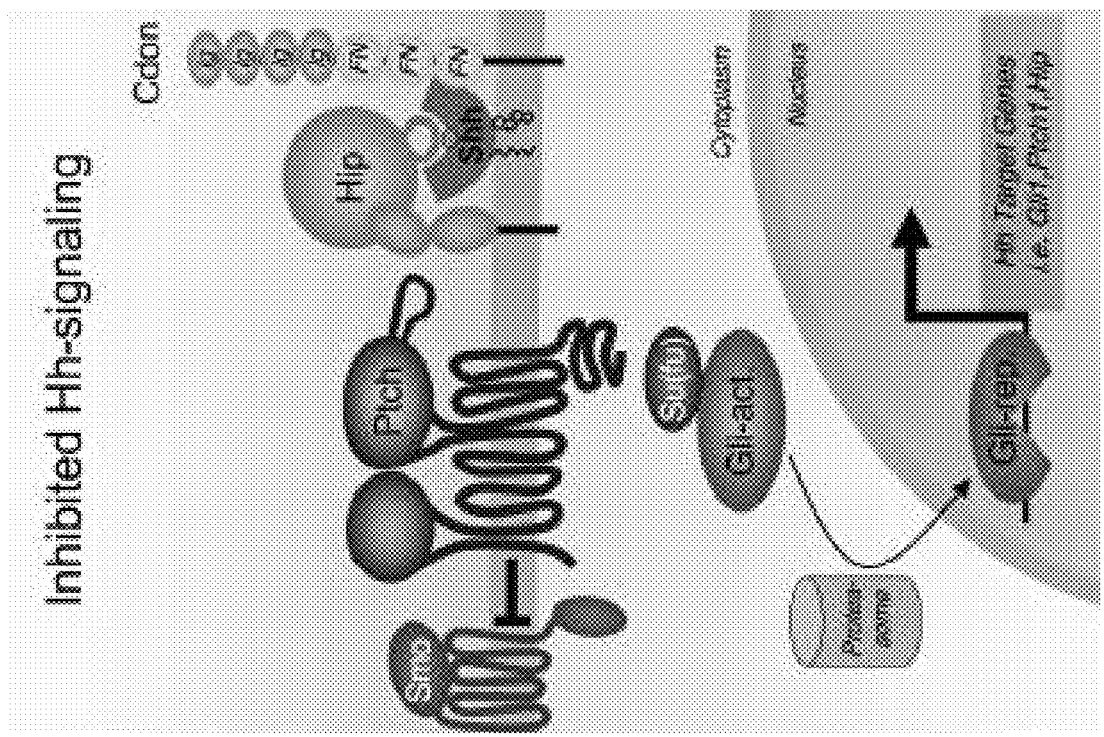
FIG. 7 shows the same pathway as FIG. 6 except when Hh signaling is inhibited by Hhip1, which acts as a structural decoy receptor for Ptch by occupying the $Zn^{2+}$-containing groove on Shh. Hhip1, Cdon and Shh form a stable ternary complex leaving Ptch to repress Smo and inhibit signaling. Consequently, Gli is processed into a transcriptional repressor by the proteasome, resulting in inhibition of Hh target gene transcription. FN and Ig stand for the fibronectin type-III (FNIII) and Ig-like domains of Cdon, respectively.

Based on our structures and binding data discussed above, we propose the following simple model for Hip/Ptch regulation of the Hh pathway (FIGS. 6 and 7). Lipid-modified Shh anchored in the cell membrane first binds to Cdon/Boc. Depending upon the cellular milieu, the Shh-Cdon/Boc complex could then further interact with either Ptch or Hhip1. Complex formation of Shh with Ptch would stimulate Hh signaling (FIG. 6), while complex formation with Hhip1 would sequester Shh and inhibit the pathway (FIG. 7). This suggests a primary role for Hhip1 in Hh signaling as an inhibitory structural decoy receptor for Ptch.

Genetic data on Hh and other Hh family members highlights the importance of the Shh pseudo-active site groove and the $Ca^{2+}$ binding site. These mutations can have a profound effect, although it is unclear for most of them whether this is due to impaired interactions with Ptch1 and/or with modulatory receptors. For instance, deletion of E176-K178, which contributes to one wall of the pseudo-active site groove, is associated with microcephaly and a partial corpus collosum.

Prophetic Examples

Example 11

Expression of Hhip1$_{\beta12}$ in *E. coli*

This example illustrates preparation of an unglycosylated form of Hhip1$_{\beta12}$ by recombinant expression in *E. coli*.

The DNA sequence encoding Hhip1$_{\beta12}$ is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., (1977) *Gene*, 2:95) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the Hhip1$_{\beta12}$ coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on After culturing the cells for several more hours, the cells can be harvested by centrifugation. The cell pellet obtained by the centrifugation can be solubilized using various agents known in the art, and the solubilized Hhip1$_{\beta12}$ protein can then be purified using a metal chelating column under conditions that allow tight binding of the protein.

Hhip1$_{\beta12}$ may be expressed in *E. coli* in a poly-His tagged form, using the following procedure. The DNA encoding Hhip1$_{\beta12}$ is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) lon galE rpoHts(htpRts) clpP(lacIq). Transformants are first grown in LB containing 50 mg/ml carbenicillin at 30° C. with shaking until an $OD_{600}$ of 3-5 is reached. Cultures are then diluted 50-100 fold into CRAP media (prepared by mixing 3.57 g $(NH_4)_2SO_4$, 0.71 g sodium citrate.$2H_2O$, 1.07 g KCl, 5.36 g Difco yeast extract, 5.36 g Sheffield hycase SF in 500 ml water, as well as 110 mM MPOS, pH 7.3, 0.55% (w/v) glucose and 7 mM MgSO4) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1 M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded Hhip1 polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Example 12

Expression of $Hhip1_{\beta12}$ in Mammalian Cell

This example illustrates preparation of a potentially glycosylated form of $Hhip1_{\beta12}$ by recombinant expression in mammalian cells.

The vector, pRK5 (see EP 307,247, published Mar. 15, 1989), is employed as the expression vector. Optionally, a $Hhip1_{\beta12}$ construct DNA is ligated into pRK5 with selected restriction enzymes to allow insertion of the $Hhip1_{\beta12}$ DNA using ligation methods such as described in Sambrook et al., supra.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-$Hhip1_{\beta12}$ DNA is mixed with about 1 μg DNA encoding the VA RNA gene (Thimmappaya et al. (1982) *Cell* 31:543) and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of $Hhip1_{\beta12}$ polypeptide. The cultures containing transfected cells may undergo further incubation (in serum free medium) and the medium is tested in selected bioassays.

In an alternative technique, a $Hhip1_{\beta12}$ construct may be introduced into 293 cells transiently using the dextran sulfate method described by Somparyrac et al. (1981) *Proc. Natl. Acad. Sci. USA* 12:7575. The 293 cells are grown to maximal density in a spinner flask and 700 μg pRK5-$Hhip1_{\beta12}$ DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed $Hhip1_{\beta12}$ can then be concentrated and purified by any selected method, such as dialysis and/or column chromatography.

In another embodiment, $Hhip1_{\beta12}$ can be expressed in CHO cells. The pRK5-$Hhip1_{\beta12}$ can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of a $Hhip1_{\beta12}$ polypeptide, the culture medium may be replaced with serum free medium. Preferably, the cultures are incubated for about 6 days, and then the conditioned medium is harvested. The medium containing the expressed $Hhip1_{\beta12}$ can then be concentrated and purified by any selected method.

An epitope-tagged $Hhip1_{\beta12}$ polypeptide may also be expressed in host CHO cells. The $Hhip1_{\beta12}$ construct may be subcloned out of the pRK5 vector. The subclone insert can undergo PCR to fuse in frame with a selected epitope tag such as a poly-his tag into a Baculovirus expression vector. The poly-his tagged $Hhip1_{\beta12}$ insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged $Hhip1_{\beta12}$ can then be concentrated and purified by any selected method, such as by $Ni^{2+}$-chelate affinity chromatography.

A $Hhip1_{\beta12}$ construct may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g., extracellular domains) of the respective proteins are fused to an IgG1 constant region sequence containing the hinge, $CH_2$ and CH2 domains and/or is a poly-His tagged form.

Following PCR amplification, the respective DNAs are subcloned in a CHO expression vector using standard techniques as described in Ausubel et al., CURRENT PROTOCOLS OF MOLECULAR BIOLOGY, Unit 3.16, John Wiley and Sons (1997). CHO expression vectors are constructed to have compatible restriction sites 5' and 3' of the DNA of interest to allow the convenient shuttling of cDNA's. The vector used for expression in CHO cells is as described in Lucas et al. (1996) *Nucl. Acids Res.* 24:9 1774-1779, and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents SUPERFECT® (Quiagen), DOSPER® or FUGENE® (Boehringer Mannheim). The cells are grown as described in Lucas et al., supra. Approximately $3 \times 10^7$ cells are frozen in an ampule for further growth and production as described below.

The ampules containing the plasmid DNA are thawed by placement into water bath and mixed by vortexing. The contents are pipetted into a centrifuge tube containing 10 ml of media and centrifuged at 1000 rpm for 5 minutes. The supernatant is aspirated and the cells are resuspended in 10 ml of selective media (0.2 μm filtered PS20 with 5% 0.2 μm diafiltered fetal bovine serum). The cells are then aliquoted into a 100 ml spinner containing 90 ml of selective media. After 1-2 days, the cells are transferred into a 250 ml spinner filled with 150 ml selective growth medium and incubated at 37° C. After another 2-3 days, 250 ml, 500 ml and 2000 ml spinners are seeded with $3 \times 10^5$ cells/ml. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2 \times 10^6$ cells/ml. On day 0, the cell number pH ie determined. On day 1, the spinner is sampled and sparging with filtered air is commenced. On day 2, the spinner is sampled, the temperature shifted to 33° C., and 30 ml of 500 g/L glucose and 0.6 ml of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 µm filter. The filtrate is either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 13

Expression of Hhip1$_{\beta 12}$ in Yeast

The following method describes recombinant expression of a Hhip1$_{\beta 12}$ construct in yeast.

First, yeast expression vectors are constructed for intracellular production or secretion of Hhip1$_{\beta 12}$ from the ADH2/GAPDH promoter. DNA encoding a Hhip1$_{\beta 12}$ polypeptide and the promoter is inserted into suitable restriction enzyme sites in the selected plasmid to direct intracellular expression of Hhip1. For secretion, DNA encoding Hhip1$_{\beta 12}$ can be cloned into the selected plasmid, together with DNA encoding the ADH2/GAPDH promoter, a native Hhip1$_{\beta 12}$ signal peptide or other mammalian signal peptide, or, for example, a yeast alpha-factor or invertase secretory signal/leader sequence, and linker sequences (if needed) for expression of Hip.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant Hhip1$_{\beta 12}$ can subsequently be isolated and purified by removing the yeast cells from the fermentation medium by centrifugation and then concentrating the medium using selected cartridge filters. The concentrate containing Hhip1$_{\beta 12}$ may further be purified using selected column chromatography resins.

Example 14

Preparation of Antibodies that Bind Hhip1$_{\beta 12}$

This example illustrates preparation of monoclonal antibodies which can specifically bind Hip.

Techniques for producing the monoclonal antibodies are known in the art and are described, for instance, in Goding, supra Immunogens that may be employed include purified Hhip1$_{\beta 12}$ polypeptides, fusion proteins containing Hhip1$_{\beta 12}$ polypeptides, and cells expressing recombinant Hhip1$_{\beta 12}$ on the cell surface. Selection of the immunogen can be made by the skilled artisan without undue experimentation.

Mice, such as Balb/c, are immunized with the Hhip1$_{\beta 12}$ immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-Hhip1$_{\beta 12}$ antibodies.

After a suitable antibody titer has been detected, the animals "positive" for antibodies can be injected with a final intravenous injection of Hhip1. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against Hhip1. Determination of "positive" hybridoma cells secreting the desired monoclonal antibodies against Hhip1$_{\beta 12}$ is within the skill in the art.

The positive hybridoma cells can be injected intraperitoneally into syngeneic Balb/c mice to produce ascites containing the anti-Hhip1$_{\beta 12}$ monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 15

Preparation of Toxin-Conjugated Antibodies that Bind Hhip1$_{\beta 12}$

The use of antibody-drug conjugates (ADC), i.e. immunoconjugates, for the local delivery of cytotoxic or cytostatic agents, i.e. drugs to kill or inhibit tumor cells in the treatment of cancer (Payne (2003) *Cancer Cell* 3:207-212; Syrigos and Epenetos (1999) *Anticancer Research* 19:605-614; Niculescu-Duvaz and Springer (1997) *Adv. Drug Del. Rev.* 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet (Mar. 15, 1986) pp. 603-05; Thorpe, (1985) "Antibody Carriers of Cytotoxic Agents in Cancer Therapy: A Review," in MONOCLONAL ANTIBODIES '84: BIOLOGICAL AND CLINICAL APPLICATIONS, Pinchera et al. (eds.), pp. 475-506). Maximal efficacy with minimal toxicity is sought thereby. Efforts to design and refine ADC have focused on the selectivity of monoclonal antibodies (mAbs) as well as drug-linking and drug-releasing properties. Both polyclonal antibodies and monoclonal antibodies have been reported as useful in these strategies (Rowland et al. (1986) *Cancer Immunol. Immunother.* 21:183-87). The drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al. (2000) *J. of the Nat. Cancer Inst.* 92(19): 1573-1581; Mandler et al. (2000) *Bioorganic & Med. Chem. Letters* 10: 1025-1028; Mandler et al. (2002) *Bioconjugate Chem.* 13:786-791), maytansinoids (EP 1391213; Liu et al., (1996) *Proc. Natl. Acad. Sci. USA* 93:8618-8623), and calicheamicin (Lode et al. (1998) *Cancer Res.* 58:2928; Hinman et al. (1993) *Cancer Res.* 53:3336-3342).

In the antibody drug conjugates (ADC) of the invention, an antibody (Ab) is conjugated to one or more drug moieties (D), e.g. about 1 to about 20 drug moieties per antibody, through a linker (L). The ADC having the formula: Ab-(L-D)p may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl)cyclohexane-1 carboxylate ("SMCC"), and N-Succinimidyl (4-iodo-acetyl) aminobenzoate ("SIAB"). Additional linker components are known in the art and some are described herein.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, hydroxyl, hydrazide, oxime, hydrazine, thiosemicarbazone, hydrazine carboxylate, and arylhydrazide groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates of the invention may also be produced by modification of the antibody to introduce electrophilic moieties, which can react with nucleophilic subsituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such aldehyde can be reacted with a drug moiety or linker nucleophile.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Specific techniques for producing antibody-drug conjugates by linking toxins to purified antibodies are well known and routinely employed in the art. For example, conjugation of a purified monoclonal antibody to the toxin DM1 may be accomplished as follows. Purified antibody is derivatized with N-succinimidyl-4-(2-pyridylthio) pentanoate to introduce dithiopyridyl groups. Antibody (376.0 mg, 8 mg/ml) in 44.7 ml of 50 mM potassium phosphate buffer (pH 6.5) containing NaCl (50 mM) and EDTA (1 mM) is treated with SPP (5.3 molar equivalents in 2.3 ml ethanol). After incubation for 90 minutes under argon at ambient temperature, the reaction mixture is gel filtered through a Sephadex® G25 column equilibrated with 35 mM sodium citrate, 154 mM NaCl and 2 mM EDTA. Antibody containing fractions are then pooled and assayed. Antibody-SPP-Py (337.0 mg with releasable 2-thiopyridine groups) is diluted with the above 35 mM sodium citrate buffer, pH 6.5, to a final concentration of 2.5 mg/ml. DM1 (1.7 equivalents, 16.1 mols) in 3.0 mM dimethylacetamide (DMA, 3% v/v in the final reaction mixture) is then added to the antibody solution. The reaction is allowed to proceed at ambient temperature under argon for 20 hours. The reaction is loaded on a Sephacryl® S300 gel filtration column (5.0 cm.times.90.0 cm, 1.77 L) equilibrated with 35 mM sodium citrate, 154 mM NaCl, pH 6.5. The flow rate is 5.0 ml/min and 65 fractions (20.0 ml each) are collected. Fractions are pooled and assayed, wherein the number of DM1 drug molecules linked per antibody molecule (p') is determined by measuring the absorbance at 252 nm and 280 nm.

For illustrative purposes, conjugation of a purified monoclonal antibody to the toxin DM1 may also be accomplished as follows. Purified antibody is derivatized with (Succinimidyl 4-(N-maleimidomethyl)cyclohexane-1-carboxylate (SMCC, Pierce Biotechnology, Inc) to introduce the SMCC linker. The antibody is treated at 20 mg/ml in 50 mM potassium phosphate/50 mM sodium chloride/2 mM EDTA, pH 6.5 with 7.5 molar equivalents of SMCC (20 mM in DMSO, 6.7 mg/ml). After stirring for 2 hours under argon at ambient temperature, the reaction mixture is filtered through a Sephadex®G25 column equilibrated with 50 mM potassium phosphate/50 mM sodium chloride/2 mM EDTA, pH 6.5. Antibody containing fractions are pooled and assayed. Antibody-SMCC is then diluted with 50 mM potassium phosphate/50 mM sodium chloride/2 mM EDTA, pH 6.5, to a final concentration of 10 mg/ml, and reacted with a 10 mM solution of DM1 (1.7 equivalents assuming 5 SMCC/antibody, 7.37 mg/ml) in dimethylacetamide. The reaction is stirred at ambient temperature under argon 16.5 hours. The conjugation reaction mixture is then filtered through a Sephadex® G25 gel filtration column (1.5.times.4.9 cm) with 1.times.PBS at pH 6.5. The DM1/antibody ratio (p) is then measured by the absorbance at 252 nm and at 280 nm.

Moreover, a free cysteine on an antibody of choice may be modified by the bis-maleimido reagent BM(PEO)4 (Pierce Chemical), leaving an unreacted maleimido group on the surface of the antibody. This may be accomplished by dissolving BM(PEO)4 in a 50% ethanol/water mixture to a concentration of 10 mM and adding a tenfold molar excess to a solution containing the antibody in phosphate buffered saline at a concentration of approximately 1.6 mg/ml (10 micromolar) and allowing it to react for 1 hour. Excess BM (PEO)4 is removed by gel filtration in 30 mM citrate, pH 6 with 150 mM NaCl buffer. An approximate 10 fold molar excess DM1 is dissolved in dimethyl acetamide (DMA) and added to the antibody-BMPEO intermediate. Dimethyl formamide (DMF) may also be employed to dissolve the drug moiety reagent. The reaction mixture is allowed to react overnight before gel filtration or dialysis into PBS to remove unreacted drug. Gel filtration on S200 columns in PBS is used to remove high molecular weight aggregates and furnish purified antibody-BMPEO-DM1 conjugate.

Cytotoxic drugs have typically been conjugated to antibodies through the often numerous lysine residues of the antibody. Conjugation through thiol groups present, or engineered into, the antibody of interest has also been accomplished. For example, cysteine residues have been introduced into proteins by genetic engineering techniques to form covalent attachment sites for ligands (Better et al. (1994) *J. Biol. Chem.* 13:9644-9650; Bernhard et al. (1994) *Bioconjugate Chem.* 5:126-132; Greenwood et al. (1994) *Therapeutic Immunol.* 1:247-255; Tu et al. (1999) *Proc. Natl. Acad. Sci. USA* 96:4862-4867; Kanno et al. (2000) *J. Biotechnology*, 76:207-214; Chmura et al. (2001) *Proc. Nat. Acad. Sci. USA* 98(15):8480-8484; U.S. Pat. No. 6,248,564). Once a free cysteine residue exists in the antibody of interest, toxins can be linked to that site. As an example, the drug linker reagents, maleimidocaproyl-monomethyl auristatin E (MMAE), i.e. MC-MMAE, maleimidocaproyl-monomethyl auristatin F (MMAF), i.e. MC-MMAF, MC-val-cit-PAB-MMAE or MC-val-cit-PAB-MMAF, dissolved in DMSO, is diluted in acetonitrile and water at known concentration, and added to chilled cysteine-derivatized antibody in phosphate buffered saline (PBS). After about one hour, an excess of maleimide is added to quench the reaction and cap any unreacted antibody thiol groups. The reaction mixture is concentrated by centrifugal ultrafiltration and the toxin conjugated antibody is purified and desalted by elution through G25 resin in PBS, filtered through 0.2 m filters under sterile conditions, and frozen for storage.

Additionally, anti-Hhip1$_{\beta 12}$ antibodies of the present invention may be conjugated to auristatin and dolostatin toxins (such as MMAE and MMAF) using the following technique. Antibody, dissolved in 500 mM sodium borate and 500 mM sodium chloride at pH 8.0 is treated with an excess of 100 mM dithiothreitol (DTT). After incubation at 37° C. for about 30 minutes, the buffer is exchanged by elution over Sephadex® G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm. The reduced antibody dissolved in PBS is chilled on ice.

The drug linker reagent, (1) maleimidocaproyl-monomethyl auristatin E (MMAE), i.e. MC-MMAE, (2) MC-MMAF, (3) MC-val-cit-PAB-MMAE, or (4) MC-val-cit-PAB-MMAF dissolved in DMSO, is diluted in acetonitrile and water at known concentration, and added to the chilled reduced antibody in PBS. After about one hour, an excess of maleimide is added to quench the reaction and cap any unreacted antibody thiol groups. The reaction mixture is concentrated by centrifugal ultrafiltration and the conjuagted antibody is purified and desalted by elution through G25 resin in PBS, filtered through 0.2 m filters under sterile conditions, and frozen for storage.

Example 16

Purification of Hhip1 polypeptides Using Specific Antibodies

Native or recombinant Hhip1 polypeptides may be purified by a variety of standard techniques in the art of protein purification. For example, pro-Hhip1$_{\beta 12}$ polypeptide, mature Hhip1$_{\beta 12}$ polypeptide, or pre-Hhip1 polypeptide is purified by immunoaffinity chromatography using antibodies specific for the Hhip1 polypeptide of interest. In general, an immunoaffinity column is constructed by covalently coupling the anti-Hhip1 polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of Hhip1 polypeptide by preparing a fraction from cells containing Hhip1 polypeptide in a soluble form. This preparation is derived by solubilization of the whole cell or of a subcellular fraction obtained via differential centrifugation by the addition of detergent or by other methods well known in the art. Alternatively, soluble Hhip1 polypeptide containing a signal sequence may be secreted in useful quantity into the medium in which the cells are grown.

A soluble $Hhip1_{\beta12}$ polypeptide-containing preparation is passed over the immunoaffinity column, and the column is washed under conditions that allow the preferential absorbance of Hhip1 polypeptide (e.g., high ionic strength buffers in the presence of detergent). Then, the column is eluted under conditions that disrupt antibody/Hhip1 polypeptide binding (e.g., a low pH buffer such as approximately pH 2-3, or a high concentration of a chaotrope such as urea or thiocyanate ion), and $Hhip1_{\beta12}$ polypeptide is collected.

The foregoing written specification is considered to be sufficient to enable one skilled in the art to practice the invention. The present invention is not to be limited in scope by the specific illustrations disclosed herein. Indeed, various modifications of the invention in addition to those shown and described herein will become apparent to those skilled in the art from the foregoing description and fall within the scope of the appended claims.

What is claimed is:

1. An isolated polypeptide comprising an amino acid sequence having at least 90% amino acid sequence identity to the amino acid sequence of SEQ ID NO: 13, wherein said isolated polypeptide does not comprise one or both of a frizzled domain having the amino acid sequence set forth in SEQ ID NO: 4 and an EGF2 domain having the amino acid sequence set forth in SEQ ID NO: 9; and wherein said polypeptide is capable of binding Shh polypeptide.

2. An isolated polypeptide having an amino acid sequence comprising the amino acid sequence of SEQ ID NO: 13, wherein said isolated polypeptide does not comprise one or both of a frizzled domain having the amino acid sequence set forth in SEQ ID NO: 4 and an EGF2 domain having the amino acid sequence set forth in SEQ ID NO: 9; and wherein said polypeptide is capable of binding Shh polypeptide.

3. A chimeric polypeptide comprising the polypeptide of claim 1 or 2 fused to a heterologous polypeptide.

4. A composition of matter comprising: (a) the polypeptide of claim 1; or (b) the polypeptide of claim 2; in combination with a pharmaceutically acceptable carrier.

5. An article of manufacture comprising: (a) a container; and (b) the composition of matter of claim 4 contained within said container.

6. The polypeptide of claim 1, wherein the polypeptide does not comprise a putative GPI signal sequence as set forth in SEQ ID NO: 10.

7. The polypeptide of claim 1, wherein the polypeptide does not comprise a putative frizzled domain as set forth in SEQ ID NO: 4.

8. The polypeptide of claim 1, wherein the polypeptide does not comprise an EGF2 domain as set forth in SEQ ID NO: 9.

9. The polypeptide of claim 8, wherein the polypeptide comprises the amino acid sequence SEQ ID NO: 13.

10. The polypeptide of claim 9, wherein the polypeptide consists of the amino acid sequence SEQ ID NO: 13.

11. The polypeptide of claim 2, wherein the polypeptide does not comprise a putative GPI signal sequence as set forth in SEQ ID NO: 10.

12. The polypeptide of claim 2, wherein the polypeptide does not comprise a putative frizzled domain as set forth in SEQ ID NO: 4.

13. The polypeptide of claim 2, wherein the polypeptide does not comprise an EGF2 domain as set forth in SEQ ID NO: 9.

14. A composition of matter comprising the chimeric polypeptide of claim 3; in combination with a pharmaceutically acceptable carrier.

15. The polypeptide of claim 7, wherein the polypeptide comprises the amino acid sequence SEQ ID NO: 12.

16. The polypeptide of claim 15, wherein the polypeptide consists of the amino acid sequence SEQ ID NO: 12.

* * * * *

SEQUENCE LISTING

```
<160> NUMBER OF SEQ ID NOS: 87

<210> SEQ ID NO 1
<211> LENGTH: 2680
<212> TYPE: DNA
<213> ORGANISM: Homo sapiens

<400> SEQUENCE: 1
gagaagctgc agccgccggc agaggagacc tcagcatcat ctagagccca gcgctggccc      60
tgcctccgcc tgccccgccg ccgccgtcgc cgtttctgtt cctgctactg tcccacctaa     120
acaactcccg ttacacggac aagtgaacat ctgtggctgt cctctccttt tcttcctcct     180
cttccaactc cttctcctcc tcccacttcc cagccgcagc agaaagcccc caacccaact     240
gacactggca caactgcaaa cggtgtcatc cgcacaactt tatctcgctc ctcgggctcc     300
cctaaggcat tggacccatc gccgcgtctt ttatttttg  caaagttgca tcgctgtaca     360 tattttgtc  cccgccacct ccctctgtct ctggagtgcc ctacagcccc gcaaactcct     420
cctggagctg cgccctagtg cccctgctgg gcagtggcgt tccccccat  cctcccgcgc     480 ccagcccctg ctgctctggg cagacgatgc tgaagatgct ctcctttaag ctgctgctgc     540
tggccgtggc tctgggcttc tttgaaggag atgctaagtt tggggaaaga aacgaaggga     600
gcggagcaag gaggagaagg tgcctgaatg ggaaccccccc gaagcgcctg aaaaggagag     660
acaggaggat gatgtcccag ctggagctgc tgagtggggg agagatgctg tgcggtggct     720
tctaccctcg gctgtcctgc tgcctgcgga gtgacagccc ggggctaggg cgcctggaga     780
ataagatatt ttctgttacc aacaacacag aatgtgggaa gttactggag gaaatcaaat     840
gtgcactttg ctctccacat tctcaaagcc tgttccactc acctgagaga gaagtcttgg     900
aaagagacct agtacttcct ctgctctgca aagactattg caaagaattc ttttacactt     960
gccgaggcca tattccaggt ttccttcaaa caactgcgga tgagttttgc ttttactatg    1020
caagaaaaga tggtgggttg tgctttccag attttccaag aaaacaagtc agaggaccag    1080
catctaacta cttggaccag atggaagaat atgacaaagt ggaagagatc agcagaaagc    1140
acaaacacaa ctgcttctgt attcaggagg ttgtgagtgg gctgcggcag cccgttggtg    1200
ccctgcatag tgggatggc  tcgcaacgtc tcttcattct ggaaaaagaa ggttatgtga    1260
```

| | | |
|---|---|---|
| agatacttac ccctgaagga gaaattttca aggagcctta tttggacatt cacaaacttg | 1320 | |
| ttcaaagtgg aataaaggga ggagatgaaa gaggactgct aagcctcgca ttccatccca | 1380 | |
| attacaagaa aaatggaaag ttgtatgtgt cctataccac caaccaagaa cggtgggcta | 1440 | |
| tcgggcctca tgaccacatt cttagggttg tggaatacac agtatccaga aaaaatccac | 1500 | |
| accaagttga tttgagaaca gccagagtct ttcttgaagt tgcagaactc cacagaaagc | 1560 | |
| atctgggagg acaactgctc tttggccctg acggcttttt gtacatcatt cttggtgatg | 1620 | |
| ggatgattac actggatgat atggaagaaa tggatgggtt aagtgatttc acaggctcag | 1680 | |
| tgctacggct ggatgtggac acagacatgt gcaacgtgcc ttattccata ccaaggagca | 1740 | |
| acccacactt caacagcacc aaccagcccc ccgaagtgtt tgctcatggg ctccacgatc | 1800 | |
| caggcagatg tgctgtggat agacatccca ctgatataaa catcaattta acgatactgt | 1860 | |
| gttcagactc caatggaaaa aacagatcat cagccagaat tctacagata ataaagggga | 1920 | |
| aagattatga aagtgagcca tcactttttag aattcaagcc attcagtaat ggtcctttgg | 1980 | |
| ttggtggatt tgtataccgg ggctgccagt cagaaagatt gtatggaagc tacgtgtttg | 2040 | |
| gagatcgtaa tgggaattc ctaactctcc agcaaagtcc tgtgacaaag cagtggcaag | 2100 | |
| aaaaaccact ctgtctcggc actagtgggt cctgtagagg ctacttttcc ggtcacatct | 2160 | |
| tgggatttgg agaagatgaa ctaggtgaag tttacatttt atcaagcagt aaaagtatga | 2220 | |
| cccagactca caatggaaaa ctctacaaaa ttgtagatcc caaaagacct ttaatgcctg | 2280 | |
| aggaatgcag agccacggta caacctgcac agacactgac ttcagagtgc tccaggctct | 2340 | |
| gtcgaaacgg ctactgcacc cccacgggaa agtgctgctg cagtccaggc tgggaggggg | 2400 | |
| acttctgcag aactgcaaaa tgtgagccag catgtcgtca tggaggtgtc tgtgttagac | 2460 | |
| cgaacaagtg cctctgtaaa aaaggatatc ttggtcctca atgtgaacaa gtggacagaa | 2520 | |
| acatccgcag agtgaccagg gcaggtattc ttgatcagat cattgacatg acatcttact | 2580 | |
| tgctggatct aacaagttac attgtatagt ttctgggact gtttgaatat tctattccaa | 2640 | |
| tgggcattta ttttttatcc tgtcattaaa aaaaaaaaa | 2680 | |

<210> SEQ ID NO 2
<211> LENGTH: 700
<212> TYPE: PRT
<213> ORGANISM: Homo sapiens

<400> SEQUENCE: 2

Met Leu Lys Met Leu Ser Phe Lys Leu Leu Leu Ala Val Ala Leu
1               5                   10                  15

Gly Phe Phe Glu Gly Asp Ala Lys Phe Gly Glu Arg Asn Gly Ser
                20                  25                  30

Gly Ala Arg Arg Arg Cys Leu Asn Gly Asn Pro Pro Lys Arg Leu
        35                  40                  45

Lys Arg Arg Asp Arg Arg Met Met Ser Gln Leu Glu Leu Ser Gly
    50                  55                  60

Gly Glu Met Leu Cys Gly Gly Phe Tyr Pro Arg Leu Ser Cys Cys Leu
65                  70                  75                  80

Arg Ser Asp Ser Pro Gly Leu Gly Arg Leu Glu Asn Lys Ile Phe Ser
                85                  90                  95

Val Thr Asn Asn Thr Glu Cys Gly Lys Leu Leu Glu Glu Ile Lys Cys
                100                 105                 110

Ala Leu Cys Ser Pro His Ser Gln Ser Leu Phe His Ser Pro Glu Arg
            115                 120                 125

-continued

Glu Val Leu Glu Arg Asp Leu Val Pro Leu Leu Cys Lys Asp Tyr
            130             135             140

Cys Lys Glu Phe Phe Tyr Thr Cys Arg Gly His Ile Pro Gly Phe Leu
145             150                 155                 160

Gln Thr Thr Ala Asp Glu Phe Cys Phe Tyr Tyr Ala Arg Lys Asp Gly
                165                 170                 175

Gly Leu Cys Phe Pro Asp Phe Pro Arg Lys Gln Val Arg Gly Pro Ala
                180                 185                 190

Ser Asn Tyr Leu Asp Gln Met Glu Glu Tyr Asp Lys Val Glu Glu Ile
                195                 200                 205

Ser Arg Lys His Lys His Asn Cys Phe Cys Ile Gln Glu Val Val Ser
                210                 215                 220

Gly Leu Arg Gln Pro Val Gly Ala Leu His Ser Gly Asp Gly Ser Gln
225                 230                 235                 240

Arg Leu Phe Ile Leu Glu Lys Glu Gly Tyr Val Lys Ile Leu Thr Pro
                245                 250                 255

Glu Gly Glu Ile Phe Lys Glu Pro Tyr Leu Asp Ile His Lys Leu Val
                260                 265                 270

Gln Ser Gly Ile Lys Gly Gly Asp Glu Arg Gly Leu Leu Ser Leu Ala
                275                 280                 285

Phe His Pro Asn Tyr Lys Lys Asn Gly Lys Leu Tyr Val Ser Tyr Thr
290                 295                 300

Thr Asn Gln Glu Arg Trp Ala Ile Gly Pro His Asp His Ile Leu Arg
305                 310                 315                 320

Val Val Glu Tyr Thr Val Ser Arg Lys Asn Pro His Gln Val Asp Leu
                325                 330                 335

Arg Thr Ala Arg Val Phe Leu Glu Val Ala Glu Leu His Arg Lys His
                340                 345                 350

Leu Gly Gly Gln Leu Leu Phe Gly Pro Asp Gly Phe Leu Tyr Ile Ile
                355                 360                 365

Leu Gly Asp Gly Met Ile Thr Leu Asp Asp Met Glu Glu Met Asp Gly
                370                 375                 380

Leu Ser Asp Phe Thr Gly Ser Val Leu Arg Leu Asp Val Asp Thr Asp
385                 390                 395                 400

Met Cys Asn Val Pro Tyr Ser Ile Pro Arg Ser Asn Pro His Phe Asn
                405                 410                 415

Ser Thr Asn Gln Pro Pro Glu Val Phe Ala His Gly Leu His Asp Pro
                420                 425                 430

Gly Arg Cys Ala Val Asp Arg His Pro Thr Asp Ile Asn Ile Asn Leu
                435                 440                 445

Thr Ile Leu Cys Ser Asp Ser Asn Gly Lys Asn Arg Ser Ser Ala Arg
                450                 455                 460

Ile Leu Gln Ile Ile Lys Gly Lys Asp Tyr Glu Ser Glu Pro Ser Leu
465                 470                 475                 480

Leu Glu Phe Lys Pro Phe Ser Asn Gly Pro Leu Val Gly Gly Phe Val
                485                 490                 495

Tyr Arg Gly Cys Gln Ser Glu Arg Leu Tyr Gly Ser Tyr Val Phe Gly
                500                 505                 510

Asp Arg Asn Gly Asn Phe Leu Thr Leu Gln Gln Ser Pro Val Thr Lys
                515                 520                 525

Gln Trp Gln Glu Lys Pro Leu Cys Leu Gly Thr Ser Gly Ser Cys Arg
530                 535                 540

Gly Tyr Phe Ser Gly His Ile Leu Gly Phe Gly Glu Asp Glu Leu Gly

```
                      545                 550                 555                 560
Glu Val Tyr Ile Leu Ser Ser Lys Ser Met Thr Gln Thr His Asn
                565                 570                 575
Gly Lys Leu Tyr Lys Ile Val Asp Pro Lys Arg Pro Leu Met Pro Glu
            580                 585                 590
Glu Cys Arg Ala Thr Val Gln Pro Ala Gln Thr Leu Thr Ser Glu Cys
        595                 600                 605
Ser Arg Leu Cys Arg Asn Gly Tyr Cys Thr Pro Thr Gly Lys Cys Cys
    610                 615                 620
Cys Ser Pro Gly Trp Glu Gly Asp Phe Cys Arg Thr Ala Lys Cys Glu
625                 630                 635                 640
Pro Ala Cys Arg His Gly Gly Val Cys Val Arg Pro Asn Lys Cys Leu
                645                 650                 655
Cys Lys Lys Gly Tyr Leu Gly Pro Gln Cys Glu Gln Val Asp Arg Asn
            660                 665                 670
Ile Arg Arg Val Thr Arg Ala Gly Ile Leu Asp Gln Ile Asp Met
        675                 680                 685
Thr Ser Tyr Leu Leu Asp Leu Thr Ser Tyr Ile Val
    690                 695                 700

<210> SEQ ID NO 3
<211> LENGTH: 19
<212> TYPE: PRT
<213> ORGANISM: Homo sapiens

<400> SEQUENCE: 3

Met Leu Lys Met Leu Ser Phe Lys Leu Leu Leu Ala Val Ala Leu
1               5                   10                  15

Gly Phe Phe

<210> SEQ ID NO 4
<211> LENGTH: 131
<212> TYPE: PRT
<213> ORGANISM: Homo sapiens

<400> SEQUENCE: 4

Met Met Ser Gln Leu Glu Leu Ser Gly Gly Glu Met Leu Cys Gly
1               5                   10                  15

Gly Phe Tyr Pro Arg Leu Ser Cys Cys Leu Arg Ser Asp Ser Pro Gly
                20                  25                  30

Leu Gly Arg Leu Glu Asn Lys Ile Phe Ser Val Thr Asn Asn Thr Glu
            35                  40                  45

Cys Gly Lys Leu Leu Glu Glu Ile Lys Cys Ala Leu Cys Ser Pro His
    50                  55                  60

Ser Gln Ser Leu Phe His Ser Pro Glu Arg Glu Val Leu Glu Arg Asp
65                  70                  75                  80

Leu Val Leu Pro Leu Leu Cys Lys Asp Tyr Cys Lys Glu Phe Phe Tyr
                85                  90                  95

Thr Cys Arg Gly His Ile Pro Gly Phe Leu Gln Thr Thr Ala Asp Glu
            100                 105                 110

Phe Cys Phe Tyr Tyr Ala Arg Lys Asp Gly Gly Leu Cys Phe Pro Asp
        115                 120                 125

Phe Pro Arg
    130

<210> SEQ ID NO 5
<211> LENGTH: 7
```

```
<212> TYPE: PRT
<213> ORGANISM: Homo sapiens

<400> SEQUENCE: 5

Lys Gln Val Arg Gly Pro Ala
1               5

<210> SEQ ID NO 6
<211> LENGTH: 415
<212> TYPE: PRT
<213> ORGANISM: Homo sapiens

<400> SEQUENCE: 6

Ser Asn Tyr Leu Asp Gln Met Glu Glu Tyr Asp Lys Val Glu Glu Ile
1               5                   10                  15

Ser Arg Lys His Lys His Asn Cys Phe Cys Ile Gln Glu Val Val Ser
            20                  25                  30

Gly Leu Arg Gln Pro Val Gly Ala Leu His Ser Gly Asp Gly Ser Gln
        35                  40                  45

Arg Leu Phe Ile Leu Glu Lys Glu Gly Tyr Val Lys Ile Leu Thr Pro
    50                  55                  60

Glu Gly Glu Ile Phe Lys Glu Pro Tyr Leu Asp Ile His Lys Leu Val
65                  70                  75                  80

Gln Ser Gly Ile Lys Gly Gly Asp Glu Arg Gly Leu Leu Ser Leu Ala
                85                  90                  95

Phe His Pro Asn Tyr Lys Lys Asn Gly Lys Leu Tyr Val Ser Tyr Thr
            100                 105                 110

Thr Asn Gln Glu Arg Trp Ala Ile Gly Pro His Asp His Ile Leu Arg
        115                 120                 125

Val Val Glu Tyr Thr Val Ser Arg Lys Asn Pro His Gln Val Asp Leu
    130                 135                 140

Arg Thr Ala Arg Val Phe Leu Glu Val Ala Glu Leu His Arg Lys His
145                 150                 155                 160

Leu Gly Gly Gln Leu Leu Phe Gly Pro Asp Gly Phe Leu Tyr Ile Ile
                165                 170                 175

Leu Gly Asp Gly Met Ile Thr Leu Asp Asp Met Glu Glu Met Asp Gly
            180                 185                 190

Leu Ser Asp Phe Thr Gly Ser Val Leu Arg Leu Asp Val Asp Thr Asp
        195                 200                 205

Met Cys Asn Val Pro Tyr Ser Ile Pro Arg Ser Asn Pro His Phe Asn
    210                 215                 220

Ser Thr Asn Gln Pro Pro Glu Val Phe Ala His Gly Leu His Asp Pro
225                 230                 235                 240

Gly Arg Cys Ala Val Asp Arg His Pro Thr Asp Ile Asn Ile Asn Leu
                245                 250                 255

Thr Ile Leu Cys Ser Asp Ser Asn Gly Lys Asn Arg Ser Ser Ala Arg
            260                 265                 270

Ile Leu Gln Ile Ile Lys Gly Lys Asp Tyr Glu Ser Glu Pro Ser Leu
        275                 280                 285

Leu Glu Phe Lys Pro Phe Ser Asn Gly Pro Leu Val Gly Gly Phe Val
    290                 295                 300

Tyr Arg Gly Cys Gln Ser Glu Arg Leu Tyr Gly Ser Tyr Val Phe Gly
305                 310                 315                 320

Asp Arg Asn Gly Asn Phe Leu Thr Leu Gln Gln Ser Pro Val Thr Lys
                325                 330                 335

Gln Trp Gln Glu Lys Pro Leu Cys Leu Gly Thr Ser Gly Ser Cys Arg
```

```
                340                 345                 350
Gly Tyr Phe Ser Gly His Ile Leu Gly Phe Gly Glu Asp Glu Leu Gly
            355                 360                 365

Glu Val Tyr Ile Leu Ser Ser Ser Lys Ser Met Thr Gln Thr His Asn
370                 375                 380

Gly Lys Leu Tyr Lys Ile Val Asp Pro Lys Arg Pro Leu Met Pro Glu
385                 390                 395                 400

Glu Cys Arg Ala Thr Val Gln Pro Ala Gln Thr Leu Thr Ser Glu
                405                 410                 415

<210> SEQ ID NO 7
<211> LENGTH: 18
<212> TYPE: PRT
<213> ORGANISM: Homo sapiens

<400> SEQUENCE: 7

Met Ile Thr Leu Asp Asp Met Glu Glu Met Asp Gly Leu Ser Asp Phe
1               5                   10                  15

Thr Gly

<210> SEQ ID NO 8
<211> LENGTH: 30
<212> TYPE: PRT
<213> ORGANISM: Homo sapiens

<400> SEQUENCE: 8

Cys Ser Arg Leu Cys Arg Asn Gly Tyr Cys Thr Pro Thr Gly Lys Cys
1               5                   10                  15

Cys Cys Ser Pro Gly Trp Glu Gly Asp Phe Cys Arg Thr Ala
            20                  25                  30

<210> SEQ ID NO 9
<211> LENGTH: 30
<212> TYPE: PRT
<213> ORGANISM: Homo sapiens

<400> SEQUENCE: 9

Lys Cys Glu Pro Ala Cys Arg His Gly Gly Val Cys Val Arg Pro Asn
1               5                   10                  15

Lys Cys Leu Cys Lys Lys Gly Tyr Leu Gly Pro Gln Cys Glu
            20                  25                  30

<210> SEQ ID NO 10
<211> LENGTH: 33
<212> TYPE: PRT
<213> ORGANISM: Homo sapiens

<400> SEQUENCE: 10

Gln Val Asp Arg Asn Ile Arg Arg Val Thr Arg Ala Gly Ile Leu Asp
1               5                   10                  15

Gln Ile Ile Asp Met Thr Ser Tyr Leu Leu Asp Leu Thr Ser Tyr Ile
            20                  25                  30

Val

<210> SEQ ID NO 11
<211> LENGTH: 475
<212> TYPE: PRT
<213> ORGANISM: Homo sapiens

<400> SEQUENCE: 11

Ser Asn Tyr Leu Asp Gln Met Glu Glu Tyr Asp Lys Val Glu Glu Ile
```

-continued

```
1               5                   10                  15
Ser Arg Lys His Lys His Asn Cys Phe Cys Ile Gln Glu Val Val Ser
                20                  25                  30

Gly Leu Arg Gln Pro Val Gly Ala Leu His Ser Gly Asp Gly Ser Gln
                35                  40                  45

Arg Leu Phe Ile Leu Glu Lys Glu Gly Tyr Val Lys Ile Leu Thr Pro
50                  55                  60

Glu Gly Glu Ile Phe Lys Glu Pro Tyr Leu Asp Ile His Lys Leu Val
65                  70                  75                  80

Gln Ser Gly Ile Lys Gly Gly Asp Glu Arg Gly Leu Leu Ser Leu Ala
                85                  90                  95

Phe His Pro Asn Tyr Lys Asn Gly Lys Leu Tyr Val Ser Tyr Thr
                100                 105                 110

Thr Asn Gln Glu Arg Trp Ala Ile Gly Pro His Asp His Ile Leu Arg
                115                 120                 125

Val Val Glu Tyr Thr Val Ser Arg Lys Asn Pro His Gln Val Asp Leu
                130                 135                 140

Arg Thr Ala Arg Val Phe Leu Glu Val Ala Glu Leu His Arg Lys His
145                 150                 155                 160

Leu Gly Gly Gln Leu Leu Phe Gly Pro Asp Gly Phe Leu Tyr Ile Ile
                165                 170                 175

Leu Gly Asp Gly Met Ile Thr Leu Asp Asp Met Glu Glu Met Asp Gly
                180                 185                 190

Leu Ser Asp Phe Thr Gly Ser Val Leu Arg Leu Asp Val Asp Thr Asp
                195                 200                 205

Met Cys Asn Val Pro Tyr Ser Ile Pro Arg Ser Asn Pro His Phe Asn
                210                 215                 220

Ser Thr Asn Gln Pro Pro Glu Val Phe Ala His Gly Leu His Asp Pro
225                 230                 235                 240

Gly Arg Cys Ala Val Asp Arg His Pro Thr Asp Ile Asn Ile Asn Leu
                245                 250                 255

Thr Ile Leu Cys Ser Asp Ser Asn Gly Lys Asn Arg Ser Ser Ala Arg
                260                 265                 270

Ile Leu Gln Ile Ile Lys Gly Lys Asp Tyr Glu Ser Glu Pro Ser Leu
                275                 280                 285

Leu Glu Phe Lys Pro Phe Ser Asn Gly Pro Leu Val Gly Gly Phe Val
                290                 295                 300

Tyr Arg Gly Cys Gln Ser Glu Arg Leu Tyr Gly Ser Tyr Val Phe Gly
305                 310                 315                 320

Asp Arg Asn Gly Asn Phe Leu Thr Leu Gln Gln Ser Pro Val Thr Lys
                325                 330                 335

Gln Trp Gln Glu Lys Pro Leu Cys Leu Gly Thr Ser Gly Ser Cys Arg
                340                 345                 350

Gly Tyr Phe Ser Gly His Ile Leu Gly Phe Gly Glu Asp Glu Leu Gly
                355                 360                 365

Glu Val Tyr Ile Leu Ser Ser Ser Lys Ser Met Thr Gln Thr His Asn
370                 375                 380

Gly Lys Leu Tyr Lys Ile Val Asp Pro Lys Arg Pro Leu Met Pro Glu
385                 390                 395                 400

Glu Cys Arg Ala Thr Val Gln Pro Ala Gln Thr Leu Thr Ser Glu Cys
                405                 410                 415

Ser Arg Leu Cys Arg Asn Gly Tyr Cys Thr Pro Thr Gly Lys Cys Cys
                420                 425                 430
```

```
Cys Ser Pro Gly Trp Glu Gly Asp Phe Cys Arg Thr Ala Lys Cys Glu
        435                 440                 445

Pro Ala Cys Arg His Gly Gly Val Cys Val Arg Pro Asn Lys Cys Leu
450                 455                 460

Cys Lys Lys Gly Tyr Leu Gly Pro Gln Cys Glu
465                 470                 475

<210> SEQ ID NO 12
<211> LENGTH: 475
<212> TYPE: PRT
<213> ORGANISM: Homo sapiens

<400> SEQUENCE: 12

Ser Asn Tyr Leu Asp Gln Met Glu Glu Tyr Asp Lys Val Glu Glu Ile
1               5                   10                  15

Ser Arg Lys His Lys His Asn Cys Phe Cys Ile Gln Glu Val Val Ser
                20                  25                  30

Gly Leu Arg Gln Pro Val Gly Ala Leu His Ser Gly Asp Gly Ser Gln
            35                  40                  45

Arg Leu Phe Ile Leu Glu Lys Glu Gly Tyr Val Lys Ile Leu Thr Pro
50                  55                  60

Glu Gly Glu Ile Phe Lys Glu Pro Tyr Leu Asp Ile His Lys Leu Val
65                  70                  75                  80

Gln Ser Gly Ile Lys Gly Gly Asp Glu Arg Gly Leu Leu Ser Leu Ala
                85                  90                  95

Phe His Pro Asn Tyr Lys Lys Asn Gly Lys Leu Tyr Val Ser Tyr Thr
            100                 105                 110

Thr Asn Gln Glu Arg Trp Ala Ile Gly Pro His Asp His Ile Leu Arg
        115                 120                 125

Val Val Glu Tyr Thr Val Ser Arg Lys Asn Pro His Gln Val Asp Leu
130                 135                 140

Arg Thr Ala Arg Val Phe Leu Glu Val Ala Glu Leu His Arg Lys His
145                 150                 155                 160

Leu Gly Gly Gln Leu Leu Phe Gly Pro Asp Gly Phe Leu Tyr Ile Ile
                165                 170                 175

Leu Gly Asp Gly Met Ile Thr Leu Asp Asp Met Glu Glu Met Asp Gly
            180                 185                 190

Leu Ser Asp Phe Thr Gly Ser Val Leu Arg Leu Asp Val Asp Thr Asp
        195                 200                 205

Met Cys Asn Val Pro Tyr Ser Ile Pro Arg Ser Asn Pro His Phe Asn
210                 215                 220

Ser Thr Asn Gln Pro Pro Glu Val Phe Ala His Gly Leu His Asp Pro
225                 230                 235                 240

Gly Arg Cys Ala Val Asp Arg His Pro Thr Asp Ile Asn Ile Asn Leu
                245                 250                 255

Thr Ile Leu Cys Ser Asp Ser Asn Gly Lys Asn Arg Ser Ser Ala Arg
            260                 265                 270

Ile Leu Gln Ile Ile Lys Gly Lys Asp Tyr Glu Ser Glu Pro Ser Leu
        275                 280                 285

Leu Glu Phe Lys Pro Phe Ser Asn Gly Pro Leu Val Gly Gly Phe Val
290                 295                 300

Tyr Arg Gly Cys Gln Ser Glu Arg Leu Tyr Gly Ser Tyr Val Phe Gly
305                 310                 315                 320

Asp Arg Asn Gly Asn Phe Leu Thr Leu Gln Gln Ser Pro Val Thr Lys
                325                 330                 335
```

```
Gln Trp Gln Glu Lys Pro Leu Cys Leu Gly Thr Ser Gly Ser Cys Arg
                340                 345                 350

Gly Tyr Phe Ser Gly His Ile Leu Gly Phe Gly Glu Asp Glu Leu Gly
            355                 360                 365

Glu Val Tyr Ile Leu Ser Ser Ser Lys Ser Met Thr Gln Thr His Asn
        370                 375                 380

Gly Lys Leu Tyr Lys Ile Val Asp Pro Lys Arg Pro Leu Met Pro Glu
385                 390                 395                 400

Glu Cys Arg Ala Thr Val Gln Pro Ala Gln Thr Leu Thr Ser Glu Cys
                405                 410                 415

Ser Arg Leu Cys Arg Asn Gly Tyr Cys Thr Pro Thr Gly Lys Cys Cys
            420                 425                 430

Cys Ser Pro Gly Trp Glu Gly Asp Phe Cys Arg Thr Ala Lys Cys Glu
        435                 440                 445

Pro Ala Cys Arg His Gly Gly Val Cys Val Arg Pro Asn Lys Cys Leu
    450                 455                 460

Cys Lys Lys Gly Tyr Leu Gly Pro Gln Cys Glu
465                 470                 475

<210> SEQ ID NO 13
<211> LENGTH: 445
<212> TYPE: PRT
<213> ORGANISM: Homo sapiens

<400> SEQUENCE: 13

Ser Asn Tyr Leu Asp Gln Met Glu Glu Tyr Asp Lys Val Glu Glu Ile
1               5                   10                  15

Ser Arg Lys His Lys His Asn Cys Phe Cys Ile Gln Glu Val Val Ser
            20                  25                  30

Gly Leu Arg Gln Pro Val Gly Ala Leu His Ser Gly Asp Gly Ser Gln
        35                  40                  45

Arg Leu Phe Ile Leu Glu Lys Glu Gly Tyr Val Lys Ile Leu Thr Pro
    50                  55                  60

Glu Gly Glu Ile Phe Lys Glu Pro Tyr Leu Asp Ile His Lys Leu Val
65                  70                  75                  80

Gln Ser Gly Ile Lys Gly Gly Asp Glu Arg Gly Leu Leu Ser Leu Ala
                85                  90                  95

Phe His Pro Asn Tyr Lys Lys Asn Gly Lys Leu Tyr Val Ser Tyr Thr
            100                 105                 110

Thr Asn Gln Glu Arg Trp Ala Ile Gly Pro His Asp His Ile Leu Arg
        115                 120                 125

Val Val Glu Tyr Thr Val Ser Arg Lys Asn Pro His Gln Val Asp Leu
    130                 135                 140

Arg Thr Ala Arg Val Phe Leu Glu Val Ala Glu Leu His Arg Lys His
145                 150                 155                 160

Leu Gly Gly Gln Leu Leu Phe Gly Pro Asp Gly Phe Leu Tyr Ile Ile
                165                 170                 175

Leu Gly Asp Gly Met Ile Thr Leu Asp Asp Met Glu Glu Met Asp Gly
            180                 185                 190

Leu Ser Asp Phe Thr Gly Ser Val Leu Arg Leu Asp Val Asp Thr Asp
        195                 200                 205

Met Cys Asn Val Pro Tyr Ser Ile Pro Arg Ser Asn Pro His Phe Asn
    210                 215                 220

Ser Thr Asn Gln Pro Pro Glu Val Phe Ala His Gly Leu His Asp Pro
225                 230                 235                 240
```

```
Gly Arg Cys Ala Val Asp Arg His Pro Thr Asp Ile Asn Ile Asn Leu
                245                 250                 255

Thr Ile Leu Cys Ser Asp Ser Asn Gly Lys Asn Arg Ser Ser Ala Arg
            260                 265                 270

Ile Leu Gln Ile Ile Lys Gly Lys Asp Tyr Glu Ser Glu Pro Ser Leu
        275                 280                 285

Leu Glu Phe Lys Pro Phe Ser Asn Gly Pro Leu Val Gly Gly Phe Val
290                 295                 300

Tyr Arg Gly Cys Gln Ser Glu Arg Leu Tyr Gly Ser Tyr Val Phe Gly
305                 310                 315                 320

Asp Arg Asn Gly Asn Phe Leu Thr Leu Gln Gln Ser Pro Val Thr Lys
                325                 330                 335

Gln Trp Gln Glu Lys Pro Leu Cys Leu Gly Thr Ser Gly Ser Cys Arg
            340                 345                 350

Gly Tyr Phe Ser Gly His Ile Leu Gly Phe Gly Glu Asp Glu Leu Gly
        355                 360                 365

Glu Val Tyr Ile Leu Ser Ser Ser Lys Ser Met Thr Gln Thr His Asn
        370                 375                 380

Gly Lys Leu Tyr Lys Ile Val Asp Pro Lys Arg Pro Leu Met Pro Glu
385                 390                 395                 400

Glu Cys Arg Ala Thr Val Gln Pro Ala Gln Thr Leu Thr Ser Glu Cys
                405                 410                 415

Ser Arg Leu Cys Arg Asn Gly Tyr Cys Thr Pro Thr Gly Lys Cys Cys
            420                 425                 430

Cys Ser Pro Gly Trp Glu Gly Asp Phe Cys Arg Thr Ala
        435                 440                 445

<210> SEQ ID NO 14
<211> LENGTH: 415
<212> TYPE: PRT
<213> ORGANISM: Homo sapiens

<400> SEQUENCE: 14

Ser Asn Tyr Leu Asp Gln Met Glu Glu Tyr Asp Lys Val Glu Glu Ile
1               5                   10                  15

Ser Arg Lys His Lys His Asn Cys Phe Cys Ile Gln Glu Val Val Ser
            20                  25                  30

Gly Leu Arg Gln Pro Val Gly Ala Leu His Ser Gly Asp Gly Ser Gln
        35                  40                  45

Arg Leu Phe Ile Leu Glu Lys Glu Gly Tyr Val Lys Ile Leu Thr Pro
    50                  55                  60

Glu Gly Glu Ile Phe Lys Glu Pro Tyr Leu Asp Ile His Lys Leu Val
65                  70                  75                  80

Gln Ser Gly Ile Lys Gly Gly Asp Glu Arg Gly Leu Leu Ser Leu Ala
                85                  90                  95

Phe His Pro Asn Tyr Lys Lys Asn Gly Lys Leu Tyr Val Ser Tyr Thr
            100                 105                 110

Thr Asn Gln Glu Arg Trp Ala Ile Gly Pro His Asp His Ile Leu Arg
        115                 120                 125

Val Val Glu Tyr Thr Val Ser Arg Lys Asn Pro His Gln Val Asp Leu
    130                 135                 140

Arg Thr Ala Arg Val Phe Leu Glu Val Ala Glu Leu His Arg Lys His
145                 150                 155                 160

Leu Gly Gly Gln Leu Leu Phe Gly Pro Asp Gly Phe Leu Tyr Ile Ile
                165                 170                 175
```

-continued

```
Leu Gly Asp Gly Met Ile Thr Leu Asp Asp Met Glu Met Asp Gly
            180                 185                 190

Leu Ser Asp Phe Thr Gly Ser Val Arg Leu Asp Val Asp Thr Asp
            195                 200                 205

Met Cys Asn Val Pro Tyr Ser Ile Pro Arg Ser Asn Pro His Phe Asn
210                 215                 220

Ser Thr Asn Gln Pro Pro Glu Val Phe Ala His Gly Leu His Asp Pro
225                 230                 235                 240

Gly Arg Cys Ala Val Asp Arg His Pro Thr Asp Ile Asn Ile Asn Leu
                245                 250                 255

Thr Ile Leu Cys Ser Asp Ser Asn Gly Lys Asn Arg Ser Ala Arg
            260                 265                 270

Ile Leu Gln Ile Ile Lys Gly Lys Asp Tyr Glu Ser Glu Pro Ser Leu
            275                 280                 285

Leu Glu Phe Lys Pro Phe Ser Asn Gly Pro Leu Val Gly Gly Phe Val
            290                 295                 300

Tyr Arg Gly Cys Gln Ser Glu Arg Leu Tyr Gly Ser Tyr Val Phe Gly
305                 310                 315                 320

Asp Arg Asn Gly Asn Phe Leu Thr Leu Gln Gln Ser Pro Val Thr Lys
                325                 330                 335

Gln Trp Gln Glu Lys Pro Leu Cys Leu Gly Thr Ser Gly Ser Cys Arg
            340                 345                 350

Gly Tyr Phe Ser Gly His Ile Leu Gly Phe Gly Glu Asp Glu Leu Gly
            355                 360                 365

Glu Val Tyr Ile Leu Ser Ser Lys Ser Met Thr Gln Thr His Asn
            370                 375                 380

Gly Lys Leu Tyr Lys Ile Val Asp Pro Lys Arg Pro Leu Met Pro Glu
385                 390                 395                 400

Glu Cys Arg Ala Thr Val Gln Pro Ala Gln Thr Leu Thr Ser Glu
                405                 410                 415

<210> SEQ ID NO 15
<211> LENGTH: 588
<212> TYPE: PRT
<213> ORGANISM: Homo sapiens

<400> SEQUENCE: 15

Glu Gly Asp Ala Lys Phe Gly Glu Arg Asn Gly Ser Gly Ala Arg
1               5                   10                  15

Arg Arg Arg Cys Leu Asn Gly Asn Pro Pro Lys Arg Leu Lys Arg Arg
                20                  25                  30

Asp Arg Arg Met Met Ser Gln Leu Glu Leu Leu Ser Gly Gly Glu Met
            35                  40                  45

Leu Cys Gly Gly Phe Tyr Pro Arg Leu Ser Cys Cys Leu Arg Ser Asp
50                  55                  60

Ser Pro Gly Leu Gly Arg Leu Glu Asn Lys Ile Phe Ser Val Thr Asn
65                  70                  75                  80

Asn Thr Glu Cys Gly Lys Leu Leu Glu Glu Ile Lys Cys Ala Leu Cys
                85                  90                  95

Ser Pro His Ser Gln Ser Leu Phe His Ser Pro Glu Arg Glu Val Leu
            100                 105                 110

Glu Arg Asp Leu Val Leu Pro Leu Leu Cys Lys Asp Tyr Cys Lys Glu
            115                 120                 125

Phe Phe Tyr Thr Cys Arg Gly His Ile Pro Gly Phe Leu Gln Thr Thr
130                 135                 140
```

-continued

```
Ala Asp Glu Phe Cys Phe Tyr Tyr Ala Arg Lys Asp Gly Gly Leu Cys
145                 150                 155                 160

Phe Pro Asp Phe Pro Arg Lys Gln Val Arg Gly Pro Ala Ser Asn Tyr
            165                 170                 175

Leu Asp Gln Met Glu Glu Tyr Asp Lys Val Glu Glu Ile Ser Arg Lys
        180                 185                 190

His Lys His Asn Cys Phe Cys Ile Gln Glu Val Val Ser Gly Leu Arg
    195                 200                 205

Gln Pro Val Gly Ala Leu His Ser Gly Asp Gly Ser Gln Arg Leu Phe
210                 215                 220

Ile Leu Glu Lys Glu Gly Tyr Val Lys Ile Leu Thr Pro Glu Gly Glu
225                 230                 235                 240

Ile Phe Lys Glu Pro Tyr Leu Asp Ile His Lys Leu Val Gln Ser Gly
            245                 250                 255

Ile Lys Gly Gly Asp Glu Arg Gly Leu Leu Ser Leu Ala Phe His Pro
        260                 265                 270

Asn Tyr Lys Asn Gly Lys Leu Tyr Val Ser Tyr Thr Thr Asn Gln
    275                 280                 285

Glu Arg Trp Ala Ile Gly Pro His Asp His Ile Leu Arg Val Val Glu
290                 295                 300

Tyr Thr Val Ser Arg Lys Asn Pro His Gln Val Asp Leu Arg Thr Ala
305                 310                 315                 320

Arg Val Phe Leu Glu Val Ala Glu Leu His Arg Lys His Leu Gly Gly
            325                 330                 335

Gln Leu Leu Phe Gly Pro Asp Gly Phe Leu Tyr Ile Ile Leu Gly Asp
        340                 345                 350

Gly Met Ile Thr Leu Asp Asp Met Glu Glu Met Asp Gly Leu Ser Asp
    355                 360                 365

Phe Thr Gly Ser Val Leu Arg Leu Asp Val Asp Thr Asp Met Cys Asn
370                 375                 380

Val Pro Tyr Ser Ile Pro Arg Ser Asn Pro His Phe Asn Ser Thr Asn
385                 390                 395                 400

Gln Pro Pro Glu Val Phe Ala His Gly Leu His Asp Pro Gly Arg Cys
            405                 410                 415

Ala Val Asp Arg His Pro Thr Asp Ile Asn Ile Asn Leu Thr Ile Leu
        420                 425                 430

Cys Ser Asp Ser Asn Gly Lys Asn Arg Ser Ser Ala Arg Ile Leu Gln
    435                 440                 445

Ile Ile Lys Gly Lys Asp Tyr Glu Ser Glu Pro Ser Leu Leu Glu Phe
450                 455                 460

Lys Pro Phe Ser Asn Gly Pro Leu Val Gly Gly Phe Val Tyr Arg Gly
465                 470                 475                 480

Cys Gln Ser Glu Arg Leu Tyr Gly Ser Tyr Val Phe Gly Asp Arg Asn
            485                 490                 495

Gly Asn Phe Leu Thr Leu Gln Gln Ser Pro Val Thr Lys Gln Trp Gln
        500                 505                 510

Glu Lys Pro Leu Cys Leu Gly Thr Ser Gly Ser Cys Arg Gly Tyr Phe
    515                 520                 525

Ser Gly His Ile Leu Gly Phe Gly Glu Asp Glu Leu Gly Glu Val Tyr
530                 535                 540

Ile Leu Ser Ser Ser Lys Ser Met Thr Gln Thr His Asn Gly Lys Leu
545                 550                 555                 560

Tyr Lys Ile Val Asp Pro Lys Arg Pro Leu Met Pro Glu Glu Cys Arg
            565                 570                 575
```

```
Ala Thr Val Gln Pro Ala Gln Thr Leu Thr Ser Glu
            580                 585

<210> SEQ ID NO 16
<211> LENGTH: 170
<212> TYPE: PRT
<213> ORGANISM: Homo sapiens

<400> SEQUENCE: 16

Glu Gly Asp Ala Lys Phe Gly Glu Arg Asn Glu Ser Gly Ala Arg
1               5                   10                  15

Arg Arg Arg Cys Leu Asn Gly Asn Pro Lys Arg Leu Lys Arg Arg
                20                  25                  30

Asp Arg Arg Met Met Ser Gln Leu Glu Leu Leu Ser Gly Gly Glu Met
            35                  40                  45

Leu Cys Gly Gly Phe Tyr Pro Arg Leu Ser Cys Cys Leu Arg Ser Asp
    50                  55                  60

Ser Pro Gly Leu Gly Arg Leu Glu Asn Lys Ile Phe Ser Val Thr Asn
65                  70                  75                  80

Asn Thr Glu Cys Gly Lys Leu Leu Glu Glu Ile Lys Cys Ala Leu Cys
                85                  90                  95

Ser Pro His Ser Gln Ser Leu Phe His Ser Pro Glu Arg Glu Val Leu
            100                 105                 110

Glu Arg Asp Leu Val Leu Pro Leu Leu Cys Lys Asp Tyr Cys Lys Glu
        115                 120                 125

Phe Phe Tyr Thr Cys Arg Gly His Ile Pro Gly Phe Leu Gln Thr Thr
130                 135                 140

Ala Asp Glu Phe Cys Phe Tyr Tyr Ala Arg Lys Asp Gly Gly Leu Cys
145                 150                 155                 160

Phe Pro Asp Phe Pro Arg Lys Gln Val Arg
                165                 170

<210> SEQ ID NO 17
<211> LENGTH: 18
<212> TYPE: PRT
<213> ORGANISM: Homo sapiens

<400> SEQUENCE: 17

Gln Leu Thr Lys Gln Arg Leu Val Asp Ala Asp Gly Ile Ile Asn Pro
1               5                   10                  15

Ser Ala

<210> SEQ ID NO 18
<211> LENGTH: 18
<212> TYPE: PRT
<213> ORGANISM: Mus musculus

<400> SEQUENCE: 18

Gln Leu Thr Lys Gln Arg Leu Val Asp Ala Asp Gly Ile Ile Asn Pro
1               5                   10                  15

Ser Ala

<210> SEQ ID NO 19
<211> LENGTH: 18
<212> TYPE: PRT
<213> ORGANISM: Gallus gallus

<400> SEQUENCE: 19

Gln Leu Thr Lys Gln Arg Leu Val Asp Ala Asp Gly Ile Ile Asn Pro
```

-continued

```
                1               5                   10                  15
Asn Ala

<210> SEQ ID NO 20
<211> LENGTH: 18
<212> TYPE: PRT
<213> ORGANISM: Danio rerio

<400> SEQUENCE: 20

Gln Leu Thr Ser Arg Arg Leu Val Asp Gly Asp Gly Leu Ile Pro Pro
1               5                   10                  15

Glu Val

<210> SEQ ID NO 21
<211> LENGTH: 18
<212> TYPE: PRT
<213> ORGANISM: Drosophila melanogaster

<400> SEQUENCE: 21

Leu Val Leu Thr Asn Arg Leu Val Asn Ser Asp Gly Ile Ile Asn Gln
1               5                   10                  15

Arg Ala

<210> SEQ ID NO 22
<211> LENGTH: 18
<212> TYPE: PRT
<213> ORGANISM: Caenorhabditis elegans

<400> SEQUENCE: 22

Arg Val Gly Lys Ile Arg Leu Val Asp Ala Ser Gly Ile Ile Asn Ser
1               5                   10                  15

Asp Gly

<210> SEQ ID NO 23
<211> LENGTH: 18
<212> TYPE: PRT
<213> ORGANISM: Homo sapiens

<400> SEQUENCE: 23

Gln Leu Thr Thr Arg Lys Leu Val Asp Arg Glu Gly Leu Ile Pro Pro
1               5                   10                  15

Glu Leu

<210> SEQ ID NO 24
<211> LENGTH: 18
<212> TYPE: PRT
<213> ORGANISM: Mus musculus

<400> SEQUENCE: 24

Gln Leu Thr Thr Arg Lys Leu Val Asp Lys Glu Gly Leu Ile Pro Pro
1               5                   10                  15

Glu Leu

<210> SEQ ID NO 25
<211> LENGTH: 18
<212> TYPE: PRT
<213> ORGANISM: Macaca mulatta

<400> SEQUENCE: 25

Met Ile Thr Leu Asp Asp Met Glu Glu Met Asp Gly Leu Ser Asp Phe
1               5                   10                  15
```

Thr Gly

<210> SEQ ID NO 26
<211> LENGTH: 18
<212> TYPE: PRT
<213> ORGANISM: Pan troglodytes

<400> SEQUENCE: 26

Met Ile Thr Leu Asp Asp Met Glu Glu Met Asp Gly Leu Ser Asp Phe
1               5                   10                  15

Thr Gly

<210> SEQ ID NO 27
<211> LENGTH: 18
<212> TYPE: PRT
<213> ORGANISM: Equus caballus

<400> SEQUENCE: 27

Met Ile Thr Leu Asp Asp Met Glu Glu Met Asp Gly Leu Ser Asp Phe
1               5                   10                  15

Thr Gly

<210> SEQ ID NO 28
<211> LENGTH: 18
<212> TYPE: PRT
<213> ORGANISM: Monodelphis domestica

<400> SEQUENCE: 28

Met Ile Thr Leu Asp Asp Met Glu Glu Met Asp Gly Leu Ser Asp Phe
1               5                   10                  15

Thr Gly

<210> SEQ ID NO 29
<211> LENGTH: 18
<212> TYPE: PRT
<213> ORGANISM: Mus musculus

<400> SEQUENCE: 29

Met Ile Thr Leu Asp Asp Met Glu Glu Met Asp Gly Leu Ser Asp Phe
1               5                   10                  15

Thr Gly

<210> SEQ ID NO 30
<211> LENGTH: 18
<212> TYPE: PRT
<213> ORGANISM: Bos taurus

<400> SEQUENCE: 30

Met Ile Thr Leu Asp Asp Met Glu Glu Met Asp Gly Leu Ser Asp Phe
1               5                   10                  15

Thr Gly

<210> SEQ ID NO 31
<211> LENGTH: 18
<212> TYPE: PRT
<213> ORGANISM: Canis familiaris

<400> SEQUENCE: 31

Met Ile Thr Leu Asp Asp Met Glu Glu Met Asp Gly Leu Ser Asp Phe
1               5                   10                  15

Thr Gly

<210> SEQ ID NO 32
<211> LENGTH: 18
<212> TYPE: PRT
<213> ORGANISM: Rattus rattus

<400> SEQUENCE: 32

Met Ile Thr Leu Asp Asp Met Glu Glu Met Asp Gly Leu Ser Asp Phe
1               5                   10                  15

Thr Gly

<210> SEQ ID NO 33
<211> LENGTH: 18
<212> TYPE: PRT
<213> ORGANISM: Ornithorhynchus anatinus

<400> SEQUENCE: 33

Met Ile Thr Leu Asp Asp Met Glu Glu Met Asp Gly Leu Ser Asp Phe
1               5                   10                  15

Thr Gly

<210> SEQ ID NO 34
<211> LENGTH: 18
<212> TYPE: PRT
<213> ORGANISM: Fugu rubripes

<400> SEQUENCE: 34

Met Ile Thr Leu Asp Asp Met Glu Glu Met Asp Gly Leu Ser Asp Phe
1               5                   10                  15

Thr Gly

<210> SEQ ID NO 35
<211> LENGTH: 18
<212> TYPE: PRT
<213> ORGANISM: Tetraodon fluviatilis

<400> SEQUENCE: 35

Met Ile Thr Leu Asp Asp Met Glu Glu Met Asp Gly Leu Ser Asp Phe
1               5                   10                  15

Thr Gly

<210> SEQ ID NO 36
<211> LENGTH: 18
<212> TYPE: PRT
<213> ORGANISM: Danio rerio

<400> SEQUENCE: 36

Met Ile Thr Leu Asp Asn Met Glu Glu Met Asp Gly Leu Ser Asp Phe
1               5                   10                  15

Thr Gly

<210> SEQ ID NO 37
<211> LENGTH: 18
<212> TYPE: PRT
<213> ORGANISM: Gallus gallus

<400> SEQUENCE: 37

Met Ile Thr Leu Asp Asp Met Glu Glu Met Asp Gly Leu Ser Asp Phe
1               5                   10                  15

Thr Gly

<210> SEQ ID NO 38

```
<211> LENGTH: 18
<212> TYPE: PRT
<213> ORGANISM: Xenopus laevis

<400> SEQUENCE: 38

Met Ile Thr Ile Asp Asp Met Glu Glu Met Asp Gly Leu Ser Asp Phe
1               5                   10                  15

Thr Gly

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MISC_FEATURE
<222> LOCATION: (1)..(1)
<223> OTHER INFORMATION: Ile, Leu or Val
<220> FEATURE:
<221> NAME/KEY: MISC_FEATURE
<222> LOCATION: (2)..(5)
<223> OTHER INFORMATION: Any amino acid
<220> FEATURE:
<221> NAME/KEY: MISC_FEATURE
<222> LOCATION: (6)..(6)
<223> OTHER INFORMATION: Met or Leu
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (8)..(8)
<223> OTHER INFORMATION: Asp, Glu or Asn
<220> FEATURE:
<221> NAME/KEY: MISC_FEATURE
<222> LOCATION: (9)..(9)
<223> OTHER INFORMATION: Any amino acid
<220> FEATURE:
<221> NAME/KEY: MISC_FEATURE
<222> LOCATION: (10)..(10)
<223> OTHER INFORMATION: Asp, Ser, or Glu
<220> FEATURE:
<221> NAME/KEY: MISC_FEATURE
<222> LOCATION: (12)..(12)
<223> OTHER INFORMATION: Leu or Ile

<400> SEQUENCE: 39

Xaa Xaa Xaa Xaa Xaa Xaa Xaa Xaa Xaa Xaa Gly Xaa
1               5                   10

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 40

Lys Phe Leu Val Asn Val Ala Leu Val Phe Met Val Val Tyr Ile Ser
1               5                   10                  15

Tyr Ile Tyr Ala
            20

<210> SEQ ID NO 41
<211> LENGTH: 25
<212> TYPE: PRT
<213> ORGANISM: Artificial Sequence
<220> FEATURE:
```

```
<223> OTHER INFORMATION: Description of Artificial Sequence: Synthetic
      construct

<400> SEQUENCE: 41

Met Gly Gly Ala Ala Ala Arg Leu Gly Ala Val Ile Leu Phe Val Val
1               5                   10                  15

Ile Val Gly Leu His Gly Val Arg Gly
            20                  25

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 42

Gln Val Thr Asp Lys Thr His Thr
1               5

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 43

Arg Leu Glu Val Leu Phe Gln Gly Pro Asp Lys Thr His Thr
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 44

Asp Tyr Lys Asp Asp Asp Asp Lys
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 45

Met Lys His His His His His His
1               5

<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 46

Gly Asp Gly Met Ile Thr Leu Asp Asp Met Glu Glu Met Asp Gly Leu
1               5                   10                  15
```

Ser Asp Phe Thr Gly
            20

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 47

Glu Asp Gly Ala Lys Phe Gly Glu
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 48

Tyr Leu Asp Gln Met Glu Glu
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 49

Lys Val Glu Glu Ile Ser Arg
1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 50

Ser Gly Ala Arg Arg Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 51

Ser Gly Gly Glu Met Leu Cys
1               5

<210> SEQ ID NO 52
<211> LENGTH: 2103
<212> TYPE: DNA
<213> ORGANISM: Homo sapiens -continued

```
<400> SEQUENCE: 52
atgctgaaga tgctctcctt taagctgctg ctgctggccg tggctctggg cttctttgaa      60
ggagatgcta agtttgggga agaaacgaa gggagcggag caaggaggag aaggtgcctg     120
aatgggaacc ccccgaagcg cctgaaaagg agagacagga ggatgatgtc ccagctggag    180
ctgctgagtg ggggagagat gctgtgcggt ggcttctacc ctcggctgtc ctgctgcctg    240
cggagtgaca gcccggggct agggcgcctg gagaataaga tattttctgt taccaacaac    300
acagaatgtg ggaagttact ggaggaaatc aaatgtgcac tttgctctcc acattctcaa    360
agcctgttcc actcacctga gagagaagtc ttggaaagag acctagtact tcctctgctc    420
tgcaaagact attgcaaaga attcttttac acttgccgag ccatattcc aggtttcctt     480
caaacaactg cggatgagtt ttgcttttac tatgcaagaa aagatggtgg gttgtgcttt    540
ccagattttc caagaaaaca agtcagagga ccagcatcta actacttgga ccagatggaa    600
gaatatgaca aagtggaaga gatcagcaga aagcacaaac acaactgctt ctgtattcag    660
gaggttgtga gtgggctgcg gcagcccgtt ggtgccctgc atagtgggga tggctcgcaa    720
cgtctcttca ttctggaaaa agaaggttat gtgaagatac ttacccctga aggaaaatt    780
ttcaaggagc cttatttgga cattcacaaa cttgttcaaa gtggaataaa gggaggagat    840
gaaagaggac tgctaagcct cgcattccat cccaattaca agaaaaatgg aaagttgtat    900
gtgtcctata ccaccaacca agaacggtgg gctatcgggc tcatgacca cattcttagg     960
gttgtggaat acacagtatc cagaaaaaat ccacaccaag ttgatttgag aacagccaga   1020
gtctttcttg aagttgcaga actccacaga aagcatctgg gaggacaact gctctttggc   1080
cctgacggct ttttgtacat cattcttggt gatgggatga ttacactgga tgatatggaa   1140
gaaatggatg ggttaagtga tttcacaggc tcagtgctac ggctggatgt ggacacagac   1200
atgtgcaacg tgccttattc cataccaagg agcaacccac acttcaacag caccaaccag   1260
cccccccgaag tgtttgctca tgggctccac gatccaggca gatgtgctgt ggatagacat   1320
cccactgata taaacatcaa tttaacgata ctgtgttcag actccaatgg aaaaaacaga   1380
tcatcagcca gaattctaca gataataaag gggaaagatt atgaaagtga gccatcactt   1440
ttagaattca agccattcag taatggtcct ttggttggtg gatttgtata ccggggctgc   1500
cagtcagaaa gattgtatgg aagctacgtg ttttggagatc gtaatgggaa tttcctaact   1560
ctccagcaaa gtcctgtgac aaagcagtgg caagaaaaac cactctgtct cggcactagt   1620
gggtcctgta gaggctactt ttccggtcac atcttgggat ttggagaaga tgaactaggt   1680
gaagtttaca ttttatcaag cagtaaaagt atgacccaga ctcacaatgg aaaactctac   1740
aaaattgtag atcccaaaag acctttaatg cctgaggaat gcagagccac ggtacaacct   1800
gcacagacac tgacttcaga gtgctccagg ctctgtcgaa acggctactg cacccccacg   1860
ggaaagtgct gctgcagtcc aggctgggag ggggacttct gcagaactgc aaaatgtgag   1920
ccagcatgtc gtcatggagg tgtctgtgtt agaccgaaca agtgcctctg taaaaaagga   1980
tatcttggtc tcaatgtgaa acaagtggac agaaacatcc gcagagtgac cagggcaggt   2040
attcttgatc agatcattga catgacatct tacttgctgg atctaacaag ttacattgta   2100
tag                                                                 2103
```

<210> SEQ ID NO 53
<211> LENGTH: 20
<212> TYPE: PRT
<213> ORGANISM: Homo sapiens -continued

```
<400> SEQUENCE: 53

Gly Cys Gln Leu Thr Lys Gln Arg Leu Val Asp Ala Asp Gly Ile Ile
1               5                   10                  15

Asn Pro Cys Gly
            20

<210> SEQ ID NO 54
<211> LENGTH: 21
<212> TYPE: PRT
<213> ORGANISM: Homo sapiens

<400> SEQUENCE: 54

Gly Cys Gly Met Ile Thr Leu Asp Asp Met Glu Glu Met Asp Gly Leu
1               5                   10                  15

Ser Asp Phe Cys Gly
            20

<210> SEQ ID NO 55
<211> LENGTH: 14
<212> TYPE: PRT
<213> ORGANISM: Homo sapiens

<400> SEQUENCE: 55

Ile Thr Leu Asp Asp Met Glu Glu Met Asp Gly Leu Ser Asp
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MISC_FEATURE
<222> LOCATION: (2)..(5)
<223> OTHER INFORMATION: Any amino acid
<220> FEATURE:
<221> NAME/KEY: MISC_FEATURE
<222> LOCATION: (6)..(6)
<223> OTHER INFORMATION: Met or Leu
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (8)..(8)
<223> OTHER INFORMATION: Asp, Glu or Asn
<220> FEATURE:
<221> NAME/KEY: MISC_FEATURE
<222> LOCATION: (9)..(9)
<223> OTHER INFORMATION: Any amino acid
<220> FEATURE:
<221> NAME/KEY: MISC_FEATURE
<222> LOCATION: (10)..(10)
<223> OTHER INFORMATION: Asp, Ser or Glu
<220> FEATURE:
<221> NAME/KEY: MISC_FEATURE
<222> LOCATION: (12)..(12)
<223> OTHER INFORMATION: Leu or Ile

<400> SEQUENCE: 56

Ile Xaa Xaa Xaa Xaa Xaa Xaa Xaa Xaa Xaa Gly Xaa
1               5                   10

<210> SEQ ID NO 57
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      construct
<220> FEATURE:
<221> NAME/KEY: MISC_FEATURE
<222> LOCATION: (2)..(5)
<223> OTHER INFORMATION: Any amino acid
<220> FEATURE:
<221> NAME/KEY: MISC_FEATURE
<222> LOCATION: (6)..(6)
<223> OTHER INFORMATION: Met or Leu
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (8)..(8)
<223> OTHER INFORMATION: Asp, Glu or Asn
<220> FEATURE:
<221> NAME/KEY: MISC_FEATURE
<222> LOCATION: (9)..(9)
<223> OTHER INFORMATION: Any amino acid
<220> FEATURE:
<221> NAME/KEY: MISC_FEATURE
<222> LOCATION: (10)..(10)
<223> OTHER INFORMATION: Asp, Ser or Glu
<220> FEATURE:
<221> NAME/KEY: MISC_FEATURE
<222> LOCATION: (12)..(12)
<223> OTHER INFORMATION: Leu or Ile

<400> SEQUENCE: 57

Leu Xaa Xaa Xaa Xaa Xaa Xaa Xaa Xaa Xaa Gly Xaa
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MISC_FEATURE
<222> LOCATION: (2)..(5)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (8)..(8)
<223> OTHER INFORMATION: Asp, Glu or Asn
<220> FEATURE:
<221> NAME/KEY: MISC_FEATURE
<222> LOCATION: (9)..(9)
<223> OTHER INFORMATION: Any amino acid
<220> FEATURE:
<221> NAME/KEY: MISC_FEATURE
<222> LOCATION: (10)..(10)
<223> OTHER INFORMATION: Asp, Ser or Glu
<220> FEATURE:
<221> NAME/KEY: MISC_FEATURE
<222> LOCATION: (12)..(12)
<223> OTHER INFORMATION: Leu or Ile

<400> SEQUENCE: 58

Ile Xaa Xaa Xaa Xaa Met Xaa Xaa Xaa Xaa Gly Xaa
1               5                   10

<210> SEQ ID NO 59
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      construct
<220> FEATURE:
<221> NAME/KEY: MISC_FEATURE
<222> LOCATION: (2)..(5)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (8)..(8)
<223> OTHER INFORMATION: Asp, Glu or Asn
<220> FEATURE:
<221> NAME/KEY: MISC_FEATURE
<222> LOCATION: (9)..(9)
<223> OTHER INFORMATION: Any amino acid
<220> FEATURE:
<221> NAME/KEY: MISC_FEATURE
<222> LOCATION: (10)..(10)
<223> OTHER INFORMATION: Asp, Ser or Glu
<220> FEATURE:
<221> NAME/KEY: MISC_FEATURE
<222> LOCATION: (12)..(12)
<223> OTHER INFORMATION: Leu or Ile

<400> SEQUENCE: 59

Leu Xaa Xaa Xaa Xaa Leu Xaa Xaa Xaa Xaa Gly Xaa
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MISC_FEATURE
<222> LOCATION: (2)..(5)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (9)..(9)
<223> OTHER INFORMATION: Any amino acid
<220> FEATURE:
<221> NAME/KEY: MISC_FEATURE
<222> LOCATION: (10)..(10)
<223> OTHER INFORMATION: Asp, Ser or Glu
<220> FEATURE:
<221> NAME/KEY: MISC_FEATURE
<222> LOCATION: (12)..(12)
<223> OTHER INFORMATION: Leu or Ile

<400> SEQUENCE: 60

Ile Xaa Xaa Xaa Xaa Met Xaa Glu Xaa Xaa Gly Xaa
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MISC_FEATURE
<222> LOCATION: (2)..(5)
<223> OTHER INFORMATION: Any amino acid
<220> FEATURE:
```

```
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (9)..(9)
<223> OTHER INFORMATION: Any amino acid
<220> FEATURE:
<221> NAME/KEY: MISC_FEATURE
<222> LOCATION: (10)..(10)
<223> OTHER INFORMATION: Asp, Ser or Glu
<220> FEATURE:
<221> NAME/KEY: MISC_FEATURE
<222> LOCATION: (12)..(12)
<223> OTHER INFORMATION: Leu or Ile

<400> SEQUENCE: 61

Leu Xaa Xaa Xaa Xaa Leu Xaa Asp Xaa Xaa Gly Xaa
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MISC_FEATURE
<222> LOCATION: (2)..(5)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (9)..(9)
<223> OTHER INFORMATION: Any amino acid
<220> FEATURE:
<221> NAME/KEY: MISC_FEATURE
<222> LOCATION: (12)..(12)
<223> OTHER INFORMATION: Leu or Ile

<400> SEQUENCE: 62

Ile Xaa Xaa Xaa Xaa Met Xaa Glu Xaa Asp Gly Xaa
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MISC_FEATURE
<222> LOCATION: (2)..(5)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (9)..(9)
<223> OTHER INFORMATION: Any amino acid
<220> FEATURE:
<221> NAME/KEY: MISC_FEATURE
<222> LOCATION: (12)..(12)
<223> OTHER INFORMATION: Leu or Ile

<400> SEQUENCE: 63

Leu Xaa Xaa Xaa Xaa Leu Xaa Asp Xaa Asp Gly Xaa
1               5                   10
```

```
<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MISC_FEATURE
<222> LOCATION: (2)..(5)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (9)..(9)
<223> OTHER INFORMATION: Any amino acid
<220> FEATURE:
<221> NAME/KEY: MISC_FEATURE
<222> LOCATION: (12)..(12)
<223> OTHER INFORMATION: Leu or Ile

<400> SEQUENCE: 64

Leu Xaa Xaa Xaa Xaa Leu Xaa Asp Xaa Ser Gly Xaa
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MISC_FEATURE
<222> LOCATION: (2)..(5)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (9)..(9)
<223> OTHER INFORMATION: Any amino acid
<220> FEATURE:
<221> NAME/KEY: MISC_FEATURE
<222> LOCATION: (12)..(12)
<223> OTHER INFORMATION: Leu or Ile

<400> SEQUENCE: 65

Leu Xaa Xaa Xaa Xaa Leu Xaa Asp Xaa Glu Gly Xaa
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MISC_FEATURE
<222> LOCATION: (2)..(5)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (9)..(9)
```

```
<223> OTHER INFORMATION: Any amino acid

<400> SEQUENCE: 66

Ile Xaa Xaa Xaa Xaa Met Xaa Glu Xaa Asp Gly Leu
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MISC_FEATURE
<222> LOCATION: (2)..(5)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (9)..(9)
<223> OTHER INFORMATION: Any amino acid

<400> SEQUENCE: 67

Leu Xaa Xaa Xaa Xaa Leu Xaa Asp Xaa Asp Gly Leu
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MISC_FEATURE
<222> LOCATION: (2)..(5)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (9)..(9)
<223> OTHER INFORMATION: Any amino acid

<400> SEQUENCE: 68

Leu Xaa Xaa Xaa Xaa Leu Xaa Asp Xaa Ser Gly Leu
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MISC_FEATURE
<222> LOCATION: (2)..(5)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (9)..(9)
<223> OTHER INFORMATION: Any amino acid
```

```
<400> SEQUENCE: 69

Leu Xaa Xaa Xaa Xaa Leu Xaa Asp Xaa Glu Gly Leu
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MISC_FEATURE
<222> LOCATION: (2)..(5)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (9)..(9)
<223> OTHER INFORMATION: Any amino acid

<400> SEQUENCE: 70

Leu Xaa Xaa Xaa Xaa Leu Xaa Asp Xaa Asp Gly Ile
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MISC_FEATURE
<222> LOCATION: (2)..(5)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (9)..(9)
<223> OTHER INFORMATION: Any amino acid

<400> SEQUENCE: 71

Leu Xaa Xaa Xaa Xaa Leu Xaa Asp Xaa Ser Gly Ile
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MISC_FEATURE
<222> LOCATION: (2)..(5)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (9)..(9)
<223> OTHER INFORMATION: Any amino acid

<400> SEQUENCE: 72
```

```
Leu Xaa Xaa Xaa Xaa Leu Xaa Asp Xaa Glu Gly Ile
1               5                   10
```

<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 73

```
Ile Thr Leu Asp Asp Met Glu Glu Met Asp Gly Leu
1               5                   10
```

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 74

```
Leu Thr Lys Gln Arg Leu Val Asp Ala Asp Gly Leu
1               5                   10
```

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 75

```
Leu Thr Thr Arg Lys Leu Val Asp Arg Glu Gly Leu
1               5                   10
```

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 76

```
Leu Leu Thr Asn Arg Leu Val Asn Ser Asp Gly Ile
1               5                   10
```

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 77

```
Leu Thr Thr Arg Lys Leu Val Asp Lys Glu Gly Leu
1               5                   10
```

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic -continued

```
        construct
<220> FEATURE:
<221> NAME/KEY: MISC_FEATURE
<222> LOCATION: (3)..(5)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (9)..(9)
<223> OTHER INFORMATION: Any amino acid

<400> SEQUENCE: 78

Leu Val Xaa Xaa Xaa Gly Xaa Ile Xaa
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MISC_FEATURE
<222> LOCATION: (4)..(5)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (9)..(9)
<223> OTHER INFORMATION: Any amino acid

<400> SEQUENCE: 79

Leu Val Asp Xaa Xaa Gly Xaa Ile Xaa
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MISC_FEATURE
<222> LOCATION: (5)..(5)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid

<400> SEQUENCE: 80

Leu Val Asp Ala Xaa Gly Xaa Ile Asn
1               5

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MISC_FEATURE
<222> LOCATION: (5)..(5)
<223> OTHER INFORMATION: Any amino acid
<220> FEATURE:
```

```
<221> NAME/KEY: MISC_FEATURE
<222> LOCATION: (7)..(7)
<223> OTHER INFORMATION: Any amino acid

<400> SEQUENCE: 81

Leu Val Asp Ala Xaa Gly Xaa Ile Asn Pro
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 82

Leu Val Asp Ala Asp Gly Ile Ile Asn Pro
1               5                   10

<210> SEQ ID NO 83
<211> LENGTH: 508
<212> TYPE: PRT
<213> ORGANISM: Homo sapiens

<400> SEQUENCE: 83

Ser Asn Tyr Leu Asp Gln Met Glu Glu Tyr Asp Lys Val Glu Ile
1               5                   10                  15

Ser Arg Lys His Lys His Asn Cys Phe Cys Ile Gln Glu Val Val Ser
                20                  25                  30

Gly Leu Arg Gln Pro Val Gly Ala Leu His Ser Gly Asp Gly Ser Gln
            35                  40                  45

Arg Leu Phe Ile Leu Glu Lys Glu Gly Tyr Val Lys Ile Leu Thr Pro
        50                  55                  60

Glu Gly Glu Ile Phe Lys Glu Pro Tyr Leu Asp Ile His Lys Leu Val
65                  70                  75                  80

Gln Ser Gly Ile Lys Gly Gly Asp Glu Arg Gly Leu Leu Ser Leu Ala
                85                  90                  95

Phe His Pro Asn Tyr Lys Lys Asn Gly Lys Leu Tyr Val Ser Tyr Thr
            100                 105                 110

Thr Asn Gln Glu Arg Trp Ala Ile Gly Pro His Asp His Ile Leu Arg
        115                 120                 125

Val Val Glu Tyr Thr Val Ser Arg Lys Asn Pro His Gln Val Asp Leu
130                 135                 140

Arg Thr Ala Arg Val Phe Leu Glu Val Ala Glu Leu His Arg Lys His
145                 150                 155                 160

Leu Gly Gly Gln Leu Leu Phe Gly Pro Asp Gly Phe Leu Tyr Ile Ile
                165                 170                 175

Leu Gly Asp Gly Met Ile Thr Leu Asp Asp Met Glu Glu Met Asp Gly
            180                 185                 190

Leu Ser Asp Phe Thr Gly Ser Val Leu Arg Leu Asp Val Asp Thr Asp
        195                 200                 205

Met Cys Asn Val Pro Tyr Ser Ile Pro Arg Ser Asn Pro His Phe Asn
    210                 215                 220

Ser Thr Asn Gln Pro Pro Glu Val Phe Ala His Gly Leu His Asp Pro
225                 230                 235                 240

Gly Arg Cys Ala Val Asp Arg His Pro Thr Asp Ile Asn Ile Asn Leu
                245                 250                 255

Thr Ile Leu Cys Ser Asp Ser Asn Gly Lys Asn Arg Ser Ser Ala Arg
```

```
            260                 265                 270
Ile Leu Gln Ile Ile Lys Gly Lys Asp Tyr Glu Ser Glu Pro Ser Leu
            275                 280                 285
Leu Glu Phe Lys Pro Phe Ser Asn Gly Pro Leu Val Gly Gly Phe Val
            290                 295                 300
Tyr Arg Gly Cys Gln Ser Glu Arg Leu Tyr Gly Ser Tyr Val Phe Gly
305                 310                 315                 320
Asp Arg Asn Gly Asn Phe Leu Thr Leu Gln Gln Ser Pro Val Thr Lys
                325                 330                 335
Gln Trp Gln Glu Lys Pro Leu Cys Leu Gly Thr Ser Gly Ser Cys Arg
            340                 345                 350
Gly Tyr Phe Ser Gly His Ile Leu Gly Phe Gly Glu Asp Glu Leu Gly
            355                 360                 365
Glu Val Tyr Ile Leu Ser Ser Ser Lys Ser Met Thr Gln Thr His Asn
            370                 375                 380
Gly Lys Leu Tyr Lys Ile Val Asp Pro Lys Arg Pro Leu Met Pro Glu
385                 390                 395                 400
Glu Cys Arg Ala Thr Val Gln Pro Ala Gln Thr Leu Thr Ser Glu Cys
                405                 410                 415
Ser Arg Leu Cys Arg Asn Gly Tyr Cys Thr Pro Thr Gly Lys Cys Cys
            420                 425                 430
Cys Ser Pro Gly Trp Glu Gly Asp Phe Cys Arg Thr Ala Lys Cys Glu
            435                 440                 445
Pro Ala Cys Arg His Gly Gly Val Cys Val Arg Pro Asn Lys Cys Leu
            450                 455                 460
Cys Lys Lys Gly Tyr Leu Gly Pro Gln Cys Glu Gln Val Asp Arg Asn
465                 470                 475                 480
Ile Arg Arg Val Thr Arg Ala Gly Ile Leu Asp Gln Ile Ile Asp Met
                485                 490                 495
Thr Ser Tyr Leu Leu Asp Leu Ser Tyr Ile Val
                500                 505

<210> SEQ ID NO 84
<211> LENGTH: 174
<212> TYPE: PRT
<213> ORGANISM: Homo sapiens

<400> SEQUENCE: 84

Cys Gly Pro Gly Arg Gly Phe Gly Lys Arg Arg His Pro Lys Lys Leu
1               5                   10                  15
Thr Pro Leu Ala Tyr Lys Gln Phe Ile Pro Asn Val Ala Glu Lys Thr
            20                  25                  30
Leu Gly Ala Ser Gly Arg Tyr Glu Gly Lys Ile Ser Arg Asn Ser Glu
        35                  40                  45
Arg Phe Lys Glu Leu Thr Pro Asn Tyr Asn Pro Asp Ile Ile Phe Lys
    50                  55                  60
Asp Glu Glu Asn Thr Gly Ala Asp Arg Leu Met Thr Gln Arg Cys Lys
65                  70                  75                  80
Asp Lys Leu Asn Ala Leu Ala Ile Ser Val Met Asn Gln Trp Pro Gly
                85                  90                  95
Val Lys Leu Arg Val Thr Glu Gly Trp Asp Glu Asp Gly His His Ser
            100                 105                 110
Glu Glu Ser Leu His Tyr Glu Gly Arg Ala Val Asp Ile Thr Thr Ser
        115                 120                 125
Asp Arg Asp Arg Ser Lys Tyr Gly Met Leu Ala Arg Leu Ala Val Glu
```

```
                130                 135                 140
Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly
                165                 170
```

<210> SEQ ID NO 85
<211> LENGTH: 175
<212> TYPE: PRT
<213> ORGANISM: Homo sapiens

<400> SEQUENCE: 85

```
Cys Gly Pro Gly Arg Val Gly Ser Arg Arg Pro Pro Arg Lys
1               5                   10                  15

Leu Val Pro Leu Ala Tyr Lys Gln Phe Ser Pro Asn Val Pro Glu Lys
                20                  25                  30

Thr Leu Gly Ala Ser Gly Arg Tyr Glu Gly Lys Ile Ala Arg Ser Ser
                35                  40                  45

Glu Arg Phe Lys Glu Leu Thr Pro Asn Tyr Asn Pro Asp Ile Ile Phe
50                  55                  60

Lys Asp Glu Glu Asn Thr Gly Ala Asp Arg Leu Met Thr Gln Arg Cys
65                  70                  75                  80

Lys Asp Arg Leu Asn Ser Leu Ala Ile Ser Val Met Asn Gln Trp Pro
                85                  90                  95

Gly Val Lys Leu Arg Val Thr Glu Gly Trp Asp Glu Asp Gly His His
                100                 105                 110

Ser Glu Glu Ser Leu His Tyr Glu Gly Arg Ala Val Asp Ile Thr Thr
                115                 120                 125

Ser Asp Arg Asp Arg Asn Lys Tyr Gly Leu Leu Ala Arg Leu Ala Val
                130                 135                 140

Glu Ala Gly Phe Asp Trp Val Tyr Tyr Glu Ser Lys Ala His Val His
145                 150                 155                 160

Cys Ser Val Lys Ser Glu His Ser Ala Ala Lys Thr Gly Gly
                165                 170                 175
```

<210> SEQ ID NO 86
<211> LENGTH: 176
<212> TYPE: PRT
<213> ORGANISM: Homo sapiens

<400> SEQUENCE: 86

```
Cys Gly Pro Gly Arg Gly Pro Val Gly Arg Arg Arg Tyr Ala Arg Lys
1               5                   10                  15

Gln Leu Val Pro Leu Leu Tyr Lys Gln Phe Val Pro Gly Val Pro Glu
                20                  25                  30

Arg Thr Leu Gly Ala Ser Gly Pro Ala Glu Gly Arg Val Ala Arg Gly
                35                  40                  45

Ser Glu Arg Phe Arg Asp Leu Val Pro Asn Tyr Asn Pro Asp Ile Ile
                50                  55                  60

Phe Lys Asp Glu Glu Asn Ser Gly Ala Asp Arg Leu Met Thr Glu Arg
65                  70                  75                  80

Cys Lys Glu Arg Val Asn Ala Leu Ala Ile Ala Val Met Asn Met Trp
                85                  90                  95

Pro Gly Val Arg Leu Arg Val Thr Glu Gly Trp Asp Glu Asp Gly His
                100                 105                 110

His Ala Gln Asp Ser Leu His Tyr Glu Gly Arg Ala Leu Asp Ile Thr
                115                 120                 125
```

```
Thr Ser Asp Arg Asp Arg Asn Lys Tyr Gly Leu Leu Ala Arg Leu Ala
    130                 135                 140

Val Glu Ala Gly Phe Asp Trp Val Tyr Tyr Glu Ser Arg Asn His Val
145                 150                 155                 160

His Val Ser Val Lys Ala Asp Asn Ser Leu Ala Val Arg Ala Gly Gly
                165                 170                 175

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 87

His His His His His His
1               5
```